(12) United States Patent
Stanton et al.

(10) Patent No.: US 7,202,344 B2
(45) Date of Patent: Apr. 10, 2007

(54) SECRETED FACTORS

(75) Inventors: Lawrence W. Stanton, Redwood City, CA (US); R. Tyler White, Fremont, CA (US)

(73) Assignee: Scios Inc., Fremont, CA (US)

( * ) Notice: Subject to any disclaimer, the term of this patent is extended or adjusted under 35 U.S.C. 154(b) by 204 days.

(21) Appl. No.: 10/959,440

(22) Filed: Oct. 5, 2004

(65) Prior Publication Data

US 2005/0208605 A1 Sep. 22, 2005

Related U.S. Application Data

(62) Division of application No. 09/809,545, filed on Mar. 14, 2001, now Pat. No. 6,800,455.

(60) Provisional application No. 60/193,548, filed on Mar. 31, 2000.

(51) Int. Cl.
*C07K 16/00* (2006.01)
*C07K 16/18* (2006.01)
*G01N 33/53* (2006.01)
*G01N 33/563* (2006.01)

(52) U.S. Cl. .............. 530/387.1; 530/388.1; 435/7.1

(58) Field of Classification Search .......... None
See application file for complete search history.

(56) References Cited

U.S. PATENT DOCUMENTS

| 4,873,191 A | 10/1989 | Wagner et al. ............. 800/25 |
| 5,716,785 A | 2/1998 | Van Gelder et al. ........... 435/6 |
| 5,744,305 A | 4/1998 | Fodor et al. ................. 435/6 |
| 5,800,992 A | 9/1998 | Fodor et al. ................. 435/6 |
| 5,807,522 A | 9/1998 | Brown et al. ............... 422/50 |

FOREIGN PATENT DOCUMENTS

| EP | 0373203 B | 8/1994 |
| WO | WO 00/11942 A1 | 3/2000 |
| WO | WO 00/35473 A2 | 6/2000 |

OTHER PUBLICATIONS

Arola et al., J. Med. Virol. (1995) 47:251-259.
Bonaldo et al., Genome Res. (1996) 6:791.
Branch, Trends in Biological Sciences (1998) 23:45.
Chow et al., Lab. Invest. (1991) 64:55-64.
Cohen et al., Nature (1993) 266:698-701.
Copeland et al., Trends in Genetics (1991) 7:113-118.
Cowley et al., Kidney Int. (1993) 43:522-534.
Database EBI/SWALL 'online! (Mar. 1, 2002) Cros et al., Gene Expression Alterations Revealed by Supression Substractive Hybridization in Rat Soleus Muscle Disuse Atrophy: Database Accession No. Q8VD50XP002195683.
DeRisi et al., Nat. Genet. (1996) 14(4):457-460.
Gordon, Intl. Rev. Cytol. (1989) 115:171-229.
Gu et al., Science (1994) 265:103-106.
Heller et al., PNAS (1997) 94(6):2150-2155.
Hohenadl et al., Mol. Cell. Probes (1991) 5:11-20.
Hubank and Schatz, Nucl. Acids Res. (1994) 22(25):5640-5648.
Jiang and Fisher, Mol. Cell. Different. (1993) 1:285-299.
Jiang et al., Oncogene (1995) 10:1855-1864.
Kaspareit-Rittinghaus et al., Transplant Proc. (1990) 6:2582-2583.
Kennell et al., Progr. Nucl. Acid Res. Mol. Biol. (1971) 11:259.
Lavitrano et al., Cell (1989) 57:717-723.
Liang and Pardee, Science (1992) 257:967-971.
Lo, Mol. Cell. Biol. (1983) 3:1803-1814.
McClelland and Welsh, PCR Methods and Applications (1994) 4:S66-81.
McManus et al., Clin. Immunol. Immunopathol. (1993) 68:159-169.
Melnick et al., J. Expert. Med. (1951) 93:247-266.
Ralph et al., PNAS (1993) 90:10710-10714.
Sagerstrom et al., Annu. Rev. Biochem. (1997) 66:751-783.
Schena et al., Science (1995) 270:467-470.
Schunkert et al., J. Clin. Invest. (1990) 86(6):1913-1920.
Small et al., Mol. Cell Biol (1985) 5:642-648.
Stanton, Cardiovascular Genomics (Jan. 30, 2000) 1-8.
Stanton et al., Circ. Res. (2000) 86(9):939-945.
Stanton et al., Circulation, American Heart Association (1998) 98(17):1746.
Thompson et al., Cell (1989) 56:313-321.
Velculescu et al., Science (1995) 270:484-487.
Wan et al., Nature Biotechnology (1996) 14:1685-1691.
Wang and Hanson, J. of Parenteral Science and Technology, Technical Report No. 10, Supp. 42-2S (1988).
Watson et al., Development Neuroscience (1993) 15:77-86.
Willenbrock, Life Sciences (1999) 65(21):2247-2249.
Zhang et al., Science (1997) 276:1268-1272.

Primary Examiner—James Martinell
(74) Attorney, Agent, or Firm—Morrison & Foerster LLP

(57) ABSTRACT

The invention concerns new secreted factors encoded by clones P00184_D11 (SEQ ID NO: 1), P00185_D11 (SEQ ID NO: 3), P00188_D12 (SEQ ID NO: 5), P00188_E01 (SEQ ID NO: 7), P00194_G01 (SEQ ID NO: 9), P00194_G05 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_E05 (SEQ ID NO: 45), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00269_H08 (SEQ ID NO: 62), P00628_H02 (SEQ ID NO: 66), P00629_C08 (SEQ ID NO: 68), P00641_G11 (SEQ ID NO: 71), P00648_E12 (SEQ ID NO: 73), P00697_C03 (SEQ ID NO: 75), and other mammalian homologues and variants of such factor, as well as polynucleotides encoding them. The invention further concerns methods and means for producing such factors and their use in the diagnosis and treatment of various cardiac, renal or inflammatory diseases.

20 Claims, 59 Drawing Sheets

FIGURE 1

```
gcggccgccc ctgacacaat ggctcagctt atgcctcagc gcagttcgct ccacccagga     60
atggcatcct gcagaataca cggcccctca tccccatccc gcgccagaga caccggccag    120
cccactgtcc ccgccacaca ttaaacttga tcctcctaca cagacgcact cggagcagag    180
cgcttataca agcgcacagc cgtctccggc accgccacac agacagatga tgccgccccg    240
accgacggcc agcccagac acaaccttct gaaaacacag aaaacaagtc ccagcccaag     300
cggctgcatg tgtccaacat ccccttccgg ttccgggatc cagacctccg acaaatgttt    360
ggccaatttg gtaaaatatt agatgttgaa attatttta atgagcgggg ctcgaaggga     420
tttggtttcg taactttcga aaatagtgcg gatgcggaca gggcgaggga gaaattgcac    480
ggtaccgtgg tagagggccg taaaatcgag gttaataatg cgacagcacg cgtg atg     537
                                                                Met
                                                                  1
```

| | | | | | | | | | | | | | | | | |
|---|---|---|---|---|---|---|---|---|---|---|---|---|---|---|---|---|
| act | aat | aaa | aag | gcc | gtg | aac | ccc | tac | acc | aat | ggc | tgg | aaa | tta | aat | 585 |
| Thr | Asn | Lys | Lys | Ala | Val | Asn | Pro | Tyr | Thr | Asn | Gly | Trp | Lys | Leu | Asn | |
| | | | 5 | | | | 10 | | | | | 15 | | | | |

| | | | | | | | | | | | | | | | | |
|---|---|---|---|---|---|---|---|---|---|---|---|---|---|---|---|---|
| cca | gtt | gtg | ggc | gcg | gtc | tac | agc | ccc | gac | ttc | tat | gca | ggc | acg | gtg | 633 |
| Pro | Val | Val | Gly | Ala | Val | Tyr | Ser | Pro | Asp | Phe | Tyr | Ala | Gly | Thr | Val | |
| | | 20 | | | | | 25 | | | | | 30 | | | | |

| | | | | | | | | | | | | | | | | |
|---|---|---|---|---|---|---|---|---|---|---|---|---|---|---|---|---|
| ctg | ttg | tgc | cag | gcc | aac | cag | gag | gga | tct | tcc | atg | tac | agt | ggc | ccc | 681 |
| Leu | Leu | Cys | Gln | Ala | Asn | Gln | Glu | Gly | Ser | Ser | Met | Tyr | Ser | Gly | Pro | |
| | 35 | | | | | 40 | | | | | 45 | | | | | |

| | | | | | | | | | | | | | | | | |
|---|---|---|---|---|---|---|---|---|---|---|---|---|---|---|---|---|
| agt | tca | ctt | gta | tat | act | tct | gca | atg | cct | ggc | ttt | cca | tat | ccg | gcc | 729 |
| Ser | Ser | Leu | Val | Tyr | Thr | Ser | Ala | Met | Pro | Gly | Phe | Pro | Tyr | Pro | Ala | |
| 50 | | | | | 55 | | | | | 60 | | | | | 65 | |

| | | | | | | | | | | | | | | | | |
|---|---|---|---|---|---|---|---|---|---|---|---|---|---|---|---|---|
| gcc | act | gct | gca | gct | gca | tac | cga | ggg | gct | cac | ctt | cga | ggc | cgt | ggt | 777 |
| Ala | Thr | Ala | Ala | Ala | Ala | Tyr | Arg | Gly | Ala | His | Leu | Arg | Gly | Arg | Gly | |
| | | | 70 | | | | | 75 | | | | | 80 | | | |

| | | | | | | | | | | | | | | | | |
|---|---|---|---|---|---|---|---|---|---|---|---|---|---|---|---|---|
| cgc | acc | gtg | tac | aac | acc | ttc | aga | gct | gcg | gcg | ccc | cca | ccc | cca | atc | 825 |
| Arg | Thr | Val | Tyr | Asn | Thr | Phe | Arg | Ala | Ala | Ala | Pro | Pro | Pro | Pro | Ile | |
| | | | 85 | | | | | 90 | | | | | 95 | | | |

| | | | | | | | | | | | | | | | | |
|---|---|---|---|---|---|---|---|---|---|---|---|---|---|---|---|---|
| ccg | gcc | tat | ggc | gga | gta | gtg | tat | caa | gag | cca | gtg | tat | ggc | aat | aaa | 873 |
| Pro | Ala | Tyr | Gly | Gly | Val | Val | Tyr | Gln | Glu | Pro | Val | Tyr | Gly | Asn | Lys | |
| | | | 100 | | | | | 105 | | | | | 110 | | | |

| | | | | | | | | | | | | | | | | |
|---|---|---|---|---|---|---|---|---|---|---|---|---|---|---|---|---|
| ttg | cta | cag | ggt | ggt | tac | gct | gca | tac | cgc | tac | gcc | cag | ccc | acc | cct | 921 |
| Leu | Leu | Gln | Gly | Gly | Tyr | Ala | Ala | Tyr | Arg | Tyr | Ala | Gln | Pro | Thr | Pro | |
| | | 115 | | | | | 120 | | | | | 125 | | | | |

| | | | | | | | | | | | | | | | | |
|---|---|---|---|---|---|---|---|---|---|---|---|---|---|---|---|---|
| gcc | act | gct | gct | gcc | tac | agt | gac | agt | tac | gga | cga | gtt | tat | gct | gcc | 969 |
| Ala | Thr | Ala | Ala | Ala | Tyr | Ser | Asp | Ser | Tyr | Gly | Arg | Val | Tyr | Ala | Ala | |
| 130 | | | | | 135 | | | | | 140 | | | | | 145 | |

| | | | | | | | | | | | | | | | | |
|---|---|---|---|---|---|---|---|---|---|---|---|---|---|---|---|---|
| gac | ccc | tac | cac | cac | aca | ctt | gct | cca | gcc | ccc | acc | tac | ggc | gtt | ggt | 1017 |
| Asp | Pro | Tyr | His | His | Thr | Leu | Ala | Pro | Ala | Pro | Thr | Tyr | Gly | Val | Gly | |
| | | | 150 | | | | | 155 | | | | | 160 | | | |

| | | | | | | | | | | | | | | | | |
|---|---|---|---|---|---|---|---|---|---|---|---|---|---|---|---|---|
| gcc | atg | aat | gct | ttt | gcg | ccc | ttg | acc | gat | gcc | aag | act | agg | agc | cat | 1065 |

FIGURE 1 (cont.)

```
Ala Met Asn Ala Phe Ala Pro Leu Thr Asp Ala Lys Thr Arg Ser His
            165                 170                 175 gct gat gat gtg ggt ctc gtt ctt tct tca ttg cag gct agt ata tac    1113
Ala Asp Asp Val Gly Leu Val Leu Ser Ser Leu Gln Ala Ser Ile Tyr
            180                 185                 190 caa ggg gga tac aac cgt ttt gct cca tat taaatgataa aaccattaaa     1163
Gln Gly Gly Tyr Asn Arg Phe Ala Pro Tyr
        195                 200 caaacaagca aaaaacaaaa caaaaacaaa aaaaccaacc ttccaatgtg gggagagagg    1223
aagctttccg aggcccgagt gttgcgacac atgcagtagg acatcacttt agcaactcaa    1283
agaaacaacg aaaaaaaaaa aaaaaaaaaa aataagcggc cgaaggggtt cgctaga       1340
```

FIGURE 2

```
tctagcgaac cccttcgcga agggggttcgc ctgtgctggt gggcgcggtg gcccgaagcc      60
ttggactcac tgcaggactg tgcagggaac cactgtccaa gcatcgggct aatagggggc     120
gcctgcctcg gtttaccctt cagcgtctgg tgaaatcccg cagcgtctag ggaaagatcc     180
gttctgctcc gcgagggaaa cagagccgtt gacc atg gtt gca acg ggc agt ttg     235
                                        Met Val Ala Thr Gly Ser Leu
                                        1                 5 agc agt aag aac acg gcc agc att tca gag ttg ctg gac ggt ggc tct       283
Ser Ser Lys Asn Thr Ala Ser Ile Ser Glu Leu Leu Asp Gly Gly Ser
        10                  15                  20 cac cct ggg agt ctg cta agt gat ttc gac tac tgg gat tat gtc gtc       331
His Pro Gly Ser Leu Leu Ser Asp Phe Asp Tyr Trp Asp Tyr Val Val
        25                  30                  35 cct gag ccc aac ctc aac gag gtg gtg ttt gaa gag aca aca tgc cag       379
Pro Glu Pro Asn Leu Asn Glu Val Val Phe Glu Glu Thr Thr Cys Gln
40                  45                  50                  55 aat ttg gtt aaa atg ttg gag aac tgt ctg tcc aag tca aag caa acc       427
Asn Leu Val Lys Met Leu Glu Asn Cys Leu Ser Lys Ser Lys Gln Thr
            60                  65                  70 aaa ctc ggt tgc tct aag gtc ctg gtt cct gag aaa ctg acc cag aga       475
Lys Leu Gly Cys Ser Lys Val Leu Val Pro Glu Lys Leu Thr Gln Arg
            75                  80                  85 att gcc caa gat gtc ctg cgg ctc tca tcc aca gag ccc tgc ggc ctt       523
Ile Ala Gln Asp Val Leu Arg Leu Ser Ser Thr Glu Pro Cys Gly Leu
        90                  95                  100 cgg ggc tgt gtt atg cac gtg aac ttg gaa att gaa aat gtg tgt aaa       571
Arg Gly Cys Val Met His Val Asn Leu Glu Ile Glu Asn Val Cys Lys
105                 110                 115 aag ctg gat agg att gtg tgt gat gct agt gtg gtg ccg acc ttt gag       619
Lys Leu Asp Arg Ile Val Cys Asp Ala Ser Val Val Pro Thr Phe Glu
120                 125                 130                 135 ctc acg ctg gtg ttc aag cag gag agc tgc tcc tgg acc agc ctc aag       667
Leu Thr Leu Val Phe Lys Gln Glu Ser Cys Ser Trp Thr Ser Leu Lys
        140                 145                 150 gac ttc ttt agc gga ggt cgc ttc tcg tcg ggc ctt aag cga act         715
Asp Phe Phe Phe Ser Gly Gly Arg Phe Ser Ser Gly Leu Lys Arg Thr
            155                 160                 165 ctg atc ctc agc tcg gga ttt cga ctt gtt aag aaa aaa ctg tac tct       763
Leu Ile Leu Ser Ser Gly Phe Arg Leu Val Lys Lys Lys Leu Tyr Ser
        170                 175                 180 ctg att gga acg aca gtc att gag gag tgc tga ggaggaaaaa acaattaaag    816
Leu Ile Gly Thr Thr Val Ile Glu Glu Cys *
```

gtccctaatg agtggctaac aaaaanaaaa nnnnnnnnnn nnnnngcggn c        867

FIGURE 3

```
tctagcgaac cccttcggtg gacagaacag cctgagtcag g atg aaa gct ctc agg              56
                                              Met Lys Ala Leu Arg
                                               1               5 gct gtc ctc ctg atc ttg cta ctc agt gga cag cca ggg agc agc tgg             104
Ala Val Leu Leu Ile Leu Leu Leu Ser Gly Gln Pro Gly Ser Ser Trp
             10                  15                  20 gca caa gaa gct ggc gat gtg gac ctg gag cta gag cgc tac agc tac             152
Ala Gln Glu Ala Gly Asp Val Asp Leu Glu Leu Glu Arg Tyr Ser Tyr
             25                  30                  35 gat gat gac ggt gat gac gat gat gac gat gat gaa gaa gag gaa gag             200
Asp Asp Asp Gly Asp Asp Asp Asp Asp Asp Asp Glu Glu Glu Glu Glu
             40                  45                  50 gag gag acc aac atg atc cct ggc agc agg gac aga gca ccg cct cta             248
Glu Glu Thr Asn Met Ile Pro Gly Ser Arg Asp Arg Ala Pro Pro Leu
     55                  60                  65 cag tgc tac ttc tgc caa gtg ctt cac agc ggg gag agc tgc aac gag             296
Gln Cys Tyr Phe Cys Gln Val Leu His Ser Gly Glu Ser Cys Asn Glu
 70                  75                  80                  85 aca cag aga tgc tcc agc agc aag ccc ttc tgt atc aca gtc atc tcc             344
Thr Gln Arg Cys Ser Ser Ser Lys Pro Phe Cys Ile Thr Val Ile Ser
             90                  95                 100 cat ggc aaa act gac aca ggt gtc ctg acg acc tac tcc atg tgg tgt             392
His Gly Lys Thr Asp Thr Gly Val Leu Thr Thr Tyr Ser Met Trp Cys
            105                 110                 115 act gat acc tgc cag ccc atc gtg aag aca gtg gac agc acc caa atg             440
Thr Asp Thr Cys Gln Pro Ile Val Lys Thr Val Asp Ser Thr Gln Met
            120                 125                 130 acc cag acc tgt tgc cag tcc aca ctc tgc aat att cca ccc tgg cag             488
Thr Gln Thr Cys Cys Gln Ser Thr Leu Cys Asn Ile Pro Pro Trp Gln
    135                 140                 145 agc ccc caa atc cac aac cct ctg ggt ggc cgg gca gac agc ccc ttg             536
Ser Pro Gln Ile His Asn Pro Leu Gly Gly Arg Ala Asp Ser Pro Leu
150                 155                 160                 165 aag ggt ggg acc aga cat cct caa ggt gac agg ttt agc cac ccc cag             584
Lys Gly Gly Thr Arg His Pro Gln Gly Asp Arg Phe Ser His Pro Gln
            170                 175                 180 gtt gtc aag gtt act cat cct cag agt gat ggg gct cac ttg tct aag             632
Val Val Lys Val Thr His Pro Gln Ser Asp Gly Ala His Leu Ser Lys
            185                 190                 195 ggt ggc aag gct aac cag ccc cag gga aat ggg gcc gga ttc cct gca             680
```

FIGURE 3 (cont.)

```
Gly Gly Lys Ala Asn Gln Pro Gln Gly Asn Gly Ala Gly Phe Pro Ala
        200                 205                 210 ggc tgg agc aaa ttt ggt aac gta gtt ctc ctg ctc acc ttc ctc acc    728
Gly Trp Ser Lys Phe Gly Asn Val Val Leu Leu Leu Thr Phe Leu Thr
    215                 220                 225 agt ctg tgg gca tca ggg gcc taa agactcgtcc tcccccaacc aggacccttc   782
Ser Leu Trp Ala Ser Gly Ala  *
230                 235 agcctttcct ccctgacaac cagcttcaga gaataaactt gaatgtcttt tgccatctaa  842
aaaaaaaaaa aaaaaaaaaa aaagcggccg cc                                874
```

FIGURE 4

```
tctagcgaac cccttcgagc gaaccccttc ggccagtacc ctgagccctg gtccctcctg      60
gagctgcccc acagctctga ctgtggactg agggatgtta ggcggatcac ctgagcctcc     120
agaggctcac acta atg agc ggg cgc tct ctt ctt agc cac tgt tgc att       170
              Met Ser Gly Arg Ser Leu Leu Ser His Cys Cys Ile
               1           5                      10 tgg ttt tca ttg act cct ggg cct cgt ttg agt gac act gtc ctt gtc       218
Trp Phe Ser Leu Thr Pro Gly Pro Arg Leu Ser Asp Thr Val Leu Val
         15              20              25 ttt tgt ttc aga gct ctc cca gtg tta gtg gac tca gat gag gaa att       266
Phe Cys Phe Arg Ala Leu Pro Val Leu Val Asp Ser Asp Glu Glu Ile
     30              35              40 atg acc aga tct gaa ata gct gaa aaa atg ttc tct tca gaa aag ata       314
Met Thr Arg Ser Glu Ile Ala Glu Lys Met Phe Ser Ser Glu Lys Ile
 45              50              55              60 atg tga tcagggcccc agtgggtcca gtgtgcatgg gagcgcggtc aggtgatggg        370
Met * aaaggcctgg ctctcgtcaa aactgacagc tgcgctatga tacatgtctc actttgttgt     430
cttggagatc tgtgtatgca ggtgaagaac tcaagtgtgg gagggtctgc cgcctcagaa     490
agccatcttt gaaacggact cataaagtca gttttgttgc cattaagttg cctgattttg     550
gaaacaattt aagaagtgtt aaagacatgt gttcagatgc ctcttaggcg gcagccacag     610
gcatgccagg ttgtgtccct cagttttctc cagacaaaag aatctgcagc tgggcgtggc     670
ggcacactac tggcagttga aagtctgtaa tttcaaggcc aagcctggtc tacatagttc     730
caggacaacc agagagatct acatagtgag accctgcctc aaaacacaga aaccnnanna    790
naaaaaaaaa aaaaaaaaag cggccgc                                         817
```

FIGURE 5

```
tctagcgaac cccttcgcac atgggttcct gctgaccaag gggacatggc tctgaagatg     60
atgaggctgg ttactcagca ggagtagctg agctgagctg gccctggagg ccctggaggc    120
cctggagtag ggcccagg atg cag gtg cta atg tct atc ccc ggc gct ctt     171
                    Met Gln Val Leu Met Ser Ile Pro Gly Ala Leu
                     1               5                   10 ctt ccc gac tct acc atg gga tgt aac tcc agg agc ccc tgc cat ctc      219
Leu Pro Asp Ser Thr Met Gly Cys Asn Ser Arg Ser Pro Cys His Leu
            15                  20                  25 ccg tac caa aag act gtg gct tcc gtg tct act cag aaa tca gtt cta      267
Pro Tyr Gln Lys Thr Val Ala Ser Val Ser Thr Gln Lys Ser Val Leu
        30                  35                  40 ctt cgt aaa cag tgt tta aaa cca gac tca ttt aat cag agt gaa gga      315
Leu Arg Lys Gln Cys Leu Lys Pro Asp Ser Phe Asn Gln Ser Glu Gly
    45                  50                  55 ttg cag tcc att ggc ttc tta gca cag aag cag ctg ata aca caa gta      363
Leu Gln Ser Ile Gly Phe Leu Ala Gln Lys Gln Leu Ile Thr Gln Val
60                  65                  70                  75 aac ccc agc cct tga gaggtagaag caagaggatc agaggttcaa gcgcatcctc      418
Asn Pro Ser Pro * ggctccatca caagttcaaa agccgcctgc accaaatggg agtccttgtc tcaaaaaaaa    478
aaaaaaaaaa agcaaagaaa gcaaggact cgatgacatg atttatagac aaaagcagtg    538
ggagaaaata ctaaagcccc actgagctgc cagccaggtg tctgtgacta caggtctttt    598
atctgctcat atatattttt acaaaaaatg aaattcatat tggtcgctat tttgctggct    658
gctttgctcc cgatcaacat gatttgcacg ttttttccat caataaatgt gccatgatat    718
ttttaaaaaa aaaaaaaaaa aaaaaaaaaa gggcncc                             755
```

FIGURE 6

```
tctagcgaac cccttcgcag ctctctgacc tgcgtcgccg ccgctctccg ctcttgattt      60
cgccgtg atg tcg acc gca atg aac ttc ggg acc aaa agc ttc cag ccg      109
        Met Ser Thr Ala Met Asn Phe Gly Thr Lys Ser Phe Gln Pro
         1       5                  10 cgg ccc cca gac aaa ggc agc ttc ccg cta gac cac ttc ggt gag tgt      157
Arg Pro Pro Asp Lys Gly Ser Phe Pro Leu Asp His Phe Gly Glu Cys
 15              20                  25                      30 aaa agc ttt aag gaa aaa ttc atg aag tgt ctc cgc gac aag aac tat      205
Lys Ser Phe Lys Glu Lys Phe Met Lys Cys Leu Arg Asp Lys Asn Tyr
                 35                  40                  45 gaa aat gct ctg tgc aga aat gaa tct aaa gag tat tta atg tgc agg      253
Glu Asn Ala Leu Cys Arg Asn Glu Ser Lys Glu Tyr Leu Met Cys Arg
             50                  55                  60 atg caa agg cag ctg atg gca cca gaa cca cta gag aaa ctc ggc ttt      301
Met Gln Arg Gln Leu Met Ala Pro Glu Pro Leu Glu Lys Leu Gly Phe
         65                  70                  75 aga gac ata atg gag gag aaa ccg gag gca aag gac aaa tgt tga          346
Arg Asp Ile Met Glu Glu Lys Pro Glu Ala Lys Asp Lys Cys  *
     80                  85                  90 gaatcactgg gctgtgtccc cctacctgga gcagagctga gcccttctgc ccaccgtgga    406
gagagctgag ccatcctgtg ctgcccagag gagggctct ccgtgtcgac tttggctcat    466
ccctgcagca cagaccaaac tgctttctct actgaccaca cttctgcttc agagagnggt    526
ttctcctgtc tgngtgtggc acaggatctg ctcanggctg aacactgatg tgatatgata    586
tcccacctag tgtggccgca caccaaaagg cctggacagg atttcacagt gactcaacct    646
gagtcctcac acccggaacc tgtcagcgaa accaancga agcaaaatgn ctggcttttg    706
gcttacaaac cccatnattt gntttccctt ctcttgggtc tttgttttga caaanctggc    766
atacaaagtn ggaaggggga aataaaaaaa aaaaaaaaaa                          806
```

FIGURE 7

```
tctagcgaac ccctcncga aggggttcgc cgagaggtgg gagccaaaag gatggagcat      60
ccgccggtgg tggctggtgg ccgcaatctt ggtggtcctg atcggggttg tcttagtctg     120
cctgatagtc tacttcgcca acgcagcgca cagcgaggcc tgtaagaacg ggttgcggtt     180
gcaggatgag tgccgaaaca ccacgcacct gttgaagcac cagctnaccc gcgcccagga     240
cagcctgctg cagacggag atg cag gca aac tcc tgc aac cag acc gtg atg      292
                     Met Gln Ala Asn Ser Cys Asn Gln Thr Val Met
                      1               5                      10 gac ctt cgg gat tcc ctg aag aag aag gtg tct naa acc cag gag caa       340
Asp Leu Arg Asp Ser Leu Lys Lys Lys Val Ser Xaa Thr Gln Glu Gln
             15                  20                  25 can gcc cgc atc aag gaa ctt gag aat aag atc gag agg ctg aac caa       388
Xaa Ala Arg Ile Lys Glu Leu Glu Asn Lys Ile Glu Arg Leu Asn Gln
         30                  35                  40 gag ctg gag aaa ttt gag gac cca aaa gga aat ttc tac cac agt gca       436
Glu Leu Glu Lys Phe Glu Asp Pro Lys Gly Asn Phe Tyr His Ser Ala
     45                  50                  55 ngt gaa ctc aag cgg gtt cgt ggt ggn ctt can cct act tgt gct ttg       484
Xaa Glu Leu Lys Arg Val Arg Gly Gly Leu Xaa Pro Thr Cys Ala Leu
 60              65                  70                  75 tgg cgg gac tgt tct nca ctt ttt ang acc caa taa ttgggangta            530
Trp Arg Asp Cys Ser Xaa Leu Phe Xaa Thr Gln  *
                 80                  85 caaacctgtg taggcattgn nggtngtaat ggcttttgag ggggtcctgg cacccttaag     590
atgtgaanac cattangnng gacccaaaat gnnttttctt gntttgaact ggggcggacc     650
cggagtgggg ggcnggaaat aanntattnn ggnnggaaan aaaaaaaaaa aaaaaaaaa      710
gcggccc                                                              717
```

FIGURE 8

```
tctagcgaac ccttcgccc agctgctaga agccaggctg gcctggtgag gc atg agc        58
                                                          Met Ser
                                                            1 atg aag atg aac cca ggt gac aag gac aag atg ttg ctc ttc tcc cca        106
Met Lys Met Asn Pro Gly Asp Lys Asp Lys Met Leu Leu Phe Ser Pro
         5               10              15 ccc ttt gac ccc tgt ctt cta agg cat cta gga agg aac cag tgt cct        154
Pro Phe Asp Pro Cys Leu Leu Arg His Leu Gly Arg Asn Gln Cys Pro
     20              25              30 tgg tac tga tttacttaga ttcaacctaa gggtccagcc actgactaag               203
Trp Tyr  *
 35
```

```
gccaaggcca ttttccata cctgggaggg tagagattca gggttgtggg taagtgggca        263
ctaaacatgg atttgcaagg gaaaacgaca gggcatcgag ctaaatttga atttacatga      323
aattctgaaa tgtacttgta tgaagaaact gttatctgaa acctaactta aatgggcatc      383
ctgccttttg tctggtgaga aatgaaagtg atctacaata agtgtcaaag caacaaggcc      443
cctctggata tgtctaggcc aggatgagga tactaagtgc cttcaaagcg agagggaggc      503
aggccaagaa cactgcccta ctgaaaggca ggcttggccg gctagggcct ccaaggccct      563
gatccctgag gcaccacagc cacaacttgt gtaggcctgg cccaggtcag tgaataggtt      623
ctaggcagtg gttctcaacc ttcctaatgc tgcaaccctt caatacagtt tctcctgttg      683
tagtaatccc caaccataaa attattttca ttgcgacttc ataactggac ttttgctact      743
gttatgaatc ataatgtaaa tatttttggg agctagaggt ttaccaaggg ggttgtgagc      803
cataggttga aaaccattgt tctaggaata gctccagggg tggtttctga ggcccccgca      863
aggtgggatc tatgggcag ggttggatct tctccaagag cccccaacag gatatatata       923
tatatatata tatatatata tatatatata tatatatata tactttgata gcatcccatg      983
gaacgactgt ctcctgatac taaagggagc ttggaagaaa ccaaggctga gagaagttgt     1043
agagtgggaa ggtaggcgaa gggattgagg tgacacagtg atagccccctt cagggtgggg    1103
tctacccnag acagcagata aaggccttag gatgggagat tactctggct gctcagaggg     1163
gaacacaggg acacagcacc aataaaatct ctttcttttc aaaaaaaaaa aaaaaaaaa      1223
aaaaagcggn cc                                                         1235
```

FIGURE 9

```
tctagcgaac ccettcgatt ttattagctc ttgcttctcc attcctcata atttatgaat    60
tatacagcct tcgcttgaat acgcgtctga agttatgctt tgtgttgttg tgggttttt    120
ttttttttc ttttcttttt ttttggagct ggggaccgaa cccagggcct tgttgctcta    180
ccactgagct aaatccccaa ccctgttgt gtgttttaaa taagtctctt actgtccatt    240
ttgtaattag tgttgttacc ttgtaataat agacatcata caaagtttcc tcttttttgt    300
gccagtgctg agaacatgag aaacatttaa tgagtatttg tttgttaaat aatatttata    360
acggctagaa tggcagacac ac atg gta gca cat gat ggt gat ttt cgg ggg    412
                        Met Val Ala His Asp Gly Asp Phe Arg Gly
                         1            5                      10 cct ttt gtt tgc tca gag ctg gta atc tct gcc ggt tgg ttt gct ttg    460
Pro Phe Val Cys Ser Glu Leu Val Ile Ser Ala Gly Trp Phe Ala Leu
             15                  20                  25 cct ggt ctg gga cta acc tca cat ttt ctc act ctt gct ttc cga gag    508
Pro Gly Leu Gly Leu Thr Ser His Phe Leu Thr Leu Ala Phe Arg Glu
             30                  35                  40 att agt cat cct tcc tgt cct act ggg ctc tcg ata gcg ctc atc agc    556
Ile Ser His Pro Ser Cys Pro Thr Gly Leu Ser Ile Ala Leu Ile Ser
             45                  50                  55 ata ctg cat ttc aat ccc agc gaa ggg gtt cgc cga agg ggt tcg cta    604
Ile Leu His Phe Asn Pro Ser Glu Gly Val Arg Arg Arg Gly Ser Leu
             60                  65                  70 ggc cag tgt gat gga tat ctg cag aat tc                              633
Gly Gln Cys Asp Gly Tyr Leu Gln Asn
 75                  80
```

FIGURE 10

```
tctagcgaac cccttcgcct ttctccaaag ccttcccgtt tcctcttgac agctacgggc    60
tgaggcagcc attcctgcag cagcgctcgg ccggtgaagg gccgaactga cgcctcctag   120
atctgtctcg gctgaattac tctcacccgt ttccattctg tgtgcaccag aaatctgaga   180
tccaggagta tcaacagcaa ag atg tct aat gag cca ccc cct cct tat cca   232
                         Met Ser Asn Glu Pro Pro Pro Pro Tyr Pro
                          1               5                  10 gga ggg cct aca gcc cca cta ctg gag gaa aaa agt gga gcc cca cat    280
Gly Gly Pro Thr Ala Pro Leu Leu Glu Glu Lys Ser Gly Ala Pro His
             15                  20                  25 acc cca ggc cga acc ttt cca gct gtg atg cag cca cca cca ggc atg    328
Thr Pro Gly Arg Thr Phe Pro Ala Val Met Gln Pro Pro Pro Gly Met
             30                  35                  40 cca ctg ccc tct gtt gac att gcc ccc ccg ccc tat gag ccg cct ggc    376
Pro Leu Pro Ser Val Asp Ile Ala Pro Pro Pro Tyr Glu Pro Pro Gly
             45                  50                  55 cat cca ggg cct aag cct ggt ttw atg ccc ccc acn tta cca cac att    424
His Pro Gly Pro Lys Pro Gly Xaa Met Pro Pro Thr Leu Pro His Ile
             60                  65                  70 cna ana acc ttn ntn tgt aaa agt taa ataanaangg agggattcga           471
Xaa Xaa Thr Xaa Xaa Cys Lys Ser  *
 75                  80 nccccctnca acnggtttca agccaatttty mtaaccattt tgtttttttc wtttaaaaaa  531
aaaaaaaaaa aaaaaaaaaa aaaaaaaaaa aaaaaaaaag gggaaaaaaa aaaaaaaaaa  591
aaaaaagggg ggcccc                                                   607
```

FIGURE 11

```
tctagcgaac ccct tcgcaa agtcctaagc cttac atg aga aaa ttt aag aca        53
                                          Met Arg Lys Phe Lys Thr
                                           1                5 ccc tta atg att gcg gaa gaa aaa tac aga caa caa agg gaa gag ctt       101
Pro Leu Met Ile Ala Glu Glu Lys Tyr Arg Gln Gln Arg Glu Glu Leu
            10              15                      20 gag aaa cag aga cgg gag agt tct tgc cat agc atc atc aaa aca gaa       149
Glu Lys Gln Arg Arg Glu Ser Ser Cys His Ser Ile Ile Lys Thr Glu
        25              30                      35 acc cag cac cgc agc tta tca gag aaa gag aaa gaa aca gag tta caa       197
Thr Gln His Arg Ser Leu Ser Glu Lys Glu Lys Glu Thr Glu Leu Gln
    40              45                      50 aaa gca gct gag gca atg tcc act ccc aga aag gat tca gac ttc act       245
Lys Ala Ala Glu Ala Met Ser Thr Pro Arg Lys Asp Ser Asp Phe Thr
55              60                      65                  70 agg gca cag ccc aac ctg gaa cct aaa agc aag gct gtg atc gcc agt       293
Arg Ala Gln Pro Asn Leu Glu Pro Lys Ser Lys Ala Val Ile Ala Ser
                75              80                      85 gaa tgc tct gaa agc cag ctc tct aca gct tcc gca ttg aca gtc gct       341
Glu Cys Ser Glu Ser Gln Leu Ser Thr Ala Ser Ala Leu Thr Val Ala
            90              95                     100 acc gag agg ctc cag cat gtt cta gcc gct tca gac gat aag ctt acc       389
Thr Glu Arg Leu Gln His Val Leu Ala Ala Ser Asp Asp Lys Leu Thr
        105             110                     115 ctg cga cgg gaa ggc aca cag aac tca agt gac acc cta caa tcg aaa       437
Leu Arg Arg Glu Gly Thr Gln Asn Ser Ser Asp Thr Leu Gln Ser Lys
    120             125                     130 aca gct tgt gag att aac cag agt cac aag gaa tgt agg aca gag caa       485
Thr Ala Cys Glu Ile Asn Gln Ser His Lys Glu Cys Arg Thr Glu Gln
135             140                     145                 150 aca ttt gag caa cac gtg gag aag ttg ccc ttc ccc caa acc aaa ccc       533
Thr Phe Glu Gln His Val Glu Lys Leu Pro Phe Pro Gln Thr Lys Pro
                155                     160                 165 att tcc ccg agt ttc aaa gtg aaa act atc agg ctt cca gct cta gat       581
Ile Ser Pro Ser Phe Lys Val Lys Thr Ile Arg Leu Pro Ala Leu Asp
            170             175                     180 cat acg ctg act gaa aca gat ctc agt tct gaa cgc cgc gta aag caa       629
His Thr Leu Thr Glu Thr Asp Leu Ser Ser Glu Arg Arg Val Lys Gln
        185             190                     195 tcc gaa att gac gtt caa acc agt act aaa gaa atg aat aag gaa att       677
```

```
Ser Glu Ile Asp Val Gln Thr Ser Thr Lys Glu Met Asn Lys Glu Ile
    200                 205                 210
```
FIGURE 11 (cont.)

```
aag aaa acc gaa gtg agc aca cag tgt gat aat aag caa tct gtg gct      725
Lys Lys Thr Glu Val Ser Thr Gln Cys Asp Asn Lys Gln Ser Val Ala
215             220                 225                 230 gaa aaa tat ttt caa tta cct aaa aca gag aaa cgg gtg acg gta caa      773
Glu Lys Tyr Phe Gln Leu Pro Lys Thr Glu Lys Arg Val Thr Val Gln
                235                 240                 245 atg ccc aaa gac tat gca gcg aaa agt cat caa agc aaa ctc caa aca      821
Met Pro Lys Asp Tyr Ala Ala Lys Ser His Gln Ser Lys Leu Gln Thr
            250                 255                 260 gtt ccc aag aag cat gga gga ttg ggg gag ttt gac aga ggg aat gtc      869
Val Pro Lys Lys His Gly Gly Leu Gly Glu Phe Asp Arg Gly Asn Val
        265                 270                 275 ctg ggg agg gaa gga aaa aat cag gac tcc tcc atg agc agt aca aaa      917
Leu Gly Arg Glu Gly Lys Asn Gln Asp Ser Ser Met Ser Ser Thr Lys
    280                 285                 290 gaa agc agg gta ata gtt gaa aga aag caa gaa cat cta cag gac cag      965
Glu Ser Arg Val Ile Val Glu Arg Lys Gln Glu His Leu Gln Asp Gln
295                 300                 305                 310 agc gta cca agg tta gtc caa caa aag att atc ggt gaa agc ctg gac     1013
Ser Val Pro Arg Leu Val Gln Gln Lys Ile Ile Gly Glu Ser Leu Asp
                315                 320                 325 tca cgg gtt cag aat ttt cag cag aca caa aca caa act tct agg att     1061
Ser Arg Val Gln Asn Phe Gln Gln Thr Gln Thr Gln Thr Ser Arg Ile
            330                 335                 340 gag cat aaa gaa ctg tcc caa cct tac agt gag aaa aaa tgt ctt aga     1109
Glu His Lys Glu Leu Ser Gln Pro Tyr Ser Glu Lys Lys Cys Leu Arg
        345                 350                 355 gac aag gac aaa caa caa aaa cag gtc tcc tct aac act gac gat tca     1157
Asp Lys Asp Lys Gln Gln Lys Gln Val Ser Ser Asn Thr Asp Asp Ser
    360                 365                 370 aag caa gag ata aca caa aaa caa tct tca ttt tcc tct gtg aga gaa     1205
Lys Gln Glu Ile Thr Gln Lys Gln Ser Ser Phe Ser Ser Val Arg Glu
375                 380                 385                 390 tcc cag cag gat gga gaa aaa tgt gcc ata aaa ata ttg gaa ttc ttg     1253
Ser Gln Gln Asp Gly Glu Lys Cys Ala Ile Lys Ile Leu Glu Phe Leu
                395                 400                 405 aga aaa cgt gaa gaa cta cag cag att ttg tct agg gta aaa cag ttt     1301
Arg Lys Arg Glu Glu Leu Gln Gln Ile Leu Ser Arg Val Lys Gln Phe
            410                 415                 420 gaa gca gat tca aat aaa agt ggc ctt aaa aca ttt cag aca ctg tta     1349
```

```
Glu Ala Asp Ser Asn Lys Ser Gly Leu Lys Thr Phe Gln Thr Leu Leu
        425                 430                 435
```
FIGURE 11 (cont.)

```
aat att gct ccg gtg tgg ctg ata agt gag gag aaa aga gaa tat gga    1397
Asn Ile Ala Pro Val Trp Leu Ile Ser Glu Glu Lys Arg Glu Tyr Gly
    440                 445                 450 gtt cgt gtt gcc atg gag aat aat tag aaaaaataaa aaaaaaaaa           1444
Val Arg Val Ala Met Glu Asn Asn  *
455                 460 aaaagcggcg nc                                                      1456
```

FIGURE 12

```
gaattgtaat acgactcact ataggg cgaa ttgggcccct agcgaacccc ttcgacaaca      60
tcaaagagga cagatctaac cctagactga ggccggaggc ctggaccaat tacctgaggg     120
atgtccacag agcctttgca ctgctgaaca gtcaccctga tccaaaccaa gtaaatggga     180
ctccaactgc accaagcagt ggcctccag tcacctctgc tgagctcttg gtgccggcag     240
ag atg gct tct gca gag tca ggt gaa gac cca agt cat gtg gtt ggg       287
   Met Ala Ser Ala Glu Ser Gly Glu Asp Pro Ser His Val Val Gly
     1           5                  10                  15 gaa acg cct cct ttg acc ttg cca gcc aac ctc caa acc ctg cat ccg      335
Glu Thr Pro Pro Leu Thr Leu Pro Ala Asn Leu Gln Thr Leu His Pro
                 20                  25                  30 aac aga cca acg ttg agt cca gag aga aaa ctt gaa tgg aat aac gac      383
Asn Arg Pro Thr Leu Ser Pro Glu Arg Lys Leu Glu Trp Asn Asn Asp
             35                  40                  45 att cca gaa gtg aat cgt ttg aat tct gaa cac tgg aga aaa act gag      431
Ile Pro Glu Val Asn Arg Leu Asn Ser Glu His Trp Arg Lys Thr Glu
         50                  55                  60 gag cag cca gga cgg ggg gag gtg ctt ctc ccc gaa ggt gac gtc agt      479
Glu Gln Pro Gly Arg Gly Glu Val Leu Leu Pro Glu Gly Asp Val Ser
     65                  70                  75 ggc aac ggt atg aca gag ctg ttg ccc atc ggt cgg cac caa caa aag      527
Gly Asn Gly Met Thr Glu Leu Leu Pro Ile Gly Arg His Gln Gln Lys
 80                  85                  90                  95 cgt ccc cac gat gcg ggg cca gag gac cat gct ttt gaa gat caa ttg      575
Arg Pro His Asp Ala Gly Pro Glu Asp His Ala Phe Glu Asp Gln Leu
                 100                 105                 110 cat cct ctc gtc cac tct gac aga act ccc gtt cat cgg gtg ttc gat      623
His Pro Leu Val His Ser Asp Arg Thr Pro Val His Arg Val Phe Asp
             115                 120                 125 gtg tcc cac ttg gag cag cct gtt cac tcc agc cac gtg gaa gga atg      671
Val Ser His Leu Glu Gln Pro Val His Ser Ser His Val Glu Gly Met
         130                 135                 140 ttg gcc aag atg gag ggg atg gca caa agg agt ggg cac caa gtc tcg      719
Leu Ala Lys Met Glu Gly Met Ala Gln Arg Ser Gly His Gln Val Ser
     145                 150                 155 aag gca gcg cct cct ctc cag tca ctt ctt gct tag attacatgtt           765
Lys Ala Ala Pro Pro Leu Gln Ser Leu Leu Ala  *
160                 165                 170 gcctaacaat gtttctttcc atgttttgat tagtaaacta actcgtggtg gcaatcatga     825
ctcccaacct tctgagctcc cccgggtacg cttgcaccgt agacgctcat gtgcgcaccg     885
tgcgggtgat gctcacacac agactcattg taattcaccg ttttaccgag aaggggggggg    945
gggcgaattt tctgtgttga tgctttgttt ttggtactaa aacagnatta tcttttgaat    1005
attgtaggga catgagtata taaagtctat ccagtcaaaa tggctagaat tgngcctttg    1065
```

```
taagttttaa aaacttgatg cccacatgag tctgtgagca catntttccc gcctgcctaa   1125
cggagttgga atttgtttct aaccactgta attcttcaac atcatcacct ttggttcagt   1185
```
FIGURE 12 (cont.)

```
gattttgcac tttgagtttg gatactgtgt ctgcttggtt ggtagtgtta gtattttct    1245
tttaaacagg cttatcagag ttgcacactt tgtcctaggc agggcaaagg aatagacgcc.  1305
cagcaaggac acacagtata ggtaacatac tgcttatcgt acgcttttcc cacaaagcat   1365
tgcatgtgtt tttacctcga cgtgctaaag ttgattagca gaaaggcatg actcacaatt   1425
ttggtggtaa aaataaacc  ctgagggagc aagcaataac taaaacaaga ttgagctgct   1485
ctctctgtgc ttactaaata gatgctcgcc tgctaatgc  ttgccctctt gaaagaagaa   1545
acaggatgca cactgcttta tttcaatctt cctctttttt tcttggtttc accagtgagc   1605
gtaagcattg gaaaaatatg tgtagtctta tctttctata agacgatttt aataaactaa   1665
aatcacaaat gctgtaaagt ttgtgcgcac cagaatggag gctaacttca taaacattgt   1725
gctgtgcgaa tattcctaaa atgatcccca agctgtggtt ttctagaaga catagttcag   1785
aaccgctttt gaaaaatctg tcctcgtgag ctcactcagt ttctgtcgga cttttagaga   1845
cagtggaagg attacctcat tgagacgttt ccgtgtcctc ttcaactcca cagggtcttg   1905
acggtggctt tgttttcct  tctagactat tcaaacatgt agataagtta tattttctt    1965
taagtgttta aagtaaacac ttttcaaaaa aaaaaaaaaa aaaaaaaaa  gcggccgc     2023
```

FIGURE 13

| | |
|---|---|
| tctagcgaac cccttcgggg gttttcatc atg gag ctg tcg cgg cgg att tgt<br>                                                                Met Glu Leu Ser Arg Arg Ile Cys<br>                                                           -25                    -20 | 53 |
| ctc gtc cga ctg tgg ctg ttg cta ctg tca ttc tta ctg ggc ttc agc<br>Leu Val Arg Leu Trp Leu Leu Leu Leu Ser Phe Leu Leu Gly Phe Ser<br>         -15                     -10                      -5 | 101 |
| gcg gga tct gcc ctc aac tgg cgg gaa caa gaa ggc aag gaa gta tgg<br>Ala Gly Ser Ala Leu Asn Trp Arg Glu Gln Glu Gly Lys Glu Val Trp<br>    1                     5                         10 | 149 |
| gat tac gtg act gtt cga gag gat gca cgc atg ttc tgg tgg ctc tac<br>Asp Tyr Val Thr Val Arg Glu Asp Ala Arg Met Phe Trp Trp Leu Tyr<br>15                 20                   25                     30 | 197 |
| tat gcc acc aac cct tgc aag aac ttc tca gag ctg cct ctg gtc atg<br>Tyr Ala Thr Asn Pro Cys Lys Asn Phe Ser Glu Leu Pro Leu Val Met<br>               35                   40                     45 | 245 |
| tgg ctt cag ggt ggt cca ggt ggt tct agc act gga ttt gga aac ttt<br>Trp Leu Gln Gly Gly Pro Gly Gly Ser Ser Thr Gly Phe Gly Asn Phe<br>           50                       55                   60 | 293 |
| gag gaa atc ggc cct ctt gac acc cga ctc aag cca cgg aac act acc<br>Glu Glu Ile Gly Pro Leu Asp Thr Arg Leu Lys Pro Arg Asn Thr Thr<br>        65                       70                      75 | 341 |
| tgg ctg cag tgg gcc agt ctc ctg ttc gtg gac aat cct gtg ggc acg<br>Trp Leu Gln Trp Ala Ser Leu Leu Phe Val Asp Asn Pro Val Gly Thr<br>     80                     85                    90 | 389 |
| ggc ttc agt tac gtg aac acg aca gat gcc tac gca aag gac ctg gac<br>Gly Phe Ser Tyr Val Asn Thr Thr Asp Ala Tyr Ala Lys Asp Leu Asp<br>95                 100                105               110 | 437 |
| acg gtg gct tcc gac atg atg gtc ctc ctg aaa tcc ttc ttt gat tgt<br>Thr Val Ala Ser Asp Met Met Val Leu Leu Lys Ser Phe Phe Asp Cys<br>             115                 120                125 | 485 |
| cat aaa gaa ttc cag acg gtt ccg ttc tac att ttc tca gaa tcc tac<br>His Lys Glu Phe Gln Thr Val Pro Phe Tyr Ile Phe Ser Glu Ser Tyr<br>          130                      135              140 | 533 |
| gga gga aag atg gct gct ggc atc agt tta gaa ctt cac aag gct att<br>Gly Gly Lys Met Ala Ala Gly Ile Ser Leu Glu Leu His Lys Ala Ile<br>        145                    150               155 | 581 |
| cag caa ggg acc atc aag tgc aac ttc tct ggg gtt gct ttg ggt gac<br>Gln Gln Gly Thr Ile Lys Cys Asn Phe Ser Gly Val Ala Leu Gly Asp<br>160                 165                170 | 629 |
| tcc tgg atc tcc cct gtg gat tca gtg ctg tcc tgg gga cct tac ctg | 677 |

```
Ser Trp Ile Ser Pro Val Asp Ser Val Leu Ser Trp Gly Pro Tyr Leu
175                 180                 185                 190
```
FIGURE 13 (cont.)

```
tac agc gtg tct ctc ctt gat aat aaa ggc ttg gct gag gtg tcc gac    725
Tyr Ser Val Ser Leu Leu Asp Asn Lys Gly Leu Ala Glu Val Ser Asp
                195                 200                 205 att gcg gag caa gtc ctc aat gaa aaa caa ggg ctt cta caa gga agc    773
Ile Ala Glu Gln Val Leu Asn Glu Lys Gln Gly Leu Leu Gln Gly Ser
            210                 215                 220 cac tca gct gtg ggg gaa agc aga aat gat cat tga aaagaacacc         819
His Ser Ala Val Gly Glu Ser Arg Asn Asp His *
            225                 230 gacggggtaa acttctataa catcttaact aaaagcaccc ccgacacctc tatggagtcg   879
agcctcgagt tcttccggag ccccttagtt cgtctctgtc agcgccacgt gagacaccta   939
caaggagacg ccttaagtca gctcatgaac ggtcccatca aaaagaagct caaaattatc   999
cctgacgacg tctcctgggg agcccagtcg tcctccgtct tcataagcat ggaagaggac  1059
ttcatgaagc ctgtcatcga catcgtggat acgttgctgg aactcggggt caatgtgact  1119
gtgtacaatg ggcagctgga tctcattgtg gacaccatag tcaggagtc ctgggttcag   1179
aagctgaagt ggccacagct gtccagattc aatcagctaa aatggaaggc cctgtacacc  1239
gatcctaagt cttcagaaac atctgcattt gtcaagtcct atgagaacct agcgttctac  1299
tggatcctaa aggcgggtca catggttcct gctgaccaag gggacatggc tctgaagatg  1359
atgaggctgg ttactcagca ggagtagctg agctgagctg ccctggagg ccctggaggc   1419
cctggagtag ggcccaggat gcaggtgcta atgtctatcc ccggcgctct tcttcccgac  1479
tctaccatgg gatgtaactc caggagcccc tgccatctcc cgtaccaaaa gactgtggct  1539
tccgtgtcta ctcagaaatc agttctactt cgtaaacagt gtttaaaacc agactcattt  1599
aatcagagtg aaggattgca gtccattggc ttcttagcac agaagcagct gataacacaa  1659
gtaaacccca gcccttgaga ggtagaagca agaggatcag aggttcaagc gcatcctcgg  1719
ctccatcaca agttcaaaag ccgcctgcac caaatgggag tccttgtctc aaaaaaaaaa  1779
aaaaaaaaaa aaaagcggc cgc                                          1802
```

FIGURE 14

```
tctagcgaac cccttcgcga aggggttcgc taggttgcgt ttgtggagaa aaatctgttc    60
tacctcaggg ctgtgagaac ggcactcctg atg tct gag aaa gag aaa caa gat   114
                                 Met Ser Glu Lys Glu Lys Gln Asp
                                  1               5 tgg ctg aag gat cct ccg ttc ctt cag aga cct ggg tgg aga gca tta   162
Trp Leu Lys Asp Pro Pro Phe Leu Gln Arg Pro Gly Trp Arg Ala Leu
    10              15                  20 ggg aca cga aga aca gag tag cggaagaaga gttcttaagt aataagttta       213
Gly Thr Arg Arg Thr Glu  *
 25              30 cctcctgact ggctcacatc actgccttac tctgtagaaa gcaggtcatc tcatggattt   273
ccccctccca cccccccagc tggatcattt tttgactcag ggaaaataat taaattattg   333
tccaactgtt agtgttgatc ggtaacagca gaaaggcaga aagttcctga taatctcaat   393
attatctttt caaaagtatt ttcctggaat gttgtttgct ttggcattac aaagttctgt   453
actcttaaaa atatttgac ttgctgggca tggaggtcac acctttaatc cagaggcagg   513
catggatcca caggagttca aggccgcctg gctacaaagc gagttcaagg gcagccaggg   573
ctacacagag agaccttgtc tcntnaccnn tnannaaaaa acnaaaaagc cggccgc      630
```

FIGURE 15

```
tctagcgaac cccttcggta tagtctttag gtagtggctt agtccctgga agctctggtt        60
gcttggcatt tcaacgtgct tcttaaataa ctgttttatt agtcagtaca ag atg ctt       118
                                                         Met Leu
                                                          1 tgt ata tca gat ctg aaa tat ctt aaa att atc act tgc att gta aat         166
Cys Ile Ser Asp Leu Lys Tyr Leu Lys Ile Ile Thr Cys Ile Val Asn
         5                   10                  15 tac tat tcc ttt cgc aga aat aat gaa tgc ttc aag aaa aaa aaa agc         214
Tyr Tyr Ser Phe Arg Arg Asn Asn Glu Cys Phe Lys Lys Lys Lys Ser
     20                  25                  30 tgt ttg tat tgg gtt taa aacgtttcca acaccaatt attctttact                 262
Cys Leu Tyr Trp Val  *
 35 taagtcatcc gatctagtta ttaaattatt attactgcct tcacactatc aaagatggta       322
aatatctgat agaatcatat tcaaaatact tctgtttcac atttcttgag aaagtactga       382
ctgtctgagt tctttctcaa gaaatgtgaa acagaagtat tttgaatcga aggggttcgc       442
tag                                                                     445
```

FIGURE 16

```
tctagcgaac cccttcggaa gaactgtata tttgtgcctt gttctgcaag ttaaaaagct        60
ggtccagaca gtgtcataga attaactttt catttctgta ttaattttag gactgcaaaa       120
atcccaaagc tgtatactta gattggattc aataaaaagt ttaagtttac tnaanaaaaa       180
aaaaaaaaaa aaaaaaaaaa aaaaaaaaaa aaaaaaaaaa aaaanaaaaa aaaaaaaagg       240
aaaaaaaaaa ncggncnnaa aaaaggnggc cgc                                    273
```

FIGURE 17

```
tctagcgaac ccettcgggg gaacccaagc ggcttcgccc aggcattcgc gcgggcgccc    60
gcggtctggg tcccacctcc tctgctttcg caccettgaa gttttggagc accaggaaaa   120
gagggcaagg aaggagaggg gaagcgaaag catatcctaa aacatttact taaaggagga   180
aagaaaaggg gtcgcagaa atg gct ggg gca att ata gaa aac atg agc acc   232
                      Met Ala Gly Ala Ile Ile Glu Asn Met Ser Thr
                       1               5                      10 aag aag ctc tgc att gtt gga ggg att ctt ctg gtt ttc caa atc gtt   280
Lys Lys Leu Cys Ile Val Gly Gly Ile Leu Leu Val Phe Gln Ile Val
             15                  20                  25 gcc ttt ctg gtg gga ggc ttg atc gct cca gca ccc aca acg gca gtg   328
Ala Phe Leu Val Gly Gly Leu Ile Ala Pro Ala Pro Thr Thr Ala Val
         30                  35                  40 tcc tac gtg gca gca aaa tgt gtg gat gtc cgg aag aac cac cat aaa   376
Ser Tyr Val Ala Ala Lys Cys Val Asp Val Arg Lys Asn His His Lys
     45                  50                  55 aca aga tgg ctg atg ccc tgg gga cca aac aag tgt aac aag atc aat   424
Thr Arg Trp Leu Met Pro Trp Gly Pro Asn Lys Cys Asn Lys Ile Asn
 60                  65                  70                  75 gac ttc gaa gaa gca att cca agg gaa att gaa gcg aat gac att gtg   472
Asp Phe Glu Glu Ala Ile Pro Arg Glu Ile Glu Ala Asn Asp Ile Val
                 80                  85                  90 ttt tct gta cac att ccc ctc cct tct atg gag atg agc cca tgg ttc   520
Phe Ser Val His Ile Pro Leu Pro Ser Met Glu Met Ser Pro Trp Phe
             95                 100                 105 cag ttt atg ctg ttt atc ctg cag ata gac att gct ttc aag cta aac   568
Gln Phe Met Leu Phe Ile Leu Gln Ile Asp Ile Ala Phe Lys Leu Asn
        110                 115                 120 aac caa atc aga gaa aat gca gaa gtt tcc atg gat gtt tcc ctg ggt   616
Asn Gln Ile Arg Glu Asn Ala Glu Val Ser Met Asp Val Ser Leu Gly
    125                 130                 135 tac cgt gat gat atg ttt tct gag tgg act gaa atg gcg cac gaa aga   664
Tyr Arg Asp Asp Met Phe Ser Glu Trp Thr Glu Met Ala His Glu Arg
140                 145                 150                 155 gta cca cgt aaa ctc aga tgc act ttc aca tcc ccc aag acc cca gag   712
Val Pro Arg Lys Leu Arg Cys Thr Phe Thr Ser Pro Lys Thr Pro Glu
                160                 165                 170 cat gaa ggt cgt cat tat gaa tgt gat gtc ctt cct ttc atg gaa att   760
His Glu Gly Arg His Tyr Glu Cys Asp Val Leu Pro Phe Met Glu Ile
            175                 180                 185 ggg tca gtg gct cat aag tat tac ctt cta aat atc cgg cta cct gta   808
Gly Ser Val Ala His Lys Tyr Tyr Leu Leu Asn Ile Arg Leu Pro Val
```

FIGURE 17 (cont.)

```
                    190                      195                      200 aat gag aag aag aaa atc aat gtt gga att ggg gaa ata aag gac att       856
Asn Glu Lys Lys Lys Ile Asn Val Gly Ile Gly Glu Ile Lys Asp Ile
    205                 210                 215 cgg ttg gtg gga atc cac caa aat gga ggt ttc act aag gta tgg ttt       904
Arg Leu Val Gly Ile His Gln Asn Gly Gly Phe Thr Lys Val Trp Phe
220                 225                 230                 235 gct atg aag acc ttc ctc aca ccc agc atc ttc atc att atg gtg tgg       952
Ala Met Lys Thr Phe Leu Thr Pro Ser Ile Phe Ile Ile Met Val Trp
                240                 245                 250 tat tgg aga agg atc acc atg atg tcc cga cct cca gtg ctt ctg gaa      1000
Tyr Trp Arg Arg Ile Thr Met Met Ser Arg Pro Pro Val Leu Leu Glu
            255                 260                 265 aaa gtc atc ttt gcc ctt ggg att tcc atg acc ttt atc aat atc cct      1048
Lys Val Ile Phe Ala Leu Gly Ile Ser Met Thr Phe Ile Asn Ile Pro
        270                 275                 280 gtg gaa tgg ttt tcc att gga ttt gat tgg acc tgg atg ctg tta ttt      1096
Val Glu Trp Phe Ser Ile Gly Phe Asp Trp Thr Trp Met Leu Leu Phe
    285                 290                 295 ggt gac ata cga cag ggc atc ttc tat gca atg ctt ctt tcc ttc tgg      1144
Gly Asp Ile Arg Gln Gly Ile Phe Tyr Ala Met Leu Leu Ser Phe Trp
300                 305                 310                 315 atc atc ttc tgt ggc gag cac atg atg gat caa cat gag cgg aat cac      1192
Ile Ile Phe Cys Gly Glu His Met Met Asp Gln His Glu Arg Asn His
                320                 325                 330 att gca ggg tat tgg aag caa gtt gga cca att gct gtt ggc tct ttc      1240
Ile Ala Gly Tyr Trp Lys Gln Val Gly Pro Ile Ala Val Gly Ser Phe
            335                 340                 345 tgc ctc ttc ata ttt gac atg tgt gag aga gga gtg caa ctc aca aat      1288
Cys Leu Phe Ile Phe Asp Met Cys Glu Arg Gly Val Gln Leu Thr Asn
        350                 355                 360 cct ttc tac agt atc tgg act aca gat gtt gga aca gaa ctg gct atg      1336
Pro Phe Tyr Ser Ile Trp Thr Thr Asp Val Gly Thr Glu Leu Ala Met
    365                 370                 375 gct ttc atc att gtg gca ggt atc tgc ctc tgc ctc tac ttc ctg ttt      1384
Ala Phe Ile Ile Val Ala Gly Ile Cys Leu Cys Leu Tyr Phe Leu Phe
380                 385                 390                 395 ctg tgt ttc atg gta ttt caa gta ttc aga aac atc agt ggg aaa cag      1432
Leu Cys Phe Met Val Phe Gln Val Phe Arg Asn Ile Ser Gly Lys Gln
                400                 405                 410 tct agc ctc cca gcc atg agc aaa gtc cgg agg ctg cac tat gag ggt      1480
```

```
Ser Ser Leu Pro Ala Met Ser Lys Val Arg Arg Leu His Tyr Glu Gly
            415                 420                 425
FIGURE 17 (cont.)

ctg att ttc agg ttc aag ttc ctc atg ctg atc acc ttg gct tgt gct      1528
Leu Ile Phe Arg Phe Lys Phe Leu Met Leu Ile Thr Leu Ala Cys Ala
            430                 435                 440 gcc atg act gtt atc ttc ttc att gtt agt cag gtg aca gaa ggc cat      1576
Ala Met Thr Val Ile Phe Phe Ile Val Ser Gln Val Thr Glu Gly His
            445                 450                 455 tgg aaa tgg ggt ggg gtc aca gtt caa gtg agc agt gct ttc ttc act      1624
Trp Lys Trp Gly Gly Val Thr Val Gln Val Ser Ser Ala Phe Phe Thr
460             465                 470                     475 gga atc tat ggg atg tgg aac ctg tat gtc ttt gct ttg atg ttc ttg      1672
Gly Ile Tyr Gly Met Trp Asn Leu Tyr Val Phe Ala Leu Met Phe Leu
                480                 485                 490 tat gca cca tcc cat aag aac tat ggg gaa gac cag tct aat ggt gac      1720
Tyr Ala Pro Ser His Lys Asn Tyr Gly Glu Asp Gln Ser Asn Gly Asp
            495                 500                 505 ctg ggt gtc cac agc ggg gaa gaa ctg cag ctc act acc aca atc acc      1768
Leu Gly Val His Ser Gly Glu Glu Leu Gln Leu Thr Thr Thr Ile Thr
            510                 515                 520 cat gta gat gga ccg act gag atc tac aag ttg acc cgt aaa gaa gca      1816
His Val Asp Gly Pro Thr Glu Ile Tyr Lys Leu Thr Arg Lys Glu Ala
            525                 530                 535 cag gag tag taggctatgg cattcatcct cagggcaggt gatgaagcca              1865
Gln Glu *
540 agttgctggt gcatgctgac cctcatgaat atgctttcgt atctttatgt cccaggatca    1925
ttttttatcct gtcacgttta caagaacatt tctgacatgc atacgtttac ttttaccatg  1985
tattagttac ttttatattt ctgtgataaa acaccatgag aaatacaatt tacagaagca   2045
aaaaaaaaaa aaaaaaaaaa aaaagcggcc gc                                  2077
```

FIGURE 18

```
tctaacgaac cccttcggag cgatgga atg aga aag gcc cag aat gtg tta agt       54
                              Met Arg Lys Ala Gln Asn Val Leu Ser
                               1                   5 ctg tgc agg gga agt gtc ctg agg gga ggg tct ttg gga ggg tcg aag        102
Leu Cys Arg Gly Ser Val Leu Arg Gly Gly Ser Leu Gly Gly Ser Lys
 10              15                  20                  25 gcc agg atg gca aag tga aggtagctga ggttgcagtc ttgggtgccc               150
Ala Arg Met Ala Lys  *
                30 actgctgtgc atctgtctgg ttatctaccc ctactttggg ctgacaactg cagggttggg      210
tgtaggctgt ctcactgcat gccgggaagc tggagaagct ccacgggaac attgagggcc      270
atggctttga gacactgcag agcatccttg gtctctgtaa ccacgtcacc taaccctgac      330
aattccagac ccttcttcca ttgtccttgt gaaccatttg ggcttatctt tccctcttag      390
tcgcaagggt caaaccaagg gtcagtcaag tagatgactg tcaccttggg cctccccaga      450
ctctgctgcc ggggttggga gaccaaagta gaaactgcca ctacaaggcc ccaggatgag      510
gtctctgttc tgtggacctg ctccccagat acaggcctca gacccatagg acgtggccgg      570
tgctcaggga cacccaatcc ccggcctcac tccatcgagt actgacttct ttctctagtg      630
ccttgggggt ctccatcctt cagttatggt atgaagaatc tatgcaaact gtataagctt      690
ctgctcacca ataaacgctt tatttaaagc ttannnnnnn nnnannnnnn nnnnnaagcg      750
gncgc                                                                  755
```

FIGURE 19

```
tctagcgaac cccttcgcag aaacccaaag ttacagacca gaccctaccc aacatccagt      60
cagcaatcca gctggagaaa cgcttgag atg aca agg gac ttt cag aag caa        112
                                Met Thr Arg Asp Phe Gln Lys Gln
                                 1               5 gcc ttg ata aga cag gaa aag cag aat tct aat aaa gat atg agg aaa       160
Ala Leu Ile Arg Gln Glu Lys Gln Asn Ser Asn Lys Asp Met Arg Lys
     10              15                  20 aat gac atg ggc ctt caa cct ctg cct gta ggg aag gac gca cac agt       208
Asn Asp Met Gly Leu Gln Pro Leu Pro Val Gly Lys Asp Ala His Ser
 25              30                  35                  40 gca cca gga gtg aca gtc tct ggg aaa aac cac aaa aga act cag gca       256
Ala Pro Gly Val Thr Val Ser Gly Lys Asn His Lys Arg Thr Gln Ala
                 45                  50                  55 cct gac aag aaa cag aga att gat gtt tgt cta gaa agc cag gac ttt       304
Pro Asp Lys Lys Gln Arg Ile Asp Val Cys Leu Glu Ser Gln Asp Phe
             60                  65                  70 cta atg aag aca aat act tcc aag gag tta aaa atg gca atg gag agg       352
Leu Met Lys Thr Asn Thr Ser Lys Glu Leu Lys Met Ala Met Glu Arg
         75                  80                  85 tcc ttt aat cca gtc aac ctt tcc ctg act gtg gtg taa aagaaaatga       401
Ser Phe Asn Pro Val Asn Leu Ser Leu Thr Val Val *
     90                  95                 100 ggacgccctt ctctccatct tccctccttc cttctccttc caattgcgtc atctgaaatt     461
gaatttcctc tcctcctcca ccacctataa tgctgtgcct gaaaaaatg agtttcctcc     521
ctcatcaccc acagagaagt caagggctga acttgagagc ctcccaaccc tgcctcttcc     581
tccaccacca ggagatgaga aatctgatca ggaatgtcta ccaacatccc tacctcctcc     641
ccctcccaca gctccatccc aaccagcaca tcttctttcc tcctctgttc tagaacatca     701
cagtgaagca tttttacaac agtattcccg aaaagaaacc ttggactctc atcggcttca     761
ctcacaggct aaaatcctaa caggaaaatc accaccccca acactcccca aacccaaact     821
tcccgagaga atcaaagcta agatgagcca ggattcacca agcggtgaat tggaaagatc     881
tctgtcagat gtggaaatta aaactaccct ctcaaaggat cagaaaagtt cgctggtggc     941
agaaagccgt gagcacacag aggccaagca agaagtattc cgaaaaagcc ttggaagaaa    1001
acagctgtcc attagctctg caaactccct ctctcagaca gttccagaaa tcccagcacc    1061
caaggaaaaa cagacagcac cccttgttaa atctcactca ttcccatcag gttcagaaca    1121
acaaagtcct aagccttaca tgagaaaatt taagacaccc ttaatgattg cggaagaaaa    1181
atacagacaa caaagggaag agcttgagaa acagagacgg gagagttctt gccatagcat    1241
catcaaaaca gaaacccagc accgcagctt atcaaanntt aaaaaaaaaa aaaannnagc    1301
ggncgcccg                                                            1310
```

FIGURE 20

```
tctagcgaac ccattcgctt tttttttttt tttttttttt ttttccccc tttcctattt    60
attaatgggg ggaagtatgt ttatgtggga tttatccact tcttttagat tctcctacct  120
gttgatctgt aattattcct agtagtctct tagagttctt agaagcatgc tgttaccgct  180
aatatttcct tttggtttgg atcttactta aacatattgt ttccttactc tcttttcat  240
cccagcttgt ctaactgaaa ggccagaccc aacttgatct atccctttaa aacttc atg  299
                                                                Met
                                                                  1
```

```
tct tgg cct gtt gat ttc tct gct cca ggt gtc acc gaa ggg gtt cgc    347
Ser Trp Pro Val Asp Phe Ser Ala Pro Gly Val Thr Glu Gly Val Arg
            5                  10                  15
```

```
cta gcg aac ccc ttc gta aca gcc aag gtt ttt gag aca gag gtt tca    395
Leu Ala Asn Pro Phe Val Thr Ala Lys Val Phe Glu Thr Glu Val Ser
        20                  25                  30
```

```
aca gca ttc ctg gag gag aca caa agg aca gat gag tca cat gaa gga    443
Thr Ala Phe Leu Glu Glu Thr Gln Arg Thr Asp Glu Ser His Glu Gly
    35                  40                  45
```

```
tgg gag gag gga agg tgg ctg ttg ata ggt att ttg aga cac tct att    491
Trp Glu Glu Gly Arg Trp Leu Leu Ile Gly Ile Leu Arg His Ser Ile
50                  55                  60                  65
```

```
tga gtcctacaca acactcccc ctccccccaa accattttta tgtctattga           544
 *
```

```
cctttcctct agtcatacag ggaaattcac agttacctac aaagaaccac taattgtaac  604
aagtcaagag gaaacttatt tttgataatg actcattgaa gatgttttga aaatttaaaa  664
ataagctctg ttagcagaag tctgtnngaa aagcangaag gaantgtttg tttattanat  724
aataaaagg cggcgaggac aacaaaaaaa aaaaaaaaaa aagcggccgc              774
```

FIGURE 21

```
tctagcgaac cccttcgcga aggggttcgc cgaaggggtt cgcttcagga gttaatgtag      60
acttgactta agcatcctga tttaaccaag a atg gtg gca cac aac ttt aac       112
                                  Met Val Ala His Asn Phe Asn
                                   1               5 ccc cat gct ggg gaa gca gag gca cac tta atc tgt gtg agt ccc agg      160
Pro His Ala Gly Glu Ala Glu Ala His Leu Ile Cys Val Ser Pro Arg
         10                  15                      20 cca tcc agg gat acc gta gta gtg aga ccc tgt ctc aca aaa caa aga      208
Pro Ser Arg Asp Thr Val Val Val Arg Pro Cys Leu Thr Lys Gln Arg
     25                  30                      35 atg gga att tag ggctggtggg gctcagcatg caactgtgcc tgttacctag          260
Met Gly Ile *
 40 tctggcctga gttcaattcc caagactcaa tgtatgagga gagaaacgat ttctgaactc    320
attcattgat ctccaaatgt gtggtatagg tgcccttccc ttaaataaaa caaacaaaca    380
aaaaacaaca aaaacaacaa acccccaata aatgtatatt taattttaaa agactgtact    440
tgggcatggt acttcacatc tacagttacg acattctaga ggctcaggcc tgggaattgc    500
tatgaatttg aggccagtct gggttagagt gacttctcat ctaggcagga ctacgtaata    560
agtctttgcc caaaaataaa cagcaaccca ataagagca acaagaattc ccctccaaa      620
tagtaacctg ggcctggaga gacagcttag caactgagtg cttgccgagc catcgaggac    680
tggagtctgg attccagcac ccgtgtgaca gacaagctgg gcgttcactc atgctgatga    740
accccaaggc tgaggagaca ctgactcttc tctggccctg ttcatgctgt ccacaggtgc    800
ccaagtagca gttaagtaga ctgtcagaca acatggctgg cttttaagc aagaacagta     860
actgaagaaa tacactttg aagtactgtt aattttgctt aaaacttggt agggagctgg     920
aggatggctc agtggttaag agcactgact gctcttccag aggtcctgag ttcaattccc    980
agcaaccaca tggtggctca caaccatctg taatgagctc tgatgccctc ttttggtgt    1040
gtctgaagac agcgacagtg tactcatata aaataaaata aatcttttt ttttttaaaa    1100
gaaatttgtc agagatatgg caggaagggt atattttac ctatttacct ggtgggctaa    1160
tcctggtatt tttttcaaaa ttaagatact atataggagc cgcgaagggg tcgctaggcc    1220
agtgtgatgg atatctgcag aattcggtta gccgaattc                          1259
```

FIGURE 22

```
tctagcgaac cccttcgtct cctcttaaac atcttaagac aagctgttat catctacact      60
gctcttagta ctgttctttt ctaagattct tctaatatga cacattaaga ctttcttaaa     120
atgtacaact gctacgctga tctaaacatt caaagtgcac acatttcgct atgaagccac     180
gtgaccagag tcctggggac taatttctgt cttagtcaga ttcctattgc tatatgaaga     240
aatacc atg ata gtg tca act ttt ata aag aaa aag tat tcc ttt ggg        288
       Met Ile Val Ser Thr Phe Ile Lys Lys Lys Tyr Ser Phe Gly
        1               5                  10 aat agt tta aag gat cag agg gtt agt gca tta tca tca cag cag gaa       336
Asn Ser Leu Lys Asp Gln Arg Val Ser Ala Leu Ser Ser Gln Gln Glu
 15              20                  25                  30 gcg tgg cag tgg gag ccc aga ttt cta tat cca gat ttt cat gaa gca       384
Ala Trp Gln Trp Glu Pro Arg Phe Leu Tyr Pro Asp Phe His Glu Ala
                 35                  40                  45 tga cgagagctcc tgggcctggc gcgagcttct gaaacctgaa agtgacatat            437
 * ttcttccaat aaggccacaa ctactgctat aaggccacat ctcctaactg tgtcactatc     497
tatgagcctg tacagtctat ttcttttaca ccactgcatc atctaagagc tgatacccgt     557
taagttagtc atgaaaatat tcaacttcta gggttctgtt ttcttctcta taaaatattg     617
aaaatgataa ttaatgtata ctttacagaa ctgtatttga agtacaactt gatggacata     677
aatcaccaca gttgggtcaa aattgtatat atatatatat atatatatat atatatatat     737
atatatcaaa aaaaaaaaaa aaaaaaaaaa aagcggccgc                           777
```

FIGURE 23

```
tctagcgaac cccttcgtac atttcaccct agaaataaat agaccttcta gctctgacag     60
aaagtagtgc ttgcctagga ggagctgggc tggccagttc ctccttcttg cacacttagc    120
ctgtttgctg aaggcttgtt tcaatggaaa actgaaatgg acccactaat gtctcgattc    180
ttctctcctt cactaagtct gtgaagtcat cagcgttttg tcttttgtgt gtgaataccg    240
aggagaattt cctcacccag tgccttcagg agccatgatg gctgcctcag aataagcaca    300
gatacacttg agcaactggt gcagaaaacc cgacttctaa attattaagg aacaggataa    360
ttgcttgtta caataattag aataatgtaa ttaggataat tgcttttaaa aaatcttccc    420
accttttcccc ccccaaatat taataattcc aactaaatcc tctggggccc ttccagtttc    480
cacaacggaa agagcctaac gtattctaaa gactgggcat attttttttt tccagattag    540
tgagtgttca tgagctatta agaggccaag tgttttttca agatggtgtc atttcattct    600
aacatatcta acatgcaaag gacttaaaaa aataatttgc aaaataatct gtttcaagtc    660
tatgaggaag ctgaagagcc tactccggag gaaactccag aagagcctcc tagcatagag    720
gaagaagaga tagtggagga agaggaggag gaggaggtgc ccccgcccag aggtacagcc    780
gctttgatga gttcagcatt ccaaagcctt ggtgctgctg gaccctactc attagccata    840
tactttcctg gaagcacagc cacgaggcct ggagggtgca cactcgtaat gactggagct    900
ttgtgggcct ttcctttccc ctaacgtttc ctccttcccc gcaatctgac cataaatgag    960
gagatttttt ttttctctta ctacactttt tgcaatccta gtttgcaatc ctcagtgtgg   1020
ctggctttca gttcaaatgc tggagaacca tgtatctgtg tggtgagagc attcatttc    1080
aagactaatt cttaaaccgc ttatccccgg agacagaaac cgtggcagag ttgctatcct   1140
ctgagctggg gtggtcatga tgatcagtta ggttactaac atcttcctaa atgaatcggt   1200
gttttgtgtt gctctgtttt catttggatg acagggtgtt gttctgttta atgcgtgtgg   1260
gtttttccaa catgtccgta aaaatatctt ttaagcacca gangtagtga agaaagctgt   1320
gcaaacagca cccgctcctg tccccaagaa awccgaggcg cccccccaaa ggtatatc     1378
```

FIGURE 24

```
tctagcgaac cccttcgcga accccttcgc tgcatcctca taaagctacc tcaagacaga      60
gcgtaactgc ctcattctag gagtggactc ggggaagaca gcagacacac catcagggag     120
cccctgggta tctccagaac atg gca agc cgt gga tac ctg cat cac ctg ctg     173
                     Met Ala Ser Arg Gly Tyr Leu His His Leu Leu
                      1               5                      10 act gca gag gga gcc tgg gag gag ttt gta tca aag gcc aag ttg ccc       221
Thr Ala Glu Gly Ala Trp Glu Glu Phe Val Ser Lys Ala Lys Leu Pro
            15                  20                  25 agg gat agg gca gtg gcc ctc cac aaa gca ctg agg gat ctg aca gca       269
Arg Asp Arg Ala Val Ala Leu His Lys Ala Leu Arg Asp Leu Thr Ala
        30                  35                  40 ctc ttg gcc ata gca gaa aga ggc aga tct cgg aaa ggc tgg aaa ggc       317
Leu Leu Ala Ile Ala Glu Arg Gly Arg Ser Arg Lys Gly Trp Lys Gly
    45                  50                  55 aag gag aag ttt gtg aaa gca ttt cct tgc ttg aaa gca gac ttg gag       365
Lys Glu Lys Phe Val Lys Ala Phe Pro Cys Leu Lys Ala Asp Leu Glu
60                  65                  70                  75 gag cac atc agc cag ctc tat gcc cta gcc gac cat gct gag gaa ctg       413
Glu His Ile Ser Gln Leu Tyr Ala Leu Ala Asp His Ala Glu Glu Leu
                80                  85                  90 cac agg ggc tgc acc gtc tcc aac atg gtg gct gac tcc ttc agt gtt       461
His Arg Gly Cys Thr Val Ser Asn Met Val Ala Asp Ser Phe Ser Val
            95                 100                 105 gcc tcc gac atc ctg aac atc ttt ggt ctc ttt ctg gca cct gag tca       509
Ala Ser Asp Ile Leu Asn Ile Phe Gly Leu Phe Leu Ala Pro Glu Ser
        110                 115                 120 gca gag gga agt ctg gtg ctc tcg gca gca ggc ttg ggg ctg ggg gta       557
Ala Glu Gly Ser Leu Val Leu Ser Ala Ala Gly Leu Gly Leu Gly Val
    125                 130                 135 gca gct act gtg act aat gtt gct act tca atc atg aag gaa aca agc       605
Ala Ala Thr Val Thr Asn Val Ala Thr Ser Ile Met Lys Glu Thr Ser
140                 145                 150                 155 agg gtt ttg gat gga gtc gaa gct ggt cac cat ggt tca acc gcc atg       653
Arg Val Leu Asp Gly Val Glu Ala Gly His His Gly Ser Thr Ala Met
                160                 165                 170 gat ata ctg gag gaa gct ggc aca agt gtg gct agg att gcc agc gag       701
Asp Ile Leu Glu Glu Ala Gly Thr Ser Val Ala Arg Ile Ala Ser Glu
            175                 180                 185 atc cct cag gct acc aga gat atc acc aga gac ctg gaa gcc ctt gag       749
Ile Pro Gln Ala Thr Arg Asp Ile Thr Arg Asp Leu Glu Ala Leu Glu
        190                 195                 200
```

```
cag cac atg aat gcc ctc agt ctg gtc aga gcc aac cct cgc cta gaa      797
Gln His Met Asn Ala Leu Ser Leu Val Arg Ala Asn Pro Arg Leu Glu
    205                 210                 215 gaa gat gcc agg gcc ctc atc aat gca ggt agc atc cct gcc caa cgg      845
Glu Asp Ala Arg Ala Leu Ile Asn Ala Gly Ser Ile Pro Ala Gln Arg
220                 225                 230                 235 gct aaa cag gtg cgg gcc agt ctg aaa gga acc cct ctg gca atg agc      893
Ala Lys Gln Val Arg Ala Ser Leu Lys Gly Thr Pro Leu Ala Met Ser
                240                 245                 250 aag gaa gac cgg atc cgc agt gcc acc acc act ggg gtc acc ctc ttg      941
Lys Glu Asp Arg Ile Arg Ser Ala Thr Thr Thr Gly Val Thr Leu Leu
                255                 260                 265 cgt gat gtg ggg agc ctt gtg aac gag tcg aag cag ttg tac gaa ggg      989
Arg Asp Val Gly Ser Leu Val Asn Glu Ser Lys Gln Leu Tyr Glu Gly
                270                 275                 280 tct gct tcc gaa tcg gca gca gca cta agg aag ctg gct cag gag ctg     1037
Ser Ala Ser Glu Ser Ala Ala Ala Leu Arg Lys Leu Ala Gln Glu Leu
285                 290                 295 gag gag aag cta ggg gag ctc atg aaa ttc tac gag aca atc tga         1082
Glu Glu Lys Leu Gly Glu Leu Met Lys Phe Tyr Glu Thr Ile  *
300                 305                 310 tcaggtttca gccagtcacc ccatccccaa gacatgcaga catcanggga gaggatctgg   1142
acagaggtag ggaccatgga ggtgctgtta gaaggagagc aagactacag tcaggtccga   1202
gggacatagt gtggaggcct gtttgatgaa cacarcaggt taraggatgg agcagtggat   1262
caaagtgaga tccactggag cctgagacsa gggaccagag gatgtgctgc aagagggact   1322
gggaaaattg aaatctanac taaacatgga aaaaggcag tttcgaaaga ctagaaaacc   1382
ctccccatct gagccattgg aaaccccaca aaacacaaac cagagagaaa agtgtgtgct   1442
ctctaaacaa gtcgtggccc ccagttcccc agcccactcc caccctcagg ggtggcatca   1502
aataaattgt ttccatttca aaaaaaaaan naaanaaaaa aaaagcggcc gc           1554
```

```
tctagcgaac cccttcggct ttttctgatt taaagtgaag aaatggccat atttgcttga    60
taatcttcag ttgtgtctct ggaactcaac aaagaacgca ttttatgaaa tatacagctg   120
tcttcggtaa agccaacttt cttacacata tttcgggaag taattaacta caatttggac   180
ttatagttac aaggttgcct tcgaaacact gctctaaatg tgtctcgtgt tggggtgcta   240
ctttgcttat gtgtaaattt cacagtaatg caatagagaa agggtgtttg tgggtgtggc   300
ttgtgggggg gattgttttg ttgttgttgt ttgagataaa gcttcattct gtagccagga   360
aagcctggaa tttactgtgt catcccaggt agcttcaaac tggtgcctat cctgcctcag   420
cctccaacgt gttgcaattg caggagtaac ctaccacatc ctgcagctac agtgatctag   480
aacctccccg tcgaagcccc accaccatag aaaccaattt gcattaagtt ttagaattcc   540
caacccaact aaagtttaat aaaaaagaa aaacaaaaca agatttaaat cattctttcc    600
ctcattcttt ttnnagatnc agggctcncc tagttttnaa caaaacagtn ngcagngnng   660
ggnncccncg gngggnttt tttncnttgn gccncntngc anccacccn cccaggcngg    720
atngggnggg gtataaaagt nttancnggc anatgnnctn ggngcanacc caagtntatc   780
aggncctnan ttnccnccca ganaactaga nanctntngc atagtanang ccccntgtgn   840
agatttnaaa nccncctgtn cacaganana gaancttana tagaaaantc aaaatatttn   900
ggngcccaan gttnccacc ctgtagagng ggnccccaaa ancngccncc aganagcnng    960
atatntgagt tntgacctnt attctttact acnacgcntt gagagaatat tntgntgggg  1020
ccctanccac atgttttgnc ccaagantgt aaanccactt naannctgng ggatatctcn  1080
ctgcanacag aagtgcccng cgggatttta aaaaaaaaaa taaaaaaaaa aaggngccn   1140
cc                                                                1142
```

FIGURE 26

```
tctagcgaac cccttcgtgg agactgtgga agttatgtat gaataggaga gtgtgtgttg      60
tgtaacacag acagaaggac attggatcat gttgaacccg cacccccaac tatgagtgat     120
ggtatggaaa gaatgcgaac atttaaactg cgccaatgcg gcggccatct tggtggagaa     180
gttcctagcc gagctttgat gtgattttt tgatggtaca atgcagcgag catggccacg      240
ggagctttga atccagccga cagctccgag atttgccctt ccagtgctct tgcctaccgt     300
agagaggact gctgagatgg gattccttgt gacaagccta cttacccttta actgccagca    360
tttgtaaggt gcaatcttgt gtattggttt tttattttga cagttttgaa aacatgtttg     420
ntgntcttgg tgttttttcca gtaaaagtaa tcacaaagga aaaaaaatt aaaaaaaaaa     480
aaaaaaaaaa aaaagcggcc gc                                              502
```

FIGURE 27

```
tctagcgaac cccttcgcct tcatatggtt ttacactgta tgcatctcac cgcggcccgg      60
aacctttctt ctcatcccaa tcctgtttga ggggacgggg ggcagggacg gacaacccaa     120
gacaagggat atttgtgctg tgggtattgc atcttatgga gggctgtagc taactgggac     180
tcctgggtga ccccaacagg cctttgatcc tctgtctctc cccgcccca ctccaaacac      240
ttatgcttcc ccaagtgcag ctgagggact acacagtggc tcccgcccca ctccaaacac     300
aggaaatcaa tctcagggag aggagataag aagtgaggag aagccaagat tcaaccaata     360
gatggtaatt gctcctggga ccgccccccc aagcatcatt tccataggaa ggactgagtt     420
tggctcctga agcccagtgg agtacctttc tctgcctgaa ttctgttgtg atccctggcc     480
aagtcctctt tccagaaacc ccacctttaa aaccagctga aaggaccttt cttctctatg     540
tttaataggt aactttccat agcttagctt ccctgcagtc tcccgagtgc ccagttaaaa     600
ttctgccata ggtcaaaagt ggggttgaga ggtgaagtca gaggccatgc atggagctca     660
gaacgtttct aaacctcctg tgattcattg agtagcccct agactctaga aggctcagat     720
gccaaaaagg ktgactttat aatttcttag ggtcttctca tgggatcgkt ttcagagtgg     780
gcattcacta aatgatagca agtttattaa ttgtttccca gygcctgatc tctttatttn     840
cccagggctt ccaaccagag cccttggttg aaagtctccc acccaccccc caccctgaga     900
cttggtggnt ttctgagatt ccccagggat ggcaaaattg gcattcttac agggagccct     960
gacttctagc acgttaccta gatttttac cctgctctct ctgcctattt tactatggga    1020
tcactgntct ctttggactt aaggaaccac cttgaagtag agtgaggtga ccacgtgttg    1080
gtggcgaaga atataagcat tggtccttaa aagagaactt ctatgaagtc aggctgcaag    1140
ctttaacatg gcacaagttg caccttactg gctgctaagt ctggatgtca accaaaggtc    1200
aactctntaa ttaaagaaaa gcaagggaga aganaggtgg aagnggcttn cataaacttt    1260
attcaaaatg tctaccagga atggtggtga caccaataat cccacatgtt ggatgtngag    1320
gcaggaagaa tgatggtaag gggcatcctc actacataat gagttgaggc tngactaggt    1380
taactntgct tnaaaaaaaa aaaaaaaaa aaaaaaagg ggngcc                     1426
```

FIGURE 28

```
tctagcgaac cccttcgcaa gaactcagac tgctcctgcc tgacttccta ggtgtcatag      60
ctctcttctg ccgccagt atg aca tca tca agg aca acg agc cca ata aca      111
                    Met Thr Ser Ser Arg Thr Thr Ser Pro Ile Thr
                     1           5                      10 aca agg aaa aaa cca aga gtg cat cag aga cca gca ccc cag agc acc      159
Thr Arg Lys Lys Pro Arg Val His Gln Arg Pro Ala Pro Gln Ser Thr
         15                  20                  25 agg gtg ggg gtc tcc tcc gaa gca aga tat gaa acc ctt tca gtg ctt      207
Arg Val Gly Val Ser Ser Glu Ala Arg Tyr Glu Thr Leu Ser Val Leu
         30                  35                  40 gct ctg agc agc tca gaa gta gaa tgc gag agg acc tca ctg ttc tga      255
Ala Leu Ser Ser Ser Glu Val Glu Cys Glu Arg Thr Ser Leu Phe  *
         45                  50                  55 cgatgattgt ccaacacaca tccggccctc tccgtgtctc ctcccaccac catcttctcc    315
tatcaccggg cttactatct tctctcctgg ctttcctctt tctgatggcg gttcctgaag    375
cctccaacta accccctaact cggggagcgc ctcgacagtg tttgtggcta aggctacact   435
cagagacaga gttgcagaat gagggagacc cagcccgagg acgccattg ctgggaggta     495
gactgggtgc gagggccctt ggcacaggac tcacatctgg gctgttcagc ttgacccgaa    555
ggctgtgtgt gaaaggggga aaaagacaag attgccaggc agggctgttg ttttgtggc    615
ttcgagggac aagaacctgg ctaaaaggca gcagccctgc tgttctttt ctcctctgtc     675
ctgtttccta ccttacaaga agtccatgca accaaccggg gctctggcac ttttcttgtt    735
tatttccctc ctggcttcca aacaagccct ctgtggacat catcaaagca tggataaccc    795
cctctgcagg ggtgggcttc attctccgct ggtccctgta gccttcctgg acacagggtg   855
aaagttgtaa aagtggtagg agtgcagcta gccacaggtt ctccttttcc catctcagtc    915
tgaccaagga ggctgaacta ccaacccaaa ttcagcgaaa aaaaaaaaaa aaaaaaaaa    975
aagcggccgc                                                             985
```

FIGURE 29

```
tctagcgaac ccct tcgcgg ggacagacat ggagaaggag atggaggacc ccctggctgg    60
agcagaccaa cagaataggc aactatggct ggagaaccgg gtatcagagt aatgcttgac   120
ctcgggaaac accaaatttc ttcttccgat cgcagaagta gtactcggcg aaattcacta   180
ggtaggaggc tcctcatctg gaagaaccg gtgcctgggg ggacctggct ggataggt      238
```

| | | | | | | | | | | | | | | | |
|---|---|---|---|---|---|---|---|---|---|---|---|---|---|---|---|
| atg | ggg | gat | cga | ggc | cgg | tcc | cct | agt | ctc | cgg | tcc | ccc | cat | ggc | agt | 286 |
| Met | Gly | Asp | Arg | Gly | Arg | Ser | Pro | Ser | Leu | Arg | Ser | Pro | His | Gly | Ser |
| -35 | | | | -30 | | | | -25 | | | | -20 | | | |

```
cct cca act cta agc acc ctc act ctc ctg ctg ctc ctc tgt gga cag      334
Pro Pro Thr Leu Ser Thr Leu Thr Leu Leu Leu Leu Leu Cys Gly Gln
         -15                 -10                  -5 gct cac tcc cag tgc aag atc ctc cgc tgc aat gcc gag tac gtc tcg      382
Ala His Ser Gln Cys Lys Ile Leu Arg Cys Asn Ala Glu Tyr Val Ser
              1               5                  10 tcc act ctg agc ctt cgg gga ggg ggc tca ccg gac acg cca cat gga      430
Ser Thr Leu Ser Leu Arg Gly Gly Gly Ser Pro Asp Thr Pro His Gly
         15                 20                  25 ggc ggc cgt ggt ggg ccg gcc tca ggt ggc ttg tgt cgc gcc ctg cgc      478
Gly Gly Arg Gly Gly Pro Ala Ser Gly Gly Leu Cys Arg Ala Leu Arg
 30                  35                  40                  45 tcc tac gct ctc tgc acg cgg cgc acc gcc cgc acc tgc cgc ggg gac      526
Ser Tyr Ala Leu Cys Thr Arg Arg Thr Ala Arg Thr Cys Arg Gly Asp
              50                  55                  60 ctc gct ttc cac tcc gcg gtg cat ggc ata gag gac ctg atg atc cag      574
Leu Ala Phe His Ser Ala Val His Gly Ile Glu Asp Leu Met Ile Gln
              65                  70                  75 cac aac tgc tca cgc cag ggt ccc acg gcc tcg ccc ccg gcc cgg ggt      622
His Asn Cys Ser Arg Gln Gly Pro Thr Ala Ser Pro Pro Ala Arg Gly
         80                  85                  90 cct gcc ctg ccc ggg gcc ggc cca gcg ccc ctg acc cca gat ccc tgt      670
Pro Ala Leu Pro Gly Ala Gly Pro Ala Pro Leu Thr Pro Asp Pro Cys
         95                 100                 105 gac tat gaa gcc cgg ttt tcc agg ctg cac ggt cga acc ccg ggt ttc      718
Asp Tyr Glu Ala Arg Phe Ser Arg Leu His Gly Arg Thr Pro Gly Phe
110                 115                 120                 125 ttg cat tgt gct tcc ttt gga gac ccc cat gtg cgc agc ttc cac aat      766
Leu His Cys Ala Ser Phe Gly Asp Pro His Val Arg Ser Phe His Asn
              130                 135                 140 cac ttt cac aca tgc cgc gtc caa gga gct tgg ccc cta cta gat aac      814
His Phe His Thr Cys Arg Val Gln Gly Ala Trp Pro Leu Leu Asp Asn
         145                 150                 155 gac ttc ctc ttt gtc caa gcc acc agc tcc ccg gta gca tcg gga gcc      862
```

Asp Phe Leu Phe Val Gln Ala Thr Ser Ser Pro Val Ala Ser Gly Ala
            160                 165                 170

FIGURE 29 (cont.)

| | |
|---|---|
| aac gct acc acc atc cgg aag atc act atc ata ttt aaa aac atg cag<br>Asn Ala Thr Thr Ile Arg Lys Ile Thr Ile Ile Phe Lys Asn Met Gln<br>    175                 180                 185 | 910 |
| gaa tgc att gac cag aaa gtc tac cag gct gag gta gac aat ctt cct<br>Glu Cys Ile Asp Gln Lys Val Tyr Gln Ala Glu Val Asp Asn Leu Pro<br>190                 195                 200                 205 | 958 |
| gca gcc ttt gaa gat ggt tct gtc aat ggg ggc gac cga cct ggg ggc<br>Ala Ala Phe Glu Asp Gly Ser Val Asn Gly Gly Asp Arg Pro Gly Gly<br>                210                 215                 220 | 1006 |
| tcg agt ttg tcc att caa act gct aac ctt ggg agc cac gtg gag att<br>Ser Ser Leu Ser Ile Gln Thr Ala Asn Leu Gly Ser His Val Glu Ile<br>            225                 230                 235 | 1054 |
| cga gct gcc tac att gga aca act ata atc gtt cgt cag aca gct gga<br>Arg Ala Ala Tyr Ile Gly Thr Thr Ile Ile Val Arg Gln Thr Ala Gly<br>        240                 245                 250 | 1102 |
| cag ctc tcc ttc tcc atc agg gta gcg gag gat gtg gca cgg gcc ttc<br>Gln Leu Ser Phe Ser Ile Arg Val Ala Glu Asp Val Ala Arg Ala Phe<br>    255                 260                 265 | 1150 |
| tct gct gag cag gat cta cag ctg tgt gtt ggg gga tgc cct ccg agc<br>Ser Ala Glu Gln Asp Leu Gln Leu Cys Val Gly Gly Cys Pro Pro Ser<br>270                 275                 280                 285 | 1198 |
| cag cga ctc tct cgc tca gag cgc aat cgc cgt ggg gcg ata gcc ata<br>Gln Arg Leu Ser Arg Ser Glu Arg Asn Arg Arg Gly Ala Ile Ala Ile<br>                290                 295                 300 | 1246 |
| gat act gcc aga agg ttg tgt aag gaa ggg ctt ccg gtt gaa gat gcc<br>Asp Thr Ala Arg Arg Leu Cys Lys Glu Gly Leu Pro Val Glu Asp Ala<br>            305                 310                 315 | 1294 |
| tac ttc caa tcc tgc gtc ttt gat gtt tca gtc tcc ggt gac ccc aac<br>Tyr Phe Gln Ser Cys Val Phe Asp Val Ser Val Ser Gly Asp Pro Asn<br>        320                 325                 330 | 1342 |
| ttt act gtg gca gct cag tca gct ctg gac gat gcc cga gtc ttc ttg<br>Phe Thr Val Ala Ala Gln Ser Ala Leu Asp Asp Ala Arg Val Phe Leu<br>    335                 340                 345 | 1390 |
| acc gat ttg gag aac ttg cac ctt ttc cca gta gat gcg ggg cct ccc<br>Thr Asp Leu Glu Asn Leu His Leu Phe Pro Val Asp Ala Gly Pro Pro<br>350                 355                 360                 365 | 1438 |
| ctc tct cca gcc acc tgc cta gtc cgg ctt ctt tcg gtc ctc ttt gtt<br>Leu Ser Pro Ala Thr Cys Leu Val Arg Leu Leu Ser Val Leu Phe Val<br>                370                 375                 380 | 1486 |
| ctg tgg ttt tgc att cag taa gtaggccagc aacccgtgac tagtttggaa | 1537 |

```
Leu Trp Phe Cys Ile Gln   *
              385
FIGURE 29 (cont.)

acggtttgag gagagaggtt gatgtgagaa aacacaaaga tgtgccaaag gaaacagtgg   1597
ggacaggaga caacgacctt actcaatcac acgaggttgc agtccagggc tgaaatgacc   1657
ctagaataaa gattctgaga cagggttttg cactccagac cttggtatgg gctccccatg   1717
aatttcccca ttagtgattt cccacttgta gtgaaattct actctctgta cacctgatat   1777
cactcctgca aggctagaga ttgtgagagc gctaagggcc agcaaaacat taaagggctg   1837
agatatctta aaggcagaaa ctagaaaagg ggaaaccatg attatctata agaaaatcaa   1897
aagagggggtt tgggaattta gctcagtggt agagcacttg cctagcaagc gcaaggccct   1957
gggttcggtc cccagctcct aaaaaaaaaa aaaaaaaaaa aaaaagcggc cgc          2010
```

FIGURE 30

```
tctagcgaac cccttcgtgg ggattaaggt tctctatagc taagcctgtc nga atg         56
                                                            Met
                                                            1 aca aca ccc aga gat ctc acc tgg ggt ggt ggg agc act ctc tgt ctt       104
Thr Thr Pro Arg Asp Leu Thr Trp Gly Gly Gly Ser Thr Leu Cys Leu
            5               10                  15 gag gga aca tgt acc tac tct ctc ctt cca caa gag cca cat aca ctt       152
Glu Gly Thr Cys Thr Tyr Ser Leu Leu Pro Gln Glu Pro His Thr Leu
        20              25                  30 aga agt tcc agt gaa gat cta tgt gct tca gaa gag agg gga ctt gga       200
Arg Ser Ser Ser Glu Asp Leu Cys Ala Ser Glu Glu Arg Gly Leu Gly
    35              40                  45 ggt gaa agg ggg agt ggg agg ggg gct tga ggacctanct gaaagatttt        250
Gly Glu Arg Gly Ser Gly Arg Gly Ala  *
50                  55 angctgaaag aacttccttg attcaaagac atatgtcagt ngacccaaca atgagaatga    310
atatgagggc caggaaaact tgtgggaatc agtctcaaga cngaaacnga gaaagaaaga    370
aaagtggnta ggactcanat tggggaacct gggtagacag gagtggcnag ggaagaaagg   430
gatcttgggt tntccacagt ttgagacaca tccggngntc gacoctattc ccngaagccn    490
cannanatgt tgcttccccn tcnntnnaat gggcctggng gtcctnctcc ctttncccng   550
gacatgaaaa ngtnttctgc nnanataacc cccntctttc ctcccccttn antntgtccc    610
taccnttttg tccctttttn ttttnaaaaa annaaaataa aggggnncnn tnttcccttn    670
gaaaaaaaaa aaaaaaaaaa aaaaaaccgc ccncc                               705
```

FIGURE 31

```
tctagcgaac cccttcgcga aggggttcgc ttacattcac gcttaagcat attaactgta      60
catattaact gatttagagg atact atg gat tcc aca tct tcc ctg agc ata      112
                            Met Asp Ser Thr Ser Ser Leu Ser Ile
                            1               5 ggg att gat ttg aaa aat gac agg gtt ggc tgt cga ccc cca tcg gag      160
Gly Ile Asp Leu Lys Asn Asp Arg Val Gly Cys Arg Pro Pro Ser Glu
10              15                  20                  25 gaa gca ggt aag gaa tca ctt agg aga act gat ctc aac att ctt cag      208
Glu Ala Gly Lys Glu Ser Leu Arg Arg Thr Asp Leu Asn Ile Leu Gln
            30                  35                  40 ttc ttt cta tta ttt act tgt tta gcc tgg agt taa attcccactc           254
Phe Phe Leu Leu Phe Thr Cys Leu Ala Trp Ser *
                45                  50 cttgtgagca cttctaattt gaaaatccac tttcttcaat attttcgaaa tttaaaactg     314
atggatgacg tgacaaaact tccacgagtt aagaattctc cacctctgat ctcatcgcag     374
cagggcacaa tccaaggcat gtgaattgac ttccaggttt atgtgacata taaatgaatt     434
ctgtctctag atttggatcc cattctccta aatatctcac catgcatgtg cagatattct     494
aaagtctaaa aatatctgat attgcaaact tttctggtca aaacattttg gatgagccat     554
ttaacagcca aggtatttga gacagaggtt tcaacagcat tcctggagga gacacaaagg     614
acagatgagt cacatgaagg atgggaggag ggaaggtggc tgttgatagg tattttgaga     674
cactctattt gagtcctaca caacactccc cctcccccc ctcccccaa accattttta      734
tgtctattga cctttcctct agtcatacag ggacattcac agttacctac aaagaaccag     794
aattgtaaca agtcaagagg aaacttattt ttgataatga ctcattgaag atgttttgaa     854
aatttaaaaa taagctcttg taagcagaag tctgtgagaa aagcaagaag gaattgtttg     914
tttattaaat aaataaaagg cnnannnnaa aaaaaaaaaa aaaaangcgg ccgc           968
```

FIGURE 32

```
tctagcgaac cccttcggca gacagcatcc ctcccaaggc tactcagggt ttaaaccctg    60
cttctgaagt gacatgtcct gcaaagaaag tccccacgtg ggtgtttcca ccaccactgt   120
cagctctgta gctgtgcaag ctggggactc caagatcgtg atagccgttg tcaagtgtgg   180
caaatgggtg cggctccaac tggctgaggc acagcccaat ctcctagaaa ttgggagcag   240
tcaag atg aaa cca gaa aac tgc ttc acg atc acg agc tcc ttc tgg cca   290
      Met Lys Pro Glu Asn Cys Phe Thr Ile Thr Ser Ser Phe Trp Pro
       1               5                  10                  15
```

```
agc tta agg cct tgg aag atc gtg tgt ggg gac tct tac agg aag cag    338
Ser Leu Arg Pro Trp Lys Ile Val Cys Gly Asp Ser Tyr Arg Lys Gln
                20                  25                  30
```

```
aca gga cgg ctg aag caa aca agg agc aaa gtg agg tgt cga tgc cat    386
Thr Gly Arg Leu Lys Gln Thr Arg Ser Lys Val Arg Cys Arg Cys His
            35                  40                  45
```

```
ggc cag act ctg ggc gaa gca tgg gcc acc ctg gtc ttc atg ctt gaa    434
Gly Gln Thr Leu Gly Glu Ala Trp Ala Thr Leu Val Phe Met Leu Glu
        50                  55                  60
```

```
aga aga agg gag ctc ctc gga ctg aca tct gag ttt ttt caa agc gcc    482
Arg Arg Arg Glu Leu Leu Gly Leu Thr Ser Glu Phe Phe Gln Ser Ala
    65                  70                  75
```

```
ttg gag ttt gct ata aaa ata gac caa gct gaa gat ttt ctg cag aat    530
Leu Glu Phe Ala Ile Lys Ile Asp Gln Ala Glu Asp Phe Leu Gln Asn
80                  85                  90                  95
```

```
cct cac gag ttt gag agt gcc gaa gcc tta cag tca ctt ctt ctg ctt    578
Pro His Glu Phe Glu Ser Ala Glu Ala Leu Gln Ser Leu Leu Leu Leu
                100                 105                 110
```

```
cat gac cga cac gcc aaa gaa ctc tta gaa cga tct cta gtc ctt tta    626
His Asp Arg His Ala Lys Glu Leu Leu Glu Arg Ser Leu Val Leu Leu
            115                 120                 125
```

```
aac aaa agc caa caa ctc act gac ttc ata gaa aaa ttc aag tgt gat    674
Asn Lys Ser Gln Gln Leu Thr Asp Phe Ile Glu Lys Phe Lys Cys Asp
        130                 135                 140
```

```
gga tct cct gtg aat tct gag ctc atc cag gga gct cag agc agt tgt    722
Gly Ser Pro Val Asn Ser Glu Leu Ile Gln Gly Ala Gln Ser Ser Cys
    145                 150                 155
```

```
ctg aag atc gac agc ctc ctt gaa ctt ctg caa gac agg aga agg cag    770
Leu Lys Ile Asp Ser Leu Leu Glu Leu Leu Gln Asp Arg Arg Arg Gln
160                 165                 170                 175
```

```
ctg gac aag cac ttg cag caa cag agg cag gag ttg tct cag gtt ctg    818
Leu Asp Lys His Leu Gln Gln Gln Arg Gln Glu Leu Ser Gln Val Leu
                180                 185                 190
```

```
cag tta tgt ctg tgg gac caa caa gaa agc cag gtt tct tgt tgg ttt    866
```

```
Gln Leu Cys Leu Trp Asp Gln Gln Glu Ser Gln Val Ser Cys Trp Phe
            195                 200                 205
```
FIGURE 32 (cont.)

```
cag aaa aca ata aga gat ctg cag gaa cag agt ctg ggt tca tcc ctt      914
Gln Lys Thr Ile Arg Asp Leu Gln Glu Gln Ser Leu Gly Ser Ser Leu
        210                 215                 220 tca gac aac aaa gag tta atc cgt aag cac gag gac ctg cca tca aag      962
Ser Asp Asn Lys Glu Leu Ile Arg Lys His Glu Asp Leu Pro Ser Lys
        225                 230                 235 caa aga gtc cct gca gtt tag gaattgaaca gaacagtttc ctgattgaat        1013
Gln Arg Val Pro Ala Val  *
240                 245 gatcttggcg cctyyttanc ggntgcagat ggtggggctt cctctggntt ctcatcctct   1073
tccactaatc tggatttttg ttcccctggt gtgccacatc actttaattt gaaagaaaaa   1133
aaataaattg ggccggaaaa aaaaaaaaaa aaaaaaaaar rrscggccnc              1183
```

FIGURE 33

```
tctagcgaac cccttcgcgc aagatggccg cttcccagac cgctccgcgg catcttcaag      60
atgcgcgaga agaacgtgca atctcgcgag atcaggctcg ctcgcgggca gtctgctcgc     120
agcctaccct tcctaggagt tggaggaggg aaagctagat tcgattaaga gcaaaaaatt     180
gttccagcag cagagcagct gtccaaggaa gtatccaaag gaactgcacc tcagtaaact     240
cctggcaagt cttaggatat gacaaagggc acaggatgca ttatgagaaa ggaaggctaa     300
ggttttcaag aacacagatt tacatcaaac ttgcgttctg aattaatctt tgagaatact     360
ggactgtgag ctagacattg agtaagaggt ttgttatatc aagaatgtga tctaaaaaaa     420
aaacattcat atcttcctcc cacaagagga tattttgaaa ctgtgggtca aagtcagact     480
acaggagagc cctcaaatat gccaaatgtg acagacagca ggattttgaa aatatagtgg     540
gagtatgtga agatgttcca gtcaaagaga cattgtttcc aaaggaaaga aagtccagtc     600
gcctcacagg aattgtgtat tccctggtag taatgcaaat ggaccacata tggctttctt     660
ctttaaagag aatacctaat tttagctaca gagtaaaatg ctgatgatac aaaccgtgac     720
aagtggaggg acaagaaagt aaatggactg atggtgccat tgtggactgg gagggtaaaa     780
gctgtacatt tgtgaacaaa aagatttcct tgttatggtc agccatgatt ctaactgcta     840
aatggaggca gtaacaacat gacctaaaga gtaaacatcc agagatggaa tgttctcaat     900
gtctgaaaag gagcagatat ctggtgtatg tgaatgtatg ctagagattt tttacaagcc     960
tgtggtgaat tagtaattgt attttatttt gaaagttaaa caggtaatta gaaaccccaa    1020
aaaaaaaaaa aataaaaaaa aagcggccgc c                                    1051
```

FIGURE 34

```
tctagcgaac cccttcgctg aaaccaccgt tcacacggga aacctgggtt aggcttttgt      60
cctcagtgac acagaggatg tagtccacag ctaggtagaa atgtcaggtt cccaacacta     120
ctccagctgt gactttgatg cttgggggat ggggtcgcag gctatttct ctgctttaac      180
agttcataga atttaacaga taagagttag tgtctttcat gtggcctcac tctggagtta     240
tgagaacata cacacggttt acagcttttc aatatncctt tccctggcca tcaagtattt     300
tgaaagtgtg ccaccttta accttgcgc tttatttttt tttctttttt taaagntgaa       360
ggtgataatt cttctatata tgatgaaact caatgtctac tgaaataagt gtaaccttag     420
ctatncacgt ttatntttta aaaccacgct atggagatat taccccgagt tctgtcnttt     480
ngcaagattt acagnaccttt cccncccccc cttttagcat tnaataaaaa natattgggg    540
agcncnntna aaaaaaaaaa aatnaanaaa agcggc                              576
```

FIGURE 35

```
tctagcgaac cccttcgcgt gatctgatcc gagctgagac ttggggagct ctggctccgt      60
gttggctgca gcatccccca tggtcttgtc tgaggtgtcc tgtgactcga ctcttcagaa     120
ctcaatgaag tagatgactt gactacaatg tggaaacatc atg aca gaa agt gtg      175
                                              Met Thr Glu Ser Val
                                                1               5 gtt tgt acc ggg gcc gtc agc act gta aag gaa gtc tgg gaa gaa aga       223
Val Cys Thr Gly Ala Val Ser Thr Val Lys Glu Val Trp Glu Glu Arg
              10              15                  20 ata aag aaa cat cat gaa gat gtg aaa cga gag aag gaa ttt cag caa       271
Ile Lys Lys His His Glu Asp Val Lys Arg Glu Lys Glu Phe Gln Gln
          25              30              35 aag cta gtg cgg atc tgg gaa gac cga gtg agt tta act aag ctg aaa       319
Lys Leu Val Arg Ile Trp Glu Asp Arg Val Ser Leu Thr Lys Leu Lys
          40              45              50 gag aag gtg acc agg gaa gat gga aga atc att cta agg ata gag aaa       367
Glu Lys Val Thr Arg Glu Asp Gly Arg Ile Ile Leu Arg Ile Glu Lys
      55              60              65 gag gaa tgg aag act ctc cct tct tcc tta ctg aaa ctg aat cag cta       415
Glu Glu Trp Lys Thr Leu Pro Ser Ser Leu Leu Lys Leu Asn Gln Leu
70              75              80              85 cag gag tgg caa ctt cat agg acc gga ttg ttg aaa att cct gaa ttc       463
Gln Glu Trp Gln Leu His Arg Thr Gly Leu Leu Lys Ile Pro Glu Phe
              90              95              100 att gga aga ttc cag cat ctc att ggt cta gac tta tct cgg aac aca       511
Ile Gly Arg Phe Gln His Leu Ile Gly Leu Asp Leu Ser Arg Asn Thr
              105             110             115 att tca gag atc ccc ccg agg cat tgg act gnt cac tta gac ttc aag       559
Ile Ser Glu Ile Pro Pro Arg His Trp Thr Xaa His Leu Asp Phe Lys
              120             125             130 gaa ctg att ctt agc tac aca aaa tca a                                 587
Glu Leu Ile Leu Ser Tyr Thr Lys Ser
135             140
```

FIGURE 36

```
tctagcgaac cccttcggtt ctgttggcta cacagctgca gagccatggc tgaccgttca      60
ctgtcagggg cacatgttac actaagcttc atgacagtga tgtaataatg ttacacattt     120
gtcttgtagt tatgtattga agtttctgtc ctgttttgtg taaaaatgta tccactcttg     180
tatatattta gacttgaaac taccacacaa atattggaac ggtttgcttt atgaagttaa     240
aagtatcctt ccgaatggaa ctaacttgct ttgtgctcag acatatacta tgctgatgta     300
ttttgcaata tactatctta aattaaatct ggtcactttg ttgccttttt aaaaagtgtg     360
gtatttcaag tagagttatt ttcctgaaat atatttgcaa actcaagctg ctttataatc     420
aaggaatatt tttattgatt gaagaaaatg actgctgcaa ttcaaaagtg aacttatttt     480
attatataga tgatttctta aaagctattt ataccatgat acaaaatcat gtagtgatcc     540
tgggagtctg tagttcttcc tgttaataac attcaacact gtatgctaga ggcagcaatg     600
ccaacactga agttattttg ggtgaaaacc gtcgttctgn cctgtttagc tggggattat     660
taaatccata taatgtatgt gcttatgtat gctacatgtg caagttaggt gtttcctttg     720
tgttctgctt attaaatgtc attcagattc acttcctgaa ttctaataaa gagggaagct     780
attggaaaaa ataaaaaaaa aaaaaaaaaa gcggccgcc                            819
```

FIGURE 37

```
tctagcgaac cccttcggtg gcgcacgccg gtaggatttg ccacgcaaat gctggaatta      60
aagacatgca gcagcagcgc cctgtggttt tggttttta  tttgattgct tattttatc     120
taattttaa  tttttgtgt  atgaacgttt tatctgcatt tatgtctctg taccacattc     180
gtgcctggtg ctatggaggc caaaaaagga ttttaggccc gagattgtag ttatagatgg     240
ttgtgggctg ccaatctgag tgctgaaaat taaacctggg tactctgaaa gaccagccag     300
tgctcttaac tatcaggcca cctctccagc actatttat  tttatttat  ttgtggagat     360
agggtctctc tctctgtatc ctagtctaac ttaaaacata aagaatattc tgtatcagta     420
tccttgagta ctaggattct aggcacctgt cattatgcct agatttttaa cagtgtgtgt     480
taattctaca taaaaatgaa tttcattatt acattttcac acttgtgaag aatatacttt     540
gatcatattc ccttctcctg atacttttc  ctatccttcc tccccactcc attagttccc     600
ttcttctttt cagagtctac cttctacttt ttactttgat ttttttcccc ccacattctg     660
tggttgagag aatgcatatt acagttgtat ttctgaatct ggctaggtac attcacttaa     720
cataattaat gatcctgggc gagcgaaggg gttcncctan cnaaccccttt cggttcaata     780
ccatttcaga gatgggcatt tccctcaatg aaatacacaa gtaaacattc cgacattgtc     840
tttaggagtg tttgttaaaa aaaaaaaaaa aaaaaaccan ancccaaaan caaaaaaaaa     900
aaagctttgc accttgcaaa agtggtcctg gcgtgggtag attgctgtta atcctttatc     960
aataacgttc tatagagaat atataaatat atatctccta gtccctgcct                1020
cttaagagcc gaaaatgcat gggtgttgta gacattcggt tgcactaaat tcctctctga    1080
attttggctg ctgaagccgt tcatttagca actgtttata ggtggttgat gaatggttcc    1140
ttatctccat ttcttcctat gtagcttaag ccgcttcctt cacagaatct aataatctcg    1200
tctaggccat tagccctgcc ctttcttaac attcttgtat ttgttgaatt tggcctcctc    1260
gaaagcaata gcaactgggt ggcccaccca agttttaacg cccctgattc catctatggc    1320
atttgtacca aatataagtt ggatgcattt attttagaca caaagcttta tttttcgac    1380
atcgtgtttc aagaaaaaaa acaaatagaa taacaataac tatgactttg aggccaatca    1440
tttttaggtg tgtgtttgaa gcatagaacg tctnttaaac tctcaatggt tccttcaaat    1500
gatgagttag tatgtaacgt aaatagcagt ttctctctct ctctctctct ttttattttt    1560
tccanataga gcactatgta aatttagcat atcaataata caggaactat ccnccaaaaa    1620
aaaaaaaaaa aaaaaaaaa  gcggccgc                                       1648
```

FIGURE 38

```
tctagcgaac ccct tcgtag aactaggagc cagtgttgac cacggtcggt ggctggatac    60
cccactgcat gctgcagcaa ggcagtccag tgtggaggtc atcaatctgc tcactgagta   120
tggggctaac ctgaaactca gaaactcgca gggcaaaagt gctcttgagc tcgctgctcc   180
caaaagtagt gtggagcagg cactcctgct ccatgaaggt ccacctgctc tttctcagct   240
ctgccgcttg tgtgtccgga agtgcttggg ccgcac atg tca tca agc cat cta    294
                                      Met Ser Ser Ser His Leu
                                       1               5
```

```
cgc act agg tct gcc aga acc cct gga aaa att cct ctt ata cca ata    342
Arg Thr Arg Ser Ala Arg Thr Pro Gly Lys Ile Pro Leu Ile Pro Ile
            10                  15                  20
```

```
gtt gga aac atg ttg cct gct gta gga cac tta ata tac aca ttc agt    390
Val Gly Asn Met Leu Pro Ala Val Gly His Leu Ile Tyr Thr Phe Ser
        25                  30                  35
```

```
ggc tta acc cac tat cct aaa aat ctg ctt acc taa ttagaataaa          436
Gly Leu Thr His Tyr Pro Lys Asn Leu Leu Thr  *
    40                  45
```

```
gccttcataa atccaaatac ttgcgttgaa caaactcctg gttaggttaa tggntgccaa   496
gagataacca gaaacctttc aagttttaa ctcttggtaa tttaaaatca aactgaaata   556
gatggaaaat aataatctat ttttggataa ttcaaggacc cttcagtatc tggggctggg   616
gtccgcattt tgnatactgg atagacacac acacaggtag gatanggtaa atnaactact   676
taaagaatgg cctggggattt aagtcctcca gatattttt aggtngnggt ttcctaaaat   736
aaaattctgg agtgccaaaa aaaaaaaaaa aaaaaaaaag cgggcc                 782
```

FIGURE 39

```
gtctagcgaa ccccttcggg aaacttcaac aaaggtacca gcaactacag cgccttgtcc      60
acccagattt cttcagccaa aagtctcaga ctgagaaacg gttctcggag aagcattcga     120
ccctggtgaa tgatgcctac aagactcttc aggcccccgt gagcagagga ctatatcttc     180
taaagctcca aggaatagaa attcctgaag ggacagatta tagaacagac agtcagttcc     240
ttgtggaaat c atg gaa atc aat gaa aaa ctc gca gac gcc aaa agt gag      290
            Met Glu Ile Asn Glu Lys Leu Ala Asp Ala Lys Ser Glu
             1               5                  10 gca gcc atg gaa gag gta gaa gcc act gtc aga gct aaa cag aaa gaa      338
Ala Ala Met Glu Glu Val Glu Ala Thr Val Arg Ala Lys Gln Lys Glu
        15                  20                  25 ttt acg gac aat ata aac aga gct ttt gaa caa ggt gat ttt gaa aaa      386
Phe Thr Asp Asn Ile Asn Arg Ala Phe Glu Gln Gly Asp Phe Glu Lys
    30                  35                  40                  45 gcc aag gaa ctt ctt aca aaa atg aga tac ttt tca aac ata gaa gaa      434
Ala Lys Glu Leu Leu Thr Lys Met Arg Tyr Phe Ser Asn Ile Glu Glu
                50                  55                  60 aag atc aag tta agc aag aac cct ctc tag ttgctaactt aaaggtttaa        484
Lys Ile Lys Leu Ser Lys Asn Pro Leu  *
                65                  70 aaataaactt tgtatttctt cannnnnnan nnnnannntn nnnnagcggc cgcc           538
```

FIGURE 40

```
tctagcgaac cccttcgcga aggggttcgc ttcttaccct gtggagaaag gggcaggagg    60
aacctcctgt gttaggagga agctggagct taccactgtg agaggacaga tgtggactga   120
gaattttctt agtgctcagt ggcacttccc aaggactccc ctccccttgt gctctgtgcg   180
gtttttagga cagctaagat gactgccacc tgttgtggca ggcccgattt gtcttgttct   240
ccccttactg taccccgata taatctctgt tgatcaacag gactacccca agaatccaca   300
tgttctcccc cgtaaccagg cagctgtctg gttcatgcct tcttcccttc aaacccaacc   360
cagcgccctt gttagtgaag aggtggtcca tggactgatg acaagttatt agcactggat   420
gctgtttcca tagtgacaag cctatacctc ttcccaccct ttagtgcgca gtgggctgct   480
gcttcagtat cctcccagct cagttttatt agatcaaagc tgcccttggg caccatgttg   540
gccacctcaa tcaccagcca aaatggtcgc tttgtccacc agaggtcaag ccatctttct   600
ggcgctgtag ttcccagctc cttctaggga acaggaagtt gatattgcca tgggggaggt   660
ggcggggtgt ggccgtcacc tcaatagttt tactgtaaaa gggaaatttg aacaagaaca   720
acaacaaaaa aaaaaaaaaa acaaagaaaa aaataaaaaa ctttaaaagt tgaaaaaaaa   780
aaaaaaaaaa aaaaaaagcg gccgc                                        805
```

FIGURE 41

```
tctagcgaac cccttcgctg ggacccgcaa ctaccaactg ccgcctggat cctaggtgag        60
ctgtgggctc tgacagcgct gtggctaac atg gca ccc aaa aag aag act ctc        113
                                Met Ala Pro Lys Lys Lys Thr Leu
                                 1           5 aag aag aac aaa ccc gag atc aat gag atg acc atc atc gtg gaa gac        161
Lys Lys Asn Lys Pro Glu Ile Asn Glu Met Thr Ile Ile Val Glu Asp
         10              15                  20 agc ccc cta aac aag ctg aat gct cta aat ggg ctc ctg ggg gga gaa        209
Ser Pro Leu Asn Lys Leu Asn Ala Leu Asn Gly Leu Leu Gly Gly Glu
 25              30              35                  40 aac agc ctt agc tgt gtt tct ttc gaa cta aca gac act tct tat ggt        257
Asn Ser Leu Ser Cys Val Ser Phe Glu Leu Thr Asp Thr Ser Tyr Gly
                 45              50                  55 ccc aac ctc ctg gaa ggt tta agt aaa atg cgt caa gag agc ttt cta        305
Pro Asn Leu Leu Glu Gly Leu Ser Lys Met Arg Gln Glu Ser Phe Leu
             60              65                  70 tgt gac ttg gtc atc ggt cca aaa cca agt cct ttg atg tcc ata agt        353
Cys Asp Leu Val Ile Gly Pro Lys Pro Ser Pro Leu Met Ser Ile Ser
         75              80                  85 caa gtg atg gct tcc tgc agc gag tct tct ata ata tcc tta aaa cga        401
Gln Val Met Ala Ser Cys Ser Glu Ser Ser Ile Ile Ser Leu Lys Arg
 90              95                 100 tcc atc gac aaa aag ggt aga cct caa tga tatcgnccct ttagggctac         451
Ser Ile Asp Lys Lys Gly Arg Pro Gln  *
105             110 caccgtgata gcatatgcat acacnggaaa gctgcccttt ctttatacac aataaggaag      511
catcatttct gctgctgtgt acctccagat ccacactctt gtgaagatgt gcagcgactt      571
tctgatccga gagatcagtg ttgagaactg catgtatgtt gttaacatgg ctgaaacata      631
ctgcttgaaa aatgcgaaag caacggccca gaaatttatc cgggataact tcattgaatt      691
tgccgactcc gaacaattta tgaagctgac gtttgaacag attaatgagc ttctcataga      751
tgatgacttg cagttgcctt ctgagctggt agcattccag attgcaatga aatggataga      811
attcaaccaa agagagtga agcacgctgc ggatctttta agcaatattc gctttggtac       871
catctctgca caagacctgg tcaattacgt tcaaaccgta ccgagaatga tgcaagacgc      931
tgattgtcat aaactgcttg tggatgctat gaactaccac ttactacctt atcatcaaaa      991
cacgttgcaa tctaggcgga caagaattag aggcggctgc cgggttctga tcactgtcgg     1051
gggacgccct ggcctgactg agaagtccct tagtagagac gtttatatag agaccctgaa     1111
aatggatgga gcaagcttac agaaatgcca gccaagagtt tcaatcagtg tgtggctgtg     1171
atggatggat tcctttatgt agcaggtggt gaggaccaga atgatgcgag aaaccaagcc     1231
aagcatgcag tcagcaattt ctgcaggtac cgatccccgc ttcaacacgt ggatccacct     1291
gggcagcatg aaccagaagc gcacgcactt cagcctgagc gtgttcaacg gctcctgta     1351
cgccggtggn gggcnccagt gnganggata tctgcagaat tcggctagcc gaattc        1407
```

FIGURE 42

```
tctagcgaac cccttcggac actgccagca tagacagcag ccctgctac tgtcccacca        60
ctgtacccca gagccccgac tagcagt atg ccg gga gcg cca ggg cct ggg cct      114
                              Met Pro Gly Ala Pro Gly Pro Gly Pro
                               1                   5
```

```
gag gtg gct gca gcc ttt gag gaa cgg ttg agt cag gca cta cag gaa        162
Glu Val Ala Ala Ala Phe Glu Glu Arg Leu Ser Gln Ala Leu Gln Glu
 10              15                  20                  25
```

```
ctg cag gca gtg gct gaa gca ggc cgg tca gcg gtg acc cag gca gct        210
Leu Gln Ala Val Ala Glu Ala Gly Arg Ser Ala Val Thr Gln Ala Ala
             30                  35                  40
```

```
gat gca gcc cta gcc act gta gag cca gtg gct cag gca tct gaa gag        258
Asp Ala Ala Leu Ala Thr Val Glu Pro Val Ala Gln Ala Ser Glu Glu
                 45                  50                  55
```

```
ctt cgg gcc gag aca gca gcc ctg agc cgg cgg ctg gat gcc ctg acc        306
Leu Arg Ala Glu Thr Ala Ala Leu Ser Arg Arg Leu Asp Ala Leu Thr
             60                  65                  70
```

```
agg cag gtg gag gtg ctg agc cta cgg ctg ggt gtt cca ctc gtg ccg        354
Arg Gln Val Glu Val Leu Ser Leu Arg Leu Gly Val Pro Leu Val Pro
 75                  80                  85
```

```
gac ctg gag tcc gag cta gag ccc agc gag ctg ttg ctg gct gct gcc        402
Asp Leu Glu Ser Glu Leu Glu Pro Ser Glu Leu Leu Leu Ala Ala Ala
 90                  95                 100                 105
```

```
gac cct gag gcc ctc ttc cag gca agc tga ggatgctggg accccgtgg           452
Asp Pro Glu Ala Leu Phe Gln Ala Ser  *
                110
```

```
ccacccgcct gcctttagca cccgccgcag ctcttctgcg ggcccctctc gaagcagcag      512
tctcatggag cccgatccag cagagccccc ctctgccaca gtggaagcag ctaatggaac      572
agagcagact ctggacaaag tgaacaaagg cccagagggg cggagccccc tgagtgcaga      632
ggagctgatg gccattgagg acgaaggaat cctggacaag atgctggacc aggctacgaa      692
ctttgaagag cggaagctca tccgggctgc gctccgtgag ctccgacaaa gaaagagaga      752
ccagagggac aaggaacgag aacggcggct acgagaggca cgggcccggc caggcgagag      812
ccgaagcaat atggctacta cagagaccac caccaggcac aagccagagg gcggctgatg      872
gctcggcggt cagcacagtt accaaaactg agcgggtcgt ccactccaat gacggcacgc      932
agactgcgcg caccaccaca gtggagtcga gtttcgtgag cgctcggag aatggcagca       992
gcaagcaagc agcagcacca cggtccaaac caagaccttt tcctcttcct cttcctcatc     1052
caaaaaaatg ggcagtatct tcgaccgaga ggaccaaacc agctcacgtt ctggcagcct     1112
ggcggccctc gaaaaacgcc aggcagagaa gaagaaagag ctcatgaagg cacagagtct     1172
gcccaagacc taagcgtccc aagcacgcaa ggccatgatt gagaaactag agaaggaagg     1232
ctcttcgggc agtcctggca caccccgtac agcggtacag cgttctacca gcttcggagt     1292
ccccaacgcc aacagcatca agcagatgtt gctggactgg tgccgagcca agacccgtgg     1352
ctacgagcac gtggacatcc agaacttctc tccagctgga gtgatgggat ggctttctgt     1412
gccctggtgc acaatttctt ccctgaggct tttgactatg gacagcttag cccacaaaac     1472
cggcgccaga actttgaaat ggccttctca tctgctgaga cccatgcgga ctgcccgcag     1532
ctcctggata cagaggacat ggtgcggctt cgagagcctg actggaagtg cgtgtacacg     1592
tacatccagg agttctaccg ctgtctggtc cagaagggc tggtaaaaac caaaaagtcc      1652
```

```
taacccctgc ttggggcccc acggatgctg gtggactgtg tacccttggt ggaggtggag   1712
gacatgatga tcatgggcaa aaagccagac cctaagtgcg tcttcaccta cgtgcaatcg   1772
```
FIGURE 42 (cont.)

```
ctgtacaacc acctgcggcg ccatgagctg cgcctgcgcg gcaagaatgt ctagccactg   1832
ctcacaccgc ctgcgctgca ggctgctgtc ccacgccccc aacaccggnc cctncagtgn   1892
gcctgccact gntgcccgtn tgtcgaaaca cctntcccct tgtcacacgc agngntttga   1952
taaattattt gntttnaaca aaaaaaaaaa aaaaaaaaaa aaaagcggcc gc           2004
```

FIGURE 43

```
tctagcgaac cccttcgctc cagggcgttt gcctcctgct gacttgctct tcaccattag    60
acaagcctga cgtcaagacc cca atg gct aac gaa gct aac cct tgc cca tgt   113
                        Met Ala Asn Glu Ala Asn Pro Cys Pro Cys
                         1               5                  10 gac att ggt cac agg cta gac tat ggt ggc atg ggc cag gaa gtt cag     161
Asp Ile Gly His Arg Leu Asp Tyr Gly Gly Met Gly Gln Glu Val Gln
             15                  20                  25 gtt gag cac atc aag gca tat gtc acc cgg tcc cct gtg gat gca ggc     209
Val Glu His Ile Lys Ala Tyr Val Thr Arg Ser Pro Val Asp Ala Gly
             30                  35                  40 aaa gct gtg att gtt gtc cag gat ata ttt ggc tgg cag ctg tcc aac     257
Lys Ala Val Ile Val Val Gln Asp Ile Phe Gly Trp Gln Leu Ser Asn
             45                  50                  55 acc agg tat atg gct gac atg att gct gga aat gga tac aca act att     305
Thr Arg Tyr Met Ala Asp Met Ile Ala Gly Asn Gly Tyr Thr Thr Ile
         60                  65                  70 gcc cag act tct ttg tgg gtc aag agc cat ggg acc cgg ctg gtg att     353
Ala Gln Thr Ser Leu Trp Val Lys Ser His Gly Thr Arg Leu Val Ile
 75                  80                  85                  90 ggt cca cct tcc ctg agt ggt tga aatcaagaaa tgccagaaaa atcaaccgag    407
Gly Pro Pro Ser Leu Ser Gly  *
                         95 aggttgatgc tgtcttgagg tatctgaaac aacagtgtca tgcccagaag attggcattg   467
tgggcttctg ctgggggggt attgtggtgc caccgtgat gacgacatat ccagaagtca    527
gagcgggggt gtctgtctat ggtatcatca gagattctga agatgtttat aatttgaaga   587
acccaacgtt gtttatcttt gcagaaaatg atgctgtgat tccacttgag caggtttcta   647
tactgatcca gaagcttaaa gaacactgca tagttaatta ccaagttaag acattttctg   707
ggcaaactca tggctttgtg catcggaaga gagaagactg ctccccctgca gacaaaccct  767
acattgagga agcgaggagg aatctcatcg aatggctgaa caagtatatt taacagcact   827
caagcacaaa ttttgaataa ttaaattgac ccgaataatt aaattgaccc gaat          881
```

FIGURE 44

Regulated expression of Full-length novel clones:

| | | Kidney | | Heart | | | | | | | | | | |
|---|---|---|---|---|---|---|---|---|---|---|---|---|---|---|
| | | | | | LV | | | | | Spt | | | | |
| Seq ID | CloneID | PKD | Na+ Ang2 | Hyp 10w | 2w | 4w | 8w | 12w | 16w | 2w | 4w | 8w | 12w | 16w |
| 1 | P00184_D11 | — | — | — | — | ▽ | ▽ | ▽ | — | — | — | — | ▽ | ▽ |
| 2 | P00185_D11 | — | — | ▽ | ▽ | — | — | ▽ | — | — | — | — | — | — |
| 3 | P00188_D12 | — | — | ▽ | ▽ | — | — | — | — | — | — | — | — | — |
| 4 | P00188_E01 | — | — | — | ▲ | ▲ | ▲ | ▲ | ▲ | — | — | — | — | ▲ |
| 5 | P00194_G01 | — | — | — | ▲ | ▲ | — | ▲ | ▲ | — | — | — | — | — |
| 6 | P00194_G05 | — | — | — | — | — | ▲ | ▲ | ▲ | — | — | — | — | ▲ |
| 7 | P00194_H10 | | | — | ▲ | — | — | — | — | — | — | — | — | — |
| 8 | P00199_D08 | — | — | — | ▽ | ▽ | — | — | ▽ | — | — | — | — | — |
| 9 | P00203_D04 | ▲ | ▲ | ▽ | — | ▲ | — | — | — | — | — | — | — | — |
| 10 | P00203_E06 | — | — | ▽ | ▽ | ▽ | ▽ | ▽ | ▽ | — | — | — | — | — |
| 11 | P00209_F06 | — | — | ▲ | ▲ | — | ▲ | ▲ | ▲ | — | — | — | — | — |
| 12 | P00219_D02 | — | — | — | — | — | — | ▲ | — | — | — | — | — | — |
| 13 | P00219_F06 | — | — | — | ▲ | ▲ | ▲ | ▲ | — | — | — | — | — | — |
| 14 | P00220_H05 | — | — | — | — | — | — | — | ▲ | ▲ | — | — | — | — |
| 15 | P00222_G03 | | | — | — | ▽ | ▽ | ▽ | — | — | ▽ | — | ▽ | — |
| 16 | P00223_F07 | | | ▽ | — | — | — | — | — | — | — | — | — | — |
| 17 | P00225_C01 | — | — | — | — | — | ▲ | ▲ | ▲ | — | — | ▲ | ▲ | ▲ |
| 18 | P00227_D11 | — | — | — | ▲ | — | — | — | ▲ | — | — | — | — | — |
| 19 | P00228_F03 | | | — | ▲ | ▲ | — | ▲ | ▲ | — | — | — | — | — |
| 20 | P00233_H08 | — | — | — | ▲ | ▲ | ▲ | ▲ | ▲ | — | — | — | — | — |
| 21 | P00235_G08 | ▲ | — | — | — | — | — | — | — | — | ▽ | — | ▽ | — |
| 22 | P00239_C11 | — | — | ▲ | ▲ | — | — | — | ▲ | ▲ | — | — | — | — |
| 23 | P00240_B04 | — | — | ▽ | — | — | — | ▽ | — | — | ▽ | — | ▽ | — |
| 24 | P00240_E05 | — | — | ▽ | — | — | — | — | — | — | — | — | — | — |
| 25 | P00241_E12 | — | — | — | — | — | — | ▽ | — | ▽ | ▽ | — | ▽ | — |
| 26 | P00245_D06 | ▲ | — | — | ▽ | — | — | — | — | — | — | — | — | — |
| 27 | P00246_D12 | | | — | — | — | — | — | — | — | ▽ | — | ▽ | — |
| 28 | P00247_A04 | — | — | — | ▽ | ▽ | ▽ | — | ▽ | — | — | — | — | — |
| 29 | P00248_B04 | | | ▽ | — | — | — | — | — | — | — | — | — | — |

FIGURE 44 (CONT.)

| | | Kidney | | Heart | | | | | | | | | | |
|---|---|---|---|---|---|---|---|---|---|---|---|---|---|---|
| | | | Na+ | Hyp | LV | | | | | Spt | | | | |
| Seq ID | CloneID | PKD | Ang2 | 10w | 2w | 4w | 8w | 12w | 16w | 2w | 4w | 8w | 12w | 16w |
| 30 | P00249_F09 | | | — | ▲ | ▲ | ▲ | ▲ | ▲ | — | ▲ | — | ▲ | ▲ |
| 31 | P00258_A10 | | | — | ▲ | ▲ | ▲ | ▲ | ▲ | — | — | — | — | — |
| 32 | P00262_C10 | | | ▲ | — | ▽ | — | — | — | — | — | — | — | — |
| 33 | P00263_G06 | | | ▲ | — | — | — | — | — | — | — | — | — | — |
| 34 | P00267_F08 | — | — | ▽ | — | ▲ | — | ▲ | — | — | — | — | — | — |
| 35 | P00269_H08 | | | ▲ | — | ▽ | — | ▽ | ▽ | — | — | — | — | — |
| 36 | P00312_C04 | | | | — | — | ▽ | — | — | — | — | ▽ | — | — |
| 37 | P00324_H02 | | | | — | ▽ | ▽ | ▽ | — | — | ▽ | ▽ | ▽ | ▽ |
| 38 | P00628_H02 | ▲ | — | — | — | — | ▲ | ▽ | ▽ | — | — | — | — | — |
| 39 | P00629_C08 | | | — | — | ▽ | — | — | ▽ | — | — | — | — | — |
| 40 | P00634_G11 | | | | | | | | | | | | | |
| 41 | P00641_G11 | — | — | ▲ | — | — | — | — | — | — | — | — | — | — |
| 42 | P00648_E12 | | | | | | | | | | | | | |
| 43 | P00697_C03 | ▽ | — | — | — | — | — | ▽ | ▽ | — | — | — | — | — |

SEQUENCE LISTING

<160> NUMBER OF SEQ ID NOS: 84

<210> SEQ ID NO 1
<211> LENGTH: 1340
<212> TYPE: DNA
<213> ORGANISM: Rattus norvegicus

<400> SEQUENCE: 1

```
gcggccgccc ctgacacaat ggctcagctt atgcctcagc gcagttcgct ccaccccaga      60
atggcatcct gcagaataca cggcccctca tccccatccc gcgccagaga caccggccag     120
cccactgtcc ccgccacaca ttaaacttga tcctcctaca cagacgcact cggagcagag     180
cgcttataca agcgcacagc cgtctccggc accgccacac agacagatga tgccgccccg     240
accgacggcc agccccagac acaaccttct gaaaacacag aaaacaagtc ccagcccaag     300
cggctgcatg tgtccaacat ccccttccgg ttcgggatc cagacctccg acaaatgttt     360
ggccaatttg gtaaaatatt agatgttgaa attattttta atgagcgggg ctcgaaggga     420
tttggtttcg taactttcga aaatagtgcg gatgcggaca gggcgaggga gaaattgcac     480
ggtaccgtgg tagagggccg taaaatcgag gttaataatg cgacagcacg cgtgatgact     540
aataaaaagg ccgtgaaccc ctacaccaat ggctggaaat taaatccagt tgtgggcgcg     600
gtctacagcc ccgacttcta tgcaggcacg gtgctgttgt gccaggccaa ccaggaggga     660
```

```
tcttccatgt acagtggccc cagttcactt gtatatactt ctgcaatgcc tggctttcca   720
tatccggccg ccactgctgc agctgcatac cgagggctc accttcgagg ccgtggtcgc    780
accgtgtaca acaccttcag agctgcggcg ccccaccc caatcccggc ctatggcgga    840
gtagtgtatc aagagccagt gtatggcaat aaattgctac agggtggtta cgctgcatac   900
cgctacgccc agcccacccc tgccactgct gctgcctaca gtgacagtta cggacgagtt   960
tatgctgccg accctacca ccacacactt gctccagccc ccacctacgg cgttggtgcc  1020
atgaatgctt tgcgcccctt gaccgatgcc aagactagga gccatgctga tgatgtgggt  1080
ctcgttcttt cttcattgca ggctagtata taccaagggg gatacaaccg ttttgctcca  1140
tattaaatga taaaaccatt aaacaaacaa gcaaaaaaca aaacaaaaac aaaaaaacca  1200
accttccaat gtggggagag aggaagcttt ccgaggcccg agtgttgcga cacatgcagt  1260
aggacatcac tttagcaact caaagaaaca acgaaaaaaa aaaaaaaaaa aaaaataagc  1320
ggccgaaggg gttcgctaga                                               1340

<210> SEQ ID NO 2
<211> LENGTH: 203
<212> TYPE: PRT
<213> ORGANISM: Rattus norvegicus

<400> SEQUENCE: 2

Met Thr Asn Lys Lys Ala Val Asn Pro Tyr Thr Asn Gly Trp Lys Leu
 1               5                  10                  15

Asn Pro Val Val Gly Ala Val Tyr Ser Pro Asp Phe Tyr Ala Gly Thr
                20                  25                  30

Val Leu Leu Cys Gln Ala Asn Gln Glu Gly Ser Ser Met Tyr Ser Gly
            35                  40                  45

Pro Ser Ser Leu Val Tyr Thr Ser Ala Met Pro Gly Phe Pro Tyr Pro
        50                  55                  60

Ala Ala Thr Ala Ala Ala Ala Tyr Arg Gly Ala His Leu Arg Gly Arg
    65                  70                  75                  80

Gly Arg Thr Val Tyr Asn Thr Phe Arg Ala Ala Pro Pro Pro Pro Pro
                85                  90                  95

Ile Pro Ala Tyr Gly Gly Val Val Tyr Gln Glu Pro Val Tyr Gly Asn
            100                 105                 110

Lys Leu Leu Gln Gly Gly Tyr Ala Ala Tyr Arg Tyr Ala Gln Pro Thr
        115                 120                 125

Pro Ala Thr Ala Ala Ala Tyr Ser Asp Ser Tyr Gly Arg Val Tyr Ala
    130                 135                 140

Ala Asp Pro Tyr His His Thr Leu Ala Pro Ala Pro Thr Tyr Gly Val
145                 150                 155                 160

Gly Ala Met Asn Ala Phe Ala Pro Leu Thr Asp Ala Lys Thr Arg Ser
                165                 170                 175

His Ala Asp Asp Val Gly Leu Val Leu Ser Ser Leu Gln Ala Ser Ile
            180                 185                 190

Tyr Gln Gly Gly Tyr Asn Arg Phe Ala Pro Tyr
        195                 200

<210> SEQ ID NO 3
<211> LENGTH: 867
<212> TYPE: DNA
<213> ORGANISM: Rattus norvegicus
<220> FEATURE:
<221> NAME/KEY: unsure
```

<222> LOCATION: (0)...(0)
<223> OTHER INFORMATION: n = A, T, C, or G

<400> SEQUENCE: 3

| | | | | | |
|---|---|---|---|---|---|
| tctagcgaac | cccttcgcga | aggggttcgc | ctgtgctggt | gggcgcggtg | gcccgaagcc | 60 |
| ttggactcac | tgcaggactg | tgcagggaac | cactgtccaa | gcatcgggct | aatagggggc | 120 |
| gcctgcctcg | gtttacccct | cagcgtctgg | tgaaatcccg | cagcgtctag | ggaaagatcc | 180 |
| gttctgctcc | gcgagggaaa | cagagccgtt | gaccatggtt | gcaacgggca | gtttgagcag | 240 |
| taagaacacg | gccagcattt | cagagttgct | ggacggtggc | tctcaccctg | ggagtctgct | 300 |
| aagtgatttc | gactactggg | attatgtcgt | ccctgagccc | aacctcaacg | aggtggtgtt | 360 |
| tgaagagaca | acatgccaga | atttggttaa | aatgttggag | aactgtctgt | ccaagtcaaa | 420 |
| gcaaaccaaa | ctcggttgct | ctaaggtcct | ggttcctgag | aaactgaccc | agagaattgc | 480 |
| ccaagatgtc | ctgcggctct | catccacaga | gccctgcggc | cttcggggct | gtgttatgca | 540 |
| cgtgaacttg | gaaattgaaa | atgtgtgtaa | aaagctggat | aggattgtgt | gtgatgctag | 600 |
| tgtggtgccg | acctttgagc | tcacgctggt | gttcaagcag | gagagctgct | cctggaccag | 660 |
| cctcaaggac | ttcttctttta | gcggaggtcg | cttctcgtcg | ggccttaagc | gaactctgat | 720 |
| cctcagctcg | ggatttcgac | ttgttaagaa | aaaactgtac | tctctgattg | gaacgacagt | 780 |
| cattgaggag | tgctgaggag | gaaaaaacaa | ttaaaggtcc | ctaatgagtg | gctaacaaaa | 840 |
| anaaaannnn | nnnnnnnnnn | ngcggnc | | | | 867 |

<210> SEQ ID NO 4
<211> LENGTH: 193
<212> TYPE: PRT
<213> ORGANISM: Rattus norvegicus

<400> SEQUENCE: 4

Met Val Ala Thr Gly Ser Leu Ser Ser Lys Asn Thr Ala Ser Ile Ser
1               5                   10                  15

Glu Leu Leu Asp Gly Gly Ser His Pro Gly Ser Leu Leu Ser Asp Phe
            20                  25                  30

Asp Tyr Trp Asp Tyr Val Val Pro Glu Pro Asn Leu Asn Glu Val Val
        35                  40                  45

Phe Glu Glu Thr Thr Cys Gln Asn Leu Val Lys Met Leu Glu Asn Cys
    50                  55                  60

Leu Ser Lys Ser Lys Gln Thr Lys Leu Gly Cys Ser Lys Val Leu Val
65                  70                  75                  80

Pro Glu Lys Leu Thr Gln Arg Ile Ala Gln Asp Val Leu Arg Leu Ser
                85                  90                  95

Ser Thr Glu Pro Cys Gly Leu Arg Gly Cys Val Met His Val Asn Leu
            100                 105                 110

Glu Ile Glu Asn Val Cys Lys Lys Leu Asp Arg Ile Val Cys Asp Ala
        115                 120                 125

Ser Val Val Pro Thr Phe Glu Leu Thr Leu Val Phe Lys Gln Glu Ser
    130                 135                 140

Cys Ser Trp Thr Ser Leu Lys Asp Phe Phe Ser Gly Gly Arg Phe
145                 150                 155                 160

Ser Ser Gly Leu Lys Arg Thr Leu Ile Leu Ser Ser Gly Phe Arg Leu
                165                 170                 175

Val Lys Lys Leu Tyr Ser Leu Ile Gly Thr Thr Val Ile Glu Glu
            180                 185                 190

Cys

<210> SEQ ID NO 5
<211> LENGTH: 874
<212> TYPE: DNA
<213> ORGANISM: Rattus norvegicus

<400> SEQUENCE: 5

```
tctagcgaac ccttcggtg acagaacag cctgagtcag gatgaaagct ctcagggctg      60
tcctcctgat cttgctactc agtggacagc cagggagcag ctgggcacaa gaagctggcg    120
atgtggacct ggagctagag cgctacagct acgatgatga cggtgatgac gatgatgacg    180
atgatgaaga agaggaagag gaggagacca acatgatccc tggcagcagg gacagagcac    240
cgcctctaca gtgctacttc tgccaagtgc ttcacagcgg ggagagctgc aacgagacac    300
agagatgctc cagcagcaag cccttctgta tcacagtcat ctcccatggc aaaactgaca    360
caggtgtcct gacgacctac tccatgtggt gtactgatac ctgccagccc atcgtgaaga    420
cagtggacag caccccaaatg acccagacct gttgccagtc cacactctgc aatattccac    480
cctggcagag cccccaaatc cacaacccctc tgggtggccg ggcagacagc cccttgaagg    540
gtgggaccag acatcctcaa ggtgacaggt ttagccaccc ccaggttgtc aaggttactc    600
atcctcagag tgatggggct cacttgtcta agggtggcaa ggctaaccag ccccagggaa    660
atggggccgg attccctgca ggctggagca aatttggtaa cgtagttctc ctgctcacct    720
tcctcaccag tctgtgggca tcaggggcct aaagactcgt cctcccccaa ccaggaccct    780
tcagcctttc ctccctgaca accagcttca gagaataaac ttgaatgtct tttgccatct    840
aaaaaaaaaa aaaaaaaaaa aaaaagcggc cgcc                                874
```

<210> SEQ ID NO 6
<211> LENGTH: 236
<212> TYPE: PRT
<213> ORGANISM: Rattus norvegicus

<400> SEQUENCE: 6

Met Lys Ala Leu Arg Ala Val Leu Leu Ile Leu Leu Leu Ser Gly Gln
 1               5                  10                  15

Pro Gly Ser Ser Trp Ala Gln Glu Ala Gly Asp Val Asp Leu Glu Leu
            20                  25                  30

Glu Arg Tyr Ser Tyr Asp Asp Gly Asp Asp Asp Asp Asp Asp
        35                  40                  45

Glu Glu Glu Glu Glu Glu Thr Asn Met Ile Pro Gly Ser Arg Asp
    50                  55                  60

Arg Ala Pro Pro Leu Gln Cys Tyr Phe Cys Gln Val Leu His Ser Gly
 65                  70                  75                  80

Glu Ser Cys Asn Glu Thr Gln Arg Cys Ser Ser Lys Pro Phe Cys
            85                  90                  95

Ile Thr Val Ile Ser His Gly Lys Thr Asp Thr Gly Val Leu Thr Thr
            100                 105                 110

Tyr Ser Met Trp Cys Thr Asp Thr Cys Gln Pro Ile Val Lys Thr Val
            115                 120                 125

Asp Ser Thr Gln Met Thr Gln Thr Cys Cys Gln Ser Thr Leu Cys Asn
        130                 135                 140

Ile Pro Pro Trp Gln Ser Pro Gln Ile His Asn Pro Leu Gly Gly Arg
145                 150                 155                 160

Ala Asp Ser Pro Leu Lys Gly Gly Thr Arg His Pro Gln Gly Asp Arg

```
                165              170              175
Phe Ser His Pro Gln Val Val Lys Val Thr His Pro Gln Ser Asp Gly
            180              185              190

Ala His Leu Ser Lys Gly Gly Lys Ala Asn Gln Pro Gln Gly Asn Gly
        195              200              205

Ala Gly Phe Pro Ala Gly Trp Ser Lys Phe Gly Asn Val Val Leu Leu
    210              215              220

Leu Thr Phe Leu Thr Ser Leu Trp Ala Ser Gly Ala
225              230              235

<210> SEQ ID NO 7
<211> LENGTH: 817
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 7
tctagcgaac cccttcgagc gaacccttc ggccagtacc ctgagccctg gtccctcctg      60
gagctgcccc acagctctga ctgtggactg agggatgtta ggcggatcac ctgagcctcc   120
agaggctcac actaatgagc gggcgctctc ttcttagcca ctgttgcatt tggttttcat   180
tgactcctgg gcctcgtttg agtgacactg tccttgtctt ttgtttcaga gctctcccag   240
tgttagtgga ctcagatgag gaaattatga ccagatctga aatagctgaa aaaatgttct   300
cttcagaaaa gataatgtga tcagggcccc agtgggtcca gtgtgcatgg gagcgcggtc   360
aggtgatggg aaaggcctgg ctctcgtcaa aactgacagc tgcgctatga tacatgtctc   420
actttgttgt cttggagatc tgtgtatgca ggtgaagaac tcaagtgtgg gagggtctgc   480
cgcctcagaa agccatcttt gaaacggact cataaagtca gttttgttgc cattaagttg   540
cctgattttg gaaacaattt aagaagtgtt aaagacatgt gttcagatgc ctcttaggcg   600
gcagccacag gcatgccagg ttgtgtccct cagtttttctc cagacaaaag aatctgcagc   660
tgggcgtggc ggcacactac tggcagttga agtctgtaa tttcaaggcc aagcctggtc     720
tacatagttc caggacaacc agagagatct acatagtgag accctgcctc aaaacacaga   780
aaccnnanna naaaaaaaaa aaaaaaaaag cggccgc                             817

<210> SEQ ID NO 8
<211> LENGTH: 61
<212> TYPE: PRT
<213> ORGANISM: Rattus norvegicus

<400> SEQUENCE: 8

Met Ser Gly Arg Ser Leu Leu Ser His Cys Cys Ile Trp Phe Ser Leu
1               5                  10                  15

Thr Pro Gly Pro Arg Leu Ser Asp Thr Val Leu Val Phe Cys Phe Arg
            20                  25                  30

Ala Leu Pro Val Leu Val Asp Ser Asp Glu Glu Ile Met Thr Arg Ser
        35                  40                  45

Glu Ile Ala Glu Lys Met Phe Ser Ser Glu Lys Ile Met
    50                  55                  60

<210> SEQ ID NO 9
<211> LENGTH: 755
<212> TYPE: DNA
<213> ORGANISM: Rattus norvegicus
```

```
<220> FEATURE:
<221> NAME/KEY: unsure
<222> LOCATION: (0)...(0)
<223> OTHER INFORMATION: n = A, T, C, or G

<400> SEQUENCE: 9
tctagcgaac cccttcgcac atgggttcct gctgaccaag ggacatggc tctgaagatg      60
atgaggctgg ttactcagca ggagtagctg agctgagctg ccctggagg ccctggaggc     120
cctggagtag ggcccaggat gcaggtgcta atgtctatcc ccggcgctct tcttcccgac    180
tctaccatgg gatgtaactc caggagcccc tgccatctcc cgtaccaaaa gactgtggct    240
tccgtgtcta ctcagaaatc agttctactt cgtaaacagt gtttaaaacc agactcattt    300
aatcagagtg aaggattgca gtccattggc ttcttagcac agaagcagct gataacacaa    360
gtaaacccca gcccttgaga ggtagaagca agaggatcag aggttcaagc gcatcctcgg    420
ctccatcaca agttcaaaag ccgcctgcac caaatgggag tccttgtctc aaaaaaaaaa    480
aaaaaaaaag caaagaaagc aaaggactcg atgacatgat ttatagacaa aagcagtggg    540
agaaaatact aaagccccac tgagctgcca gccaggtgtc tgtgactaca ggtcttttat    600
ctgctcatat atattttac aaaaaatgaa attcatattg gtcgctattt tgctggctgc     660
tttgctcccg atcaacatga tttgcacgtt ttttccatca ataaatgtgc catgatattt    720
ttaaaaaaaa aaaaaaaaa aaaaaaaagg gcncc                                755

<210> SEQ ID NO 10
<211> LENGTH: 79
<212> TYPE: PRT
<213> ORGANISM: Rattus norvegicus

<400> SEQUENCE: 10

Met Gln Val Leu Met Ser Ile Pro Gly Ala Leu Leu Pro Asp Ser Thr
1               5                   10                  15

Met Gly Cys Asn Ser Arg Ser Pro Cys His Leu Pro Tyr Gln Lys Thr
            20                  25                  30

Val Ala Ser Val Ser Thr Gln Lys Ser Val Leu Leu Arg Lys Gln Cys
        35                  40                  45

Leu Lys Pro Asp Ser Phe Asn Gln Ser Glu Gly Leu Gln Ser Ile Gly
    50                  55                  60

Phe Leu Ala Gln Lys Gln Leu Ile Thr Gln Val Asn Pro Ser Pro
65                  70                  75

<210> SEQ ID NO 11
<211> LENGTH: 806
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 11
tctagcgaac cccttcgcag ctctctgacc tgcgtcgccg ccgctctccg ctcttgattt      60
cgccgtgatg tcgaccgcaa tgaacttcgg gaccaaaagc ttccagccgc ggccccccaga   120
caaaggcagc ttcccgctag accacttcgg tgagtgtaaa agctttaagg aaaaattcat    180
gaagtgtctc cgcgacaaga actatgaaaa tgctctgtgc agaaatgaat ctaaagagta    240
tttaatgtgc aggatgcaaa ggcagctgat ggcaccagaa ccactagaga aactcggctt    300
tagagacata atggaggaga aaccggaggc aaaggacaaa tgttgagaat cactgggctg    360
```

```
tgtcccccta cctggagcag agctgagccc ttctgcccac cgtggagaga gctgagccat    420
cctgtgctgc ccagaggagg ggctctccgt gtcgactttg gctcatccct gcagcacaga    480
ccaaactgct ttctctactg accacacttc tgcttcagag agnggtttct cctgtctgng    540
tgtggcacag gatctgctca nggctgaaca ctgatgtgat atgatatccc acctagtgtg    600
gccgcacacc aaaaggcctg gacaggattt cacagtgact caacctgagt cctcacaccc    660
ggaacctgtc agcgaaaacc aancgaagca aaatgnctgg cttttggctt acaaacccca    720
tnatttgntt tcccttctct tgggtctttg ttttgacaaa nctggcatac aaagtnggaa    780
gggggaaata aaaaaaaaaa aaaaaa                                        806
```

```
<210> SEQ ID NO 12
<211> LENGTH: 92
<212> TYPE: PRT
<213> ORGANISM: Rattus norvegicus

<400> SEQUENCE: 12

Met Ser Thr Ala Met Asn Phe Gly Thr Lys Ser Phe Gln Pro Arg Pro
1               5                   10                  15

Pro Asp Lys Gly Ser Phe Pro Leu Asp His Phe Gly Glu Cys Lys Ser
            20                  25                  30

Phe Lys Glu Lys Phe Met Lys Cys Leu Arg Asp Lys Asn Tyr Glu Asn
        35                  40                  45

Ala Leu Cys Arg Asn Glu Ser Lys Glu Tyr Leu Met Cys Arg Met Gln
    50                  55                  60

Arg Gln Leu Met Ala Pro Glu Pro Leu Glu Lys Leu Gly Phe Arg Asp
65                  70                  75                  80

Ile Met Glu Glu Lys Pro Glu Ala Lys Asp Lys Cys
                85                  90
```

```
<210> SEQ ID NO 13
<211> LENGTH: 717
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 13
tctagcgaac cccttcncga aggggttcgc cgagaggtgg gagccaaaag gatggagcat     60
ccgccggtgg tggctggtgg ccgcaatctt ggtggtcctg atcggggttg tcttagtctg    120
cctgatagtc tacttcgcca acgcagcgca cagcgaggcc tgtaagaacg ggttgcggtt    180
gcaggatgag tgccgaaaca ccacgcacct gttgaagcac cagctnaccc gcgcccagga    240
cagcctgctg cagacggaga tgcaggcaaa ctcctgcaac cagaccgtga tggaccttcg    300
ggattccctg aagaagaagg tgtctnaaac ccaggagcaa cangcccgca tcaaggaact    360
tgagaataag atcgagaggc tgaaccaaga gctggaaaaa tttgaggacc caaaaggaaa    420
tttctaccac agtgcangtg aactcaagcg ggttcgtggt ggncttcanc ctacttgtgc    480
tttgtggcgg gactgttctn cacttttan gacccaataa ttgggangta caaacctgtg    540
taggcattgn nggtngtaat ggcttttgag gggtcctgg cacccttaag atgtgaaaac    600
cattangnng gacccaaaat gnttttctt gntttgaact ggggcggacc cggagtgggg    660
ggcnggaaat aanntattnn ggnnggaaan aaaaaaaaaa aaaaaaaaa gcggccc       717
```

<210> SEQ ID NO 14
<211> LENGTH: 86
<212> TYPE: PRT
<213> ORGANISM: Rattus norvegicus
<220> FEATURE:
<221> NAME/KEY: UNSURE
<222> LOCATION: (0)...(0)
<223> OTHER INFORMATION: Xaa = any amino acid

<400> SEQUENCE: 14

Met Gln Ala Asn Ser Cys Asn Gln Thr Val Met Asp Leu Arg Asp Ser
 1               5                  10                  15

Leu Lys Lys Lys Val Ser Xaa Thr Gln Glu Gln Xaa Ala Arg Ile Lys
                20                  25                  30

Glu Leu Glu Asn Lys Ile Glu Arg Leu Asn Gln Glu Leu Glu Lys Phe
            35                  40                  45

Glu Asp Pro Lys Gly Asn Phe Tyr His Ser Ala Xaa Glu Leu Lys Arg
        50                  55                  60

Val Arg Gly Gly Leu Xaa Pro Thr Cys Ala Leu Trp Arg Asp Cys Ser
65                  70                  75                  80

Xaa Leu Phe Xaa Thr Gln
                85

<210> SEQ ID NO 15
<211> LENGTH: 1235
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C or G

<400> SEQUENCE: 15
tctagcgaac cccttcgccc agctgctaga agccaggctg gcctggtgag gcatgagcat      60
gaagatgaac ccaggtgaca aggacaagat gttgctcttc tccccaccct ttgacccctg     120
tcttctaagg catctaggaa ggaaccagtg tccttggtac tgatttactt agattcaacc     180
taagggtcca gccactgact aaggccaagg ccatttttcc atacctggga gggtagagat     240
tcagggttgt gggtaagtgg gcactaaaca tggatttgca agggaaaacg acagggcatc     300
gagctaaatt tgaatttaca tgaaattctg aaatgtactt gtatgaagaa actgttatct     360
gaaacctaac ttaaatgggc atcctgcctt ttgtctggtg agaaatgaaa gtgatctaca     420
ataagtgtca aagcaacaag gcccctctgg atatgtctag gccaggatga ggatactaag     480
tgccttcaaa gcgagaggga ggcaggccaa gaacactgcc ctactgaaag gcaggcttgg     540
ccggctaggg cctccaaggc cctgatccct gaggcaccac agccacaact tgtgtaggcc     600
tggcccaggt cagtgaatag gttctaggca gtggttctca accttcctaa tgctgcaacc     660
cttcaataca gtttctcctg ttgtagtaat ccccaaccat aaaattattt tcattgcgac     720
ttcataactg gacttttgct actgttatga atcataatgt aaatattttt tggagctaga     780
ggtttaccaa gggggttgtg agccataggt tgaaaaccat tgttctagga atagctccag     840
ggtggtttc tgaggccccc gcaaggtggg atctatgggg cagggttgga tcttctccaa     900
gagcccccaa caggatatat atatatatat atatatatat atatatatat atatatatat     960
atatactttg atagcatccc atggaacgac tgtctcctga tactaaaggg agcttggaag    1020
aaaccaaggc tgagagaagt tgtagagtgg aaggtaggc gaaggattg aggtgacaca    1080
gtgatagccc cttcagggtg gggtctaccc nagacagcag ataaaggcct taggatggga    1140

```
gattactctg gctgctcaga ggggaacaca gggacacagc accaataaaa tctctttctt    1200
ttcaaaaaaa aaaaaaaaaa aaaaaaaagc ggncc                              1235
```

<210> SEQ ID NO 16
<211> LENGTH: 36
<212> TYPE: PRT
<213> ORGANISM: Rattus norvegicus

<400> SEQUENCE: 16

```
Met Ser Met Lys Met Asn Pro Gly Asp Lys Asp Lys Met Leu Leu Phe
 1               5                  10                  15

Ser Pro Pro Phe Asp Pro Cys Leu Leu Arg His Leu Gly Arg Asn Gln
             20                  25                  30

Cys Pro Trp Tyr
         35
```

<210> SEQ ID NO 17
<211> LENGTH: 633
<212> TYPE: DNA
<213> ORGANISM: Rattus norvegicus

<400> SEQUENCE: 17

```
tctagcgaac cccttcgatt ttattagctc ttgcttctcc attcctcata atttatgaat      60
tatacagcct tcgcttgaat acgcgtctga agttatgctt tgtgttgttg tgggtttttt     120 ttttttttc ttttctttt ttttggagct ggggaccgaa cccagggcct tgttgctcta       180
ccactgagct aaatccccaa ccctgttgt gtgttttaaa taagtctctt actgtccatt      240
ttgtaattag tgttgttacc ttgtaataat agacatcata caaagtttcc tctttttgt     300 gccagtgctg agaacatgag aaacatttaa tgagtatttg tttgttaaat aatatttata    360
acggctagaa tggcagacac acatggtagc acatgatggt gattttcggg ggccttttgt    420
ttgctcagag ctggtaatct ctgccggttg gtttgctttg cctggtctgg gactaacctc    480 acatttctc actcttgctt tccgagagat tagtcatcct tcctgtccta ctgggctctc     540
gatagcgctc atcagcatac tgcatttcaa tcccagcgaa ggggttcgcc gaaggggttc    600
gctaggccag tgtgatggat atctgcagaa ttc                                 633
```

<210> SEQ ID NO 18
<211> LENGTH: 83
<212> TYPE: PRT
<213> ORGANISM: Rattus norvegicus

<400> SEQUENCE: 18

```
Met Val Ala His Asp Gly Asp Phe Arg Gly Pro Phe Val Cys Ser Glu
 1               5                  10                  15

Leu Val Ile Ser Ala Gly Trp Phe Ala Leu Pro Gly Leu Gly Leu Thr
             20                  25                  30

Ser His Phe Leu Thr Leu Ala Phe Arg Glu Ile Ser His Pro Ser Cys
         35                  40                  45

Pro Thr Gly Leu Ser Ile Ala Leu Ile Ser Ile Leu His Phe Asn Pro
     50                  55                  60

Ser Glu Gly Val Arg Arg Arg Gly Ser Leu Gly Gln Cys Asp Gly Tyr
65                  70                  75                  80

Leu Gln Asn
```

<210> SEQ ID NO 19

```
<211> LENGTH: 607
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 19
tctagcgaac cccttcgcct ttctccaaag ccttcccgtt tcctcttgac agctacgggc      60
tgaggcagcc attcctgcag cagcgctcgg ccggtgaagg gccgaactga cgcctcctag     120
atctgtctcg gctgaattac tctcacccgt ttccattctg tgtgcaccag aaatctgaga     180
tccaggagta tcaacagcaa agatgtctaa tgagccaccc cctccttatc caggagggcc     240
tacagcccca ctactggagg aaaaaagtgg agccccacat accccaggcc gaacctttcc     300
agctgtgatg cagccaccac caggcatgcc actgccctct gttgacattg ccccccccgcc    360 ctatgagccg cctggccatc cagggcctaa gcctggtttw atgcccccca cnttaccaca     420
cattcnaana accttnntnt gtaaaagtta aataanaang gagggattcg anccccctnc     480
aacnggtttc aagccaattt ymtaaccatt ttgttttttt cwtttaaaaa aaaaaaaaa     540 aaaaaaaaa aaaaaaaaa aaaaaaaaa gggaaaaaa aaaaaaaaa aaaaaaaggg         600 gggcccc                                                               607

<210> SEQ ID NO 20
<211> LENGTH: 82
<212> TYPE: PRT
<213> ORGANISM: Rattus norvegicus
<220> FEATURE:
<221> NAME/KEY: UNSURE
<222> LOCATION: (0)...(0)
<223> OTHER INFORMATION: Xaa = any amino acid

<400> SEQUENCE: 20

Met Ser Asn Glu Pro Pro Pro Tyr Pro Gly Gly Pro Thr Ala Pro
 1               5                  10                  15

Leu Leu Glu Glu Lys Ser Gly Ala Pro His Thr Pro Gly Arg Thr Phe
            20                  25                  30

Pro Ala Val Met Gln Pro Pro Gly Met Pro Leu Pro Ser Val Asp
        35                  40                  45

Ile Ala Pro Pro Pro Tyr Glu Pro Pro Gly His Pro Gly Pro Lys Pro
        50                  55                  60

Gly Xaa Met Pro Pro Thr Leu Pro His Ile Xaa Xaa Thr Xaa Xaa Cys
65                  70                  75                  80

Lys Ser

<210> SEQ ID NO 21
<211> LENGTH: 1456
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 21
tctagcgaac ccttcgcaa agtcctaagc cttacatgag aaatttaag acacccttaa        60 tgattgcgga agaaaaatac agacaacaaa gggaagagct tgagaaacag agacgggaga    120
gttcttgcca tagcatcatc aaaacagaaa cccagcaccg cagcttatca gagaaagaga    180
```

-continued

```
aagaaacaga gttacaaaaa gcagctgagg caatgtccac tcccagaaag gattcagact    240
tcactagggc acagcccaac ctggaaccta aaagcaaggc tgtgatcgcc agtgaatgct    300
ctgaaagcca gctctctaca gcttccgcat tgacagtcgc taccgagagg ctccagcatg    360
ttctagccgc ttcagacgat aagcttaccc tgcgacggga aggcacacag aactcaagtg    420
acaccctaca atcgaaaaca gcttgtgaga ttaaccagag tcacaaggaa tgtaggacag    480
agcaaacatt tgagcaacac gtggagaagt tgcccttccc ccaaaccaaa cccatttccc    540
cgagtttcaa agtgaaaact atcaggcttc cagctctaga tcatacgctg actgaaacag    600
atctcagttc tgaacgccgc gtaaagcaat ccgaaattga cgttcaaacc agtactaaag    660
aaatgaataa ggaaattaag aaaaccgaag tgagcacaca gtgtgataat aagcaatctg    720
tggctgaaaa atattttcaa ttacctaaaa cagagaaacg ggtgacggta caaatgccca    780
aagactatgc agcgaaaagt catcaaagca aactccaaac agttcccaag aagcatggag    840
gattggggga gtttgacaga gggaatgtcc tggggaggga aggaaaaaat caggactcct    900
ccatgagcag tacaaaagaa agcagggtaa tagttgaaag aaagcaagaa catctacagg    960
accagagcgt accaaggtta gtccaacaaa agattatcgg tgaaagcctg gactcacggg    1020
ttcagaattt tcagcagaca caaacacaaa cttctaggat tgagcataaa gaactgtccc    1080
aaccttacag tgagaaaaaa tgtcttagag acaaggacaa acaacaaaaa caggtctcct    1140
ctaacactga cgattcaaag caagagataa cacaaaaaca atcttcattt tcctctgtga    1200
gagaatccca gcaggatgga gaaaaatgtg ccataaaaat attggaattc ttgagaaaac    1260
gtgaagaact acagcagatt ttgtctaggg taaaacagtt tgaagcagat tcaaataaaa    1320
gtggccttaa acatttcag acactgttaa atattgctcc ggtgtggctg ataagtgagg    1380
agaaaagaga atatggagtt cgtgttgcca tggagaataa ttagaaaaaa taaaaaaaaa    1440
aaaaaaaagc ggcgnc                                                    1456
```

<210> SEQ ID NO 22
<211> LENGTH: 462
<212> TYPE: PRT
<213> ORGANISM: Rattus norvegicus

<400> SEQUENCE: 22

```
Met Arg Lys Phe Lys Thr Pro Leu Met Ile Ala Glu Glu Lys Tyr Arg
 1               5                  10                  15

Gln Gln Arg Glu Glu Leu Glu Lys Gln Arg Arg Glu Ser Ser Cys His
            20                  25                  30

Ser Ile Ile Lys Thr Glu Thr Gln His Arg Ser Leu Ser Glu Lys Glu
        35                  40                  45

Lys Glu Thr Glu Leu Gln Lys Ala Ala Glu Ala Met Ser Thr Pro Arg
    50                  55                  60

Lys Asp Ser Asp Phe Thr Arg Ala Gln Pro Asn Leu Glu Pro Lys Ser
65                  70                  75                  80

Lys Ala Val Ile Ala Ser Glu Cys Ser Glu Ser Gln Leu Ser Thr Ala
                85                  90                  95

Ser Ala Leu Thr Val Ala Thr Glu Arg Leu Gln His Val Leu Ala Ala
            100                 105                 110

Ser Asp Asp Lys Leu Thr Leu Arg Arg Glu Gly Thr Gln Asn Ser Ser
        115                 120                 125

Asp Thr Leu Gln Ser Lys Thr Ala Cys Glu Ile Asn Gln Ser His Lys
    130                 135                 140
```

```
Glu Cys Arg Thr Glu Gln Thr Phe Glu Gln His Val Glu Lys Leu Pro
145                 150                 155                 160

Phe Pro Gln Thr Lys Pro Ile Ser Pro Ser Phe Lys Val Lys Thr Ile
            165                 170                 175

Arg Leu Pro Ala Leu Asp His Thr Leu Thr Glu Thr Asp Leu Ser Ser
        180                 185                 190

Glu Arg Arg Val Lys Gln Ser Glu Ile Asp Val Gln Thr Ser Thr Lys
    195                 200                 205

Glu Met Asn Lys Glu Ile Lys Lys Thr Glu Val Ser Thr Gln Cys Asp
210                 215                 220

Asn Lys Gln Ser Val Ala Glu Lys Tyr Phe Gln Leu Pro Lys Thr Glu
225                 230                 235                 240

Lys Arg Val Thr Val Gln Met Pro Lys Asp Tyr Ala Ala Lys Ser His
                245                 250                 255

Gln Ser Lys Leu Gln Thr Val Pro Lys Lys His Gly Gly Leu Gly Glu
            260                 265                 270

Phe Asp Arg Gly Asn Val Leu Gly Arg Glu Gly Lys Asn Gln Asp Ser
        275                 280                 285

Ser Met Ser Ser Thr Lys Glu Ser Arg Val Ile Val Glu Arg Lys Gln
290                 295                 300

Glu His Leu Gln Asp Gln Ser Val Pro Arg Leu Val Gln Gln Lys Ile
305                 310                 315                 320

Ile Gly Glu Ser Leu Asp Ser Arg Val Gln Asn Phe Gln Gln Thr Gln
                325                 330                 335

Thr Gln Thr Ser Arg Ile Glu His Lys Glu Leu Ser Gln Pro Tyr Ser
            340                 345                 350

Glu Lys Lys Cys Leu Arg Asp Lys Asp Lys Gln Gln Lys Gln Val Ser
        355                 360                 365

Ser Asn Thr Asp Asp Ser Lys Gln Glu Ile Thr Gln Lys Gln Ser Ser
370                 375                 380

Phe Ser Ser Val Arg Glu Ser Gln Gln Asp Gly Glu Lys Cys Ala Ile
385                 390                 395                 400

Lys Ile Leu Glu Phe Leu Arg Lys Arg Glu Glu Leu Gln Gln Ile Leu
                405                 410                 415

Ser Arg Val Lys Gln Phe Glu Ala Asp Ser Asn Lys Ser Gly Leu Lys
            420                 425                 430

Thr Phe Gln Thr Leu Leu Asn Ile Ala Pro Val Trp Leu Ile Ser Glu
        435                 440                 445

Glu Lys Arg Glu Tyr Gly Val Arg Val Ala Met Glu Asn Asn
    450                 455                 460

<210> SEQ ID NO 23
<211> LENGTH: 2023
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 23
gaattgtaat acgactcact atagggcgaa ttgggcccct agcgaacccc ttcgacaaca      60
tcaaagagga cagatctaac cctagactga ggccggaggc ctggaccaat tacctgaggg     120
atgtccacag agcctttgca ctgctgaaca gtcaccctga tccaaaccaa gtaaatggga     180
ctccaactgc accaagcagt ggcctcccag tcacctctgc tgagctcttg gtgccggcag     240
```

-continued

```
agatggcttc tgcagagtca ggtgaagacc caagtcatgt ggttggggaa acgcctcctt    300
tgaccttgcc agccaacctc caaaccctgc atccgaacag accaacgttg agtccagaga    360
gaaaacttga atggaataac gacattccag aagtgaatcg tttgaattct gaacactgga    420
gaaaaactga ggagcagcca ggacgggggg aggtgcttct ccccgaaggt gacgtcagtg    480
gcaacggtat gacagagctg ttgcccatcg gtcggcacca caaaagcgt ccccacgatg     540 cggggccaga ggaccatgct tttgaagatc aattgcatcc tctcgtccac tctgacagaa    600
ctcccgttca tcgggtgttc gatgtgtccc acttggagca gcctgttcac tccagccacg    660
tggaaggaat gttggccaag atggagggga tggcacaaag gagtgggcac caagtctcga    720
aggcagcgcc tcctctccag tcacttcttg cttagattac atgttgccta acaatgtttc    780
tttccatgtt ttgattagta aactaactcg tggtggcaat catgactccc aaccttctga    840 gctccccgg gtacgcttgc accgtagacg ctcatgtgcg caccgtgcgg gtgatgctca     900
cacacagact cattgtaatt caccgtttta ccgagaaggg gggggggcg aatttctgt      960 gttgatgctt tgttttggt actaaaacag nattatcttt tgaatattgt agggacatga    1020
gtatataaag tctatccagt caaaatggct agaattgngc ctttgtaagt tttaaaaact   1080
tgatgcccac atgagtctgt gagcacatnt ttcccgcctg cctaacggag ttggaatttg   1140
tttctaacca ctgtaattct tcaacatcat cacctttggt tcagtgattt tgcactttga   1200
gtttggatac tgtgtctgct tggttggtag tgttagtatt tttcttttaa acaggcttat   1260
cagagttgca cactttgtcc taggcagggc aaaggaatag acgcccagca aggacacaca   1320
gtataggtaa catactgctt atcgtacgct tttcccacaa agcattgcat gtgtttttac   1380
ctcgacgtgc taaagttgat tagcagaaag gcatgactca caattttggt ggtaaaaaat   1440
aaaccctgag ggagcaagca ataactaaaa caagattgag ctgctctctc tgtgcttact   1500
aaatagatgc tcgccctgct aatgcttgcc ctcttgaaag aagaaacagg atgcacactg   1560
ctttatttca atcttcctct ttttttcttg gtttcaccag tgagcgtaag cattggaaaa   1620
atatgtgtag tcttatcttt ctataagacg atttaataa actaaaatca caaatgctgt    1680
aaagtttgtg cgcaccagaa tggaggctaa cttcataaac attgtgctgt gcgaatattc   1740
ctaaaatgat ccccaagctg tggttttcta gaagacatag ttcagaaccg cttttgaaaa   1800
atctgtcctc gtgagctcac tcagtttctg tcggactttt agagacagtg gaaggattac   1860
ctcattgaga cgtttccgtg tcctcttcaa ctccacaggg tcttgacggt ggctttgttt   1920
ttccttctag actattcaaa catgtagata agttatattt ttctttaagt gtttaaagta   1980 aacactttc aaaaaaaaa aaaaaaaaa aaaaagcggc cgc                        2023
```

<210> SEQ ID NO 24
<211> LENGTH: 170
<212> TYPE: PRT
<213> ORGANISM: Rattus norvegicus

<400> SEQUENCE: 24

Met Ala Ser Ala Glu Ser Gly Glu Asp Pro Ser His Val Val Gly Glu
1               5                   10                  15

Thr Pro Pro Leu Thr Leu Pro Ala Asn Leu Gln Thr Leu His Pro Asn
            20                  25                  30

Arg Pro Thr Leu Ser Pro Glu Arg Lys Leu Glu Trp Asn Asn Asp Ile
        35                  40                  45

Pro Glu Val Asn Arg Leu Asn Ser Glu His Trp Arg Lys Thr Glu Glu

|   |   |   | 50 |   |   |   | 55 |   |   |   | 60 |   |   |
Gln Pro Gly Arg Gly Glu Val Leu Leu Pro Gly Asp Val Ser Gly
 65                  70                  75                  80

Asn Gly Met Thr Glu Leu Leu Pro Ile Gly Arg His Gln Gln Lys Arg
                 85                  90                  95

Pro His Asp Ala Gly Pro Glu Asp His Ala Phe Glu Asp Gln Leu His
                100                 105                 110

Pro Leu Val His Ser Asp Arg Thr Pro Val His Arg Val Phe Asp Val
            115                 120                 125

Ser His Leu Glu Gln Pro Val His Ser Ser His Val Glu Gly Met Leu
        130                 135                 140

Ala Lys Met Glu Gly Met Ala Gln Arg Ser Gly His Gln Val Ser Lys
145                 150                 155                 160

Ala Ala Pro Pro Leu Gln Ser Leu Leu Ala
                165                 170

<210> SEQ ID NO 25
<211> LENGTH: 1802
<212> TYPE: DNA
<213> ORGANISM: Rattus norvegicus

<400> SEQUENCE: 25
tctagcgaac cccttcgggg gttttcatca tggagctgtc gcggcggatt tgtctcgtcc      60
gactgtggct gttgctactg tcattcttac tgggcttcag cgcgggatct gccctcaact     120
ggcgggaaca agaaggcaag gaagtatggg attacgtgac tgttcgagag gatgcacgca     180
tgttctggtg gctctactat gccaccaacc cttgcaagaa cttctcagag ctgcctctgg     240
tcatgtggct tcagggtggt ccaggtggtt ctagcactgg atttggaaac tttgaggaaa     300
tcggccctct tgacacccga ctcaagccac ggaacactac ctggctgcag tgggccagtc     360
tcctgttcgt ggacaatcct gtgggcacgg gcttcagtta cgtgaacacg acagatgcct     420
acgcaaagga cctggacacg gtggcttccg acatgatggt cctcctgaaa tccttctttg     480
attgtcataa agaattccag acggttccgt tctacatttt ctcagaatcc tacgaggaa      540
agatggctgc tggcatcagt ttagaacttc acaaggctat tcagcaaggg accatcaagt     600
gcaacttctc tggggttgct ttgggtgact cctggatctc ccctgtggat tcagtgctgt     660
cctggggacc ttacctgtac agcgtgtctc tccttgataa taaaggcttg gctgaggtgt     720
ccgacattgc ggagcaagtc ctcaatgaaa acaagggct tctacaagga agccactcag      780
ctgtggggga agcagaaat gatcattgaa aagaacaccg acggggtaaa cttctataac      840
atcttaacta aaagcacccc cgacacctct atggagtcga gcctcgagtt cttccggagc     900
cccttagttc gtctctgtca gcgccacgtg agacacctac aaggagacgc cttaagtcag     960
ctcatgaacg gtcccatcaa aaagaagctc aaaattatcc ctgacgacgt ctcctgggga    1020
gcccagtcgt cctccgtctt cataagcatg gaagaggact tcatgaagcc tgtcatcgac    1080
atcgtggata cgttgctgga actcggggtc aatgtgactg tgtacaatgg cagctggat     1140
ctcattgtgg acaccatagg tcaggagtcc tgggttcaga gctgaagtg gccacagctg     1200
tccagattca atcagctaaa atggaaggcc ctgtacaccg atcctaagtc ttcagaaaca    1260
tctgcatttg tcaagtccta tgagaaccta gcgttctact ggatcctaaa ggcgggtcac    1320
atggttcctg ctgaccaagg ggacatggct ctgaagatga tgaggctggt tactcagcag    1380
gagtagctga gctgagctgg ccctggaggc cctggaggcc ctggagtagg gcccaggatg    1440

```
caggtgctaa tgtctatccc cggcgctctt cttcccgact ctaccatggg atgtaactcc    1500
aggagcccct gccatctccc gtaccaaaag actgtggctt ccgtgtctac tcagaaatca    1560
gttctacttc gtaaacagtg tttaaaacca gactcattta atcagagtga aggattgcag    1620
tccattggct tcttagcaca gaagcagctg ataacacaag taaaccccag cccttgagag    1680
gtagaagcaa gaggatcaga ggttcaagcg catcctcggc tccatcacaa gttcaaaagc    1740
cgcctgcacc aaatgggagt ccttgtctca aaaaaaaaa aaaaaaaaaa aaaagcggcc    1800
gc                                                                   1802
```

<210> SEQ ID NO 26
<211> LENGTH: 259
<212> TYPE: PRT
<213> ORGANISM: Rattus norvegicus

<400> SEQUENCE: 26

```
Met Glu Leu Ser Arg Arg Ile Cys Leu Val Arg Leu Trp Leu Leu
 1               5                  10                  15

Leu Ser Phe Leu Leu Gly Phe Ser Ala Gly Ser Ala Leu Asn Trp Arg
            20                  25                  30

Glu Gln Glu Gly Lys Glu Val Trp Asp Tyr Val Thr Val Arg Glu Asp
        35                  40                  45

Ala Arg Met Phe Trp Trp Leu Tyr Tyr Ala Thr Asn Pro Cys Lys Asn
    50                  55                  60

Phe Ser Glu Leu Pro Leu Val Met Trp Leu Gln Gly Pro Gly Gly
65                  70                  75                  80

Ser Ser Thr Gly Phe Gly Asn Phe Glu Glu Ile Gly Pro Leu Asp Thr
                85                  90                  95

Arg Leu Lys Pro Arg Asn Thr Thr Trp Leu Gln Trp Ala Ser Leu Leu
            100                 105                 110

Phe Val Asp Asn Pro Val Gly Thr Gly Phe Ser Tyr Val Asn Thr Thr
        115                 120                 125

Asp Ala Tyr Ala Lys Asp Leu Asp Thr Val Ala Ser Asp Met Met Val
    130                 135                 140

Leu Leu Lys Ser Phe Phe Asp Cys His Lys Glu Phe Gln Thr Val Pro
145                 150                 155                 160

Phe Tyr Ile Phe Ser Glu Ser Tyr Gly Gly Lys Met Ala Ala Gly Ile
                165                 170                 175

Ser Leu Glu Leu His Lys Ala Ile Gln Gln Gly Thr Ile Lys Cys Asn
            180                 185                 190

Phe Ser Gly Val Ala Leu Gly Asp Ser Trp Ile Ser Pro Val Asp Ser
        195                 200                 205

Val Leu Ser Trp Gly Pro Tyr Leu Tyr Ser Val Ser Leu Leu Asp Asn
    210                 215                 220

Lys Gly Leu Ala Glu Val Ser Asp Ile Ala Glu Gln Val Leu Asn Glu
225                 230                 235                 240

Lys Gln Gly Leu Leu Gln Gly Ser His Ser Ala Val Gly Glu Ser Arg
                245                 250                 255

Asn Asp His
```

<210> SEQ ID NO 27
<211> LENGTH: 630
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 27

| | | | | | |
|---|---|---|---|---|---|
| tctagcgaac | cccttcgcga | aggggttcgc | taggttgcgt | ttgtggagaa | aaatctgttc | 60 |
| tacctcaggg | ctgtgagaac | ggcactcctg | atgtctgaga | agagaaaaca | agattggctg | 120 |
| aaggatcctc | cgttccttca | gagacctggg | tggagagcat | tagggacacg | aagaacagag | 180 |
| tagcggaaga | agagttctta | agtaataagt | ttacctcctg | actggctcac | atcactgcct | 240 |
| tactctgtag | aaagcaggtc | atctcatgga | tttcccctc | ccaccccccc | agctggatca | 300 |
| ttttttgact | cagggaaaat | aattaaatta | ttgtccaact | gttagtgttg | atcggtaaca | 360 |
| gcagaaaggc | agaaagttcc | tgataatctc | aatattatct | tttcaaaagt | attttcctgg | 420 |
| aatgttgttt | gctttggcat | tacaaagttc | tgtactctta | aaaatatttt | gacttgctgg | 480 |
| gcatggaggt | cacaccttta | atccagaggc | aggcatggat | ccacaggagt | tcaaggccgc | 540 |
| ctggctacaa | agcgagttca | agggcagcca | gggctacaca | gagagacctt | gtctcntnac | 600 |
| cnntnannaa | aaaacnaaaa | agccggccgc | | | | 630 |

<210> SEQ ID NO 28
<211> LENGTH: 30
<212> TYPE: PRT
<213> ORGANISM: Rattus norvegicus

<400> SEQUENCE: 28

Met Ser Glu Lys Glu Lys Gln Asp Trp Leu Lys Asp Pro Pro Phe Leu
1               5                   10                  15
Gln Arg Pro Gly Trp Arg Ala Leu Gly Thr Arg Arg Thr Glu
            20                  25                  30

<210> SEQ ID NO 29
<211> LENGTH: 445
<212> TYPE: DNA
<213> ORGANISM: Rattus norvegicus

<400> SEQUENCE: 29

| | | | | | |
|---|---|---|---|---|---|
| tctagcgaac | cccttcggta | tagtctttag | gtagtggctt | agtccctgga | agctctggtt | 60 |
| gcttggcatt | tcaacgtgct | tcttaaataa | ctgttttatt | agtcagtaca | agatgctttg | 120 |
| tatatcagat | ctgaaatatc | ttaaaattat | cacttgcatt | gtaaattact | attcctttcg | 180 |
| cagaaataat | gaatgcttca | agaaaaaaaa | aagctgtttg | tattgggttt | aaaacgtttc | 240 |
| caaacaccaa | ttattcttta | cttaagtcat | ccgatctagt | tattaaatta | ttattactgc | 300 |
| cttcacacta | tcaaagatgg | taaatatctg | atagaatcat | attcaaaata | cttctgtttc | 360 |
| acatttcttg | agaaagtact | gactgtctga | gttctttctc | aagaaatgtg | aaacagaagt | 420 |
| attttgaatc | gaagggggttc | gctag | | | | 445 |

<210> SEQ ID NO 30
<211> LENGTH: 39
<212> TYPE: PRT
<213> ORGANISM: Rattus norvegicus

<400> SEQUENCE: 30

Met Leu Cys Ile Ser Asp Leu Lys Tyr Leu Lys Ile Ile Thr Cys Ile
1               5                   10                  15
Val Asn Tyr Tyr Ser Phe Arg Arg Asn Asn Glu Cys Phe Lys Lys Lys
            20                  25                  30

Lys Ser Cys Leu Tyr Trp Val
         35

<210> SEQ ID NO 31
<211> LENGTH: 273
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 31
tctagcgaac cccttcggaa gaactgtata tttgtgcctt gttctgcaag ttaaaaagct      60
ggtccagaca gtgtcataga attaactttt catttctgta ttaattttag gactgcaaaa     120
atcccaaagc tgtatactta gattggattc aataaaaagt ttaagtttac tnaanaaaaa     180
aaaaaaaaaa aaaaaaaaaa aaaaaaaaaa aaaaaaaaaa aaaanaaaaa aaaaaaaagg     240
aaaaaaaaaa ncggncnnaa aaaaggnggc cgc                                  273

<210> SEQ ID NO 32
<211> LENGTH: 2077
<212> TYPE: DNA
<213> ORGANISM: Rattus norvegicus

<400> SEQUENCE: 32
tctagcgaac cccttcgggg gaacccaagc ggcttcgccc aggcattcgc gcgggcgccc      60
gcggtctggg tcccacctcc tctgctttcg caccccttgaa gttttggagc accaggaaaa    120
gagggcaagg aaggagaggg gaagcgaaag catatcctaa acatttact taaaggagga     180 aagaaaaggg gtcgcagaaa tggctgrggc aattatagaa aacatgagca ccaagaagct    240
ctgcattgtt ggagggattc ttctggtttt ccaaatcgtt gcctttctgg tgggaggctt    300
gatcgctcca gcacccacaa cggcagtgtc ctacgtggca gcaaaatgtg tggatgtccg    360
gaagaaccac cataaaacaa gatggctgat gccctgggga ccaaacaagt gtaacaagat    420
caatgacttc gaagaagcaa ttccaaggga aattgaagcg aatgacattg tgttttctgt    480
acacattccc ctcccttcta tggagatgag cccatggttc cagtttatgc tgtttatcct    540
gcagatagac attgctttca agctaaacaa ccaaatcaga gaaatgcag aagtttccat     600 ggatgtttcc ctgggttacc gtgatgatat gttttctgag tggactgaaa tggcgcacga    660
aagagtacca cgtaaaactca gatgcacttt cacatccccc aagacccag agcatgaagg    720 tcgtcattat gaatgtgatg tccttccttt catggaaatt gggtcagtgg ctcataagta    780
ttaccttcta aatatccggc tacctgtaaa tgagaagaag aaaatcaatg ttggaattgg    840
ggaaataaag gacattcggt tggtgggaat ccaccaaaat ggaggtttca ctaaggtatg    900
gtttgctatg aagaccttcc tcacacccag catcttcatc attatggtgt ggtattggag    960
aaggatcacc atgatgtccc gacctccagt gcttctggaa aaagtcatct tgcccttgg   1020 gatttccatg accttttatca atatccctgt ggaatggttt tccattggat ttgattggac   1080
ctggatgctg ttatttggtg acatacgaca gggcatcttc tatgcaatgc ttcttttcctt   1140 ctggatcatc ttctgtggcg agcacatgat ggatcaacat gagcggaatc acattgcagg   1200
gtattggaag caagttggac caattgctgt tggctctttc tgcctcttca tatttgacat   1260
gtgtgagaga ggagtgcaac tcacaaatcc tttctacagt atctggacta cagatgttgg   1320
aacagaactg gctatggctt tcatcattgt ggcaggtatc tgcctctgcc tctacttcct   1380

```
gtttctgtgt tcatggtat ttcaagtatt cagaaacatc agtgggaaac agtctagcct    1440
cccagccatg agcaaagtcc ggaggctgca ctatgagggt ctgattttca ggttcaagtt    1500
cctcatgctg atcaccttgg cttgtgctgc catgactgtt atcttcttca ttgttagtca    1560
ggtgacagaa ggccattgga atggggtgg ggtcacagtt caagtgagca gtgctttctt    1620
cactggaatc tatgggatgt ggaacctgta tgtctttgct ttgatgttct tgtatgcacc    1680
atcccataag aactatgggg aagaccagtc taatggtgac ctgggtgtcc acagcgggga    1740
agaactgcag ctcactacca caatcaccca tgtagatgga ccgactgaga tctacaagtt    1800
gacccgtaaa gaagcacagg agtagtaggc atggcattc atcctcaggg caggtgatga    1860
agccaagttg ctggtgcatg ctgaccctca tgaatatgct ttcgtatctt tatgtcccag    1920
gatcattttt atcctgtcac gtttacaaga acatttctga catgcatacg tttactttta    1980
ccatgtatta gttactttta tatttctgtg ataaacacc atgagaaata caattttacag   2040 aagcaaaaaa aaaaaaaaa aaaaaaaaag cggccgc                              2077
```

<210> SEQ ID NO 33
<211> LENGTH: 541
<212> TYPE: PRT
<213> ORGANISM: Rattus norvegicus

<400> SEQUENCE: 33

```
Met Ala Gly Ala Ile Ile Glu Asn Met Ser Thr Lys Lys Leu Cys Ile
1               5                   10                  15

Val Gly Gly Ile Leu Leu Val Phe Gln Ile Val Ala Phe Leu Val Gly
            20                  25                  30

Gly Leu Ile Ala Pro Ala Pro Thr Thr Ala Val Ser Tyr Val Ala Ala
        35                  40                  45

Lys Cys Val Asp Val Arg Lys Asn His His Lys Thr Arg Trp Leu Met
    50                  55                  60

Pro Trp Gly Pro Asn Lys Cys Asn Lys Ile Asn Asp Phe Glu Glu Ala
65                  70                  75                  80

Ile Pro Arg Glu Ile Glu Ala Asn Asp Ile Val Phe Ser Val His Ile
                85                  90                  95

Pro Leu Pro Ser Met Glu Met Ser Pro Trp Phe Gln Phe Met Leu Phe
            100                 105                 110

Ile Leu Gln Ile Asp Ile Ala Phe Lys Leu Asn Asn Gln Ile Arg Glu
        115                 120                 125

Asn Ala Glu Val Ser Met Asp Val Ser Leu Gly Tyr Arg Asp Asp Met
    130                 135                 140

Phe Ser Glu Trp Thr Glu Met Ala His Glu Arg Val Pro Arg Lys Leu
145                 150                 155                 160

Arg Cys Thr Phe Thr Ser Pro Lys Thr Pro Glu His Glu Gly Arg His
                165                 170                 175

Tyr Glu Cys Asp Val Leu Pro Phe Met Glu Ile Gly Ser Val Ala His
            180                 185                 190

Lys Tyr Tyr Leu Leu Asn Ile Arg Leu Pro Val Asn Glu Lys Lys Lys
        195                 200                 205

Ile Asn Val Gly Ile Gly Glu Ile Lys Asp Ile Arg Leu Val Gly Ile
    210                 215                 220

His Gln Asn Gly Gly Phe Thr Lys Val Trp Phe Ala Met Lys Thr Phe
225                 230                 235                 240

Leu Thr Pro Ser Ile Phe Ile Ile Met Val Trp Tyr Trp Arg Arg Ile
                245                 250                 255
```

Thr Met Met Ser Arg Pro Val Leu Leu Glu Lys Val Ile Phe Ala
        260                 265                 270

Leu Gly Ile Ser Met Thr Phe Ile Asn Ile Pro Val Glu Trp Phe Ser
            275                 280                 285

Ile Gly Phe Asp Trp Thr Trp Met Leu Leu Phe Gly Asp Ile Arg Gln
        290                 295                 300

Gly Ile Phe Tyr Ala Met Leu Leu Ser Phe Trp Ile Ile Phe Cys Gly
305                 310                 315                 320

Glu His Met Met Asp Gln His Glu Arg Asn His Ile Ala Gly Tyr Trp
            325                 330                 335

Lys Gln Val Gly Pro Ile Ala Val Gly Ser Phe Cys Leu Phe Ile Phe
        340                 345                 350

Asp Met Cys Glu Arg Gly Val Gln Leu Thr Asn Pro Phe Tyr Ser Ile
        355                 360                 365

Trp Thr Thr Asp Val Gly Thr Glu Leu Ala Met Ala Phe Ile Ile Val
    370                 375                 380

Ala Gly Ile Cys Leu Cys Leu Tyr Phe Leu Phe Leu Cys Phe Met Val
385                 390                 395                 400

Phe Gln Val Phe Arg Asn Ile Ser Gly Lys Gln Ser Ser Leu Pro Ala
            405                 410                 415

Met Ser Lys Val Arg Arg Leu His Tyr Glu Gly Leu Ile Phe Arg Phe
        420                 425                 430

Lys Phe Leu Met Leu Ile Thr Leu Ala Cys Ala Ala Met Thr Val Ile
        435                 440                 445

Phe Phe Ile Val Ser Gln Val Thr Glu Gly His Trp Lys Trp Gly Gly
    450                 455                 460

Val Thr Val Gln Val Ser Ser Ala Phe Phe Thr Gly Ile Tyr Gly Met
465                 470                 475                 480

Trp Asn Leu Tyr Val Phe Ala Leu Met Phe Leu Tyr Ala Pro Ser His
            485                 490                 495

Lys Asn Tyr Gly Glu Asp Gln Ser Asn Gly Asp Leu Gly Val His Ser
        500                 505                 510

Gly Glu Glu Leu Gln Leu Thr Thr Thr Ile Thr His Val Asp Gly Pro
    515                 520                 525

Thr Glu Ile Tyr Lys Leu Thr Arg Lys Glu Ala Gln Glu
    530                 535                 540

<210> SEQ ID NO 34
<211> LENGTH: 755
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 34
tctaacgaac cccttcggag cgatggaatg agaaaggccc agaatgtgtt aagtctgtgc    60 agggaagtg tcctgagggg agggtctttg ggagggtcga aggccaggat ggcaaagtga   120
aggtagctga ggttgcagtc ttgggtgccc actgctgtgc atctgtctgg ttatctaccc   180
ctactttggg ctgacaactg cagggttggg tgtaggctgt ctcactgcat gccgggaagc   240
tggagaagct ccacgggaac attgagggcc atgctttga dacactgcag agcatccttg    300
gtctctgtaa ccacgtcacc taaccctgac aattccagac ccttcttcca ttgtcctttgt   360

| | | | | |
|---|---|---|---|---|
| gaaccatttg | ggcttatctt | tccctcttag | tcgcaagggt | caaaccaagg | gtcagtcaag | 420 |
| tagatgactg | tcaccttggg | cctccccaga | ctctgctgcc | ggggttggga | gaccaaagta | 480 |
| gaaactgcca | ctacaaggcc | ccaggatgag | gtctctgttc | tgtggacctg | ctccccagat | 540 |
| acaggcctca | gacccatagg | acgtggccgg | tgctcaggga | cacccaatcc | ccggcctcac | 600 |
| tccatcgagt | actgacttct | ttctctagtg | ccttgggggt | ctccatcctt | cagttatggt | 660 |
| atgaagaatc | tatgcaaact | gtataagctt | ctgctcacca | ataaacgctt | tatttaaagc | 720 |
| ttannnnnnn | nnnannnnnn | nnnnnaagcg | gncgc | | | 755 |

<210> SEQ ID NO 35
<211> LENGTH: 30
<212> TYPE: PRT
<213> ORGANISM: Rattus norvegicus

<400> SEQUENCE: 35

Met Arg Lys Ala Gln Asn Val Leu Ser Leu Cys Arg Gly Ser Val Leu
 1               5                  10                  15
Arg Gly Gly Ser Leu Gly Gly Ser Lys Ala Arg Met Ala Lys
            20                  25                  30

<210> SEQ ID NO 36
<211> LENGTH: 1310
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 36

| | | | | | | |
|---|---|---|---|---|---|---|
| tctagcgaac | cccttcgcag | aaacccaaag | ttacagacca | gaccctaccc | aacatccagt | 60 |
| cagcaatcca | gctggagaaa | cgcttgagat | gacaagggac | tttcagaagc | aagccttgat | 120 |
| aagacaggaa | aagcagaatt | ctaataaaga | tatgaggaaa | aatgacatgg | gccttcaacc | 180 |
| tctgcctgta | gggaaggacg | cacacagtgc | accaggagtg | acagtctctg | ggaaaaacca | 240 |
| caaaagaact | caggcacctg | acaagaaaca | gagaattgat | gtttgtctag | aaagccagga | 300 |
| ctttctaatg | aagacaaata | cttccaagga | gttaaaaatg | gcaatggaga | ggtcctttaa | 360 |
| tccagtcaac | ctttccctga | ctgtggtgta | aagaaaatg | aggacgccct | tctctccatc | 420 |
| ttccctcct | tcttctcctt | ccaattgcgt | catctgaaat | tgaatttcct | ctcctcctcc | 480 |
| accacctata | atgctgtgcc | tgaaaaaaat | gagtttcctc | cctcatcacc | cacagagaag | 540 |
| tcaagggctg | aacttgagag | cctcccaacc | ctgcctcttc | ctccaccacc | aggagatgag | 600 |
| aaatctgatc | aggaatgtct | accaacatcc | ctacctcctc | ccctcccac | agctccatcc | 660 |
| caaccagcac | atcttctttc | ctcctctgtt | ctagaacatc | acagtgaagc | atttttacaa | 720 |
| cagtattccc | gaaaagaaac | cttggactct | catcggcttc | actcacaggc | taaaatccta | 780 |
| acaggaaaat | caccaccccc | aacactcccc | aaacccaaac | ttcccgagag | aatcaaagct | 840 |
| aagatgagcc | aggattcacc | aagcggtgaa | ttggaaagat | ctctgtcaga | tgtgaaaatt | 900 |
| aaaactaccc | tctcaaagga | tcagaaaagt | tcgctggtgg | cagaaagccg | tgagcacaca | 960 |
| gaggccaagc | aagaagtatt | ccgaaaaagc | cttggaagaa | aacagctgtc | cattagctct | 1020 |
| gcaaactccc | tctctcagac | agttccagaa | atcccagcac | ccaaggaaaa | acagacagca | 1080 |
| cccccttgtta | aatctcactc | attcccatca | ggttcagaac | aacaaagtcc | taagccttac | 1140 |
| atgagaaaat | ttaagacacc | cttaatgatt | gcggaagaaa | aatacagaca | acaaagggaa | 1200 |

```
gagcttgaga acagagacg ggagagttct tgccatagca tcatcaaaac agaaacccag    1260
caccgcagct tatcaaannt taaaaaaaaa aaaaannnag cggncgcccg              1310
```

<210> SEQ ID NO 37
<211> LENGTH: 100
<212> TYPE: PRT
<213> ORGANISM: Rattus norvegicus

<400> SEQUENCE: 37

```
Met Thr Arg Asp Phe Gln Lys Gln Ala Leu Ile Arg Gln Glu Lys Gln
  1               5                  10                  15

Asn Ser Asn Lys Asp Met Arg Lys Asn Asp Met Gly Leu Gln Pro Leu
             20                  25                  30

Pro Val Gly Lys Asp Ala His Ser Ala Pro Gly Val Thr Val Ser Gly
         35                  40                  45

Lys Asn His Lys Arg Thr Gln Ala Pro Asp Lys Gln Arg Ile Asp
     50                  55                  60

Val Cys Leu Glu Ser Gln Asp Phe Leu Met Lys Thr Asn Thr Ser Lys
 65                  70                  75                  80

Glu Leu Lys Met Ala Met Glu Arg Ser Phe Asn Pro Val Asn Leu Ser
                 85                  90                  95

Leu Thr Val Val
            100
```

<210> SEQ ID NO 38
<211> LENGTH: 774
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 38

```
tctagcgaac cccttcgctt tttttttttt tttttttttt ttttccccccc tttcctattt    60 attaatgggg ggaagtatgt ttatgtggga tttatccact tcttttagat tctcctacct   120
gttgatctgt aattattcct agtagtctct tagagttctt agaagcatgc tgttaccgct   180
aatatttcct tttggtttgg atcttactta aacatattgt ttccttactc tcttttttcat   240 cccagcttgt ctaactgaaa ggccagaccc aacttgatct atcccttaa aacttcatgt    300 cttggcctgt tgatttctct gctccaggtg tcaccgaagg ggttcgccta gcgaacccct   360
tcgtaacagc caaggttttt gagacagagg tttcaacagc attcctggag gagacacaaa   420
ggacagatga gtcacatgaa ggatgggagg agggaaggtg gctgttgata ggtattttga   480
gacactctat ttgagtccta cacaacactc ccccctcccc ccaaaccatt tttatgtcta   540
ttgacctttc ctctagtcat acagggaaat tcacagttac ctacaaagaa ccactaattg   600
taacaagtca agaggaaact tattttttgat aatgactcat tgaagatgtt ttgaaaattt   660
aaaaataagc tctgttagca gaagtctgtn ngaaaagcan gaaggaaatg tttgtttatt   720
anataaataa aaggcggcga ggacaacaaa aaaaaaaaaa aaaaaagcgg ccgc        774
```

<210> SEQ ID NO 39
<211> LENGTH: 65
<212> TYPE: PRT
<213> ORGANISM: Rattus norvegicus

<400> SEQUENCE: 39

```
Met Ser Trp Pro Val Asp Phe Ser Ala Pro Gly Val Thr Glu Gly Val
 1               5                  10                  15

Arg Leu Ala Asn Pro Phe Val Thr Ala Lys Val Phe Glu Thr Glu Val
             20                  25                  30

Ser Thr Ala Phe Leu Glu Glu Thr Gln Arg Thr Asp Glu Ser His Glu
             35                  40                  45

Gly Trp Glu Gly Arg Trp Leu Leu Ile Gly Ile Leu Arg His Ser
         50                  55                  60

Ile
65

<210> SEQ ID NO 40
<211> LENGTH: 1259
<212> TYPE: DNA
<213> ORGANISM: Rattus norvegicus

<400> SEQUENCE: 40
tctagcgaac cccttcgcga aggggttcgc cgaaggggtt cgcttcagga gttaatgtag     60
acttgactta agcatcctga tttaaccaag aatggtggca cacaacttta acccccatgc    120
tggggaagca gaggcacact taatctgtgt gagtcccagg ccatccaggg ataccgtagt    180
agtgagaccc tgtctcacaa acaaagaat gggaatttag gctggtggg gctcagcatg     240
caactgtgcc tgttacctag tctggcctga gttcaattcc caagactcaa tgtatgagga    300
gagaaacgat ttctgaactc attcattgat ctccaaatgt gtggtatagg tgcccttccc    360
ttaaataaaa caaacaaaca aaaacaaca aaacaacaa accccaata aatgtatatt       420
taattttaaa agactgtact tgggcatggt acttcacatc tacagttacg acattctaga    480
ggctcaggcc tgggaattgc tatgaatttg aggccagtct gggttagagt gacttctcat    540
ctaggcagga ctacgtaata agtctttgcc caaaaataaa cagcaaccca ataagagca    600
acaagaattc tccctccaaa tagtaacctg gcctggaga gacagcttag caactgagtg     660
cttgccgagc catcgaggac tggagtctgg attccagcac ccgtgtgaca gacaagctgg    720
gcgttcactc atgctgatga accccaaggc tgaggagaca ctgactcttc tctggccctg    780
ttcatgctgt ccacaggtgc ccaagtagca gttaagtaga ctgtcagaca acatggctgg    840
cttttaagc aagaacagta actgaagaaa tacacttttg aagtactgtt aattttgctt     900
aaaacttggt agggagctgg aggatggctc agtggttaag agcactgact gctcttccag    960
aggtcctgag ttcaattccc agcaaccaca tggtggctca caaccatctg taatgagctc   1020
tgatgccctc ttttttggtgt gtctgaagac agcgacagtg tactcatata aaataaaata   1080
aatcttttt ttttttaaaa gaatttgtc agagatatgg caggaagggt atatttttac    1140
ctatttacct ggtgggctaa tcctggtatt ttttttcaaaa ttaagatact ataggagc    1200
cgcgaagggg tcgctaggcc agtgtgatgg atatctgcag aattcggtta gccgaattc    1259

<210> SEQ ID NO 41
<211> LENGTH: 42
<212> TYPE: PRT
<213> ORGANISM: Rattus norvegicus

<400> SEQUENCE: 41

Met Val Ala His Asn Phe Asn Pro His Ala Gly Glu Ala Glu Ala His
 1               5                  10                  15

Leu Ile Cys Val Ser Pro Arg Pro Ser Arg Asp Thr Val Val Val Arg
             20                  25                  30
```

Pro Cys Leu Thr Lys Gln Arg Met Gly Ile
        35                  40

<210> SEQ ID NO 42
<211> LENGTH: 777
<212> TYPE: DNA
<213> ORGANISM: Rattus norvegicus

<400> SEQUENCE: 42
tctagcgaac cccttcgtct cctcttaaac atcttaagac aagctgttat catctacact    60
gctcttagta ctgttctttt ctaagattct tctaatatga cacattaaga ctttcttaaa   120
atgtacaact gctacgctga tctaaacatt caaagtgcac acatttcgct atgaagccac   180
gtgaccagag tcctggggac taatttctgt cttagtcaga ttcctattgc tatatgaaga   240
aataccatga tagtgtcaac ttttataaag aaaaagtatt cctttgggaa tagtttaaag   300
gatcagaggg ttagtgcatt atcatcacag caggaagcgt ggcagtggga gcccagattt   360
ctatatccag atttttcatga agcatgacga gagctcctgg gcctggcgcg agcttctgaa   420
acctgaaagt gacatatttc ttccaataag gccacaacta ctgctataag gccacatctc   480
ctaactgtgt cactatctat gagcctgtac agtctatttc ttttacacca ctgcatcatc   540
taagagctga tacccgttaa gttagtcatg aaaatattca acttctaggg ttctgttttc   600
ttctctataa aatattgaaa atgataatta atgtatactt tacagaactg tatttgaagt   660
acaacttgat ggacataaat caccacagtt gggtcaaaat tgtatatata tatatatata   720
tatatatata tatatata tatcaaaaaa aaaaaaaaa aaaaaaaaag cggccgc         777

<210> SEQ ID NO 43
<211> LENGTH: 46
<212> TYPE: PRT
<213> ORGANISM: Rattus norvegicus

<400> SEQUENCE: 43

Met Ile Val Ser Thr Phe Ile Lys Lys Tyr Ser Phe Gly Asn Ser
 1               5                  10                  15

Leu Lys Asp Gln Arg Val Ser Ala Leu Ser Ser Gln Gln Glu Ala Trp
                20                  25                  30

Gln Trp Glu Pro Arg Phe Leu Tyr Pro Asp Phe His Glu Ala
        35                  40                  45

<210> SEQ ID NO 44
<211> LENGTH: 1378
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 44
tctagcgaac cccttcgtac atttcaccct agaaataaat agaccttcta gctctgacag    60
aaagtagtgc ttgcctagga ggagctgggc tggccagttc ctccttcttg cacacttagc   120
ctgtttgctg aaggcttgtt tcaatggaaa actgaaatgg acccactaat gtctcgattc   180
ttctctcctt cactaagtct gtgaagtcat cagcgttttg tcttttgtgt gtgaataccg   240
aggagaattt cctcacccag tgccttcagg agccatgatg gctgcctcag aataagcaca   300
gatacacttg agcaactggt gcagaaaacc cgacttctaa attattaagg aacaggataa   360

```
ttgcttgtta caataattag aataatgtaa ttaggataat tgcttttaaa aaatcttccc    420
acctttcccc ccccaaatat taataattcc aactaaatcc tctggggccc ttccagtttc    480
cacaacggaa agagcctaac gtattctaaa gactgggcat attttttttt tccagattag    540
tgagtgttca tgagctatta agaggccaag tgttttttca agatggtgtc atttcattct    600
aacatatcta acatgcaaag gacttaaaaa aataatttgc aaaataatct gtttcaagtc    660
tatgaggaag ctgaagagcc tactccggag gaaactccag aagagcctcc tagcatagag    720
gaagaagaga tagtggagga agaggaggag gaggaggtgc ccccgcccag aggtacagcc    780
gctttgatga gttcagcatt ccaaagcctt ggtgctgctg gaccctactc attagccata    840
tactttcctg gaagcacagc cacgaggcct ggagggtgca cactcgtaat gactggagct    900
ttgtgggcct ttcctttccc ctaacgtttc ctccttcccc gcaatctgac cataaatgag    960
gagatttttt ttttctctta ctacactttt tgcaatccta gtttgcaatc ctcagtgtgg   1020
ctggctttca gttcaaatgc tggagaacca tgtatctgtg tggtgagagc attcattttc   1080
aagactaatt cttaaaccgc ttatccccgg agacagaaac cgtggcagag ttgctatcct   1140
ctgagctggg gtggtcatga tgatcagtta ggttactaac atcttcctaa atgaatcggt   1200
gttttgtgtt gctctgtttt catttggatg acagggtgtt gttctgttta atgcgtgtgg   1260 gttttttccaa catgtccgta aaaatatctt ttaagcacca gangtagtga agaaagctgt   1320
gcaaacagca cccgctcctg tccccaagaa awccgaggcg ccccccaaa ggtatatc    1378

<210> SEQ ID NO 45
<211> LENGTH: 1554
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 45
tctagcgaac cccttcgcga acccctttcgc tgcatcctca taaagctacc tcaagacaga     60
gcgtaactgc ctcattctag gagtggactc ggggaagaca gcagacacac catcagggag    120
cccctgggta tctccagaac atggcaagcc gtggatacct gcatcacctg ctgactgcag    180
agggagcctg ggaggagttt gtatcaaagg ccaagttgcc cagggatagg gcagtggccc    240
tccacaaagc actgagggat ctgacagcac tcttggccat agcagaaaga ggcagatctc    300
ggaaaggctg gaaaggcaag gagaagtttg tgaaagcatt tccttgcttg aaagcagact    360
tggaggagca catcagccag ctctatgccc tagccgacca tgctgaggaa ctgcacaggg    420
gctgcaccgt ctccaacatg gtggctgact ccttcagtgt tgcctccgac atcctgaaca    480 tcttttggtct ctttctggca cctgagtcag cagagggaag tctggtgctc tcggcagcag    540
gcttggggct gggggtagca gctactgtga ctaatgttgc tacttcaatc atgaaggaaa    600
caagcagggt tttggatgga gtcgaagctg gtcaccatgg ttcaaccgcc atggatatac    660
tggaggaagc tggcacaagt gtggctagga ttgccagcga gatccctcag gctaccagag    720
atatcaccag agacctggaa gcccttgagc agcacatgaa tgccctcagt ctggtcagag    780
ccaaccctcg cctagaagaa gatgccaggg ccctcatcaa tgcaggtagc atccctgccc    840
aacgggctaa acaggtgcgg gccagtctga aaggaacccc tctggcaatg agcaaggaag    900
accggatccg cagtgccacc accactgggg tcaccctctt gcgtgatgtg gggagccttg    960
tgaacgagtc gaagcagttg tacgaagggt ctgcttccga atcggcagca gcactaagga   1020
```

```
agctggctca ggagctggag gagaagctag gggagctcat gaaattctac gagacaatct    1080
gatcaggttt cagccagtca ccccatcccc aagacatgca gacatcangg gagaggatct    1140
ggacagaggt agggaccatg gaggtgctgt tagaaggaga gcaagactac agtcaggtcc    1200
gagggacata gtgtggaggc ctgtttgatg aacacarcag gttaraggat ggagcagtgg    1260
atcaaagtga gatccactgg agcctgagac sagggaccag aggatgtgct gcaagaggga    1320
ctgggaaaat tgaaatctan actaaacatg gaaaaaaggc agtttcgaaa gactagaaaa    1380
ccctcnccat ctgagccatt ggaaacccca caaaacacaa accagagaga aaagtgtgtg    1440
ctctctaaac aagtcgtggc ccccagttcc ccagcccact cccaccctca ggggtggcat    1500
caaataaatt gtttccattt caaaaaaaaa annaaanaaa aaaaaagcgg ccgc          1554
```

<210> SEQ ID NO 46
<211> LENGTH: 313
<212> TYPE: PRT
<213> ORGANISM: Rattus norvegicus

<400> SEQUENCE: 46

```
Met Ala Ser Arg Gly Tyr Leu His His Leu Leu Thr Ala Glu Gly Ala
1               5                   10                  15

Trp Glu Glu Phe Val Ser Lys Ala Lys Leu Pro Arg Asp Arg Ala Val
            20                  25                  30

Ala Leu His Lys Ala Leu Arg Asp Leu Thr Ala Leu Leu Ala Ile Ala
        35                  40                  45

Glu Arg Gly Arg Ser Arg Lys Gly Trp Lys Gly Lys Glu Lys Phe Val
    50                  55                  60

Lys Ala Phe Pro Cys Leu Lys Ala Asp Leu Glu Glu His Ile Ser Gln
65                  70                  75                  80

Leu Tyr Ala Leu Ala Asp His Ala Glu Glu Leu His Arg Gly Cys Thr
                85                  90                  95

Val Ser Asn Met Val Ala Asp Ser Phe Ser Val Ala Ser Asp Ile Leu
            100                 105                 110

Asn Ile Phe Gly Leu Phe Leu Ala Pro Glu Ser Ala Gly Ser Leu
            115                 120                 125

Val Leu Ser Ala Ala Gly Leu Gly Leu Gly Val Ala Ala Thr Val Thr
    130                 135                 140

Asn Val Ala Thr Ser Ile Met Lys Glu Thr Ser Arg Val Leu Asp Gly
145                 150                 155                 160

Val Glu Ala Gly His His Gly Ser Thr Ala Met Asp Ile Leu Glu Glu
                165                 170                 175

Ala Gly Thr Ser Val Ala Arg Ile Ala Ser Glu Ile Pro Gln Ala Thr
            180                 185                 190

Arg Asp Ile Thr Arg Asp Leu Glu Ala Leu Glu Gln His Met Asn Ala
        195                 200                 205

Leu Ser Leu Val Arg Ala Asn Pro Arg Leu Glu Glu Asp Ala Arg Ala
    210                 215                 220

Leu Ile Asn Ala Gly Ser Ile Pro Ala Gln Ala Lys Gln Val Arg
225                 230                 235                 240

Ala Ser Leu Lys Gly Thr Pro Leu Ala Met Ser Lys Glu Asp Arg Ile
                245                 250                 255

Arg Ser Ala Thr Thr Thr Gly Val Thr Leu Leu Arg Asp Val Gly Ser
            260                 265                 270

Leu Val Asn Glu Ser Lys Gln Leu Tyr Glu Gly Ser Ala Ser Glu Ser
```

|   |   | 275 |   |   | 280 |   |   | 285 |   |
|---|---|---|---|---|---|---|---|---|---|

Ala Ala Ala Leu Arg Lys Leu Ala Gln Glu Leu Glu Glu Lys Leu Gly
    290                295                300

Glu Leu Met Lys Phe Tyr Glu Thr Ile
305                310

<210> SEQ ID NO 47
<211> LENGTH: 1142
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 47

```
tctagcgaac cccttcggct ttttctgatt taaagtgaag aaatggccat atttgcttga      60
taatcttcag ttgtgtctct ggaactcaac aaagaacgca ttttatgaaa tatacagctg     120
tcttcggtaa agccaacttt cttacacata tttcgggaag taattaacta caatttggac     180
ttatagttac aaggttgcct tcgaaacact gctctaaatg tgtctcgtgt tggggtgcta     240
ctttgcttat gtgtaaattt cacagtaatg caatagagaa agggtgtttg tgggtgtggc     300
ttgtgggggg gattgttttg ttgttgttgt ttgagataaa gcttcattct gtagccagga     360
aagcctggaa tttactgtgt catcccaggt agcttcaaac tggtgcctat cctgcctcag     420
cctccaacgt gttgcaattg caggagtaac ctaccacatc ctgcagctac agtgatctag     480
aacctccccg tcgaagcccc accaccatag aaaccaattt gcattaagtt ttagaattcc     540
caacccaact aaagtttaat aaaaaaagaa aaacaaaaca agatttaaat cattctttcc     600
ctcattcttt ttnnagatnc agggctcncc tagttttnaa caaaacagtn ngcagngnng     660
ggnnccccng gngggnnttt tttncnttgn gccncntngc ancccacccn cccaggcngg     720
atngggnggg gtataaaagt nttancnggc anatgnnctn ggngcanacc caagtntatc     780
aggnccntnan ttnccncccca ganaactaga nanctntngc atagtanang ccccntgtgn     840
agatttnaaa nccnctgtn cacagaana gaancttana tagaaantc aaatatttn      900
ggngcccaan gttncccacc ctgtagagng ggncccaaaa ancngccncc aganagcnng     960
atatntgagt tntgacctnt attctttact acnacgcntt gagagaatat tntgntgggg    1020
ccctanccac atgttttgnc caagantgt aaanccactt naannctgng ggatatctcn    1080
ctgcanacag aagtgcccng cgggattta aaaaaaaaa taaaaaaaaa aaaggngccn    1140
cc                                                                  1142
```

<210> SEQ ID NO 48
<211> LENGTH: 502
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 48

```
tctagcgaac cccttcgtgg agactgtgga agtatatgtat gaataggaga gtgtgtgttg      60
tgtaacacag acagaaggac attggatcat gttgaacccg cacccccaac tatgagtgat     120
ggtatggaaa gaatgcgaac atttaaactg cgccaatgcg gcggccatct tggtggagaa     180
gttcctagcc gagctttgat gtgattttttt tgatggtaca atgcagcgag catggccacg     240
```

-continued

```
ggagctttga atccagccga cagctccgag atttgccctt ccagtgctct tgcctaccgt      300
agagaggact gctgagatgg gattccttgt gacaagccta cttaccttta actgccagca      360
tttgtaaggt gcaatcttgt gtattggttt tttattttga cagttttgaa acatgtttg      420 ntgntcttgg tgttttcca gtaaaagtaa tcacaaagga aaaaaaatt aaaaaaaaa        480 aaaaaaaaaa aaaagcggcc gc                                              502
```

<210> SEQ ID NO 49
<211> LENGTH: 1426
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 49

```
tctagcgaac cccttcgcct tcatatggtt ttacactgta tgcatctcac cgcggcccgg      60
aacctttctt ctcatcccaa tcctgtttga ggggacgggg ggcagggacg gacaacccaa      120 gacagggat atttgtgctg tgggtattgc atcttatgga gggctgtagc taactgggac       180
tcctgggtga ccccaacagg cctttgatcc tctgtctctc cccgcttgat ctttcttacc      240
ttatgcttcc ccaagtgcag ctgagggact acacagtggc tcccgcccca ctccaaacac      300
aggaaatcaa tctcagggag aggagataag aagtgaggag aagccaagat tcaaccaata     360
gatggtaatt gctcctggga ccgccccccc aagcatcatt tccataggaa ggactgagtt      420
tggctcctga agcccagtgg agtaccttc tctgcctgaa ttctgttgtg atccctggcc       480
aagtcctctt tccagaaacc ccacctttaa accagctga aaggaccctt cttctctatg       540
tttaataggt aactttccat agcttagctt ccctgcagtc tcccgagtgc ccagttaaaa     600
ttctgccata ggtcaaaagt ggggttgaga ggtgaagtca gaggccatgc atggagctca     660
gaacgtttct aaacctcctg tgattcattg agtagcccct agactctaga aggctcagat     720
gccaaaaagg ktgactttat aatttcttag ggtcttctca tgggatcgkt ttcagagtgg    780
gcattcacta aatgatagca agtttattaa ttgtttccca gygcctgatc tctttattn     840 cccagggctt ccaaccagag cccttggttg aaagtctccc acccaccccc caccctgaga    900
cttggtggnt ttctgagatt ccccagggat ggcaaaattg gcattcttac agggagccct    960
gacttctagc acgttaccta gattttttac cctgctctct ctgcctattt tactatggga   1020
tcactgntct cttttggactt aaggaaccac cttgaagtag agtgaggtga ccacgtgttg    1080
gtggcgaaga atataagcat tggtccttaa aagagaactt ctatgaagtc aggctgcaag   1140 cttttaacatg gcacaagttg caccttactg gctgctaagt ctggatgtca accaaaggtc   1200
aactctntaa ttaaagaaaa gcaagggaga aganaggtgg aagnggcttn cataaacttt    1260
attcaaaatg tctaccagga atggtggtga caccaataat cccacatgtt ggatgtngag   1320
gcaggaagaa tgatggtaag gggcatcctc actacataat gagttgaggc tngactaggt    1380
taactntgct tnaaaaaaaa aaaaaaaaaa aaaaaaagg ggngcc                    1426
```

<210> SEQ ID NO 50
<211> LENGTH: 985
<212> TYPE: DNA
<213> ORGANISM: Rattus norvegicus

<400> SEQUENCE: 50

-continued

| | |
|---|---|
| tctagcgaac cccttcgcaa gaactcagac tgctcctgcc tgacttccta ggtgtcatag | 60 |
| ctctcttctg ccgccagtat gacatcatca aggacaacga gcccaataac aacaaggaaa | 120 |
| aaaccaagag tgcatcagag accagcaccc cagagcacca gggtgggggt ctcctccgaa | 180 |
| gcaagatatg aaaccctttc agtgcttgct ctgagcagct cagaagtaga atgcgagagg | 240 |
| acctcactgt tctgacgatg attgtccaac acacatccgg ccctctccgt gtctcctccc | 300 |
| accaccatct tctcctatca ccgggcttac tatcttctct cctggctttc ctctttctga | 360 |
| tggcggttcc tgaagcctcc aactaacccc taactcgggg agcgcctcga cagtgtttgt | 420 |
| ggctaaggct acactcagag acagagttgc agaatgaggg agacccagcc cgagggacgc | 480 |
| cattgctggg aggtagactg ggtgcgaggg cccttggcac aggactcaca tctgggctgt | 540 |
| tcagcttgac ccgaaggctg tgtgtgaaag ggggaaaaag acaagattgc caggcagggc | 600 |
| tgttgttttt gtggcttcga gggacaagaa cctggctaaa aggcagcagc cctgctgttc | 660 |
| tttttctcct ctgtcctgtt tcctaccctta caagaagtcc atgcaaccaa ccggggctct | 720 |
| ggcacttttc ttgtttattt ccctcctggc ttccaaacaa gccctctgtg acatcatca | 780 |
| aagcatggat aaccccctct gcagggttgg gcttcattct ccgctggtcc ctgtagcctt | 840 |
| cctggacaca gggtgaaagt tgtaaaagtg gtaggagtgc agctagccac aggttctcct | 900 |
| tttcccatct cagtctgacc aaggaggctg aactaccaac ccaaattcag cgaaaaaaaa | 960 |
| aaaaaaaaaa aaaaaagcg gccgc | 985 |

<210> SEQ ID NO 51
<211> LENGTH: 58
<212> TYPE: PRT
<213> ORGANISM: Rattus norvegicus

<400> SEQUENCE: 51

```
Met Thr Ser Ser Arg Thr Thr Ser Pro Ile Thr Thr Arg Lys Lys Pro
 1               5                  10                  15

Arg Val His Gln Arg Pro Ala Pro Gln Ser Thr Arg Val Gly Val Ser
            20                  25                  30

Ser Glu Ala Arg Tyr Glu Thr Leu Ser Val Leu Ala Leu Ser Ser Ser
        35                  40                  45

Glu Val Glu Cys Glu Arg Thr Ser Leu Phe
    50                  55
```

<210> SEQ ID NO 52
<211> LENGTH: 2010
<212> TYPE: DNA
<213> ORGANISM: Rattus norvegicus

<400> SEQUENCE: 52

| | |
|---|---|
| tctagcgaac cccttcgcgg ggacagacat ggagaaggag atggaggacc ccctggctgg | 60 |
| agcagaccaa cagaataggc aactatggct ggagaaccg tatcagagt aatgcttgac | 120 |
| ctcgggaaac accaaatttc ttcttccgat cgcagaagta gtactcggcg aaattcacta | 180 |
| ggtaggaggc tcctcatctg ggaagaaccg gtgcctgggg gacctggct ggataggtat | 240 |
| gggggatcga ggccggtccc ctagtctccg gtcccccccat ggcagtcctc caactctaag | 300 |
| caccctcact ctcctgctgc tcctctgtgg acaggctcac tcccagtgca agatcctccg | 360 |
| ctgcaatgcc gagtacgtct cgtccactct gagccttcgg ggagggggct caccggacac | 420 |
| gccacatgga ggcggccgtg gtgggccggc tcaggtggc ttgtgtcgcg ccctgcgctc | 480 |
| ctacgctctc tgcacgcggc gcaccgcccg cacctgccgc ggggacctcg ctttccactc | 540 |

```
cgcggtgcat ggcatagagg acctgatgat ccagcacaac tgctcacgcc agggtcccac      600
ggcctcgccc ccggcccggg gtcctgccct gcccggggcc ggcccagcgc ccctgacccc      660
agatccctgt gactatgaag cccggttttc caggctgcac ggtcgaaccc cgggtttctt      720
gcattgtgct tcctttggag accccatgt gcgcagcttc cacaatcact ttcacacatg       780
ccgcgtccaa ggagcttggc ccctactaga taacgacttc ctctttgtcc aagccaccag      840
ctccccggta gcatcgggag ccaacgctac caccatccgg aagatcacta tcatatttaa      900
aaacatgcag gaatgcattg accagaaagt ctaccaggct gaggtagaca atcttcctgc      960
agcctttgaa gatggttctg tcaatggggg cgaccgacct gggggctcga gtttgtccat     1020
tcaaactgct aaccttggga gccacgtgga gattcgagct gcctacattg aacaactat      1080
aatcgttcgt cagacagctg gacagctctc cttctccatc agggtagcgg aggatgtggc     1140
acgggccttc tctgctgagc aggatctaca gctgtgtgtt gggggatgcc ctccgagcca     1200
gcgactctct cgctcagagc gcaatcgccg tggggcgata gccatagata ctgccagaag    1260
gttgtgtaag gaagggcttc cggttgaaga tgcctacttc caatcctgcg tctttgatgt     1320
ttcagtctcc ggtgacccca actttactgt ggcagctcag tcagctctgg acgatgcccg     1380
agtcttcttg accgatttgg agaacttgca ccttttccca gtagatgcgg ggcctcccct     1440
ctctccagcc acctgcctag tccggcttct ttcggtcctc tttgttctgt ggttttgcat     1500
tcagtaagta ggccagcaac ccgtgactag tttggaaacg gtttgaggag agaggttgat     1560
gtgagaaaac acaaagatgt gccaaaggaa acagtgggga caggagacaa cgaccttact    1620
caatcacacg aggttgcagt ccagggctga aatgaccta gaataaagat tctgagacag     1680
ggttttgcac tccagacctt ggtatgggct ccccatgaat ttccccatta gtgatttccc    1740
acttgtagtg aaattctact ctctgtacac ctgatatcac tcctgcaagg ctagagattg    1800
tgagagcgct aagggccagc aaaacattaa agggctgaga tatcttaaag gcagaaacta    1860
gaaaagggga aaccatgatt atctataaga aaatcaaaag aggggtttgg gaatttagct    1920
cagtggtaga gcacttgcct agcaagcgca aggccctggg ttcggtcccc agctcctaaa    1980
aaaaaaaaaa aaaaaaaaaa aagcggccgc                                    2010
```

<210> SEQ ID NO 53
<211> LENGTH: 422
<212> TYPE: PRT
<213> ORGANISM: Rattus norvegicus

<400> SEQUENCE: 53

```
Met Gly Asp Arg Gly Arg Ser Pro Ser Leu Arg Ser Pro His Gly Ser
 1               5                  10                  15

Pro Pro Thr Leu Ser Thr Leu Thr Leu Leu Leu Leu Cys Gly Gln
             20                  25                  30

Ala His Ser Gln Cys Lys Ile Leu Arg Cys Asn Ala Glu Tyr Val Ser
         35                  40                  45

Ser Thr Leu Ser Leu Arg Gly Gly Ser Pro Asp Thr Pro His Gly
     50                  55                  60

Gly Gly Arg Gly Gly Pro Ala Ser Gly Gly Leu Cys Arg Ala Leu Arg
 65                  70                  75                  80

Ser Tyr Ala Leu Cys Thr Arg Arg Thr Ala Arg Thr Cys Arg Gly Asp
                 85                  90                  95

Leu Ala Phe His Ser Ala Val His Gly Ile Glu Asp Leu Met Ile Gln
                100                 105                 110
```

```
His Asn Cys Ser Arg Gln Gly Pro Thr Ala Ser Pro Pro Ala Arg Gly
        115                 120                 125

Pro Ala Leu Pro Gly Ala Gly Pro Ala Pro Leu Thr Pro Asp Pro Cys
    130                 135                 140

Asp Tyr Glu Ala Arg Phe Ser Arg Leu His Gly Arg Thr Pro Gly Phe
145                 150                 155                 160

Leu His Cys Ala Ser Phe Gly Asp Pro His Val Arg Ser Phe His Asn
                165                 170                 175

His Phe His Thr Cys Arg Val Gln Gly Ala Trp Pro Leu Leu Asp Asn
        180                 185                 190

Asp Phe Leu Phe Val Gln Ala Thr Ser Ser Pro Val Ala Ser Gly Ala
            195                 200                 205

Asn Ala Thr Thr Ile Arg Lys Ile Thr Ile Ile Phe Lys Asn Met Gln
        210                 215                 220

Glu Cys Ile Asp Gln Lys Val Tyr Gln Ala Glu Val Asp Asn Leu Pro
225                 230                 235                 240

Ala Ala Phe Glu Asp Gly Ser Val Asn Gly Gly Asp Arg Pro Gly Gly
                245                 250                 255

Ser Ser Leu Ser Ile Gln Thr Ala Asn Leu Gly Ser His Val Glu Ile
            260                 265                 270

Arg Ala Ala Tyr Ile Gly Thr Thr Ile Ile Val Arg Gln Thr Ala Gly
        275                 280                 285

Gln Leu Ser Phe Ser Ile Arg Val Ala Glu Asp Val Ala Arg Ala Phe
    290                 295                 300

Ser Ala Glu Gln Asp Leu Gln Leu Cys Val Gly Gly Cys Pro Pro Ser
305                 310                 315                 320

Gln Arg Leu Ser Arg Ser Glu Arg Asn Arg Arg Gly Ala Ile Ala Ile
                325                 330                 335

Asp Thr Ala Arg Arg Leu Cys Lys Glu Gly Leu Pro Val Glu Asp Ala
            340                 345                 350

Tyr Phe Gln Ser Cys Val Phe Asp Val Ser Val Ser Gly Asp Pro Asn
        355                 360                 365

Phe Thr Val Ala Ala Gln Ser Ala Leu Asp Asp Ala Arg Val Phe Leu
    370                 375                 380

Thr Asp Leu Glu Asn Leu His Leu Phe Pro Val Asp Ala Gly Pro Pro
385                 390                 395                 400

Leu Ser Pro Ala Thr Cys Leu Val Arg Leu Leu Ser Val Leu Phe Val
                405                 410                 415

Leu Trp Phe Cys Ile Gln
            420

<210> SEQ ID NO 54
<211> LENGTH: 705
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 54
tctagcgaac cccttcgtgg ggattaaggt tctctatagc taagcctgtc ngaatgacaa      60
cacccagaga tctccacctgg ggtggtggga gcactctctg tcttgaggga acatgtacct    120
actctctcct tccacaagag ccacatacac ttagaagttc cagtgaagat ctatgtgctt    180
```

-continued

```
cagaagagag gggacttgga ggtgaaaggg ggagtgggag gggggcttga ggacctanct    240
gaaagatttt angctgaaag aacttccttg attcaaagac atatgtcagt ngacccaaca    300
atgagaatga atatgagggc caggaaaact tgtgggaatc agtctcaaga cngaaacnga    360
gaaagaaaga aaagtgggta ggactcanat tggggaacct gggtagacag gagtggcnag    420
ggaagaaagg gatcttgggt tntccacagt ttgagacaca tccggngntc gaccctattc    480
ccngaagccn cannanatgt tgcttccccn tcnntnnaat gggcctggng gtcctnctcc    540
ctttncccng gacatgaaaa ngtnttctgc nnanataacc cccntctttc ctcccccttn    600
antntgtccc taccntttg tcccttttn ttttnaaaaa annaaaataa agggnncnn      660 tnttcccttn gaaaaaaaaa aaaaaaaaaa aaaaaccgc ccncc                    705
```

```
<210> SEQ ID NO 55
<211> LENGTH: 58
<212> TYPE: PRT
<213> ORGANISM: Rattus norvegicus

<400> SEQUENCE: 55
```

```
Met Thr Thr Pro Arg Asp Leu Thr Trp Gly Gly Gly Ser Thr Leu Cys
 1               5                  10                  15

Leu Glu Gly Thr Cys Thr Tyr Ser Leu Leu Pro Gln Glu Pro His Thr
            20                  25                  30

Leu Arg Ser Ser Ser Glu Asp Leu Cys Ala Ser Glu Glu Arg Gly Leu
        35                  40                  45

Gly Gly Glu Arg Gly Ser Gly Arg Gly Ala
    50                  55
```

```
<210> SEQ ID NO 56
<211> LENGTH: 968
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 56
```

```
tctagcgaac cccttcgcga aggggttcgc ttacattcac gcttaagcat attaactgta     60
catattaact gatttagagg atactatgga ttccacatct tccctgagca tagggattga    120
tttgaaaaat gacagggttg gctgtcgacc cccatcggag gaagcaggta aggaatcact    180
taggagaact gatctcaaca ttcttcagtt ctttctatta tttacttgtt tagcctggag    240
ttaaattccc actccttgtg agcacttcta atttgaaaat ccactttctt caatattttc    300
gaaatttaaa actgatggat gacgtgacaa aacttccacg agttaagaat tctccacctc    360
tgatctcatc gcagcagggc acaatccaag gcatgtgaat tgacttccag gtttatgtga    420
catataaatg aattctgtct ctagatttgg atcccattct cctaaatatc tcaccatgca    480
tgtgcagata ttctaaagtc taaaaatatc tgatattgca aacttttctg gtcaaaacat    540
tttggatgag ccattaaca gccaaggtat ttgagacaga ggtttcaaca gcattcctgg    600
aggagacaca aaggacagat gagtcacatg aaggatggga ggagggaagg tggctgttga    660
taggtatttt gagacactct atttgagtcc tacacaacac tccccctcc cccctcccc    720 ccaaaccatt tttatgtcta ttgacctttc ctctagtcat acagggacat tcacagttac    780
ctacaaagaa ccagaattgt aacaagtcaa gaggaaactt attttgata atgactcatt    840 gaagatgttt tgaaaattta aaataagct cttgtaagca gaagtctgtg agaaaagcaa    900
```

```
gaaggaattg tttgtttatt aaataaataa aaggcnnann nnaaaaaaaa aaaaaaaan       960 gcggccgc                                                              968

<210> SEQ ID NO 57
<211> LENGTH: 52
<212> TYPE: PRT
<213> ORGANISM: Rattus norvegicus

<400> SEQUENCE: 57

Met Asp Ser Thr Ser Ser Leu Ser Ile Gly Ile Asp Leu Lys Asn Asp
  1               5                  10                  15

Arg Val Gly Cys Arg Pro Pro Ser Glu Glu Ala Gly Lys Glu Ser Leu
             20                  25                  30

Arg Arg Thr Asp Leu Asn Ile Leu Gln Phe Phe Leu Leu Phe Thr Cys
         35                  40                  45

Leu Ala Trp Ser
         50

<210> SEQ ID NO 58
<211> LENGTH: 1183
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 58
tctagcgaac cccttcggca gacagcatcc ctcccaaggc tactcagggt ttaaaccctg       60
cttctgaagt gacatgtcct gcaaagaaag tccccacgtg ggtgtttcca ccaccactgt      120
cagctctgta gctgtgcaag ctgggactc caagatcgtg atagccgttg tcaagtgtgg       180
caaatgggtg cggctccaac tggctgaggc acagcccaat ctcctagaaa ttgggagcag      240
tcaagatgaa accagaaaac tgcttcacga tcacgagctc cttctggcca agcttaaggc      300
cttggaagat cgtgtgtggg gactcttaca ggaagcagac aggacggctg aagcaaacaa      360
ggagcaaagt gaggtgtcga tgccatggcc agactctggg cgaagcatgg gccaccctgg      420
tcttcatgct tgaaagaaga agggagctcc tcggactgac atctgagttt tttcaaagcg      480
ccttggagtt tgctataaaa atagaccaag ctgaagattt tctgcagaat cctcacgagt      540
ttgagagtgc cgaagcctta cagtcacttc ttctgcttca tgaccgacac gccaaagaac      600
tcttagaacg atctctagtc cttttaaaca aaagccaaca actcactgac ttcatagaaa      660
aattcaagtg tgatggatct cctgtgaatt ctgagctcat ccagggagct cagagcagtt      720
gtctgaagat cgacagcctc cttgaacttc tgcaagacag gagaaggcag ctggacaagc      780
acttgcagca acagaggcag gagttgtctc aggttctgca gttatgtctg tgggaccaac      840
aagaaagcca ggtttcttgt tggtttcaga aaacaataag agatctgcag gaacagagtc      900
tgggttcatc cctttcagac aacaaagagt taatccgtaa gcacgaggac ctgccatcaa      960
agcaaagagt ccctgcagtt taggaattga acagaacagt ttcctgattg aatgatcttg     1020
gcgcctyytt ancggntgca gatggtgggg cttcctctgg nttctcatcc tcttccacta     1080
atctggattt ttgttcccct ggtgtgccac atcactttaa tttgaaagaa aaaaaataaa     1140
ttgggccgga aaaaaaaaaa aaaaaaaaaa aarrrscggc cnc                       1183

<210> SEQ ID NO 59
```

<211> LENGTH: 245
<212> TYPE: PRT
<213> ORGANISM: Rattus norvegicus

<400> SEQUENCE: 59

Met Lys Pro Glu Asn Cys Phe Thr Ile Thr Ser Ser Phe Trp Pro Ser
1               5                   10                  15
Leu Arg Pro Trp Lys Ile Val Cys Gly Asp Ser Tyr Arg Lys Gln Thr
            20                  25                  30
Gly Arg Leu Lys Gln Thr Arg Ser Lys Val Arg Cys Arg Cys His Gly
        35                  40                  45
Gln Thr Leu Gly Glu Ala Trp Ala Thr Leu Val Phe Met Leu Glu Arg
    50                  55                  60
Arg Arg Glu Leu Leu Gly Leu Thr Ser Glu Phe Phe Gln Ser Ala Leu
65                  70                  75                  80
Glu Phe Ala Ile Lys Ile Asp Gln Ala Glu Asp Phe Leu Gln Asn Pro
                85                  90                  95
His Glu Phe Glu Ser Ala Glu Ala Leu Gln Ser Leu Leu Leu Leu His
            100                 105                 110
Asp Arg His Ala Lys Glu Leu Leu Glu Arg Ser Leu Val Leu Leu Asn
        115                 120                 125
Lys Ser Gln Gln Leu Thr Asp Phe Ile Glu Lys Phe Lys Cys Asp Gly
    130                 135                 140
Ser Pro Val Asn Ser Glu Leu Ile Gln Gly Ala Gln Ser Ser Cys Leu
145                 150                 155                 160
Lys Ile Asp Ser Leu Leu Glu Leu Leu Gln Asp Arg Arg Arg Gln Leu
                165                 170                 175
Asp Lys His Leu Gln Gln Gln Arg Gln Glu Leu Ser Gln Val Leu Gln
            180                 185                 190
Leu Cys Leu Trp Asp Gln Gln Glu Ser Gln Val Ser Cys Trp Phe Gln
        195                 200                 205
Lys Thr Ile Arg Asp Leu Gln Glu Gln Ser Leu Gly Ser Ser Leu Ser
    210                 215                 220
Asp Asn Lys Glu Leu Ile Arg Lys His Glu Asp Leu Pro Ser Lys Gln
225                 230                 235                 240
Arg Val Pro Ala Val
                245

<210> SEQ ID NO 60
<211> LENGTH: 1051
<212> TYPE: DNA
<213> ORGANISM: Rattus norvegicus

<400> SEQUENCE: 60
tctagcgaac cccttcgcgc aagatggccg cttcccagac cgctccgcgg catcttcaag      60
atgcgcgaga gaacgtgca  atctcgcgag atcaggctcg ctcgcgggca gtctgctcgc     120
agcctaccct tcctaggagt tggaggaggg aaagctagat tcgattaaga gcaaaaaatt     180
gttccagcag cagagcagct gtccaaggaa gtatccaaag gaactgcacc tcagtaaact     240
cctggcaagt cttaggatat gacaaagggc acaggatgca ttatgagaaa ggaaggctaa     300
ggttttcaag aacacagatt tacatcaaac ttgcgttctg aattaatctt tgagaatact     360
ggactgtgag ctagacattg agtaagaggt ttgttatatc aagaatgtga tctaaaaaaa     420
aaacattcat atcttcctcc cacaagagga tattttgaaa ctgtgggtca agtcagact      480
acaggagagc cctcaaatat gccaaatgtg acagacagca ggattttgaa atatatagtgg    540

```
gagtatgtga agatgttcca gtcaaagaga cattgtttcc aaaggaaaga aagtccagtc      600
gcctcacagg aattgtgtat tccctggtag taatgcaaat ggaccacata tggctttctt      660 cttttaaagag aatacctaat tttagctaca gagtaaaatg ctgatgatac aaaccgtgac     720
aagtggaggg acaagaaagt aaatggactg atggtgccat tgtggactgg gagggtaaaa     780
gctgtacatt tgtgaacaaa aagatttcct tgttatggtc agccatgatt ctaactgcta     840
aatggaggca gtaacaacat gacctaaaga gtaaacatcc agagatggaa tgttctcaat     900
gtctgaaaag gagcagatat ctggtgtatg tgaatgtatg ctagagattt tttacaagcc     960
tgtggtgaat tagtaattgt atttattttt gaaagttaaa caggtaatta gaaaccccaa    1020
aaaaaaaaaa aataaaaaaa aagcggccgc c                                   1051

<210> SEQ ID NO 61
<211> LENGTH: 576
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 61
tctagcgaac cccttcgctg aaaccaccgt tcacacggga aacctgggtt aggcttttgt      60
cctcagtgac acagaggatg tagtccacag ctaggtagaa atgtcaggtt cccaacacta     120
ctccagctgt gactttgatg cttgggggat ggggtcgcag gctatttttct ctgctttaac    180 agttcataga atttaacaga taagagttag tgtctttcat gtggcctcac tctggagtta     240
tgagaacata cacacggttt acagcttttc aatatnccttt tccctggcca tcaagtattt    300
tgaaagtgtg ccacctttta accttttgcgc tttatttttt tttcttttttt taaagntgaa   360 ggtgataatt cttctatata tgatgaaact caatgtctac tgaaataagt gtaaccttag     420
ctatncacgt ttatnttttta aaaccacgct atggagatat taccccgagt tctgtcnttt    480
ngcaagattt acagnacctt cccncccccc cttttagcat tnaataaaaa natattgggg    540 agcncnnntna aaaaaaaaaa aatnaanaaa agcggc                              576

<210> SEQ ID NO 62
<211> LENGTH: 587
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 62
tctagcgaac cccttcgcgt gatctgatcc gagctgagac ttggggagct ctggctccgt      60
gttggctgca gcatccccca tggtcttgtc tgaggtgtcc tgtgactcga ctcttcagaa     120
ctcaatgaag tagatgactt gactacaatg tggaaacatc atgacagaaa gtgtggtttg     180
taccggggcc gtcagcactg taaaggaagt ctgggaagaa agaataaaga acatcatga      240 agatgtgaaa cgagagaagg aatttcagca aaagctagtg cggatctggg aagaccgagt     300
gagtttaact aagctgaaag agaaggtgac cagggaagat ggaagaatca ttctaaggat     360
agagaaagag gaatggaaga ctctcccttc ttccttactg aaactgaatc agctacagga     420
gtggcaactt cataggaccg gattgttgaa aattcctgaa ttcattggaa gattccagca     480
```

```
tctcattggt ctagacttat ctcggaacac aatttcagag atccccccga ggcattggac      540
tgntcactta gacttcaagg aactgattct tagctacaca aaatcaa                    587
```

<210> SEQ ID NO 63
<211> LENGTH: 142
<212> TYPE: PRT
<213> ORGANISM: Rattus norvegicus
<220> FEATURE:
<221> NAME/KEY: UNSURE
<222> LOCATION: (0)...(0)
<223> OTHER INFORMATION: Xaa = any amino acid

<400> SEQUENCE: 63

```
Met Thr Glu Ser Val Val Cys Thr Gly Ala Val Ser Thr Val Lys Glu
 1               5                  10                  15

Val Trp Glu Glu Arg Ile Lys Lys His His Glu Asp Val Lys Arg Glu
             20                  25                  30

Lys Glu Phe Gln Gln Lys Leu Val Arg Ile Trp Glu Asp Arg Val Ser
         35                  40                  45

Leu Thr Lys Leu Lys Glu Lys Val Thr Arg Glu Asp Gly Arg Ile Ile
     50                  55                  60

Leu Arg Ile Glu Lys Glu Glu Trp Lys Thr Leu Pro Ser Ser Leu Leu
 65                  70                  75                  80

Lys Leu Asn Gln Leu Gln Glu Trp Gln Leu His Arg Thr Gly Leu Leu
                 85                  90                  95

Lys Ile Pro Glu Phe Ile Gly Arg Phe Gln His Leu Ile Gly Leu Asp
            100                 105                 110

Leu Ser Arg Asn Thr Ile Ser Glu Ile Pro Pro Arg His Trp Thr Xaa
        115                 120                 125

His Leu Asp Phe Lys Glu Leu Ile Leu Ser Tyr Thr Lys Ser
    130                 135                 140
```

<210> SEQ ID NO 64
<211> LENGTH: 819
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 64

```
tctagcgaac cccttcggtt ctgttggcta cacagctgca gagccatggc tgaccgttca      60
ctgtcagggg cacatgttac actaagcttc atgacagtga tgtaataatg ttacacattt     120
gtcttgtagt tatgtattga agtttctgtc ctgttttgtg taaaaatgta tccactcttg     180
tatatattta gacttgaaac taccacacaa atattggaac ggtttgcttt atgaagttaa     240
aagtatcctt ccgaatggaa ctaacttgct ttgtgctcag acatatacta tgctgatgta     300
ttttgcaata tactatctta aattaaatct ggtcactttg ttgcctttt aaaaagtgtg      360 gtatttcaag tagagttatt ttcctgaaat atatttgcaa actcaagctg ctttataatc     420
aaggaatatt tttattgatt gaagaaaatg actgctgcaa ttcaaaagtg aacttatttt     480
attatataga tgatttctta aaagctattt ataccatgat acaaaatcat gtagtgatcc     540
tgggagtctg tagttcttcc tgttaataac attcaacact gtatgctaga ggcagcaatg     600
ccaacactga agttattttg ggtgaaaacc gtcgttctgn cctgtttagc tggggattat    660
taaatccata taatgtatgt gcttatgtat gctacatgtg caagttaggt gtttcctttg     720
```

-continued

| | |
|---|---|
| tgttctgctt attaaatgtc attcagattc acttcctgaa ttctaataaa gagggaagct | 780 |
| attggaaaaa ataaaaaaaa aaaaaaaaaa gcggccgcc | 819 |

<210> SEQ ID NO 65
<211> LENGTH: 1648
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 65

| | |
|---|---|
| tctagcgaac cccttcggtg gcgcacgccg gtaggatttg ccacgcaaat gctggaatta | 60 |
| aagacatgca gcagcagcgc cctgtggttt tggttttta tttgattgct tattttatc | 120 |
| taattttaa ttttttgtgt atgaacgttt tatctgcatt tatgtctctg taccacattc | 180 |
| gtgcctggtg ctatggaggc caaaaaagga ttttaggccc gagattgtag ttatagatgg | 240 |
| ttgtgggctg ccaatctgag tgctgaaaat taaacctggg tactctgaaa gaccagccag | 300 |
| tgctcttaac tatcaggcca cctctccagc actattttat tttattttat ttgtggagat | 360 |
| agggtctctc tctctgtatc ctagtctaac ttaaaacata agaatattc tgtatcagta | 420 |
| tccttgagta ctaggattct aggcacctgt cattatgcct agattttaa cagtgtgtgt | 480 |
| taattctaca taaaaatgaa tttcattatt acattttcac acttgtgaag aatatacttt | 540 |
| gatcatattc ccttctcctg atacttttc ctatccttcc tccccactcc attagttccc | 600 |
| ttcttctttt cagagtctac cttctacttt ttactttgat ttttttcccc ccacattctg | 660 |
| tggttgagag aatgcatatt acagttgtat ttctgaatct ggctaggtac attcacttaa | 720 |
| cataattaat gatcctgggc gagcgaaggg gttcncctan cnaaccccttt cggttcaata | 780 |
| ccatttcaga gatgggcatt tccctcaatg aaatacacaa gtaaacattc cgacattgtc | 840 |
| tttaggagtg tttgttaaaa aaaaaaaaa aaaaaaccan ancccaaaan caaaaaaaaa | 900 |
| aaagctttgc accttgcaaa agtggtcctg gcgtgggtag attgctgtta atcctttatc | 960 |
| aataacgttc tatagagaat atataaatat atatataatt atatctccta gtccctgcct | 1020 |
| cttaagagcc gaaaatgcat gggtgttgta gacattcggt tgcactaaat tcctctctga | 1080 |
| attttggctg ctgaagccgt tcatttagca actgtttata ggtggttgat gaatggttcc | 1140 |
| ttatctccat ttcttcctat gtagcttaag ccgcttcctt cacagaatct aataatctcg | 1200 |
| tctaggccat tagccctgcc ctttcttaac attcttgtat ttgttgaatt tggcctcctc | 1260 |
| gaaagcaata gcaactgggt ggcccaccca agttttaacg cccctgattc catctatggc | 1320 |
| atttgtacca aatataagtt ggatgcattt attttagaca caaagcttta tttttcgac | 1380 |
| atcgtgtttc aagaaaaaaa acaaatagaa taacaataac tatgactttg aggccaatca | 1440 |
| tttttaggtg tgtgtttgaa gcatagaacg tctnttaaac tctcaatggt tccttcaaat | 1500 |
| gatgagttag tatgtaacgt aaatagcagt ttctctctct ctctctctct tttatttt | 1560 |
| tccanataga gcactatgta aatttagcat atcaataata caggaactat ccnccaaaaa | 1620 |
| aaaaaaaaaa aaaaaaaaaa gcggccgc | 1648 |

<210> SEQ ID NO 66
<211> LENGTH: 782
<212> TYPE: DNA
<213> ORGANISM: Rattus norvegicus
<220> FEATURE:
<221> NAME/KEY: unsure

```
<222> LOCATION: (0)...(0)
<223> OTHER INFORMATION: n = A, T, C, or G

<400> SEQUENCE: 66
tctagcgaac cccttcgtag aactaggagc cagtgttgac cacggtcggt ggctggatac      60
cccactgcat gctgcagcaa ggcagtccag tgtggaggtc atcaatctgc tcactgagta     120
tggggctaac ctgaaactca gaaactcgca gggcaaaagt gctcttgagc tcgctgctcc     180
caaaagtagt gtggagcagg cactcctgct ccatgaaggt ccacctgctc tttctcagct     240
ctgccgcttg tgtgtccgga agtgcttggg ccgcacatgt catcaagcca tctacgcact     300
aggtctgcca gaacccctgg aaaaattcct cttataccaa tagttggaaa catgttgcct     360
gctgtaggac acttaatata cacattcagt ggcttaaccc actatcctaa aaatctgctt     420
acctaattag aataaagcct tcataaatcc aaatacttgc gttgaacaaa ctcctggtta     480
ggttaatggn tgccaagaga taaccagaaa cctttcaagt ttttaactct tggtaattta     540
aaatcaaact gaaatagatg gaaaataata atctattttt ggataattca aggacccttc     600
agtatctggg gctggggtcc gcattttgna tactggatag acacacacac aggtaggata     660
nggtaaatna actacttaaa gaatggcctg ggatttaagt cctccagata ttttttaggt     720
ngnggtttcc taaaataaaa ttctggagtg ccaaaaaaaa aaaaaaaaa aaaaagcggg     780
cc                                                                   782

<210> SEQ ID NO 67
<211> LENGTH: 49
<212> TYPE: PRT
<213> ORGANISM: Rattus norvegicus

<400> SEQUENCE: 67

Met Ser Ser Ser His Leu Arg Thr Arg Ser Ala Arg Thr Pro Gly Lys
 1               5                  10                  15

Ile Pro Leu Ile Pro Ile Val Gly Asn Met Leu Pro Ala Val Gly His
                20                  25                  30

Leu Ile Tyr Thr Phe Ser Gly Leu Thr His Tyr Pro Lys Asn Leu Leu
            35                  40                  45

Thr

<210> SEQ ID NO 68
<211> LENGTH: 538
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 68
gtctagcgaa ccccttcggg aaacttcaac aaaggtacca gcaactacag cgccttgtcc      60
acccagattt cttcagccaa agtctcaga ctgagaaacg gttctcggag aagcattcga     120
ccctggtgaa tgatgcctac aagactcttc aggccccgt gagcagagga ctatatcttc     180
taaagctcca aggaatagaa attcctgaag ggacagatta tagaacagac agtcagttcc     240
ttgtggaaat catggaaatc aatgaaaaac tcgcagacgc caaagtgag gcagccatgg     300
aagaggtaga agccactgtc agagctaaac agaaagaatt tacggacaat ataaacagag     360
cttttgaaca aggtgatttt gaaaagcca aggaacttct tacaaaaatg agatactttt     420
caaacataga agaaaagatc aagttaagca agaaccctct ctagttgcta acttaaaggt     480
```

```
ttaaaaataa actttgtatt tcttcannnn nnannnnnan nntnnnnnag cggccgcc        538
```

<210> SEQ ID NO 69
<211> LENGTH: 70
<212> TYPE: PRT
<213> ORGANISM: Rattus norvegicus

<400> SEQUENCE: 69

```
Met Glu Ile Asn Glu Lys Leu Ala Asp Ala Lys Ser Glu Ala Ala Met
 1               5                  10                  15
Glu Glu Val Glu Ala Thr Val Arg Ala Lys Gln Lys Glu Phe Thr Asp
            20                  25                  30
Asn Ile Asn Arg Ala Phe Glu Gln Gly Asp Phe Glu Lys Ala Lys Glu
        35                  40                  45
Leu Leu Thr Lys Met Arg Tyr Phe Ser Asn Ile Glu Glu Lys Ile Lys
    50                  55                  60
Leu Ser Lys Asn Pro Leu
65                  70
```

<210> SEQ ID NO 70
<211> LENGTH: 805
<212> TYPE: DNA
<213> ORGANISM: Rattus norvegicus

<400> SEQUENCE: 70

```
tctagcgaac cccttcgcga aggggttcgc ttcttaccct gtggagaaag gggcaggagg     60
aacctcctgt gttaggagga agctggagct taccactgtg agaggacaga tgtggactga    120
gaattttctt agtgctcagt ggcacttccc aaggactccc ctccccttgt gctctgtgcg    180
gttttttagga cagctaagat gactgccacc tgttgtggca ggcccgattt gtcttgttct    240
ccccttactg tacccegata taatctctgt tgatcaacag gactacccca agaatccaca    300
tgttctcccc cgtaaccagg cagctgtctg gttcatgcct tcttcccttc aaacccaacc    360
cagcgccctt gttagtgaag aggtggtcca tggactgatg acaagttatt agcactggat    420
gctgttteca tagtgacaag cctataccte ttcccaccct ttagtgcgca gtgggctgct    480
gcttcagtat cctcccagct cagttttatt agatcaaagc tgcccttggg caccatgttg    540
gccacctcaa tcaccagcca aaatggtcgc tttgtccacc agaggtcaag ccatctttct    600
ggcgctgtag ttcccagctc cttctaggga acaggaagtt gatattgcca tgggggaggt    660
ggcgggggtgt ggccgtcacc tcaatagttt tactgtaaaa gggaaatttg aacaagaaca    720
acaacaaaaa aaaaaaaaaa acaaagaaaa aaataaaaaa ctttaaaagt tgaaaaaaaa    780
aaaaaaaaaa aaaaaaagcg gccgc                                          805
```

<210> SEQ ID NO 71
<211> LENGTH: 1407
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 71

```
tctagcgaac cccttcgctg ggacccgcaa ctaccaactg ccgcctggat cctaggtgag     60
ctgtgggctc tgacagcgct gtggctaaca tggcacccaa aagaagact ctcaagaaga    120
acaaacccga gatcaatgag atgaccatca tcgtggaaga cagccccta aacaagctga    180
```

-continued

```
atgctctaaa tgggctcctg gggggagaaa acagccttag ctgtgtttct ttcgaactaa        240
cagacacttc ttatggtccc aacctcctgg aaggtttaag taaaatgcgt caagagagct        300
ttctatgtga cttggtcatc ggtccaaaac caagtccttt gatgtccata agtcaagtga        360
tggcttcctg cagcgagtct tctataatat ccttaaaacg atccatcgac aaaaagggta        420
gacctcaatg atatcgnccc tttagggcta ccaccgtgat agcatatgca tacacnggaa        480
agctgccctt tctttataca caataaggaa gcatcatttc tgctgctgtg tacctccaga        540
tccacactct tgtgaagatg tgcagcgact ttctgatccg agagatcagt gttgagaact        600
gcatgtatgt tgttaacatg gctgaaacat actgcttgaa aaatgcgaaa gcaacggccc        660
agaaatttat ccgggataac ttcattgaat ttgccgactc cgaacaattt atgaagctga        720
cgtttgaaca gattaatgag cttctcatag atgatgactt gcagttgcct tctgagctgg        780
tagcattcca gattgcaatg aaatggatag aattcaacca aaagagagtg aagcacgctg        840
cggatctttt aagcaatatt cgctttggta ccatctctgc acaagacctg gtcaattacg        900
ttcaaaccgt accgagaatg atgcaagacg ctgattgtca taaactgctt gtggatgcta        960
tgaactacca cttactacct tatcatcaaa acacgttgca atctaggcgg acaagaatta       1020
gaggcggctg ccgggttctg atcactgtcg ggggacgccc tggcctgact gagaagtccc       1080
ttagtagaga cgtttatata gagaccctga aaatggatgg agcaagctta cagaaatgcc       1140
agccaagagt ttcaatcagt gtgtggctgt gatggatgga ttcctttatg tagcaggtgg       1200
tgaggaccag aatgatgcga gaaaccaagc caagcatgca gtcagcaatt tctgcaggta       1260
ccgatccccg cttcaacacg tggatccacc tgggcagcat gaaccagaag cgcacgcact       1320
tcagcctgag cgtgttcaac gggctcctgt acgccggtgg ngggcnccag tgnganggat       1380
atctgcagaa ttcggctagc cgaattc                                            1407
```

<210> SEQ ID NO 72
<211> LENGTH: 113
<212> TYPE: PRT
<213> ORGANISM: Rattus norvegicus

<400> SEQUENCE: 72

Met Ala Pro Lys Lys Thr Leu Lys Lys Asn Lys Pro Glu Ile Asn
1               5                   10                  15

Glu Met Thr Ile Ile Val Glu Asp Ser Pro Leu Asn Lys Leu Asn Ala
            20                  25                  30

Leu Asn Gly Leu Leu Gly Gly Glu Asn Ser Leu Ser Cys Val Ser Phe
        35                  40                  45

Glu Leu Thr Asp Thr Ser Tyr Gly Pro Asn Leu Leu Glu Gly Leu Ser
    50                  55                  60

Lys Met Arg Gln Glu Ser Phe Leu Cys Asp Leu Val Ile Gly Pro Lys
65                  70                  75                  80

Pro Ser Pro Leu Met Ser Ile Ser Gln Val Met Ala Ser Cys Ser Glu
                85                  90                  95

Ser Ser Ile Ile Ser Leu Lys Arg Ser Ile Asp Lys Lys Gly Arg Pro
            100                 105                 110

Gln

<210> SEQ ID NO 73
<211> LENGTH: 2004
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 73

```
tctagcgaac cccttcggac actgccagca tagacagcag ccctgctac tgtcccacca      60
ctgtacccca gagccccgac tagcagtatg ccgggagcgc cagggcctgg gcctgaggtg    120
gctgcagcct ttgaggaacg gttgagtcag gcactacagg aactgcaggc agtggctgaa    180
gcaggccggt cagcggtgac ccaggcagct gatgcagccc tagccactgt agagccagtg    240
gctcaggcat ctgaagagct tcgggccgag acagcagccc tgagccggcg gctggatgcc    300
ctgaccaggc aggtggaggt gctgagccta cggctgggtg ttccactcgt gccggacctg    360
gagtccgagc tagagcccag cgagctgttg ctggctgctg ccgaccctga ggccctcttc    420
caggcaagct gaggatgctg gaccccgt ggccacccgc ctgcctttag cacccgccgc    480
agctcttctg cgggcccctc tcgaagcagc agtctcatgg agcccgatcc agcagagccc    540
ccctctgcca cagtggaagc agctaatgga acagagcaga ctctggacaa agtgaacaaa    600
ggcccagagg ggcggagccc cctgagtgca gaggagctga tggccattga ggacgaagga    660
atcctggaca agatgctgga ccaggctacg aactttgaag agcggaagct catccgggct    720
gcgctccgtg agctccgaca aagaaagaga ccagagggg acaaggaacg agaacggcgg    780
ctacgagagg cacgggcccg gccaggcgag agccgaagca atatggctac tacagagacc    840
accaccaggc acaagccaga gggcggctga tggctcggcg gtcagcacag ttaccaaaac    900
tgagcgggtc gtccactcca atgacggcac gcagactgcg cgcaccacca cagtggagtc    960
gagtttcgtg aggcgctcgg agaatggcag cagcaagcaa gcagcagcac cacggtccaa   1020
accaagacct tttcctcttc ctcttcctca tccaaaaaaa tgggcagtat cttcgaccga   1080
gaggaccaaa ccagctcacg ttctggcagc ctggcggccc tcgaaaaacg ccaggcagag   1140
aagaagaaag agctcatgaa ggcacagagt ctgcccaaga cctaagcgtc ccaagcacgc   1200
aaggccatga ttgagaaact agagaaggaa ggctcttcgg gcagtcctgg cacacccgt   1260
acagcggtac agcgttctac cagcttcgga gtccccaacg ccaacagcat caagcagatg   1320
ttgctggact ggtgccgagc caagaccctg gctacgagc acgtggacat ccagaacttc   1380
tctccagctg gagtgatggg atggctttct gtgccctggt gcacaatttc ttccctgagg   1440
cttttgacta tggacagctt agcccacaaa accggcgcca gaacttttgaa atggccttct   1500
catctgctga gacccatgcg gactgcccgc agctcctgga tacagaggac atggtgcggc   1560
ttcgagagcc tgactggaag tgcgtgtaca cgtacatcca ggagttctac cgctgtctgg   1620
tccagaaggg gctggtaaaa accaaaaagt cctaaccct gcttgggggcc ccacggatgc   1680
tggtggactg tgtaccettg gtggaggtgg aggacatgat gatcatgggc aaaaagccag   1740
accctaagtg cgtcttcacc tacgtgcaat cgctgtacaa ccacctgcgg cgccatgagc   1800
tgcgcctgcg cggcaagaat gtctagccac tgctcacacc gcctgcgctg caggctgctg   1860
tcccacgccc ccaacaccgg nccctncagt gngcctgcca ctgntgcccg tntgtcgaaa   1920
cacctntccc cttgtcacac gcagngnttt gataaattat ttgnttttnaa caaaaaaaaa   1980
aaaaaaaaaa aaaaaagcgg ccgc                                         2004
```

<210> SEQ ID NO 74
<211> LENGTH: 114
<212> TYPE: PRT

<213> ORGANISM: Rattus norvegicus

<400> SEQUENCE: 74

| Met | Pro | Gly | Ala | Pro | Gly | Pro | Gly | Pro | Glu | Val | Ala | Ala | Phe | Glu |
|---|---|---|---|---|---|---|---|---|---|---|---|---|---|---|
| 1 | | | | 5 | | | | | 10 | | | | | 15 |

| Glu | Arg | Leu | Ser | Gln | Ala | Leu | Gln | Glu | Leu | Gln | Ala | Val | Ala | Glu | Ala |
|---|---|---|---|---|---|---|---|---|---|---|---|---|---|---|---|
| | | | 20 | | | | | 25 | | | | | 30 | | |

Gly Arg Ser Ala Val Thr Gln Ala Ala Asp Ala Ala Leu Ala Thr Val
            35                  40                  45

Glu Pro Val Ala Gln Ala Ser Glu Gly Leu Arg Ala Glu Thr Ala Ala
 50                  55                  60

Leu Ser Arg Arg Leu Asp Ala Leu Thr Arg Gln Val Glu Val Leu Ser
65                  70                  75                  80

Leu Arg Leu Gly Val Pro Leu Val Pro Asp Leu Glu Ser Glu Leu Glu
                85                  90                  95

Pro Ser Glu Leu Leu Leu Ala Ala Asp Pro Glu Ala Leu Phe Gln
            100                 105                 110

Ala Ser

<210> SEQ ID NO 75
<211> LENGTH: 881
<212> TYPE: DNA
<213> ORGANISM: Rattus norvegicus

<400> SEQUENCE: 75

```
tctagcgaac cccttcgctc agggcgtttt gcctcctgct gacttgctct tcaccattag    60
acaagcctga cgtcaagacc ccaatggcta acgaagctaa cccttgccca tgtgacattg   120
gtcacaggct agactatggt ggcatgggcc aggaagttca ggttgagcac atcaaggcat   180
atgtcacccg gtcccctgtg gatgcaggca agctgtgat tgttgtccag gatatatttg    240
gctggcagct gtccaacacc aggtatatgg ctgacatgat tgctggaaat ggatacacaa   300
ctattgccca gacttctttg tgggtcaaga gccatggac ccggctggtg attggtccac    360
cttccctgag tggttgaaat caagaaatgc cagaaaaatc aaccgagagg ttgatgctgt   420
cttgaggtat ctgaaacaac agtgtcatgc ccagaagatt ggcattgtgg gcttctgctg   480
gggggtatt gtggtgcacc acgtgatgac gacatatcca gaagtcagag cggggggtgtc   540
tgtctatggt atcatcagag attctgaaga tgtttataat ttgaagaacc caacgttgtt   600
tatctttgca gaaaatgatg ctgtgattcc acttgagcag gtttctatac tgatccagaa   660
gcttaaagaa cactgcatag ttaattacca agttaagaca ttttctgggc aaactcatgg   720
ctttgtgcat cggaagagag aagactgctc ccctgcagac aaaccctaca ttgaggaagc   780
gaggaggaat ctcatcgaat ggctgaacaa gtatatttaa cagcactcaa gcacaaattt   840
tgaataatta aattgacccg ataattaaa ttgacccgaa t                        881
```

<210> SEQ ID NO 76
<211> LENGTH: 97
<212> TYPE: PRT
<213> ORGANISM: Rattus norvegicus

<400> SEQUENCE: 76

Met Ala Asn Glu Ala Asn Pro Cys Pro Cys Asp Ile Gly His Arg Leu
 1               5                  10                  15

Asp Tyr Gly Gly Met Gly Gln Glu Val Gln Val Glu His Ile Lys Ala
            20                  25                  30

```
Tyr Val Thr Arg Ser Pro Val Asp Ala Gly Lys Ala Val Ile Val Val
         35                  40                  45

Gln Asp Ile Phe Gly Trp Gln Leu Ser Asn Thr Arg Tyr Met Ala Asp
 50                  55                  60

Met Ile Ala Gly Asn Gly Tyr Thr Thr Ile Ala Gln Thr Ser Leu Trp
 65                  70                  75                  80

Val Lys Ser His Gly Thr Arg Leu Val Ile Gly Pro Pro Ser Leu Ser
             85                  90                  95

Gly

<210> SEQ ID NO 77
<211> LENGTH: 25
<212> TYPE: DNA
<213> ORGANISM: Artificial Sequence
<220> FEATURE:
<223> OTHER INFORMATION: Primer specific for vector to produce "Driver
      DNA".

<400> SEQUENCE: 77
cgtatgttgt gtggaattgt gagcg                                          25

<210> SEQ ID NO 78
<211> LENGTH: 25
<212> TYPE: DNA
<213> ORGANISM: Artificial Sequence
<220> FEATURE:
<223> OTHER INFORMATION: Primer specific for vector to produce "Driver
      DNA".

<400> SEQUENCE: 78
gatgtgctgc aaggcgatta agttg                                          25

<210> SEQ ID NO 79
<211> LENGTH: 28
<212> TYPE: DNA
<213> ORGANISM: Artificial Sequence
<220> FEATURE:
<223> OTHER INFORMATION: Oligos corresponding to polylinker sequence.

<400> SEQUENCE: 79
gccgccagtg tgctggaatt cggctagc                                       28

<210> SEQ ID NO 80
<211> LENGTH: 28
<212> TYPE: DNA
<213> ORGANISM: Artificial Sequence
<220> FEATURE:
<223> OTHER INFORMATION: Oligos corresponding to polylinker sequence.

<400> SEQUENCE: 80
cgaattctgc agatatccat cacactgg                                       28

<210> SEQ ID NO 81
<211> LENGTH: 25
<212> TYPE: DNA
<213> ORGANISM: Artificial Sequence
<220> FEATURE:
<223> OTHER INFORMATION: Oligos corresponding to polylinker sequence.

<400> SEQUENCE: 81
ctagagggcc caattcgccc tatag                                          25

<210> SEQ ID NO 82
<211> LENGTH: 25
```

```
-continued

<212> TYPE: DNA
<213> ORGANISM: Artificial Sequence
<220> FEATURE:
<223> OTHER INFORMATION: Oligos corresponding to polylinker sequence.

<400> SEQUENCE: 82
tgagtcgtat tacaattcac tggcc                                        25

<210> SEQ ID NO 83
<211> LENGTH: 20
<212> TYPE: DNA
<213> ORGANISM: Artificial Sequence
<220> FEATURE:
<223> OTHER INFORMATION: Oligos corresponding to polylinker sequence.

<400> SEQUENCE: 83
gctcggatcc actagtaacg                                              20

<210> SEQ ID NO 84
<211> LENGTH: 18
<212> TYPE: DNA
<213> ORGANISM: Artificial Sequence
<220> FEATURE:
<223> OTHER INFORMATION: Oligos corresponding to polylinker sequence.

<400> SEQUENCE: 84
tttttttttt tttttttt                                                18
```

SECRETED FACTORS

CROSS-REFERENCE TO RELATED APPLICATIONS

This application is a divisional of U.S. patent application Ser. No. 09/809,545, filed Mar. 14, 2001, now U.S. Pat. No. 6,800,455, which claims the benefit of priority under Title 35, United States Code § 119(e) of U.S. provisional application No. 60/193,548 filed on Mar. 31, 2000, both of which are hereby incorporated by reference in their entirety.

TECHNICAL FIELD

The present invention concerns secreted factors encoded by genes differentially regulated in certain diseased tissues. More particularly, the invention concerns nucleic acid encoding novel secreted polypeptide factors, the encoded polypeptides, and compositions containing and methods and means for producing them. The invention further concerns methods based on the use of such nucleic acids and/or polypeptides in the diagnosis and treatment of various diseases, in particular cardiac, renal, or inflammatory diseases.

BACKGROUND ART

Gene expression patterns, including changes in gene expression between normal and diseased tissues or tissues in various stages of disease progression provide valuable insight into the molecular determinants of normal and abnormal cellular physiology. Accordingly, genes that are differentially expressed in subjects suffering from a disease, such as cardiac, renal or inflammatory disease, relative to normal subjects, are useful targets for intervention to diagnose, prevent or treat such diseases.

Techniques have been developed to efficiently analyze the level of expression of specific genes in cells and tissues. Procedures that can be used to identify and clone differentially expressed genes include, for example, subtractive hybridization (Jiang and Fisher, *Mol. Cell. Different.* (1993) 1:285–299; Jiang, et al., *Oncogene* (1995) 10:1855–1864; Sagerstrom, et al., *Annu. Rev. Biochem.* (1997) 66:751–83); differential RNA display (DDRT-PCR) (Watson, et al., *Developmental Neuroscience* (1993) 15:77–86; Liang and Pardee, *Science* (1992) 257:967–971); RNA fingerprinting by arbitrarily primed PCR (RAP-PCR) (Ralph, et al., *Proc. Natl. Acad. Sci. USA* (1993) 90:10710–10714; McClelland and Welsh, *PCR Methods and Applications* (1994) 4:S66–81); representational difference analysis (RDA) (Hubank and Schatz, *Nucl. Acids Res.* (1994) 22:5640–5648); serial analysis of gene expression (SAGE) (Velculescu, et al., *Science* (1995) 270:484–487; Zhang, et al., *Science* (1997) 276:1268–1272); electronic subtraction (Wan, et al., *Nature Biotechnology* (1996) 14:1685–1691); combinatorial gene matrix analyses (Schena, et al., *Science* (1995) 270: 467–470), and various modifications and improvements of these and similar techniques.

A particularly attractive method for assessing gene expression is the DNA microarray technique. In this method, nucleotide sequences of interest are plated, or arrayed, on a porous or non-porous substrate that can be paper, nylon or other type of membrane, filter, chip, glass slide or any other suitable solid support. The arrayed sequences are then hybridized with specific DNA probes from cells or tissues of interest. Microarrays of biological materials have been described in a number of patents and patent applications, including, for example, U.S. Pat. Nos. 5,744,305; 5,800,992; 5,807,522; and 5,716,785; and European Patent No. 0 373 203.

The DNA microarray technique can be used to monitor the expression level of large numbers of genes simultaneously (to produce a transcript image), and to identify genetic variants, mutations and polymorphisms. This information may be used to determine gene function, understanding the genetic basis of disease, diagnosing disease, and developing and monitoring the activities of therapeutic agents.

An important application of the microarray method allows for the assessment of differential gene expression in pairs of mRNA samples from two different tissues, or in the same tissue comparing normal versus disease states or time progression of the disease. Microarray analysis allows one to analyze the expression of known genes of interest, or to discover novel genes expressed differentially in tissues of interest. Thus, an attractive application of this technology is as a fundamental discovery tool to identify new genes, and their corresponding expression products, which contribute to the pathogenesis of disease and related conditions.

Microarray technology has been successfully applied to large-scale analysis of human gene expression to identify cancer-specific genes and inflammatory-specific genes (DeRisi, et al., *Nat. Genet.* (1996) 14(4):457–460; Heller, et al, *Proc. Natl. Acad. Sci. USA* (1997) 94(6):2150–2155). DeRisi, et al., examined a pre-selected set of 870 different genes for their expression in a melanoma cell line and a non-tumorigenic version of the same cell line. The microarray analysis revealed a decrease in expression for 15/870 (1.7%) and an increase in expression for 63/870 (7.3%) of the genes in non-tumorigenic relative to tumorigenic cells (differential expression values <0.52 or >2.4 were deemed significant). Heller, et al., employed microarrays to evaluate the expression of 1,000 genes in cells taken from normal and inflamed human tissues. The results indicated that altered expression was evident in genes encoding inflammatory mediators such as IL-3, and a tissue metalloprotease. These results illustrate the utility of applying microarray technology to complex human diseases.

It would be beneficial to discover differentially expressed genes that are related to diseases or various disease states. It would further be beneficial to develop methods and compositions for the diagnostic evaluation and prognosis of conditions involving such diseases, for the identification of subjects exhibiting a predisposition to such conditions, for modulating the effect of these differentially expressed genes and their expression products, for monitoring patients undergoing clinical evaluation for the prevention and treatment of a disease, specifically cardiac, kidney or inflammatory disease, and for monitoring the efficacy of compounds used in clinical trials.

Secreted proteins mediate key biological processes including cell to cell interactions as well as important cellular functions such as cell growth and differentiation, and most protein-based drugs are secreted proteins including insulin, growth hormone, interferons, tissue plasminogen activator (tPA), and erythropoietin (EPO). It would, therefore, be particularly desirable to identify novel differentially expressed genes encoding secreted proteins.

DISCLOSURE OF THE INVENTION

In one aspect, the present invention concerns an isolated nucleic acid molecule comprising a poly- or oligonucleotide selected from the group consisting of:

(a) a polynucleotide encoding a polypeptide having at least about 80% sequence identity with amino acids selected from the group consisting of: 1 to 1203 of SEQ ID NO: 2, amino acids 1 to 193 of SEQ ID NO: 4, amino acids 1 to 236 of SEQ ID NO: 6, amino acids 1 to 61 of SEQ ID NO: 8, amino acids 1 to 79 of SEQ ID NO:10, amino acids 1 to 92 of SEQ ID NO: 12, amino acids 1 to 86 of SEQ ID NO: 14, amino acids 1 to 36 of SEQ ID NO: 16, amino acids 1 to 83 of SEQ ID NO: 18, amino acids 1 to 82 of SEQ ID NO: 20, amino acids 1 to 462 of SEQ ID NO: 22, amino acids 1 to 170 of SEQ ID NO: 24, amino acids −26 to 233 of FIG. 13 (amino acids 1 to 259 of SEQ ID NO: 26), amino acids 1 to 30 of SEQ ID NO: 28, amino acids 1 to 39 of SEQ ID NO: 30, amino acids 1 to 541 of SEQ ID NO: 33, amino acids 1 to 30 of SEQ ID NO: 35, amino acids 1 to 100 of SEQ ID NO: 37, amino acids 1 to 65 of SEQ ID NO: 39, amino acids 1 to 42 of SEQ ID NO: 41, amino acids 1 to 46 of SEQ ID NO: 43, amino acids 1 to 313 of SEQ ID NO: 46, amino acids 1 to 58 of SEQ ID NO: 51, amino acids −35 to 387 of FIG. 29 (amino acids 1 to 422 of SEQ ID NO: 53), amino acids 1 to 58 of SEQ ID NO: 55, amino acids 1 to 52 of SEQ ID NO: 57, amino acids 1 to 245 of SEQ ID NO: 59, amino acids 1 to 142 of SEQ ID NO: 63, amino acids 1 to 49 of SEQ ID NO: 67, amino acids 1 to 70 of SEQ ID NO: 69, amino acids 1 to 113 of SEQ ID NO: 72, and amino acids 1 to 114 of SEQ ID NO: 74, and amino acids 1 to 97 of SEQ ID NO: 76; or a transmembrane domain (membrane spanning segment/region) deleted or inactivated variant thereof;

(b) a polynucleotide encoding a polypeptide having at least about 80% sequence identity with amino acids 1 to 233 of SEQ ID NO: 26, or amino acids 1 to 387 of SEQ ID NO: 53;

(c) a polynucleotide encoding amino acids selected from the group consisting of: 1 to 203 of SEQ ID NO: 2, amino acids 1 to 193 of SEQ ID NO: 4, amino acids 1 to 236 of SEQ ID NO: 6, amino acids 1 to 61 of SEQ ID NO: 8, amino acids 1 to 79 of SEQ ID NO: 10, amino acids 1 to 92 of SEQ ID NO: 12, amino acids 1 to 86 of SEQ ID NO: 14, amino acids 1 to 36 of SEQ ID NO: 16, amino acids 1 to 83 of SEQ ID NO: 18, amino acids 1 to 82 of SEQ ID NO: 20, amino acids 1 to 462 of SEQ ID NO: 22, amino acids 1 to 170 of SEQ ID NO: 24, amino acids −26 to 233 of FIG. 13 (amino acids 1 to 259 of SEQ ID NO: 26), amino acids 1 to 30 of SEQ ID NO: 28, amino acids 1 to 39 of SEQ ID NO: 30, amino acids 1 to 541 of SEQ ID NO: 33, amino acids 1 to 30 of SEQ ID NO: 35, amino acids 1 to 100 of SEQ ID NO: 37, amino acids 1 to 65 of SEQ ID NO: 39, amino acids 1 to 42 of SEQ ID NO: 41, amino acids 1 to 46 of SEQ ID NO: 43, amino acids 1 to 313 of SEQ ID NO: 46, amino acids 1 to 58 of SEQ ID NO: 51, amino acids −35 to 387 of FIG. 29 (amino acids 1 to 422 of SEQ ID NO: 53), amino acids 1 to 58 of SEQ ID NO: 55, amino acids 1 to 52 of SEQ ID NO: 57, amino acids 1 to 245 of SEQ ID NO: 59, amino acids 1 to 142 of SEQ ID NO: 63, amino acids 1 to 49 of SEQ ID NO: 67, amino acids 1 to 70 of SEQ ID NO: 69, amino acids 1 to 113 of SEQ ID NO: 72, and amino acids 1 to 114 of SEQ ID NO: 74, and amino acids 1 to 97 of SEQ ID NO: 76; or a transmembrane domain (membrane spanning segment/region) deleted or inactivated variant thereof;

(d) a polynucleotide selected from the group consisting of: a polynucleotide hybridizing under stringent conditions with the complement of the coding region of SEQ ID NO: 1, wherein said polynucleotide encodes a polypeptide having at least one biological activity of the polypeptide encoded by clone P00184_D11 (SEQ ID NO: 1), a polynucleotide hybridizing under stringent conditions with the complement of the coding region of SEQ ID NO: 3, wherein said polynucleotide encodes a polypeptide having at least one biological activity of the polypeptide encoded by clone P00185_D11 (SEQ ID NO: 3); a polynucleotide hybridizing under stringent conditions with the complement of the coding region of SEQ ID NO: 5, wherein said polynucleotide encodes a polypeptide having at least one biological activity of the polypeptide encoded by clone P00188_D12 (SEQ ID NO: 5), a polynucleotide hybridizing under stringent conditions with the complement of the coding region of SEQ ID NO: 7, wherein said polynucleotide encodes a polypeptide having at least one biological activity of the polypeptide encoded by clone P00188_E01 (SEQ ID NO: 7), a polynucleotide hybridizing under stringent conditions with the complement of the coding region of SEQ ID NO: 9, wherein said polynucleotide encodes a polypeptide having at least one biological activity of the polypeptide encoded by clone P00194_G01 (SEQ ID NO: 9), a polynucleotide hybridizing under stringent conditions with the complement of the coding region of SEQ ID NO: 11, wherein said polynucleotide encodes a polypeptide having at least one biological activity of the polypeptide encoded by clone P00194_G05 (SEQ ID NO: 11), a polynucleotide hybridizing under stringent conditions with the complement of the coding region of SEQ ID NO: 13, wherein said polynucleotide encodes a polypeptide having at least one biological activity of the polypeptide encoded by clone P00194_H10 (SEQ ID NO: 13), a polynucleotide hybridizing under stringent conditions with the complement of the coding region of SEQ ID NO: 15, wherein said polynucleotide encodes a polypeptide having at least one biological activity of the polypeptide encoded by clone P00199_D08 (SEQ ID NO: 15), a polynucleotide hybridizing under stringent conditions with the complement of the coding region of SEQ ID NO: 17, wherein said polynucleotide encodes a polypeptide having at least one biological activity of the polypeptide encoded by clone P00203_D04 (SEQ ID NO: 17), a polynucleotide hybridizing under stringent conditions with the complement of the coding region of SEQ ID NO: 19, wherein said polynucleotide encodes a polypeptide having at least one biological activity of the polypeptide encoded by clone P00203_E06 (SEQ ID NO: 19), a polynucleotide hybridizing under stringent conditions with the complement of the coding region of SEQ ID NO: 21, wherein said polynucleotide encodes a polypeptide having at least one biological activity of the polypeptide encoded by clone P00209_F06 (SEQ ID NO: 21), a polynucleotide hybridizing under stringent conditions with the complement of the coding region of SEQ ID NO: 23, wherein said polynucleotide encodes a polypeptide having at least one biological activity of the polypeptide encoded by clone P00219_D02 (SEQ ID NO: 23), a polynucleotide hybridizing under stringent conditions with the complement of the coding region of SEQ ID NO: 25, wherein said polynucleotide encodes a polypeptide having at least one biological activity of the polypeptide encoded by clone P00219_F06 (SEQ ID NO: 25), a polynucleotide hybridizing under stringent conditions with the complement of the coding region of SEQ ID NO: 27, wherein said polynucleotide encodes a polypeptide having at least one biological activity of the polypeptide encoded by clone P00220_HO5 (SEQ ID NO: 27), a polynucleotide hybridizing under stringent conditions with the complement of the coding region of SEQ ID NO: 29, wherein said polynucleotide encodes a polypeptide having at least one biological activity of the polypeptide encoded by clone P00222_G03 (SEQ ID NO: 29), a polynucleotide hybridizing under stringent conditions with the complement of the polynucleotide of SEQ ID NO: 31 (clone P00223_F07), a polynucleotide hybridizing under stringent conditions with the complement of the coding region of SEQ ID NO: 32, wherein said polynucleotide encodes a polypeptide having at least one biological activity of the polypeptide encoded by clone P00225_C01 (SEQ ID NO: 32), a polynucleotide hybridizing under stringent conditions with the complement of the coding region of SEQ ID NO: 34, wherein said polynucleotide encodes a polypeptide having at least one biological activity of the polypeptide encoded by clone P00227_D11 (SEQ ID NO: 34), a polynucleotide hybridizing under stringent conditions with the complement of the coding region of SEQ ID NO: 36, wherein said polynucleotide encodes a polypeptide having at least one biological activity of the polypeptide encoded by clone P00228_F03 (SEQ ID NO: 36), a polynucleotide hybridizing under stringent conditions with the complement of the coding region of SEQ ID NO: 38, wherein said polynucleotide encodes a polypeptide having at least one biological activity of the polypeptide encoded by clone P00233_H08 (SEQ ID NO: 38), a polynucleotide hybridizing under stringent conditions with the complement of the coding region of SEQ ID NO: 40, wherein said polynucleotide encodes a polypeptide having at least one biological activity of the polypeptide encoded by clone P00235_G08 (SEQ ID NO: 40), a polynucleotide hybridizing under stringent conditions with the complement of the coding region of SEQ ID NO: 42, wherein said polynucleotide encodes a polypeptide having at least one biological activity of the polypeptide encoded by clone P00239_C11 (SEQ ID NO: 42), a polynucleotide hybridizing under stringent conditions with the complement of the polynucleotide of SEQ ID NO: 44 (clone P00240_B04), a polynucleotide hybridizing under stringent conditions with the complement of the coding region of SEQ ID NO: 45, wherein said polynucleotide encodes a polypeptide having at least one biological activity of the polypeptide encoded by clone P00240_E05 (SEQ ID NO: 45), a polynucleotide hybridizing under stringent conditions with the complement of the polynucleotide of SEQ ID NO: 47 (clone P00241_E12), a polynucleotide hybridizing under stringent conditions with the complement of the polynucleotide of SEQ ID NO: 48 (clone P00245_D06), a polynucleotide hybridizing under stringent conditions with the complement of the polynucleotide of SEQ ID NO: 49 (clone P00246_D12), a polynucleotide hybridizing under stringent conditions with the complement of the coding region of SEQ ID NO: 50, wherein said polynucleotide encodes a polypeptide having at least one biological activity of the polypeptide encoded by clone P00247_A04 (SEQ ID NO: 50), a polynucleotide hybridizing under stringent conditions with the complement of the coding region of SEQ ID NO: 52, wherein said polynucleotide encodes a polypeptide having at least one biological activity of the polypeptide encoded by clone P00248_B04 (SEQ ID NO: 52), a polynucleotide hybridizing under stringent conditions with the complement of the coding region of SEQ ID NO: 54, wherein said polynucleotide encodes a polypeptide having at least one biological activity of the polypeptide encoded by clone P00249_F09 (SEQ ID NO: 54), a polynucleotide hybridizing under stringent conditions with the complement of the coding region of SEQ ID NO: 56, wherein said polynucleotide encodes a polypeptide having at least one biological activity of the polypeptide encoded by clone P00258_A10 (SEQ ID NO: 56), a polynucleotide hybridizing under stringent conditions with the complement of the coding region of SEQ ID NO: 58, wherein said polynucleotide encodes a polypeptide having at least one biological activity of the polypeptide encoded by clone P00262_C10 (SEQ ID NO: 58), a polynucleotide hybridizing under stringent conditions with the complement of the polynucleotide of SEQ ID NO: 60 (clone P00263_GO6), a polynucleotide hybridizing under stringent conditions with the complement of the polynucleotide of SEQ ID NO: 61 (clone P00267_F08), a polynucleotide hybridizing under stringent conditions with the complement of the coding region of SEQ ID NO: 62, wherein said polynucleotide encodes a polypeptide having at least one biological activity of the polypeptide encoded by clone P00269_H08 (SEQ ID NO: 62), a polynucleotide hybridizing under stringent conditions with the complement of the polynucleotide of SEQ ID NO: 64 (clone P00312_C04), a polynucleotide hybridizing under stringent conditions with the complement of the polynucleotide of SEQ ID NO: 65 (clone P00324_H02), a polynucleotide hybridizing under stringent conditions with the complement of the coding region of SEQ ID NO: 66, wherein said polynucleotide encodes a polypeptide having at least one biological activity of the polypeptide encoded by clone P00628_H02 (SEQ ID NO: 66), a polynucleotide hybridizing under stringent conditions with the complement of the coding region of SEQ ID NO: 68, wherein said polynucleotide encodes a polypeptide having at least one biological activity of the polypeptide encoded by clone P00629_C08 (SEQ ID NO: 68), a polynucleotide hybridizing under stringent conditions with the complement of the polynucleotide of SEQ ID NO: 70 (clone P00634_G11), a polynucleotide hybridizing under stringent conditions with the complement of the coding region of SEQ ID NO: 71, wherein said polynucleotide encodes a polypeptide having at least one biological activity of the polypeptide encoded by clone P00641_G11 (SEQ ID NO: 71), a polynucleotide hybridizing under stringent conditions with the complement of the coding region of SEQ ID NO: 73, wherein said polynucleotide encodes a polypeptide having at least one biological activity of the polypeptide encoded by clone P00648_E12 (SEQ ID NO: 73), and a polynucleotide hybridizing under stringent conditions with the complement of the coding region of SEQ ID NO: 75 wherein said polynucleotide encodes a polypeptide having at least one biological activity of the polypeptide encoded by clone P00697_C03 (SEQ ID NO: 75);

(e) a polynucleotide encoding at least about 50 contiguous amino acids from amino acids selected from the group consisting of: amino acids 1 to 203 of SEQ ID NO: 2, wherein said polynucleotide encodes a polypeptide having at least one biological activity of the polypeptide encoded by clone P00184_D11 (SEQ ID NO: 1), a polynucleotide encoding at least about 50 contiguous amino acids from amino acids 1 to 193 of SEQ ID NO: 4, wherein said polynucleotide encodes a polypeptide having at least one biological activity of the polypeptide encoded by clone P00185_D11 (SEQ ID NO: 3); a polynucleotide encoding at least about 50 contiguous amino acids from amino acids 1 to 236 of SEQ ID NO: 6, wherein said polynucleotide encodes a polypeptide having at least one biological activity of the polypeptide encoded by clone P00188_D12 (SEQ ID NO: 5), a polynucleotide encoding at least about 50 contiguous amino acids from amino acids 1 to 61 of SEQ ID NO: 8, wherein said polynucleotide encodes a polypeptide having at least one biological activity of the polypeptide encoded by clone P00188_E01 (SEQ ID NO: 7), a polynucleotide encoding at least about 50 contiguous amino acids from amino acids 1 to 79 of SEQ ID NO: 10, wherein said polynucleotide encodes a polypeptide having at least one biological activity of the polypeptide encoded by clone P00194_G01 (SEQ ID NO: 9), a polynucleotide encoding at least about 50 contiguous amino acids from amino acids 1 to 92 of SEQ ID NO: 12, wherein said polynucleotide encodes a polypeptide having at least one biological activity of the polypeptide encoded by clone P00194_G05 (SEQ ID NO: 11), a polynucleotide encoding at least about 50 contiguous amino acids from amino acids 1 to 86 of SEQ ID NO: 14, wherein said polynucleotide encodes a polypeptide having at least one biological activity of the polypeptide encoded by clone P00194_H10 (SEQ ID NO: 13), a polynucleotide encoding at least about 50 contiguous amino acids from amino acids 1 to 36 of SEQ ID NO: 16, wherein said polynucleotide encodes a polypeptide having at least one biological activity of the polypeptide encoded by clone P00199_D08 (SEQ ID NO: 15), a polynucleotide encoding at least about 50 contiguous amino acids from amino acids 1 to 83 of SEQ ID NO: 18, wherein said polynucleotide encodes a polypeptide having at least one biological activity of the polypeptide encoded by clone P00203_D04 (SEQ ID NO: 17), a polynucleotide encoding at least about 50 contiguous amino acids from amino acids 1 to 82 of SEQ ID NO: 20, wherein said polynucleotide encodes a polypeptide having at least one biological activity of the polypeptide encoded by clone P00203_E06 (SEQ ID NO: 19), a polynucleotide encoding at least about 50 contiguous amino acids from amino acids 1 to 462 of SEQ ID NO: 22, wherein said polynucleotide encodes a polypeptide having at least one biological activity of the polypeptide encoded by clone P00209_F06 (SEQ ID NO: 21), a polynucleotide encoding at least about 50 contiguous amino acids from amino acids 1 to 170 of SEQ ID NO: 24, wherein said polynucleotide encodes a polypeptide having at least one biological activity of the polypeptide encoded by clone P00219_D02 (SEQ ID NO: 23), a polynucleotide encoding at least about 50 contiguous amino acids from amino acids −26 to 233 of FIG. 13 (amino acids 1 to 259 of SEQ ID NO: 26), wherein said polynucleotide encodes a polypeptide having at least one biological activity of the polypeptide encoded by clone P00219_F06 (SEQ ID NO: 25), a polynucleotide encoding at least about 50 contiguous amino acids from amino acids 1 to 30 of SEQ ID NO: 28, wherein said polynucleotide encodes a polypeptide having at least one biological activity of the polypeptide encoded by clone P00220_H05 (SEQ ID NO: 27), a polynucleotide encoding at least about 50 contiguous amino acids from amino acids 1 to 39 of SEQ ID NO: 30, wherein said polynucleotide encodes a polypeptide having at least one biological activity of the polypeptide encoded by clone P00222_G03 (SEQ ID NO: 29), a polynucleotide encoding at least about 50 contiguous amino acids from amino acids 1 to 541 of SEQ ID NO: 33, wherein said polynucleotide encodes a polypeptide having at least one biological activity of the polypeptide encoded by clone P00225_C01 (SEQ ID NO: 32), a polynucleotide encoding at least about 50 contiguous amino acids from amino acids 1 to 30 of SEQ ID NO: 35, wherein said polynucleotide encodes a polypeptide having at least one biological activity of the polypeptide encoded by clone P00227_D11 (SEQ ID NO: 34), a polynucleotide encoding at least about 50 contiguous amino acids from amino acids 1 to 100 of SEQ ID NO: 37, wherein said polynucleotide encodes a polypeptide having at least one biological activity of the polypeptide encoded by clone P00228_F03 (SEQ ID NO: 36), a polynucleotide encoding at least about 50 contiguous amino acids from amino acids 1 to 65 of SEQ ID NO: 39, wherein said polynucleotide encodes a polypeptide having at least one biological activity of the polypeptide encoded by clone P00233_H08 (SEQ ID NO: 38), a polynucleotide encoding at least about 50 contiguous amino acids from amino acids 1 to 65 of SEQ ID NO: 39, wherein said polynucleotide encodes a polypeptide having at least one biological activity of the polypeptide encoded by clone P00235_G08 (SEQ ID NO: 40), a polynucleotide encoding at least about 50 contiguous amino acids from amino acids 1 to 46 of SEQ ID NO: 43, wherein said polynucleotide encodes a polypeptide having at least one biological activity of the polypeptide encoded by clone P00239_C11 (SEQ ID NO: 42), a polynucleotide encoding at least about 50 contiguous amino acids from amino acids 1 to 313 of SEQ ID NO: 46, wherein said polynucleotide encodes a polypeptide having at least one biological activity of the polypeptide encoded by clone P00240_E05 (SEQ ID NO: 45), a polynucleotide encoding at least about 50 contiguous amino acids from amino acids 1 to 58 of SEQ ID NO: 51, wherein said polynucleotide encodes a polypeptide having at least one biological activity of the polypeptide encoded by clone P00247_A04 (SEQ ID NO: 50), a polynucleotide encoding at least about 50 contiguous amino acids from amino acids −35 to 387 of FIG. 29 (amino acids 1 to 422 of SEQ ID NO: 53), wherein said polynucleotide encodes a polypeptide having at least one biological activity of the polypeptide encoded by clone P00248_B04 (SEQ ID NO: 52), a polynucleotide encoding at least about 50 contiguous amino acids from amino acids 1 to 58 of SEQ ID NO: 55, wherein said polynucleotide encodes a polypeptide having at least one biological activity of the polypeptide encoded by clone P00249_F09 (SEQ ID NO: 54), a polynucleotide encoding at least about 50 contiguous amino acids from amino acids 1 to 52 of SEQ ID NO: 57, wherein said polynucleotide encodes a polypeptide having at least one biological activity of the polypeptide encoded by clone P00258_A10 (SEQ ID NO: 56), a polynucleotide encoding at least about 50 contiguous amino acids from amino acids 1 to 245 of SEQ ID NO: 59, wherein said polynucleotide encodes a polypeptide having at least one biological activity of the polypeptide encoded by clone P00262_C10 (SEQ ID NO: 58), a polynucleotide encoding at least about 50 contiguous amino acids from amino acids 1 to 142 of SEQ ID NO: 63, wherein said polynucleotide encodes a polypeptide having at least one biological activity of the polypeptide encoded by clone P00269_H08 (SEQ ID NO: 62), a polynucleotide encoding at least about 50 contiguous amino acids from amino acids 1 to 49 of SEQ ID NO: 67, wherein said polynucleotide encodes a polypeptide having at least one biological activity of the polypeptide encoded by clone P00628_H02 (SEQ ID NO: 66), a polynucleotide encoding at least about 50 contiguous amino acids from amino acids 1 to 70 of SEQ ID NO: 69, wherein said polynucleotide encodes a polypeptide having at least one biological activity of the polypeptide encoded by clone P00629_C08 (SEQ ID NO: 68), a polynucleotide encoding at least about 50 contiguous amino acids from amino acids 1 to 113 of SEQ ID NO: 72, wherein said polynucleotide encodes a polypeptide having at least one biological activity of the polypeptide encoded by clone P006411_G11 (SEQ ID NO: 71), a polynucleotide encoding at least about 50 contiguous amino acids from amino acids 1 to 114 of SEQ ID NO: 74, wherein said polynucleotide encodes a polypeptide having at least one biological activity of the polypeptide encoded by clone P00648_E12 (SEQ ID NO: 73), a polynucleotide encoding at least about 50 contiguous amino acids from amino acids 1 to 97 of SEQ ID NO: 76, wherein said polynucleotide encodes a polypeptide having at least one biological activity of the polypeptide encoded by clone P00697_C03 (SEQ ID NO: 75);

(f) a polynucleotide encoding at least about 50 contiguous amino acids from amino acids 1 to 233 of SEQ ID NO: 26, wherein said polynucleotide encodes a polypeptide having at least one biological activity of the polypeptide encoded by clone P00219_F06 (SEQ ID NO: 25), and a polynucleotide encoding at least about 50 contiguous amino acids from amino acids 1 to 387 of SEQ ID NO: 53, wherein said polynucleotide encodes a polypeptide having at least one biological activity of the polypeptide encoded by clone P00248_B04 (SEQ ID NO: 52);

(g) a polynucleotide selected from the group consisting of SEQ ID NOS: 1, 3, 5, 7, 9, 11, 13, 15, 17, 19, 21, 23, 25, 27, 29, 31, 32, 34, 36, 38, 40, 42, 44, 45, 47, 48, 49, 50, 52, 54, 56, 58, 60, 61, 62, 64, 65, 66, 68, 70, 71, 73 and 75;

(h) the complement of a polynucleotide of (a)–(g); and (i) an antisense oligonucleotide capable of hybridizing with, and inhibiting the translation of, the mRNA encoded by a gene encoding a polypeptide selected from the group consisting of: SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74, 76, and another mammalian (e.g., human) homologue thereof.

In another aspect, the invention concerns a vector comprising any of the poly- or oligonucleotides of (a)–(i) above.

In a further aspect, the invention concerns a recombinant host cell transformed with nucleic acid comprising any of the poly- or oligonucleotides of (a)–(i) above, or with a vector comprising any of the poly- or oligonucleotides of (a)–(i) above.

In a still further aspect, the invention concerns a recombinant method for producing a polypeptide by culturing a recombinant host cell transformed with nucleic acid comprising any of the polynucleotides of (a)–(g) above under conditions such that the polypeptide is expressed, and isolating the polypeptide.

In a different aspect, the invention concerns a polypeptide comprising:

(a) a polypeptide having at least about 80% identity with amino acids 1 to 203 of SEQ ID NO: 2, amino acids 1 to 193 of SEQ ID NO: 4, amino acids 1 to 236 of SEQ ID NO: 6, amino acids 1 to 61 of SEQ ID NO: 8, amino acids 1 to 79 of SEQ ID NO: 10, amino acids 1 to 92 of SEQ ID NO: 12, amino acids 1 to 86 of SEQ ID NO: 14, amino acids 1 to 36 of SEQ ID NO: 16, amino acids 1 to 83 of SEQ ID NO: 18, amino acids 1 to 82 of SEQ ID NO: 20, amino acids 1 to 462 of SEQ ID NO: 22, amino acids 1 to 170 of SEQ ID NO: 24, amino acids −26 to 233 of FIG. 13 (amino acids 1 to 259 of SEQ ID NO: 26), amino acids 1 to 30 of SEQ ID NO: 28, amino acids 1 to 39 of SEQ ID NO: 30, amino acids 1 to 541 of SEQ ID NO: 33, amino acids 1 to 30 of SEQ ID NO: 35, amino acids 1 to 100 of SEQ ID NO: 37, amino acids 1 to 65 of SEQ ID NO: 39, amino acids 1 to 42 of SEQ ID NO: 41, amino acids 1 to 46 of SEQ ID NO: 43, amino acids 1 to 313 of SEQ ID NO: 46, amino acids 1 to 58 of SEQ ID NO: 51, amino acids −35 to 387 of FIG. 29 (amino acids 1 to 422 of SEQ ID NO: 53), amino acids 1 to 58 of SEQ ID NO: 55, amino acids 1 to 52 of SEQ ID NO: 57, amino acids 1 to 245 of SEQ ID NO: 59, amino acids 1 to 142 of SEQ ID NO: 63, amino acids 1 to 49 of SEQ ID NO: 67, amino acids 1 to 70 of SEQ ID NO: 69, amino acids 1 to 113 of SEQ ID NO: 72, amino acids 1 to 114 of SEQ ID NO: 74, amino acids 1 to 97 of SEQ ID NO: 76; or (b) a polypeptide encoded by nucleic acid hybridizing under stringent conditions with the complement of the coding region of SEQ ID NOS: 1, 3, 5, 7, 9, 11, 13, 15, 17, 19, 21, 23, 25, 27, 29, 31, 32, 34, 36, 38, 40, 42, 44, 45, 47, 48, 49, 50, 52 54, 56, 58, 60, 61, 62, 64, 65, 66, 68, 70, 71, 73, 75;

(c) the polypeptides of (a) and (b) having at least one biological activity of the polypeptide encoded by clones P00184_D11 (SEQ ID NO: 1), P00185_D11 (SEQ ID NO: 3), P00188_D12 (SEQ ID NO: 5), P00188_E01 (SEQ ID NO: 7), P00194_G01 (SEQ ID NO: 9), P00194_G05 (SEQ ID NO: 1), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00223_F07 (SEQ ID NO: 31), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_B04 (SEQ ID NO: 44), P00240_E05 (SEQ ID NO: 45), P00241_E12 (SEQ ID NO: 47), P00245_D06 (SEQ ID NO: 48), P00246_D12 (SEQ ID NO: 49), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00263_G06 (SEQ ID NO: 60), P00267_F08 (SEQ ID NO: 61), P00269_H08 (SEQ ID NO: 62), P00312_C04 (SEQ ID NO: 64), P00324_H02 (SEQ ID NO: 65), P00628_H02 (SEQ ID NO: 66), P00629_C08 (SEQ ID NO: 68), P00634_G11 (SEQ ID NO: 70), P00641_G11 (SEQ ID NO: 71), P00648_E12 (SEQ ID NO: 73), or P00697_C03 (SEQ ID NO: 75).

In another aspect, the invention concerns a composition comprising a polypeptide as hereinabove defined in admixture with a pharmaceutically acceptable carrier. In a specific embodiment, the composition is a pharmaceutical composition, preferably for the treatment of a cardiac, renal or inflammatory disease, comprising an effective amount of a polypeptide of the present invention.

In yet another aspect, the invention concerns an antibody specifically binding a polypeptide of the present invention (as hereinabove defined).

In a further aspect, the invention concerns an antagonist or agonist of a polypeptide of the present invention.

In a still further aspect, the invention concerns a composition, preferably a pharmaceutical composition, comprising an effective amount of an antibody herein, in admixture with a pharmaceutically acceptable carrier.

The invention further concerns a composition, preferably a pharmaceutical composition, comprising an effective amount of an antagonist or agonist of the present invention, in admixture with a pharmaceutically acceptable carrier.

In a further aspect, the invention concerns a method for the treatment of a cardiac, renal or inflammatory disease, comprising administering to a patient in need an effective amount of a polypeptide of the present invention or an antagonist or agonist thereof.

In a different aspect, the invention concerns a method for the treatment of a cardiac, renal or inflammatory disease, comprising administering to a patient in need an effective amount of a poly- or oligonucleotide of the present invention (as hereinabove defined).

The invention also concerns a method for the treatment of a cardiac, renal or inflammatory disease, comprising administering to a patient in need an effective amount of an antibody specifically binding to a polypeptide of the present invention.

In a further aspect, the invention concerns a method for screening a subject for a cardiac, renal or inflammatory disease characterized by the differential expression of the endogenous homologue of the proteins of SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74 or 76 comprising the steps of:
  measuring the expression in the subject of the endogenous homologue of the protein of SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74 or 76; and
  determining the relative expression of such endogenous homologue in the subject compared to its expression in normal subjects, or compared to its expression in the same subject at an earlier stage of development of the cardiac, renal or inflammatory disease. The subject is preferably human and, accordingly, the endogenous protein is a human homologue of the rat proteins of SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74 or 76.

In a still further aspect, the invention concerns an array comprising one or more oligonucleotides complementary to reference RNA or DNA encoding a protein of SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74, or 76 or another mammalian (e.g., human) homologue thereof, where the reference DNA or RNA sequences are obtained from both a biological sample from a normal subject and a biological sample from a subject exhibiting a cardiac, renal, or inflammatory disease, or from biological samples taken at different stages of a cardiac, renal, or inflammatory disease.

In yet another aspect, the invention concerns a method for detecting cardiac, kidney, or inflammatory disease in a human patient comprising the steps of:
  providing an array of oligonucleotides at known locations on a substrate, which array comprises oligonucleotides complementary to reference DNA or RNA sequences encoding a human homologue of the proteins of SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74, or 76, where the reference DNA or RNA sequences are obtained from both a biological sample from a normal patient and a biological sample from a patient potentially exhibiting cardiac, renal, or inflammatory disease, or from a patient exhibiting cardiac, renal, or inflammatory disease, taken at different stages of such disease jointly referred to as "the test patient");
  exposing the array, under hybridization conditions, to a first sample of cDNA probes constructed from mRNA obtained from a biological sample from a corresponding biological sample of a normal patient or from a test patient at a certain stage of the disease;
  exposing the array, under hybridization conditions, to a second sample of cDNA probes constructed from mRNA obtained from a biological sample obtained from the test patient (if the first sample was taken at a certain stage of the disease, the second sample is taken at a different stage of the disease);
  quantifying any hybridization between the first sample of cDNA probes and the second sample of cDNA probes with the oligonucleotide probes on the array; and
  determining the relative expression of genes encoding the human homologue of the protein of SEQ ID NO: 2 in the biological samples from the normal patient and the test patient, or in the biological samples taken from the test patient at different stages of the disease.

The invention further concerns a diagnostic kit comprising an array herein (as defined above) for detecting and diagnosing a disease, specifically cardiac, kidney or inflammatory disease. This kit may comprise control oligonucleotide probes, PCR reagents and detectable labels. In addition, this kit may comprise biological samples taken from human subjects, said samples comprising blood or tissue, preferably cardiac tissue, more preferably left ventricle cells. Such diagnostic kits may also comprise antibodies (including poly- and monoclonal antibodies) to a polypeptide of the present invention, including the polypeptide of SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74, or 76 and further mammalian (e.g., human) homologues thereof.

BRIEF DESCRIPTION OF THE DRAWINGS

FIG. 1 shows the nucleotide sequence (SEQ ID NO: 1) of the clone P0184_D11 and deduced amino acid sequence of the polypeptide (SEQ ID NO: 2) encoded by the clone.

FIG. 2 shows the nucleotide sequence (SEQ ID NO: 3) of the clone P0185_D11 and deduced amino acid sequence of the polypeptide (SEQ ID NO: 4) encoded by the clone.

FIG. 3 shows the nucleotide sequence (SEQ ID NO: 5) of the clone P0188_D12 and deduced amino acid sequence of the polypeptide (SEQ ID NO: 6) encoded by the clone.

FIG. 4 shows the nucleotide sequence (SEQ ID NO: 7) of the clone P0188_E01 and deduced amino acid sequence of the polypeptide (SEQ ID NO: 8) encoded by the clone.

FIG. 5 shows the nucleotide sequence (SEQ ID NO: 9) of the clone P0194_G01 and deduced amino acid sequence of the polypeptide (SEQ ID NO: 10) encoded by the clone.

FIG. 6 shows the nucleotide sequence (SEQ ID NO: 11) of the clone P0194_G05 and deduced amino acid sequence of the polypeptide (SEQ ID NO: 12) encoded by the clone.

FIG. 7 shows the nucleotide sequence (SEQ ID NO: 13) of the clone P0194_H10 and deduced amino acid sequence of the polypeptide (SEQ ID NO: 14) encoded by the clone.

FIG. 8 shows the nucleotide sequence (SEQ ID NO: 15) of the clone P0199_D08 and deduced amino acid sequence of the polypeptide (SEQ ID NO: 16) encoded by the clone.

FIG. 9 shows the nucleotide sequence (SEQ ID NO: 17) of the clone P0203_D04 and deduced amino acid sequence of the polypeptide (SEQ ID NO: 18) encoded by the clone.

FIG. 10 shows the nucleotide sequence (SEQ ID NO: 19) of the clone P0203_E06 and deduced amino acid sequence of the polypeptide (SEQ ID NO: 20) encoded by the clone.

FIG. 11 shows the nucleotide sequence (SEQ ID NO: 21) of the clone P0209_F06 and deduced amino acid sequence of the polypeptide (SEQ ID NO: 22) encoded by the clone.

FIG. 12 shows the nucleotide sequence (SEQ ID NO: 23) of the clone P0219_D02 and deduced amino acid sequence of the polypeptide (SEQ ID NO: 24) encoded by the clone.

FIG. 13 shows the nucleotide sequence (SEQ ID NO: 25) of the clone P0219_F06 and deduced amino acid sequence of the polypeptide (SEQ ID NO: 26) encoded by the clone. The underlined amino acid residues at the N-terminal end represent a putative signal peptide.

FIG. 14 shows the nucleotide sequence (SEQ ID NO: 27) of the clone P0220_H05 and deduced amino acid sequence of the polypeptide (SEQ ID NO: 28) encoded by the clone.

FIG. 15 shows the nucleotide sequence (SEQ ID NO: 29) of the clone P0222_G03 and deduced amino acid sequence of the polypeptide (SEQ ID NO: 30) encoded by the clone.

FIG. 16 shows the nucleotide sequence (SEQ ID NO: 31) of the clone P0184_D11.

FIG. 17 shows the nucleotide sequence (SEQ ID NO: 32) of the clone P0225_C01 and deduced amino acid sequence of the polypeptide (SEQ ID NO: 33) encoded by the clone.

FIG. 18 shows the nucleotide sequence (SEQ ID NO: 34) of the clone P0227_D11 and deduced amino acid sequence of the polypeptide (SEQ ID NO: 35) encoded by the clone.

FIG. 19 shows the nucleotide sequence (SEQ ID NO: 36) of the clone P0228_F03 and deduced amino acid sequence of the polypeptide (SEQ ID NO: 37) encoded by the clone.

FIG. 20 shows the nucleotide sequence (SEQ ID NO: 38) of the clone P0233_H08 and deduced amino acid sequence of the polypeptide (SEQ ID NO: 39) encoded by the clone.

FIG. 21 shows the nucleotide sequence (SEQ ID NO: 40) of the clone P0235_G08 and deduced amino acid sequence of the polypeptide (SEQ ID NO: 41) encoded by the clone.

FIG. 22 shows the nucleotide sequence (SEQ ID NO: 42) of the clone P0239_C11 and deduced amino acid sequence of the polypeptide (SEQ ID NO: 43) encoded by the clone.

FIG. 23 shows the nucleotide sequence (SEQ ID NO: 44) of the clone P0184_D11.

FIG. 24 shows the nucleotide sequence (SEQ ID NO: 45) of the clone P0240_E05 and deduced amino acid sequence of the polypeptide (SEQ ID NO: 46) encoded by the clone.

FIG. 25 shows the nucleotide sequence (SEQ ID NO: 47) of the clone P0241_E12.

FIG. 26 shows the nucleotide sequence (SEQ ID NO: 48) of the clone P0245_D06.

FIG. 27 shows the nucleotide sequence (SEQ ID NO: 49) of the clone P0246_D12.

FIG. 28 shows the nucleotide sequence (SEQ ID NO: 50) of the clone P0247_A04 and deduced amino acid sequence of the polypeptide (SEQ ID NO: 51) encoded by the clone.

FIG. 29 shows the nucleotide sequence (SEQ ID NO: 52) of the clone P0248_B04 and deduced amino acid sequence of the polypeptide (SEQ ID NO: 53) encoded by the clone. The underlined amino acid residues at the N-terminal end represent a putative signal peptide.

FIG. 30 shows the nucleotide sequence (SEQ ID NO: 54) of the clone P0249_F09 and deduced amino acid sequence of the polypeptide (SEQ ID NO: 55) encoded by the clone.

FIG. 31 shows the nucleotide sequence (SEQ ID NO: 56) of the clone P0258_A10 and deduced amino acid sequence of the polypeptide (SEQ ID NO: 57) encoded by the clone.

FIG. 32 shows the nucleotide sequence (SEQ ID NO: 58) of the clone P0262_C10 and deduced amino acid sequence of the polypeptide (SEQ ID NO: 59) encoded by the clone.

FIG. 33 shows the nucleotide sequence (SEQ ID NO: 60) of the clone P0263_G06.

FIG. 34 shows the nucleotide sequence (SEQ ID NO: 61) of the clone P0267_F08.

FIG. 35 shows the nucleotide sequence (SEQ ID NO: 62) of the clone P0269_H08 and deduced amino acid sequence of the polypeptide (SEQ ID NO: 63) encoded by the clone.

FIG. 36 shows the nucleotide sequence (SEQ ID NO: 64) of the clone P0312_C04.

FIG. 37 shows the nucleotide sequence (SEQ ID NO: 65) of the clone P0324_H02.

FIG. 38 shows the nucleotide sequence (SEQ ID NO: 66) of the clone P0628_H02 and deduced amino acid sequence of the polypeptide (SEQ ID NO: 67) encoded by the clone.

FIG. 39 shows the nucleotide sequence (SEQ ID NO: 68) of the clone P0629_C08 and deduced amino acid sequence of the polypeptide (SEQ ID NO: 69) encoded by the clone.

FIG. 40 shows the nucleotide sequence (SEQ ID NO: 70) of the clone P0634_G11.

FIG. 41 shows the nucleotide sequence (SEQ ID NO: 71) of the clone P0641_G11 and deduced amino acid sequence of the polypeptide (SEQ ID NO: 72) encoded by the clone.

FIG. 42 shows the nucleotide sequence (SEQ ID NO: 73) of the clone P0648_E12 and deduced amino acid sequence of the polypeptide (SEQ ID NO: 74) encoded by the clone.

FIG. 43 shows the nucleotide sequence (SEQ ID NO: 75) of the clone P0697_C03 and deduced amino acid sequence of the polypeptide (SEQ ID NO: 76) encoded by the clone.

FIG. 44 shows the results of differential expression of clones P00184_D11, P00185D11, P00188_D12, P00188_E01, P00194_$G_{05}$, P00194_G05, P00194_H10, P00199_D08, P00203_D04, P00203_E06, P00209_F06, P00219_D02, P00219_F06, P00220_H05, P00222_G03, P00223_F07, P00225_C01, P00227_D11, P00228_F03, P00233_H08, P00235_G08, P00239_C11, P00240_B04, P00240_E05, P00241_E12, P00245_D06, P00246_D12, P00247_A04, P00248_B04, P00249_F09, P00258_A10, P00262_C10, P00263_G06, P00267_F08, P00269_H08, P00312_C04, P00324_H02, P00628_H02, P00629_C08, P00634_G11, P00641_G11, P00648_E12, and P00697_C03 in various heart and kidney disease models in the rat.

DEFINITIONS

Unless defined otherwise, technical and scientific terms used herein have the same meaning as commonly understood by one of ordinary skill in the art to which this invention belongs. Singleton, et al., *Dictionary of Microbiology and Molecular Biology*, 2$^{nd}$ ed., J. Wiley & Sons (New York, N.Y. 1994), and March, *Advanced Organic Chemistry Reactions Mechanisms and Structure*, 4$^{th}$ ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNA's and RNA's that contain one or more modified bases. Thus, DNA's or RNA's with backbones modified for stability or for other reasons are "polynucleotides" as that term is intended herein. Moreover, DNA's or RNA's comprising unusual bases, such as inosine, or modified bases, such as tritylated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNA's. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNA's in cells and organisms.

The term "polypeptide," in singular or plural, is used herein to refer to any peptide or protein comprising two or more amino acids joined to each other in a linear chain by peptide bonds. As used herein, the term refers to both short chains, which also commonly are referred to in the art as peptides, oligopeptides and oligomers, and to longer chains, commonly referred to in the art as proteins. Polypeptides, as defined herein, may contain amino acids other than the 20 naturally occurring amino acids, and may include modified amino acids. The modification can be anywhere within the polypeptide molecule, such as, for example, at the terminal amino acids, and may be due to natural processes, such as processing and other post-translational modifications, or may result from chemical and/or enzymatic modification techniques which are well known to the art. The known modifications include, without limitation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature, such as, for instance, Creighton, T. E., *Proteins—Structure And Molecular Properties*, 2$^{nd}$ Ed., W. H. Freeman and Company, New York (1993); Wold, F., "Posttranslational Protein Modifications: Perspectives and Prospects," in *Posttranslational Covalent Modification of Proteins*, Johnson, B. C., ed., Academic Press, New York (1983), pp. 1–12; Seifter, et al., "Analysis for Protein Modifications and Nonprotein Cofactors," *Meth. Enzymol.* (1990) 182:626–646, and Rattan, et al., *Ann. N.Y. Acad. Sci.* (1992) 663:48–62.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

Modifications that occur in a polypeptide often will be a function of how the polypeptide is made. For polypeptides made by expressing a cloned gene in a host, for instance, the nature and extent of the modifications in large part will be determined by the host cell posttranslational modification capacity and the modification signals present in the polypeptide amino acid sequence. For instance, it is well known that glycosylation usually does not occur in certain bacterial hosts such as *E. coli*. Accordingly, when glycosylation is desired, a polypeptide is expressed in a glycosylating host, generally eukaryotic host cells. Insect cells often carry out the same posttranslational glycosylations as mammalian cells and, for this reason, insect cell expression systems have been developed to express efficiently mammalian proteins having native patterns of glycosylation.

It will be appreciated that the same type of modification may be present in the same or varying degree at several sites in a given polypeptide. Also, a given polypeptide may contain many types of modifications.

It will be appreciated that polypeptides are not always entirely linear. For instance, polypeptides may be branched as a result of ubiquitination, and they may be circular, with or without branching, generally as a result of posttranslational events, including natural processing and events brought about by human manipulation which do not occur naturally. Circular, branched and branched circular polypeptides may be synthesized by non-translation natural process and by entirely synthetic methods, as well. Such structures are within the scope of the polypeptides as defined herein.

The term "amino acid sequence variant" refers to molecules with some differences in their amino acid sequences as compared to a reference (e.g., native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

The amino acid sequence variants within the scope of the present invention may contain amino acid alterations, including substitutions and/or insertions and/or deletions in any region of the polypeptide of SEQ ID NO: 1, including the N- and C-terminal regions. The amino acid sequence variants of the present invention show at least about 75%, more preferably at least about 85%, even more preferably at least about 90%, most preferably at least about 95% amino acid sequence identity with a polypeptide of SEQ ID NO: 1 or with a native homologue thereof in another mammalian species, including humans.

"Sequence identity" is defined as the percentage of amino acid residues in a candidate sequence that are identical with the amino acid residues in a native polypeptide sequence, after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul, et al., "Gapped BLAST and PSI-BLAST: A New Generation of Protein Database Search Programs," *Nucleic Acids Res.* (1997) 25:3389–3402. The parameters are set to default values, with the exception of the Penalty for mismatch, which is set to −1.

"Stringent" hybridization conditions are sequence dependent and will be different with different environmental parameters (e.g., salt concentrations, and presence of organics). Generally, stringent conditions are selected to be about 5° C. to 20° C. lower than the thermal melting point ($T_m$) for the specific nucleic acid sequence at a defined ionic strength and pH. Preferably, stringent conditions are about 5° C. to 10° C. lower than the thermal melting point for a specific nucleic acid bound to a complementary nucleic acid. The $T_m$ is the temperature (under defined ionic strength and pH) at which 50% of a nucleic acid (e.g., tag nucleic acid) hybridizes to a perfectly matched probe.

"Stringent" wash conditions are ordinarily determined empirically for hybridization of each set of tags to a corresponding probe array. The arrays are first hybridized (typically under stringent hybridization conditions) and then washed with buffers containing successively lower concentrations of salts, or higher concentrations of detergents, or at increasing temperatures until the signal to noise ratio for specific to non-specific hybridization is high enough to facilitate detection of specific hybridization. Stringent temperature conditions will usually include temperatures in excess of about 30° C., more usually in excess of about 37° C., and occasionally in excess of about 45° C. Stringent salt conditions will ordinarily be less than about 1,000 mM, usually less than about 500 mM, more usually less than about 400 mM, typically less than about 300 mM, preferably less than about 200 mM, and more preferably less than about 150 mM. However, the combination of parameters is more important than the measure of any single parameter. See, e.g., Wetmur, et al., *J. Mol. Biol.* (1966) 31:349–370, and Wetmur, *Critical Reviews in Biochemistry and Molecular Biology* (1991) 26(34):227–259. In a preferred embodiment, "stringent conditions" or "high stringency conditions," as defined herein, may be hybridization in 50% formamide, 5 ×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

As used herein, the term "polynucleotide encoding a polypeptide" and grammatical equivalents thereof, encompass polynucleotides which include a sequence encoding a polypeptide of the present invention, including polynucleotides that comprise a single continuous region or discontinuous regions encoding the polypeptide (for example, interrupted by introns) together with additional regions, that also may contain coding and/or non-coding sequences.

"Antisense oligodeoxynucleotides" or "antisense oligonucleotides" (which terms are used interchangeably) are defined as nucleic acid molecules that can inhibit the transcription and/or translation of target genes in a sequence-specific manner. The term "antisense" refers to the fact that the nucleic acid is complementary to the coding ("sense") genetic sequence of the target gene. Antisense oligonucleotides hybridize in an anti-parallel orientation to nascent mRNA through Watson-Crick base-pairing. By binding the target mRNA template, antisense oligonucleotides block the successful translation of the encoded protein. The term specifically includes antisense agents called "ribozymes" that have been designed to induce catalytic cleavage of a target RNA by addition of a sequence that has natural self-splicing activity (Warzocha and Wotowiec, "Antisense Strategy: Biological Utility and Prospects in the Treatment of Hematological Malignancies," *Leuk. Lymphoma* (1997) 24:267–281).

The terms "vector," "polynucleotide vector," "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, conjugated with transferrin, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

The term "antagonist" is used in the broadest sense and includes any molecule that partially or fully blocks, inhibits or neutralizes a biological activity exhibited by a polypeptide of the present invention. In a similar manner, the term "agonist" is used in the broadest sense and includes any molecule that mimics a biological activity exhibited by a polypeptide of the present invention, for example, by specifically changing the function or expression of such polypeptide, or the efficiency of signaling through such polypeptide, thereby altering (increasing or inhibiting) an already existing biological activity or triggering a new biological activity.

The term "recombinant" when used with reference to a cell, animal, or virus indicates that the cell, animal, or virus encodes a foreign DNA or RNA. For example, recombinant cells optionally express nucleic acids (e.g., RNA) not found within the native (non-recombinant) form of the cell.

The term "antibody" is used in the broadest sense and specifically covers monoclonal antibodies (including agonist, antagonist, and neutralizing antibodies), polyclonal antibodies, multi-specific antibodies (e.g., bispecific antibodies), as well as antibody fragments. The monoclonal antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison, et al., *Proc. Natl. Acad. Sci. USA* (1984) 81:6851–6855). The monoclonal antibodies further include "humanized" antibodies or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones, et al., *Nature* (1986) 321:522–525; and Reichmann, et al., *Nature* (1988) 332: 323–329. The humanized antibody includes a PRIMATIZED® antibody wherein the antigen-binding region of the antibody is derived from an antibody produced by immunizing macaque monkeys with the antigen of interest.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata, et al., *Protein Eng.* (1995) 8(10): 1057–1062); single-chain antibody molecules; and multi-specific antibodies formed from antibody fragments.

The terms "differentially expressed gene," "differential gene expression" and their synonyms, which are used interchangeably, refer to a gene whose expression is activated to a higher or lower level in a subject suffering from a disease, specifically a cardiac, kidney or inflammatory disease state, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes, or a comparison of the ratios of the expression between two or more genes, or even a comparison of two differently processed products of the same gene, which differ between normal subjects and subjects suffering from a disease, specifically a cardiac, kidney or inflammatory disease state, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about 1.4-fold, preferably at least about 1.8-fold, more preferably at least about 2.0-fold, most preferably at least about 2.5-fold difference between the expression of a given gene in normal and diseased subjects, or in various stages of disease development in a diseased subject.

"Cardiac disease" includes congestive heart failure, myocarditis, dilated congestive cardiomyopathy, hypertrophic cardiomyopathy, restrictive cardiomyopathy, mitral valve disease, aortic valve disease, tricuspid valve disease, angina pectoris, myocardial infarction, cardiac arrhythmia, pulmonary hypertension, arterial hypertension, renovascular hypertension, arteriosclerosis, atherosclerosis, and cardiac tumors, along with any disease or disorder that relates to the cardiovascular system and related disorders, as well as symptoms indicative of, or related to, cardiac disease and related disorders.

As used herein, "heart failure" refers to an abnormality of cardiac function where the heart does not pump blood at the rate needed for the requirements of metabolizing tissues. The heart failure can be caused by any number of factors, including ischemic, congenital, rheumatic, or idiopathic forms.

As used herein "congestive heart failure" refers to a syndrome characterized by left ventricular dysfunction, reduced exercise tolerance, impaired quality of life, and markedly shortened life expectancy. Decreased contractility of the left ventricle leads to reduced cardiac output with consequent systemic arterial and venous vasoconstriction.

This vasoconstriction, which appears to be mediated, in part, by the renin-angiotensis system, promotes the vicious cycle of further reductions of stroke volume followed by an increased elevation of vascular resistance.

As used herein "infarct" refers to an area of necrosis resulting from an insufficiency of blood supply. "Myocardial infarction" refers to myocardial necrosis resulting from the insufficiency of coronary blood supply.

"Kidney disease" includes acute renal failure, glomerulonephritis, chronic renal failure, azotemia, uremia, immune renal disease, acute nephritic syndrome, rapidly progressive nephritic syndrome, nephrotic syndrome, Berger's Disease, chronic nephritic/proteinuric syndrome, tubulointerstitial disease, nephrotoxic disorders, renal infarction, atheroembolic renal disease, renal cortical necrosis, malignant nephroangiosclerosis, renal vein thrombosis, renal tubular acidosis, renal glucosuria, nephrogenic diabetes insipidus, Bartter's syndrome, Liddle's syndrome, polycystic kidney disease, medullary cystic disease, medullary sponge kidney, hereditary nephritis, and nail-patella syndrome, along with any disease or disorder that relates to the renal system and related disorders, as well as symptoms indicative of, or related to, renal or kidney disease and related disorders.

The phrases "polycystic kidney disease" "PKD" and "polycystic renal disease" are used interchangeably, and refer to a group of disorders characterized by a large number of cysts distributed throughout dramatically enlarged kidneys. The resultant cyst development leads to impairment of kidney function and can eventually cause kidney failure. "PKD" specifically includes autosomal dominant polycystic kidney disease (ADPKD) and recessive autosomal recessive polycystic kidney disease (ARPKD), in all stages of development, regardless of the underlying cause.

"Inflammatory disease" includes myocarditis, asthma, chronic inflammation, autoimmune diabetes, tumor angiogenesis, rheumatoid arthritis (RA), rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis restenosis, cerebral malaria, chronic pulmonary inflammatory disease, silicosis, pulmonary sarcosis, bone resorption diseases such as osteoporosis, graft versus host reaction, Crohn's Disease, ulcerative colitis including inflammatory bowel disease (IBD), Alzheimer's disease, and pyresis, along with any disease or disorder that relates to inflammation and related disorders, as well as symptoms indicative of, or related to, inflammation and related disorders.

The terms "treat" or "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

"Chronic" administration refers to administration of the agent(s) in a continuous mode as opposed to an acute mode, so as to maintain the desired effect for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

An "individual" is a vertebrate, preferably a mammal, more preferably a human.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

An "effective amount" is an amount sufficient to effect beneficial or desired therapeutic (including preventative) results. An effective amount can be administered in one or more administrations.

"Active" or "activity" means a qualitative biological and/or immunological property.

The phrase "immunological property" means immunological cross-reactivity with at least one epitope of the reference (native sequence) polypeptide molecule, wherein, "immunological cross-reactivity" means that the candidate polypeptide is capable of competitively inhibiting the qualitative biological activity of the reference (native sequence) polypeptide. The immunological cross-reactivity is preferably "specific," which means that the binding affinity of the immunologically cross-reactive molecule identified to the corresponding polypeptide is significantly higher (preferably at least about 2-times, more preferably at least about 4-times, most preferably at least about 6-times higher) than the binding affinity of that molecule to any other known native polypeptide.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONIC™.

MODES OF CARRYING OUT THE INVENTION

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, $2^{nd}$ edition (Sambrook, et al. (1989)); *Oligonucleotide Synthesis* (M. J. Gait, ed. (1984)); *Animal Cell Culture* (R. I. Freshney, ed. (1987)); *Methods in Enzymology*

(Academic Press, Inc.); *Handbook of Experimental Immunology*, 4th edition (D. M. Weir & C. C. Blackwell, eds., Blackwell Science Inc. (1987)); *Gene Transfer Vectors for Mammalian Cells* (J. M. Miller & M. P. Calos, eds. (1987)); *Current Protocols in Molecular Biology* (F. M. Ausubel, et al., eds. (1987)); *PCR: The Polymerase Chain Reaction* (Mullis, et al., eds. (1994)); and *Current Protocols in Immunology* (J. E. Coligan, et al., eds. (1991)).

1. Identification of Differential Gene Expression and Further Characterization of Differentially Expressed Genes The present invention is based on the identification of genes that are differentially expressed in the left ventricle in the Myocardial Infarction Model, as described in the Examples. Such models of differential gene expression can be utilized, among other things, for the identification of genes which are differentially expressed in normal cells versus cells in a disease state, specifically cardiac, kidney or inflammatory disease state, in cells within different diseases, among cells within a single given disease state, in cells within different stages of a disease, or in cells within different time stages of a disease.

Once a particular differentially expressed gene has been identified through the use of one model, its expression pattern can be further characterized, for example, by studying its expression in a different model. A gene may be regulated one way, i.e., the gene can exhibit one differential gene expression pattern, in a given model, but can be regulated differently in another model. The use, therefore, of multiple models can be helpful in distinguishing the roles and relative importance of particular genes in a disease, specifically cardiac, kidney or inflammatory disease.

a. In Vitro Models of Differential Gene Expression

A suitable model that can be utilized within the context of the present invention to discover differentially expressed genes is the in vitro specimen model. In a preferred embodiment, the specimen model uses biological samples from subjects, e.g., peripheral blood, cells and tissues, including surgical and biopsy specimens. Such specimens can represent normal peripheral blood and tissue or peripheral blood and tissue from patients suffering from a disease, specifically cardiac, kidney or inflammatory disease, or having undergone surgical treatment for disorders involving a disease, such as, for example, coronary bypass surgery. Surgical specimens can be procured under standard conditions involving freezing and storing in liquid nitrogen (see Karmali, et al., *Br. J. Cancer* (1983) 48:689–696). RNA from specimen cells is isolated by, for example, differential centrifugation of homogenized tissue, and analyzed for differential expression relative to other specimen cells, preferably using microarray analysis.

Cell lines can also be used to identify genes that are differentially expressed in a disease, specifically cardiac, kidney or inflammatory disease. Differentially expressed genes are detected, as described herein, by comparing the pattern of gene expression between the experimental and control conditions. In such models, genetically matched disease cell lines (e.g., variants of the same cell line) may be utilized. For example, the gene expression pattern of two variant cell lines can be compared, wherein one variant exhibits characteristics of one disease state while the other variant exhibits characteristics of another disease state.

Alternatively, two variant cell lines, both of which exhibit characteristics of the same disease, specifically cardiac, kidney or inflammatory disease, but which exhibit differing degrees of disease disorder severity may be used. Further, genetically matched cell lines can be utilized, one of which exhibits characteristics of a disease, specifically cardiac, kidney or inflammatory disease, state, while the other exhibits a normal cellular phenotype. In accordance with this aspect of the invention, the cell line variants are cultured under appropriate conditions, harvested, and RNA is isolated and analyzed for differentially expressed genes, as with the other models. In a preferred embodiment, microarray analysis is used.

b. In Vivo Models of Differential Gene Expression

In the in vivo model, animal models of a disease, specifically cardiac, kidney or inflammatory disease, and related disorders, can be utilized to discover differentially expressed gene sequences. The in vivo nature of such disease models can prove to be especially predictive of the analogous responses in living patients, particularly human patients. Animal models for a disease, specifically cardiac, kidney or inflammatory disease, which can be utilized for in vivo models include any of the animal models described below. In a preferred embodiment, RNA from both the normal and disease state model is isolated and analyzed for differentially expressed genes using microarray analysis.

As presented in the examples, three representative in vivo cardiac disease models, a representative kidney disease model, and a representative inflammatory disease model have been successfully utilized to identify differentially expressed genes, and are believed to be useful to further characterize the genes and polypeptides of the present invention. These genes are expressed at higher or lower levels in the disease state, relative to the normal state, and preferably are expressed at least about a two-fold higher or lower level relative to the normal state at at least one time point.

Representative in vivo animal models for use in the present invention include the following: general inflammation—carrageenan-induced paw edema, arachidonic acid-induced ear inflammation; arthritis—adjuvant-induced polyarthritis, collagen-induced arthritis, streptococcal cell wall-induced arthritis; multiple sclerosis—experimental autoimmune encephalomyelitis (EAE); Systemic Lupus Erythematosus (SLE); NZB—spontaneous SLE mouse, DNA/anti-DNA immune complex-induced SLE; insulin-dependent diabetes mellitus—NOD spontaneous diabetes mouse; inflammatory bowel disease—acetic acid or trinitrobenzene sulfonic (TNBS)-induced ulcerative colitis; respiratory disease—antigen-induced bronchoconstriction (asthma), lipopolysaccharide (LPS)-induced acute respiratory distress syndrome (ARDS); analgesia—acetic acid-induced or phenylquinone-induced writhing, latency of tail-withdrawal (hot plate); transplant organ rejection—allograft rejection (kidney, lung, heart)-acute and chronic arteriosclerosis; kidney disease—unilateral nephrectomy (acute renal failure), cyclosporin-induced nephropathy, accelerated crescentic anti-glomerular basement membrane (GBM) glomerulonephritis, soluble immune complex-induced nephritis (see generally Aziz, *Bioassays* (1995) 17:8 703–712); and cardiac disease—spontaneous cardiomyopathic hamsters (heart failure), myocardial infarction (MI) model. pacing-induced model of failure (Riegger model), arrhythmias following myocardial infarction (Harris model), aconitine/chloroform-induced arrhythmias, carotid artery injury (restenosis), balloon angioplasty (restenosis). One skilled in the art understands that the present invention is not limited to the in vivo models recited above and that any known models can be used within the context of the present invention.

c. Microarray Technique

In a preferred embodiment of the present invention, microarrays are utilized to assess differential expression of genes. In one aspect of the present invention, DNA microarrays are utilized to assess the expression profile of genes expressed in normal subjects and subjects suffering from a disease, specifically cardiac, kidney or inflammatory disease. Identification of the differentially expressed disease genes can be performed by: constructing normalized and subtracted cDNA libraries from mRNA extracted from the cells or tissue of healthy animals and an animal model of disease or of healthy patients and diseased patients, for example, using any of the in vitro or in vivo models described above; purifying the DNA of cDNA libraries of clones representing healthy and diseased cells or tissue, microarraying the purified DNA for expression analysis; and probing microarrays to identify the genes from the clones that are differentially expressed using labeled cDNA from healthy and diseased cells or tissues.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy. Quantitation of hybridization of each arrayed element allows for assessment of corresponding mRNA abundance. With dual color fluorescence, separately labeled cDNA probes generated from two sources of RNA are hybridized pair-wise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena, et al., Proc. Natl. Acad. Sci. USA (1996) 93(20):106–149).

In a specific embodiment, in vivo models of disease states are used to detect differentially expressed genes. By way of example, three representative cardiac disease models, a representative kidney disease model, and a representative inflammatory disease model were successfully utilized to identify specific differentially expressed genes. Summarizing the representative general protocol used for such in vivo models, separate DNA libraries were constructed from mRNA extracted from disease state tissue and normal tissue. From these libraries, at least 20,000 unidentified cDNA clones were preferably chosen for analysis and microarrayed on chips. Probes generated from normal and disease tissue, from multiple time points, were hybridized to the microarray. By this approach, genes, which are differentially expressed in normal and diseased tissue, were revealed and further identified by DNA sequencing. The analysis of the clones for differential expression reveal genes whose expression is elevated or decreased in association with a disease, specifically cardiac, kidney or inflammatory disease, in the specific in vivo model chosen.

d. Further Characterization of Differentially Expressed Genes

The differentially expressed genes of the present invention are screened to obtain more information about the biological function of such genes. This information can, in turn, lead to the designation of such genes or their gene products as potential therapeutic or diagnostic molecules, or targets for identifying such molecules.

The goal of the follow-up work after a differentially expressed gene has been identified is to identify its target cell type(s), function and potential role in disease pathology. To this end, the differentially expressed genes are screened to identify cell types responding to the gene product, to better understand the mechanism by which the identified cell types respond to the gene product, and to find known signaling pathways that are affected by the expression of the gene.

When further characterization of a differentially expressed gene indicates that a modulation of the gene's expression or a modulation of the gene product's activity can inhibit or treat a disease, specifically cardiac, kidney or inflammatory disease, the differentially expressed gene or its gene product becomes a potential drug candidate, or a target for developing a drug candidate for the treatment of a cardiac, kidney or inflammatory disease, or may be used as a diagnostic.

Where further characterization of a differentially expressed gene reveals that modulation of the gene expression or gene product cannot retard or treat a target disease, the differentially expressed gene may still contribute to developing a gene expression diagnostic pattern correlative of a disease or its disorders. Accordingly, such genes may be useful as diagnostics.

A variety of techniques can be utilized to further characterize the differentially expressed genes after they are identified.

First, the nucleotide sequence of the identified genes, which can be obtained by utilizing standard techniques well known to those of skill in the art, can be used to further characterize such genes. For example, the sequence of the identified genes can reveal homologies to one or more known sequence motifs, which can yield information regarding the biological function of the identified gene product.

Second, an analysis of the tissue or cell type distribution of the mRNA produced by the identified genes can be conducted, utilizing standard techniques well known to those of skill in the art. Such techniques can include, for example, Northern analyses, microarrays, real time (RT-coupled PCR), and RNase protection techniques. In a preferred embodiment, transcriptional screening is used, which may be based on the transfection of cells with an inducible promoter-luciferase plasmid construct, real time PCR, or microarrays, the real time PCR and microarray approached being particularly preferred. Such analyses provide information as to whether the identified genes are expressed in further tissues expected to contribute to a disease, specifically cardiac, kidney or inflammatory disease. These techniques can also provide quantitative information regarding steady state mRNA regulation, yielding data concerning which of the identified genes exhibits a high level of regulation preferably in tissues which can be expected to contribute to a disease state. Additionally, standard in situ hybridization techniques can be utilized to provide information regarding which cells within a given tissue express the identified gene. Specifically, these techniques can provide information regarding the biological function of an identified gene relative to a disease, specifically cardiac, kidney or inflammatory disease, where only a subset of the cells within the tissue is thought to be relevant to the disorder.

Third, the sequences of the identified differentially expressed genes can be used, utilizing standard techniques, to place the genes onto genetic maps, e.g., mouse (Copeland, et al., *Trends in Genetics* (1991) 7:113–118) and human genetic maps (Cohen, et al., *Nature* (1993) 266:698–701). This mapping information can yield information regarding the genes' importance to human disease by identifying genes that map within genetic regions to which known genetic disease disorders map.

After the follow-up screening is completed, relevant, targeted in vivo and in vitro systems can be used to more directly assess the biological function of the identified genes. In vivo systems can include animal systems that naturally exhibit symptoms of a disease, specifically cardiac, kidney or inflammatory disease, or ones engineered to exhibit such symptoms. Animals of any species, including, but not limited to, mice, rats, rabbits, guinea pigs, pigs, micro-pigs, goats, and non-human primates, e.g., baboons, monkeys, and chimpanzees, can be used to generate animal models of a disease, specifically cardiac, kidney or inflammatory disease. Any technique known in the art can be used to introduce a target gene transgene into animals to produce the founder lines of transgenic animals. Such techniques include, pronuclear microinjection (Hoppe, et al., U.S. Pat. No. 4,873,191 (1989)); retrovirus mediated gene transfer into germ lines (Van der Fatten, et al., *Proc. Natl. Acad. Sci. USA* (1985) 82:6148–6152); gene targeting in embryonic stem cells (Thompson, et al., *Cell* (1989) 56:313–321); electroporation of embryos (Lo, *Mol. Cell. Biol.* (1983) 3:1803–1814); and sperm-mediated gene transfer (Lavitrano, et al., *Cell* (1989) 57:717–723). For a review of such techniques, see Gordon, *Intl. Rev. Cytol.* (1989) 115:171–229. Further techniques will be detailed below, in connection with the gene therapy applications of the polynucleotides of the present invention.

The present invention provides for transgenic animals that carry the transgene in all their cells, as well as animals which carry the transgene in some, but not all their cells, i.e., mosaic animals. The transgene can be integrated, either as a single transgene or in concatemers, e.g., head-to-head tandems or head-to-tail tandems. The transgene can also be selectively introduced into and activated in a particular cell type by following, for example, the teaching of Lasko, et al., *Proc. Natl. Acad. Sci. USA* (1992) 89:6232–6236. The regulatory sequences required for such a cell-type specific activation depends upon the particular cell type of interest, and will be apparent to those of skill in the art.

When it is desired that the transgene be integrated into the chromosomal site of the endogenous target gene, gene targeting is preferred. Briefly, when such a technique is to be utilized, vectors containing some nucleotide sequences homologous to the endogenous target gene of interest are designed for the purpose of integrating, via homologous recombination with chromosomal sequences, into and disrupting the function of the nucleotide sequence of the endogenous target gene. The transgene can also be selectively introduced into a particular cell type, thus inactivating the endogenous gene of interest in only that cell type, by following the teaching of Gu, et al., *Science* (1994) 265:103–106. The regulatory sequences required for such a cell-type specific inactivation depends upon the particular cell type of interest, and will be apparent to those of skill in the art.

Once transgenic animals have been generated, the expression of the recombinant target gene and protein can be assayed using standard techniques. Initial screening can be accomplished by Southern blot analysis or PCR techniques to analyze animal tissues to assay whether integration of the transgene has taken place. The level of mRNA expression of the transgene in the tissues of the transgenic animals can also be assessed using techniques which include Northern blot analysis of tissue samples obtained from the animal, in situ hybridization analysis, and RT-coupled PCR. Samples of target gene-expressing tissue can also be evaluated immunocytochemically using antibodies specific for the transgenic product of interest.

The transgenic animals that express target gene mRNA or target gene transgene peptide (detected immunocytochemically, using antibodies directed against target gene product epitopes) at easily detectable levels should then be further evaluated to identify those animals which display disease characteristics or symptoms. Additionally, specific cell types within the transgenic animals can be analyzed for cellular phenotypes characteristic of a disease, specifically cardiac, kidney or inflammatory disease. Such cellular phenotypes can include, for example, differential gene expression characteristic of cells within a given disease state of interest. Further, such cellular phenotypes can include an assessment of a particular cell type diagnostic pattern of expression and its comparison to known diagnostic expression profiles of the particular cell type in animals exhibiting a disease, specifically cardiac, kidney or inflammatory disease. Such transgenic animals serve as suitable models. Once transgenic founder animals are produced, they can be bred, inbred, outbred, or crossbred to produce colonies of the particular animal.

The animal models described above and in the Examples, can be used to generate cell lines for use in cell-based in vitro assays to further characterize the differentially expressed genes of the invention and their gene products. Techniques that can be used to derive a continuous cell line from transgenic animals are disclosed, for example, by Small, et al., *Mol. Cell Biol.* (1985) 5:642–648.

Alternatively, cells of a cell type known to-be involved in a cardiac, kidney or inflammatory disease can be transfected with sequences capable of increasing or decreasing the amount of target gene expression within the cell. For example, sequences of the differentially expressed genes herein can be introduced into, and overexpressed in, the genome of the cell of interest, or if endogenous target gene sequences are present, they can either be overexpressed or, be disrupted in order to underexpress or inactivate target gene expression.

The information obtained through such characterizations can suggest relevant methods for the treatment of a disease, specifically cardiac, kidney or inflammatory disease, involving the gene of interest. For example, treatment can include a modulation of gene expression or gene product activity. Characterization procedures such as those described herein can indicate where such modulation should involve an increase or a decrease in the expression or activity of the gene or gene product of interest.

2. Production of Polynucleotides and Polypeptides

The polypeptides of the present invention are preferably produced by techniques of recombinant DNA technology. DNA encoding a native polypeptide herein can be obtained from cDNA libraries prepared from tissue believed to possess the corresponding mRNA and to express it at a detectable level. For example, cDNA library can be constructed by obtaining polyadenylated mRNA from a cell line known to express the desired polypeptide, and using the mRNA as a template to synthesize double-stranded cDNA. In the present case, a suitable source for the desired mRNA may be heart tissue obtained from normal heart or from the Myocardial Infarction Model (MI model) mentioned above, and described in detail in the Examples. The polypeptide genes of the present invention can also be obtained from a genomic library, such as a human genomic cosmid library.

Libraries, either cDNA or genomic, are screened with probes designed to identify the gene of interest or the protein encoded by it. For cDNA expression libraries, suitable probes include monoclonal and polyclonal antibodies that recognize and specifically bind to a polypeptide of SEQ ID NO's: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74 and 76. For cDNA libraries, suitable probes include oligonucleotide probes (generally about 20–80 bases) that encode known or suspected portions of a polypeptide herein, from the same or different species, and/or complementary or homologous cDNA's or fragments thereof that encode the same or a similar gene. Appropriate probes for screening genomic libraries include, without limitation, oligonucleotides, cDNA's, or fragments thereof that encode the same or a similar gene, and/or homologous genomic DNA's or fragments thereof. Screening the cDNA and genomic libraries with the selected probe may be conducted using standard protocols as described, for example, in chapters 10–12 of Sambrook, et al., *Molecular Cloning: A Laboratory Manual,* New York, Cold Spring Harbor Laboratory Press (1989).

According to a preferred method, carefully selected oligonucleotide probes are used to screen cDNA libraries from various tissues, preferably from heart and/or kidney tissues. The oligonucleotide sequences selected as probes should be sufficient in length and sufficiently unique and unambiguous that false positives are minimized. The actual sequences can be designed based on regions of SEQ ID NO: 2 which have the least codon redundancy. The oligonucleotides may be degenerate at one or more positions. The use of degenerate oligonucleotides is of particular importance where a library is screened from a species in which preferential codon usage is not known.

The oligonucleotides must be labeled such that they can be detected upon hybridization to DNA in the library screened. Preferably, the 5' end of the oligonucleotide is radiolabeled, using APT (e.g., $\gamma^{32}P$) and polynucleotide kinase. However, other labeling, e.g., biotinylation or enzymatic labeling are also suitable.

Alternatively, to obtain DNA encoding a homologue of rat polypeptides specifically disclosed herein in another mammalian species, e.g., in humans, one only needs to conduct hybridization screening with labeled rat DNA or fragments thereof, selected following the principles outlined above, in order to detect clones which contain homologous sequences in the cDNA libraries obtained from appropriate tissues (e.g., heart or kidney) of the particular animal, such as human (cross-species hybridization). Full-length clones can then be identified, for example, by restriction endonuclease analysis and nucleic acid sequencing. If full-length clones are not identified, appropriate fragments are recovered from the various clones and ligated at restriction sites common to the fragments to assemble a full-length clone.

cDNA's encoding the polypeptides of the present invention can also be identified and isolated by other known techniques, such as by direct expression cloning or by using the PCR technique, both of which are well known are described in textbooks, such as those referenced hereinbefore.

Once the sequence is known, the nucleic acid encoding a particular polypeptide of the present invention can also be obtained by chemical synthesis, following known methods, such as the phosphoramidite method (Beaucage and Caruthers, *Tetrahedron Letters* (1981) 22:1859; Matteucci and Caruthers, *Tetrahedron Letters* (1980) 21:719; and Matteucci and Caruthers, *J. Amer. Chem. Soc.* (1981) 103:3185), and the phosphotriester approach (Ito, et al., *Nucleic Acids Res.* (1982) 10:1755–1769).

The cDNA encoding the desired polypeptide of the present invention is inserted into a replicable vector for cloning and expression. Suitable vectors are prepared using standard techniques of recombinant DNA technology, and are, for example, described in the textbooks cited above. Isolated plasmids and DNA fragments are cleaved, tailored, and ligated together in a specific order to generate the desired vectors. After ligation, the vector containing the gene to be expressed is transformed into a suitable host cell.

Host cells can be any eukaryotic or prokaryotic hosts known for expression of heterologous proteins.

The polypeptides of the present invention can be expressed in eukaryotic hosts, such as eukaryotic microbes (yeast), cells isolated from multicellular organisms (mammalian cell cultures), plants and insect cells.

While prokaryotic host provide a convenient means to synthesize eukaryotic proteins, when made this fashion, proteins usually lack many of the immunogenic properties, three-dimensional conformation, glycosylation, and other features exhibited by authentic eukaryotic proteins. Eukaryotic expression systems overcome these limitations.

Yeasts are particularly attractive as expression hosts for a number of reasons. They can be rapidly growth on inexpensive (minimal) media, the recombinant can be easily selected by complementation, expressed proteins can be specifically engineered for cytoplasmic localization or for extracellular export, and are well suited for large-scale fermentation.

*Saccharomyces cerevisiae* is the most commonly used among lower eukaryotic hosts. However, a number of other genera, species, and strains are also available and useful herein, such as *Pichia pastoris* (EP 183,070; Sreekrishna, et al., *J. Basic Microbiol.* (1988) 28:165–278). Yeast expression systems are commercially available, and can be purchased, for example, from Invitrogen (San Diego, Calif.). Other yeasts suitable for VEGF expression include, without limitation, *Kluyveromyces* hosts (U.S. Pat. No. 4,943,529), e.g., *Kluyveromyces lactis; Schizosaccharomyces pombe* (Beach and Nurse, *Nature* (1981) 290:140; *Aspergillus* hosts, e.g., *A. niger* (Kelly and Hynes, *EMBO J.* (1985) 4:475–479) and *A. nidulans* (Ballance, et al., *Biochem. Biophys. Res. Commun.* (1983) 112:284–289), and *Hansenula* hosts, e.g., *Hansenula polymorpha*.

Preferably a methylotrophic yeast is used as a host in performing the methods of the present invention. Suitable methylotrophic yeasts include, but are not limited to, yeast capable of growth on methanol selected from the group consisting of the genera *Pichia* and *Hansenula*. A list of specific species which are exemplary of this class of yeasts may be found, for example, in Anthony, C., *The Biochemistry of Methylotrophs,* (1982) 269, Academic Press, New York, N.Y. Presently preferred are methylotrophic yeasts of the genus *Pichia* such as the auxotrophic *Pichia pastoris* GS115 (NRRL Y-15851); *Pichia pastoris* GS190 (NRRL Y-18014) disclosed in U.S. Pat. No. 4,818,700; and *Pichia pastoris* PPF1 (NRRL Y-18017) disclosed in U.S. Pat. No. 4,812,405. Auxotrophic *Pichia pastoris* strains are also advantageous to the practice of this invention for their ease of selection. It is recognized that wild type *Pichia pastoris* strains (such as NRRL Y-11430 and NRRL Y-11431) may be employed with equal success if a suitable transforming marker gene is selected, such as the use of SUC2 to transform *Pichia pastoris* to a strain capable of growth on sucrose, or if an antibiotic resistance marker is employed, such as resistance to G418. *Pichia pastoris* linear plasmids are disclosed, for example, in U.S. Pat. No. 5,665,600.

Suitable promoters used in yeast vectors include the promoters for 3-phosphoglycerate kinase (Hitzeman, et al., *J. Biol. Chem.* (1980) 255:2073); and other glycolytic enzymes (Hess, et al., *J. Adv. Enzyme Res.* (1968) 7:149; Holland, et al., *Biochemistry* (1978) 17:4900), e.g., enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the constructions of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter regions for alcohol oxidase 1 (AOX1, particularly preferred for expression in *Pichia*), alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter and termination sequences, with or without an origin of replication, is suitable. Yeast expression systems are commercially available, for example, from Clontech Laboratories, Inc. (Palo Alto, Calif., e.g., pYEX 4T family of vectors for *S. cerevisiae*), Invitrogen (Carlsbad, Calif., e.g., pPICZ series Easy Select Pichia Expression Kit) and Stratagene (La Jolla, Calif., e.g., ESP™ Yeast Protein Expression and Purification System for *S. pombe* and pESC vectors for *S. cerevisiae*).

Cell cultures derived from multicellular organisms may also be used as hosts to practice the present invention. While both invertebrate and vertebrate cell cultures are acceptable, vertebrate cell cultures, particularly mammalian cells, are preferable. Examples of suitable cell lines include monkey kidney CV1 cell line transformed by SV40 (COS-7, ATCC CRL 1651); human embryonic kidney cell line 293S (Graham, et al, *J. Gen. Virol.* (1977) 36:59); baby hamster kidney cells (BHK, ATCC CCL 10); Chinese hamster ovary (CHO) cells (Urlaub and Chasin, *Proc. Natl. Acad. Sci. USA* (1980) 77:4216; monkey kidney cells (CV1-76, ATCC CCL 70); African green monkey cells (VERO-76, ATCC CRL-1587); human cervical carcinoma cells (HELA, ATCC CCL 2); canine kidney cells (MDCK, ATCC CCL 34); human lung cells (W138, ATCC CCL 75); and human liver cells (Hep G2, HB 8065).

Suitable promoters used in mammalian expression vectors are often of viral origin. These viral promoters are commonly derived from cytomegalovirus (CMV), polyoma virus, Adenovirus2, and Simian Virus 40 (SV40). The SV40 virus contains two promoters that are termed the early and late promoters. They are both easily obtained from the virus as one DNA fragment that also contains the viral origin of replication (Fiers, et al., *Nature* (1978) 273:113). Smaller or larger SV40 DNA fragments may also be used, provided they contain the approximately 250-bp sequence extending from the HindIII site toward the BglI site located in the viral origin of replication. An origin of replication may be obtained from an exogenous source, such as SV40 or other virus, and inserted into the cloning vector. Alternatively, the host cell chromosomal mechanism may provide the origin of replication. If the vector containing the foreign gene is integrated into the host cell chromosome, the latter is often sufficient.

Eukaryotic expression systems employing insect cell hosts may rely on either plasmid or baculoviral expression systems. The typical insect host cells are derived from the fall army worm (*Spodoptera frugiperda*). For expression of a foreign protein these cells are infected with a recombinant form of the baculovirus *Autographa californica* nuclear polyhedrosis virus which has the gene of interest expressed under the control of the viral polyhedrin promoter. Other insects infected by this virus include a cell line known commercially as "High 5" (Invitrogen) which is derived from the cabbage looper (*Trichoplusia ni*). Another baculovirus sometimes used is the *Bombyx mori* nuclear polyhedrosis virus which infect the silk worm (*Bombyx mori*). Numerous baculovirus expression systems are commercially available, for example, from Invitrogen (Bac-N-Blue™), Clontech (BacPAK™ Baculovirus Expression System), Life Technologies (BAC-TO-BAC™), Novagen (Bac Vector System™), Pharmingen and Quantum Biotechnologies). Another insect cell host is common fruit fly, *Drosophila melanogaster*, for which a transient or stable plasmid based transfection kit is offered commercially by Invitrogen (The DES™ System).

Prokaryotes are the preferred hosts for the initial cloning steps, and are particularly useful for rapid production of large amounts of DNA, for production of single-stranded DNA templates used for site-directed mutagenesis, for screening many mutants simultaneously, and for DNA sequencing of the mutants generated. *E. coli* strains suitable for the production of the polypeptides of the present invention include, for example, BL21 carrying an inducible T7 RNA polymerase gene (Studier, et al., *Methods Enzymol.* (1990) 185:60–98); AD494 (DE3); EB105; and CB (*E. coli* B) and their derivatives; K12 strain 214 (ATCC 31,446); W3110 (ATCC 27,325); X1776 (ATCC 31,537); HB101 (ATCC 33,694); JM101 (ATCC 33,876); NM522 (ATCC 47,000); NM538 (ATCC 35,638); NM539 (ATCC 35,639), etc. Many other species and genera of prokaryotes may be used as well. Prokaryotes, e.g., *E. coli*, produce the polypeptides of the present invention in an unglycosylated form.

Vectors used for transformation of prokaryotic host cells usually have a replication site, marker gene providing for phenotypic selection in transformed cells, one or more promoters compatible with the host cells, and a polylinker region containing several restriction sites for insertion of foreign DNA. Plasmids typically used for transformation of *E. coli* include pBR322, pUC18, pUC19, pUC118, pUC119, and Bluescript M13, all of which are commercially available and described in sections 1.12–1.20 of Sambrook, et al., supra. The promoters commonly used in vectors for the transformation of prokaryotes are the T7 promoter (Studier, et al., supra); the tryptophan (trp) promoter (Goeddel, et al., *Nature* (1979) 281:544); the alkaline phosphatase promoter (phoA); and the β-lactamase and lactose (lac) promoter systems. In *E. coli*, some polypeptides accumulate in the form of inclusion bodies, and need to be solubilized, purified, and refolded. These steps can be carried out by methods well known in the art.

Many eukaryotic proteins, including the polypeptide of SEQ ID NO's: 26 and 53 disclosed herein, contain an endogenous signal sequence as part of the primary translation product. This sequence targets the protein for export from the cell via the endoplasmic reticulum and Golgi apparatus. The signal sequence is typically located at the amino terminus of the protein, and ranges in length from about 13 to about 36 amino acids. Although the actual sequence varies among proteins, all known eukaryotic signal sequences contain at least one positively charged residue and a highly hydrophobic stretch of 10–15 amino acids (usually rich in the amino acids leucine, isoleucine, valine and phenylalanine) near the center of the signal sequence. The signal sequence is normally absent from the secreted form of the protein, as it is cleaved by a signal peptidase located on the endoplasmic reticulum during translocation of the protein into the endoplasmic reticulum. The protein with its signal sequence still attached is often referred to as the pre-protein, or the immature form of the protein, in contrast to the protein from which the signal sequence has been cleaved off, which is usually referred to as the mature protein. Proteins may also be targeted for secretion by linking a heterologous signal sequence to the protein. This is readily accomplished by ligating DNA encoding a signal sequence to the 5' end of the DNA encoding the protein, and expressing the fusion protein in an appropriate host cell. Prokaryotic and eukaryotic (yeast and mammalian) signal sequences may be used, depending on the type of the host cell. The DNA encoding the signal sequence is usually excised from a gene encoding a protein with a signal sequence, and then ligated to the DNA encoding the protein to be secreted. Alternatively, the signal sequence can be chemically synthesized. The signal must be functional, i.e., recognized by the host cell signal peptidase such that the signal sequence is cleaved and the protein is secreted. A large variety of eukaryotic and prokaryotic signal sequences is known in the art, and can be used in performing the process of the present invention. Yeast signal sequences include, for example, acid phosphatase, alpha factor, alkaline phosphatase and invertase signal sequences. Prokaryotic signal sequences include, for example LamB, OmpA, OmpB and OmpF, MalE, PhoA, and β lactamase.

Mammalian cells are usually transformed with the appropriate expression vector using a version of the calcium phosphate method (Graham, et al., *Virology* (1978) 52:546; Sambrook, et al., supra, sections 16.32–16.37), or, more recently, lipofection. However, other methods, e.g., protoplast fusion, electroporation, direct microinjection, etc., are also suitable.

Yeast hosts are generally transformed by the polyethylene glycol method (Hinnen, *Proc. Natl. Acad. Sci. USA* (1978) 75:1929). Yeast, e.g., *Pichia pastoris*, can also be transformed by other methodologies, e.g., electroporation.

Prokaryotic host cells can, for example, be transformed using the calcium chloride method (Sambrook, et al., supra, section 1.82), or electroporation.

More recently, techniques have been developed for the expression of heterologous proteins in the milk of non-human transgenic animals. For example, Krimpenfort, et al., *Biotechnology* (1991) 9:844–847 describes microinjection of fertilized bovine oocytes with genes encoding human proteins and development of the resulting embryos in surrogate mothers. The human genes were fused to the bovine αS$_1$ casein regulatory elements. This general technology is also described in PCT application WO 91/08216 published Jun. 13, 1991. PCT application WO 88/00239, published Jan. 14, 1988, describes procedures for obtaining suitable regulatory DNA sequences for the products of the mammary glands of sheep, including beta lactoglobulin, and the construction of transgenic sheep modified so as to secrete foreign proteins in milk. PCT publication WO 88/01648, published Mar. 10, 1988, generally describes construction of transgenic animals which secrete foreign proteins into milk under control of the regulatory sequences of bovine alpha lactalbumin gene. PCT application WO 88/10118, published Dec. 29, 1988, describes construction of transgenic mice and larger mammals for the production of various recombinant human proteins in milk. Thus, techniques for construction of appropriate host vectors containing regulatory sequences effective to produce foreign proteins in mammary glands and cause the secretion of said protein into milk are known in the art.

Among the milk-specific protein promoters are the casein promoters and the beta lactoglobulin promoter. The casein promoters may, for example, be selected from an alpha casein promoter, a beta casein promoter or a kappa casein promoter. Preferably, the casein promoter is of bovine origin and is an alpha S-1 casein promoter. Among the promoters that are specifically activated in mammary is the long terminal repeat (LTR) promoter of the mouse mammary tumor virus (MMTV). The milk-specific protein promoter or the promoters that are specifically activated in mammary tissue may be derived from either cDNA or genomic sequences. Preferably, they are genomic in origin.

Signal peptides that are useful in expressing heterologous proteins in the milk of transgenic mammals include milk-specific signal peptides or other signal peptides useful in the secretion and maturation of eukaryotic and prokaryotic proteins. Preferably, the signal peptide is selected from milk-specific signal peptides or the signal peptide of the desired recombinant protein product, if any. Most preferably, the milk-specific signal peptide is related to the milk-specific promoter used in the expression system of this invention.

The present invention includes amino acid sequence variants of the native rat polypeptides specifically disclosed herein or their analogues in any other animal, e.g., mammalian species, including humans. Such amino acid sequence variants can be produced by expressing the underlying DNA sequence in a suitable recombinant host cell, as described above, or by in vitro synthesis of the desired polypeptide. The nucleic acid sequence encoding a polypeptide variant of the present invention is preferably prepared by site-directed mutagenesis of the nucleic acid sequence encoding the corresponding native (e.g., human) polypeptide. Particularly preferred is site-directed mutagenesis using polymerase chain reaction (PCR) amplification (see, for example, U.S. Pat. No. 4,683,195 issued Jul. 28, 1987; and *Current Protocols In Molecular Biology*, chapter 15 (Ausubel, et al., ed., 1991). Other site-directed mutagenesis techniques are also well known in the art and are described, for example, in the following publications: *Current Protocols In Molecular Biology*, supra, chapter 8; *Molecular Cloning: A Laboratory Manual.*, 2$^{nd}$ edition (Sambrook, et al., 1989); Zoller, et al., *Methods Enzymol.* (1983) 100: 468–500; Zoller & Smith, *DNA* (1984) 3:479–488; Zoller, et al., *Nucl. Acids Res.* (1987) 10:6487; Brake, et al., *Proc. Natl. Acad. Sci. USA* (1984) 81:4642–4646; Botstein, et al., *Science* (1985) 229:1193; Kunkel, et al., *Methods Enzymol.* (1987) 154:367–382, Adelman, et al., *DNA* (1983) 2:183; and Carter, et al., *Nucl. Acids Res.* (1986) 13:4331. Cassette mutagenesis (Wells, et al., *Gene* (1985) 34:315), and restriction selection mutagenesis (Wells, et al., *Philos. Trans. R. Soc. London Ser. A* (1986) 317:415) may also be used.

Amino acid sequence variants with more than one amino acid substitution may be generated in one of several ways. If the amino acids are located close together in the polypeptide chain, they may be mutated simultaneously, using one oligonucleotide that codes for all of the desired amino acid substitutions. If, however, the amino acids are located some distance from one another (e.g., separated by more than ten amino acids), it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

The amino acid sequence variants of the present invention include polypeptides in which the membrane spanning (transmembrane) region or regions are deleted or inactivated. Deletion or inactivation of these portions of the molecule yields soluble proteins, which are no longer capable of membrane anchorage. Inactivation may, for example, be achieved by deleting sufficient residues (but less than the entire transmembrane region) to produce a substantially hydrophilic hydropathy profile at this site, or by substituting with heterologous residues which accomplish the same result. For example, the transmembrane region(s) may be substituted by a random or predetermined sequence of about 5 to 50 serine, threonine, lysine, arginine, glutamine, aspartic acid and like hydrophilic residues, which altogether exhibit a hydrophilic hydropathy profile. Like the transmembrane region deletional variants, these variants are "soluble," i.e., secreted into the culture medium of recombinant hosts. Soluble variants of the native polypeptides of the present invention may be used to make fusions at their N- or C-terminus to immunogenic polypeptides, e.g., bacterial polypeptides such as beta-lactamase or an enzyme encoded by the E. coli trp locus, or yeast protein, and C-terminal fusions with proteins having a long half-life such as immunoglobulin regions (preferably immunoglobulin constant regions to yield immunoadhesins), albumin, or ferritin, as described in WO 89/02922 published on 6 Apr. 1989. For the production of immunoglobulin fusions see also U.S. Pat. No. 5,428,130 issued Jun. 27, 1995.

3. Production of Antibodies

The present invention includes antibodies that specifically bind a polypeptide of SEQ ID NO: 2 or another mammalian (e.g., human) homologue of such polypeptide. Such antibodies find utility as reagents used, for example, in analytical chemistry or process sciences, as diagnostic and/or therapeutics.

Methods of preparing polyclonal antibodies are known in the art. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. It may be useful to conjugate the immunizing agent to a protein known to be immunogenic in the mammal being immunized, such as serum albumin, or soybean trypsin inhibitor. Examples of adjuvants which may be employed include Freund's complete adjuvant and MPL-TDM.

According to one approach, monoclonal antibodies may be prepared using hybridoma methods, such as those described by Kohler and Milstein, Nature (1975) 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. Generally, either peripheral blood lymphocytes (PBL's) are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59–103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. Preferred immortalized cell lines are those that fuse efficiently, support stable high level expression of antibody by the selected antibody-producing cells, and are sensitive to a medium such as HAT medium.

The culture medium in which the hybridoma cells are cultured can then be assayed for the presence of monoclonal antibodies directed against the particular polypeptide used, such as a rat polypeptide of SEQ ID NO: 2 or its human homologue. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem. (1980) 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Alternatively, monoclonal antibodies may be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells discussed above serve as a preferred source of such DNA. Once isolated, the DNA may be placed into expression vectors, which are then transfected into host cells such as COS cells, Chinese hamster ovary (CHO) cells, or myeloma cells that do not otherwise produce immunoglobulin protein, to obtain the synthesis of monoclonal antibodies in the recombinant host cells.

The antibodies, including antibody fragments, such as Fv, Fab, Fab', $F(ab')_2$ or other antigen-binding subsequences of antibodies, may be humanized. Humanized antibodies contain minimal sequence derived from a non-human immunoglobulin. More specifically, in humanized antibodies residues from a complementary determining region (CDR) of a human immunoglobulin (the recipient) are replaced by residues from a CDR of a non-human species (donor antibody) such as mouse, rat or rabbit having the desired specificity, affinity and capacity. In some instances, Fv framework residues of the human immunoglobulin are also replaced by corresponding non-human residues. Humanized antibodies may additionally comprise residues that are found neither in the recipient antibody nor in the imported CDR or framework sequences (Jones, et al., *Nature* (1986) 321:522–525; Riechmann, et al., *Nature* (1988) 332:323–329).

Methods for humanizing non-human antibodies are well known in the art. Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers (Jones, et al., *Nature* (1986) 321: 522–525; Riechmann, et al., *Nature* (1988) 332:323–327; Verhoeyen, et al., *Science* (1988) 239:1534–1536), by substituting rodent CDR's or CDR sequences for the corresponding sequences of a human antibody. In addition, human antibodies can be produced using various techniques known in the art, including phage display libraries (Hoogenboom and Winter, *J. Mol. Biol.* (1991) 227:381; Marks, et al., *J. Mol. Biol.* (1991) 222:581). The techniques of Cole, et al., and Boerner, et al., are also available for the preparation of human monoclonal antibodies (Cole, et al., *Monoclonal Antibodies and Cancer Therapy*, Alan R. Liss, p. 77 (1985) and Boerner, et al., *J. Immunol.* (1991) 147(1): 86–95). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and in the following scientific publications: Marks, et al., *Bio/Technology* (1992) 10:779–783; Lonberg, et al., *Nature* (1994) 368 856–859; Morrison, *Nature* (1994) 368:812–813; Fishwild, et al., *Nature Biotechnology* (1996) 14:845–851; Neuberger, *Nature Biotechnology* (1996) 14:826; Lonberg and Huszar, *Intern. Rev. Immunol.* (1995) 13:65–93.

The antibodies may be bispecific, in which one specificity is for polypeptide of the present invention, and the other specificity for another protein, such as, a second polypeptide of the present invention or another polypeptide.

4. Uses a. Polynucleotides

The differentially expressed genes identified in accordance with the present invention may be used to design specific oligonucleotide probes and primers. In certain preferred embodiments, the term "primer" as used here includes any nucleic acid capable of priming template-dependent synthesis of a nascent nucleic acid. In certain other embodiments, the nucleic acid may be able to hybridize a template, but not be extended for synthesis of nascent nucleic acid that is complementary to the template.

In certain embodiments of the present invention the term "template" may refer to a nucleic acid that is used in the creation of a complementary nucleic acid strand to the "template" strand. The template may be either RNA or DNA, and the complementary strand may also be RNA or DNA. In certain embodiments the complementary strand may comprise all or part of the complementary sequence to the template, or may include mutations so that it is not an exact, complementary strand to the template. Strands that are not exactly complementary to the template strand may hybridize specifically to the template strand in detection assays described here, as well as other assays known in the art, and such complementary strands that can be used in detection assays are part of the invention.

When used in combination with nucleic acid amplification procedures, these probes and primers enable the rapid analysis of cell, tissue, or peripheral blood samples. In certain aspects of the invention, the term "amplification" may refer to any method or technique known in the art or described herein for duplicating or increasing the number of copies or amount of a target nucleic acid or its complement. The term "amplicon" refers to the target sequence for amplification, or that part of a target sequence that is amplified, or the amplification products of the target sequence being amplified. In certain other embodiments, an "amplicon" may include the sequence of probes or primers used in amplification. This analysis assists in detecting and diagnosing a disease, specifically cardiac, kidney or inflammatory disease, and in determining optimal treatment courses for individuals at varying stages of disease progression.

In light of the present disclosure, one skilled in the art may select segments from the identified genes for use in detection, diagnostic, or prognostic methods, vector constructs, antibody production, kits, or any of the embodiments described herein as part of the present invention. For example, in certain embodiments the sequences selected to design probes and primers may include repetitive stretches of adenine nucleotides (poly-A tails) normally attached at the ends of the RNA for the identified differentially expressed gene. In certain other embodiments, probes and primers may be specifically designed to not include these or other segments from the identified genes, as one of ordinary skill in the art may deem certain segments more suitable for use in the detection methods disclosed.

For example, where a genomic sequence is disclosed, one may use sequences that correspond to exon regions of the gene in most cases. One skilled in the art may select segments from the published exon sequences, or may assemble them into a reconstructed mRNA sequence that does not contain intronic sequences. Indeed, one skilled in the art may select or assemble segments from any of the identified gene sequences into other useful forms, such as coding segment reconstructions of mRNA sequences from published genomic sequences of the identified differentially expressed genes, as part of the present invention. Such assembled sequences would be useful in designing probes and primers, as well as providing coding segments for protein translation and for detection, diagnosis, and prognosis embodiments of the invention described herein.

Primers can be designed to amplify transcribed portions of the differentially expressed genes of the present invention that would include any length of nucleotide segment of the transcribed sequences, up to and including the full length of each gene. It is preferred that the amplified segments of identified genes be an amplicon of at least about 50 to about 500 base pairs in length. It is more preferred that the amplified segments of identified genes be an amplicon of at least about 100 to about 400 base pairs in length, or no longer in length than the amplified segment used to normalize the quantity of message being amplified in the detection assays described herein. Such assays include RNA diagnosticing methods, however, differential expression may be detected by other means, and all such methods would fall within the scope of the present invention. The predicted size of the gene segment, calculated by the location of the primers relative to the transcribed sequence, would be used to determine if the detected amplification product is indeed the gene being amplified. Sequencing the amplified or detected band that matches the expected size of the amplification product and comparison of the band's sequence to the known or disclosed sequence of the gene would confirm that the correct gene is being amplified and detected.

The identified differentially expressed genes may also be used to identify and isolate full-length gene sequences, including regulatory elements for gene expression, from genomic human DNA libraries. The cDNA sequences or portions thereof, identified in the present disclosure may be used as hybridization probes to screen genomic human (or other mammalian) DNA libraries by conventional techniques. Once partial genomic clones have been identified, "chromosomal walking" may isolate full-length genes (also called "overlap hybridization"). See Chinault, et al., *Gene* (1979) 5:111–126. Once a partial genomic clone has been isolated using a cDNA hybridization probe, non-repetitive segments at or near the ends of the partial genomic clone may be used as hybridization probes in further genomic library screening, ultimately allowing isolation of entire gene sequences for the disease, specifically cardiac, kidney or inflammatory disease, state genes of interest. It will be recognized that full-length genes may be obtained using small EST's via technology currently available and described in this disclosure (Sambrook, et al., supra; Chinault, et al., supra). Sequences identified and isolated by such means may be useful in the detection of disease genes using the detection and diagnostic methods described herein, and are part of the invention.

As described before, the identified rat gene may be used as a hybridization probe to screen human or other mammalian cDNA libraries by conventional techniques. Comparison of cloned cDNA sequences with known human or animal cDNA or genomic sequences may be performed using computer programs and databases known in the art.

The polynucleotides of the present invention are also useful in antisense-mediated gene inhibition, first introduced by Stephenson and Zamecnik, *Proc. Natl. Acad. Sci. USA* (1978) 75:285–288; see also, Zamecnik, et al., *Proc. Natl. Acad. Sci. USA* (1986) 83:4143–4146). This technique is based on the discovery that synthetic DNA fragments can inhibit the transcription and/or translation of selected genes in a sequence-specific manner. Since its inception, the technique has found important diagnostic and clinical therapeutic applications in many fields of oncology, vascular and genetic diseases, and in the treatment of HIV and other virus infections. To date, two main antisense strategies have been employed: transfection of cells with antisense cDNA and treatment of cells with antisense oligodeoxynucleotides (ODN's), the use of ODN's derived from the translation initiation site, e.g., between the −10 and +10 regions of the target gene nucleotide sequence of interest being preferred. According to the present invention, molecules can be designed to reduce or inhibit either normal or, if appropriate, mutant target gene activity, using antisense technology. For further details see, for example, Wagner, "Gene Inhibition Using Antisense Oligodeoxynucleotides," *Nature* (1992) 372:333–335; Tonkinson and Stein, "Antisense Oligodeoxynucleotides as Clinical Therapeutic Agents," *Cancer Invest.* (1996) 14:54–65; Askari and McDonnell, "Antisense-Oligonucleotide Therapy," *N. Engl. J. Med.* (1996) 334:316–318; Redekop and Naus, "Transfection With bFGF Sense and Antisense cDNA Resulting in Modification of Malignant Glioma Growth," *J. Neurosurg.* (1997) 82:83–90; Saleh, et al., "Inhibition of Growth of C6 Glioma Cells In Vivo by Expression of Antisense Vascular Endothelial Growth Factor Sequence," *Cancer Res.* (1996) 56:393–401.

Oligodeoxynucleotides can be used for the inhibition of gene transcription in the form of triple helix structures. The base composition of these oligodeoxynucleotides must be designed to promote triple helix formation via Hoogsteen base pairing rules, which generally require sizeable stretches of either purines or pyrimidines to be present on one strand of a duplex. Nucleotide sequences can be pyrimidine-based, which will result in TAT and CGC+ triplets across the three associated strands of the resulting triple helix. The pyrimidine-rich molecules provide base complementarily to a purine-rich region of a single strand of the duplex, in a parallel orientation to that strand. In addition, nucleic acid molecules can be chosen that are purine-rich and, for example, contain a stretch of G residues. These molecules form a triple helix with a DNA duplex that is rich in GC pairs, in which the majority of the purine residues are located on a single strand of the targeted duplex, resulting in GGC triplets across the three strands in the triplex. Alternatively, creating a "switchback" nucleic acid molecule can increase the potential sequences that can be targeted for triple helix formation. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also covers the use of ribozymes. Ribozymes are enzymatic RNA molecules capable of catalyzing the specific cleavage of RNA (Rossi, *Current Biology* (1994) 4:469–471). The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA and must include the well-known catalytic sequence responsible for mRNA cleavage. For this sequence, see U.S. Pat. No. 5,093,246, which is incorporated by reference herein in its entirety. Within the scope of the present invention are engineered hammerhead motif ribozyme molecules that specifically and efficiently catalyze endonucleolytic cleavage of RNA sequences encoding target gene proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site can be evaluated for predicted structural features, such as secondary structure, that can render the oligonucleotide sequence unsuitable. The suitability of candidate sequences can also be evaluated by testing their accessibility to hybridization with complementary oligonucleotides, using ribonuclease protection assays.

In instances where the antisense, ribozyme, or triple helix molecules are utilized to reduce or inhibit mutant gene expression, it is possible that the transcription or translation of mRNA produced by normal alleles is also reduced or inhibited. As a result, the concentration of normal gene product may be lower than is necessary for a normal phenotype. In such cases, to ensure that substantially normal levels of gene activity are maintained, nucleic acid molecules that encode and express the polypeptide encoded by the gene targeted, can be introduced into cells via gene therapy methods, such as those described below. The nucleic acid sequence used in gene therapy is selected such that it does not contain sequences susceptible to the antisense, ribozyme, or triple helix treatments utilized. Alternatively, where the target gene encodes an extracellular protein, it can be preferable to co-administer normal target gene protein into the cell or tissue in order to maintain the requisite level of cellular or tissue target gene activity.

The present invention also contemplates the use of "peptide nucleic acids" (PNA's). PNA's have a peptide-like backbone instead of the normal sugar and phosphate groups of DNA. PNA's may be used to turn on specific genes, by binding to a promoter region of a gene to initiate RNA transcription. This approach is particularly useful where a particular disease or disorder is characterized by the underexpression of a particular gene, or where the increased expression of an identified gene has a beneficial effect on the treatment of a disease, in particular cardiac, kidney or inflammatory disease. Chimeric molecules of PNA and DNA may also be considered. The DNA portion will allow enzymes attacking DNA-RNA hybrids to cut the RNA part of the complex into pieces (leading to dissociation of the drug molecule, which can then be reused), whereas the PNA portion will contribute stability and selectivity.

As noted before, the polynucleotides of the present invention can also be used in gene therapy. In gene therapy applications, genes are introduced into cells in order to achieve in vivo synthesis of a therapeutically effective genetic product, for example for replacement of a defective gene. Gene therapy includes both conventional gene therapy where a lasting effect is achieved by a single treatment, and the administration of gene therapeutic agents, which involves the one time or repeated administration of a therapeutically effective DNA or RNA.

There are a variety of techniques available for introducing nucleic acid into viable cells. The techniques differ depending upon whether the nucleic acid in transferred into cultured cells in vitro, or in vivo in the cells of the intended host. Techniques suitable for the transfer of the nucleic acid into mammalian cells in vitro include the use of liposomes, electroporation, microinjection, cell fusion, DEAE-dextran, the calcium phosphate method, etc. The currently preferred in vivo gene transfer methods include transfection with viral (typically retroviral) vectors and viral coat protein-liposome mediated transfection (Dzau, et al., *Trends in Biotechnology* (1993) 11:205–210). In some situations it is desirable to provide the nucleic acid source with an agent that targets the target cells, such as an antibody specific for a cell surface membrane protein or the target cells, a ligand for a receptor on the target cells, etc. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. For review of gene marking and gene therapy protocols see Anderson, et al, *Science* (1992) 256:808–813.

The information provided by the present invention can also be used to detect genetic lesions in a differentially expressed gene of the present invention, thereby determining if a subject with the lesioned gene is at risk for a disorder characterized by differentially expressed gene expression or polypeptide activity. In preferred embodiments, the methods include detecting, in a biological sample from a subject, the presence or absence of a genetic lesion characterized by, for example, an alteration affecting the integrity of a gene encoding an polypeptide or the misexpression of the gene. For example, such genetic lesions can be detected by ascertaining the existence of at least one of: a deletion of one or more nucleotides from a gene; an addition of one or more nucleotides to a gene; a substitution of one or more nucleotides of a gene; a chromosomal rearrangement of a gene; an alteration in the level of a messenger RNA transcript of a gene; aberrant modification of a gene, such as of the methylation pattern of the genomic DNA; the presence of a non-wild type splicing pattern of a messenger RNA transcript of a gene; a non-wild type level of a gene protein; allelic loss of a gene; and inappropriate post-translational modification of a gene protein. As described herein, there are a large number of assay techniques known in the art that can be used for detecting lesions in a gene.

In certain embodiments, detection of a lesion may involve the use of a probe/primer in, such as anchor PCR or RACE PCR, or, alternatively, in LCR (see, e.g., Landegran, et al., *Science* (1988) 241:1077–1080; and Nakazawa, et al., *Proc. Natl. Acad. Sci. USA* (1994) 91:360–364), the latter of which can be particularly useful for detecting point mutations in the cardiac gene (see Abravaya, et al., *Nucleic Acids Res.* (1995) 23:675–682). This method can include the steps of collecting a biological sample from a subject, isolating nucleic acid (e.g., genomic, mRNA or both) from the cells of the sample, contacting the nucleic acid sample with one or more primers which specifically hybridize to an differentially expressed gene under conditions such that hybridization and amplification of the cardiac gene (if present) occurs, and detecting the presence or absence of an amplification product, or detecting the size of the amplification product and comparing the length to a control sample.

In an alternative embodiment, mutations in a differentially expressed gene from a sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see U.S. Pat. No. 5,498,531) can be used to score for the presence of specific mutations by development or loss of a ribozyme cleavage site.

The arrays of immobilized DNA fragments may also be used for genetic diagnostics. To illustrate, a microarray containing multiple forms of a mutated gene or genes can be probed with a labeled mixture of a subject DNA, which will preferentially interact with only one of the immobilized versions of the gene.

The detection of this interaction can lead to a medical diagnosis. Arrays of immobilized DNA fragments can also be used in DNA probe diagnostics. For example, the identity of a differentially expressed gene of the present invention can be established unambiguously by hybridizing a sample of a subject's DNA to an array comprising known differentially expressed DNA. Other molecules of genetic interest, such as cDNA's and RNA's can be immobilized on the array or alternately used as the labeled probe mixture that is applied to the array.

b. Polypeptides

The native polypeptides of the present invention, and their equivalents in other mammalian (e.g., human) species, can be used to identify interacting proteins and genes encoding such proteins. Interacting proteins and their genes may be part of the signaling pathway in which the differentially expressed genes identified herein participate, and thus are valuable diagnostic and therapeutic candidates or targets. Among the traditional methods employed are co-immunoprecipitation, cross-linking and co-purification through gradients or chromatographic columns. Using procedures such as these allows for the identification of interactive gene products. Once identified, an interactive gene product can be used, using standard techniques, to identify its corresponding interactive gene. For example, at least a portion of the amino acid sequence of the interactive gene product can be ascertained using techniques well known to those of skill in the art, such as the Edman degradation technique (see, e.g., Creighton, *Proteins: Structures and Molecular Principles*, W. H. Freeman & Co. (New York, N.Y. (1983), pp. 34–49). The amino acid sequence obtained can be used as a guide for the generation of oligonucleotide mixtures that can be used to screen for interactive gene sequences. Screening can be accomplished, for example, by standard hybridization or PCR techniques. Techniques for the generation of oligonucleotide mixtures and the screening are well known.

Additionally, methods can be employed which result in the simultaneous identification of interactive genes that encode the protein interacting with a protein involved in a disease, specifically cardiac, kidney or inflammatory disease. These methods include, for example, probing expression libraries with a labeled protein known or suggested to be involved in a disease, using this protein in a manner similar to the well known technique of antibody probing of λgtll libraries.

A particularly suitable technique for studying protein-protein interactions is the yeast two-hybrid assay. Many transcriptional activators, such as yeast GAL4, consist of two physically discrete modular domains, one acting as the DNA-binding domain, while the other one functioning as the transcription activation domain. The yeast two-hybrid system takes advantage of this property, and employs two hybrid proteins, one in which the target protein is fused to the DNA-binding domain of GAL4, and another, in which candidate activating proteins are fused to the activation domain. The expression of a GAL1-calZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions using the yeast two-hybrid technique is available from Clontech. For further details see, e.g., Fields and Song, *Nature* (London) (1989) 340:245–246; Chien, et al., *Proc. Natl. Acad. Sci. USA* (1991) 88:9578–9582; and Chevray and Nathans, *Proc. Natl. Acad. Sci. USA* (1992) 89:5789–5793.

Polypeptides of the present invention may also be used to generate antibodies, using well-known techniques, some of which have been detailed above.

The polypeptides of the present invention are also useful in assays for identifying lead compounds for therapeutically active agents for the treatment of cardiac, kidney or inflammatory diseases. Candidate compounds include, for example, peptides such as soluble peptides, including Ig-tailed fusion peptides (e.g., immunoadhesins) and members of random peptide libraries (see, e.g., Lam, et al., *Nature* (1991) 354:82–84; Houghten, et al., *Nature* (1991) 354: 84–86) and combinatorial chemistry-derived molecular libraries made of D- or L-configuration amino acids; phosphopeptides (e.g., members of random and partially degenerate, directed phosphopeptide libraries, see, e.g., Songyang, et al., *Cell* (1993) 72:767–778; antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and small organic and inorganic molecules (e.g., molecules obtained from combinatorial and natural product libraries).

Such screening assays are preferably amenable to high-throughput screening of chemical libraries, and are particularly suitable for identifying small molecule drug candidates. Small molecules, which are usually less than 10K molecular weight, are desirable as therapeutics since they are more likely to be permeable to cells, are less susceptible to degradation by various cellular mechanisms, and are not as apt to elicit immune response as proteins. Small molecules include but are not limited to synthetic organic or inorganic compounds, and peptides. Many pharmaceutical companies have extensive libraries of such molecules, which can be conveniently screened by using the assays of the present invention. The assays can be performed in a variety of formats, including protein-protein binding assays, biochemical screening assays, immunoassays, cell based assays, etc. Such assay formats are well known in the art.

In a preferred embodiment, the screening assays of the present invention involve contacting a biological sample obtained from a subject having a disease, specifically cardiac, kidney or inflammatory disease, characterized by the differential expression of a gene identified herein, with a candidate compound or agent. The expression of the gene or the activity of the gene product is then determined in the presence and absence of the test compound or agent. When expression of differentially expressed gene mRNA or polypeptide is greater (preferably statistically significantly greater) in the presence of the candidate compound than in its absence, the candidate compound may be identified as a stimulator of differentially expressed gene expression. Alternatively, when differentially expressed gene expression is less (preferably statistically significantly less) in the presence of the candidate compound than in its absence, the candidate compound may be identified as an inhibitor of differentially expressed gene expression. The level of differentially expressed gene expression in the cells can be determined by methods described herein for detecting differentially expressed gene mRNA or protein.

Compounds identified via assays such as those described herein can be useful, for example, in elaborating the biological function of the target gene product, and for treating a cardiac, kidney or inflammatory disease, or ameliorating symptoms of such disease. In instances when a disease state or disorder results from a lower overall level of target gene expression, target gene product, or target gene product activity in a cell involved in the disease, compounds that interact with the target gene product can include ones accentuating or amplifying the activity of the bound target gene protein. Such compounds would bring about an effective increase in the level of target gene activity, thus treating the disease, disorder or state, or ameliorating its symptoms. Where mutations within the target gene cause aberrant target gene proteins to be made, which have a deleterious effect that leads to a disease, compounds that bind target gene protein can be identified that inhibit the activity of the bound target gene protein.

5. Pharmaceutical Compositions

Pharmaceutical compositions of the present invention can comprise a polynucleotide of the present invention, a product of the genes identified herein, or other therapeutically active compounds, including organic small molecules, peptides, polypeptides, antibodies, etc., identified with the aid of the differentially expressed genes identified herein.

Suitable forms, in part, depend upon the use or the route of entry, for example oral, transdermal, inhalation, or by injection. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms that prevent the agent or composition from exerting its effect.

The active ingredient, when appropriate, can also be formulated as pharmaceutically acceptable salts (e.g., acid addition salts) and/or complexes. Pharmaceutically acceptable salts are non-toxic at the concentration at which they are administered. Pharmaceutically acceptable salts include acid addition salts such as those containing sulfate, hydrochloride, phosphate, sulfonate, sulfamate, sulfate, acetate, citrate, lactate, tartrate, methanesulfonate, ethanesulfonate, benzenesulfonate, p-toluenesulfonate, cyclolexylsulfonate, cyclohexylsulfamate and quinate. Pharmaceutically acceptable salts can be obtained from acids such as hydrochloric acid, sulfuric acid, phosphoric acid, sulfonic acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including, but not limited to, intravenous, intra-arterial, intraperitoneal, intrapericardial, intracoronary, subcutaneous, and intramuscular, oral, topical or transmucosal.

The desired isotonicity of the compositions can be accomplished using sodium chloride or other pharmaceutically acceptable agents such as dextrose, boric acid, sodium tartrate, propylene glycol, polyols (such as mannitol and sorbitol), or other inorganic or organic solutes.

Pharmaceutical compositions can be formulated for a variety of modes of administration, including systemic and topical or localized administration. Techniques and formulations generally may be found in *Remington's Pharmaceutical Sciences*, 18$^{th}$ Edition, Mack Publishing Co., Easton, Pa. (1990). See, also, Wang and Hanson "Parenteral Formulations of Proteins and Peptides: Stability and Stabilizers," *Journal of Parenteral Science and Technology* (1988), Technical Report No. 10, Supp. 42–2S. A suitable administration format can best be determined by a medical practitioner for each patient individually.

For systemic administration, injection is preferred, e.g., intramuscular, intravenous, intra-arterial, intracoronary, intrapericardial, intraperitoneal, subcutaneous, intrathecal, or intracerebrovascular. For injection, the compounds of the invention are formulated in liquid solutions, preferably in physiologically compatible buffers such as Hank's solution or Ringer's solution. Alternatively, the compounds of the invention are formulated in one or more excipients (e.g., propylene glycol) that are generally accepted as safe as defined by USP standards. They can, for example, be suspended in an inert oil, suitably a vegetable oil such as sesame, peanut, olive oil, or other acceptable carrier. Preferably, they are suspended in an aqueous carrier, for example, in an isotonic buffer solution at pH of about 5.6 to 7.4. These compositions can be sterilized by conventional sterilization techniques, or can be sterile filtered. The compositions can contain pharmaceutically acceptable auxiliary substances as required to approximate physiological conditions, such as pH buffering agents. Useful buffers include for example, sodium acetate/acetic acid buffers. A form of repository or "depot" slow release preparation can be used so that therapeutically effective amounts of the preparation are delivered into the bloodstream over many hours or days following transdermal injection or delivery. In addition, the compounds can be formulated in solid form and redissolved or suspended immediately prior to use. Lyophilized forms are also included.

Alternatively, certain compounds identified in accordance with the present invention can be administered orally. For oral administration, the compounds are formulated into conventional oral dosage forms such as capsules, tablets and tonics.

Systemic administration can also be by transmucosal or transdermal. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be, for example, through nasal sprays or using suppositories.

For administration by inhalation, usually inhalable dry power compositions or aerosol compositions are used, where the size of the particles or droplets is selected to ensure deposition of the active ingredient in the desired part of the respiratory tract, e.g., throat, upper respiratory tract or lungs. Inhalable compositions and devices for their administration are well known in the art. For example, devices for the delivery of aerosol medications for inspiration are known. One such device is a metered dose inhaler that delivers the same dosage of medication to the patient upon each actuation of the device. Metered dose inhalers typically include a canister containing a reservoir of medication and propellant under pressure and a fixed volume metered dose chamber. The canister is inserted into a receptacle in a body or base having a mouthpiece or nosepiece for delivering medication to the patient. The patient uses the device by manually pressing the canister into the body to close a filling valve and capture a metered dose of medication inside the chamber and to open a release valve which releases the captured, fixed volume of medication in the dose chamber to the atmosphere as an aerosol mist. Simultaneously, the patient inhales through the mouthpiece to entrain the mist into the airway. The patient then releases the canister so that the release valve closes and the filling valve opens to refill the dose chamber for the next administration of medication. See, for example, U.S. Pat. No. 4,896,832 and a product available from 3M Healthcare known as Aerosol Sheathed Actuator and Cap.

Another device is the breath actuated metered dose inhaler that operates to provide automatically a metered dose in response to the patient's inspiratory effort. One style of breath actuated device releases a dose when the inspiratory effort moves a mechanical lever to trigger the release valve. Another style releases the dose when the detected flow rises above a preset threshold, as detected by a hot wire anemometer. See, for example, U.S. Pat. Nos. 3,187,748; 3,565,070; 3,814,297; 3,826,413; 4,592,348; 4,648,393; and 4,803,978.

Devices also exist to deliver dry powdered drugs to the patient's airways (see, e.g., U.S. Pat. No. 4,527,769) and to deliver an aerosol by heating a solid aerosol precursor material (see, e.g., U.S. Pat. No. 4,922,901). These devices typically operate to deliver the drug during the early stages of the patient's inspiration by relying on the patient's inspiratory flow to draw the drug out of the reservoir into the airway or to actuate a heating element to vaporize the solid aerosol precursor.

Devices for controlling particle size of an aerosol are also known, see, for example, U.S. Pat. Nos. 4,790,305; 4,926,852; 4,677,975; and 3,658,059.

For topical administration, the compounds of the invention are formulated into ointments, salves, gels, or creams, as is generally known in the art.

If desired, solutions of the above compositions can be thickened with a thickening agent such as methyl cellulose. They can be prepared in emulsified form, either water in oil or oil in water. Any of a wide variety of pharmaceutically acceptable emulsifying agents can be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components can be mixed simply in a blender or other standard device to produce a concentrated mixture which can then be adjusted to the final concentration and viscosity by the addition of water or thickening agent and possibly a buffer to control pH or an additional solute to control tonicity.

The amounts of various compounds for use in the methods of the invention to be administered can be determined by standard procedures. Generally, a therapeutically effective amount is between about 100 mg/kg and $10^{-12}$ mg/kg depending on the age and size of the patient, and the disease or disorder associated with the patient. Generally, it is an amount between about 0.05 and 50 mg/kg of the individual to be treated. The determination of the actual dose is well within the skill of an ordinary physician.

The invention is further illustrated in the following non-limiting examples.

EXAMPLES

Example 1

Identification of Differentially Expressed Rat Genes Referred to by Clone ID Number 1. In Vivo Model of Myocardial Infarction Genes P00184_D11 (SEQ ID NO: 1), P00185_D11 (SEQ ID NO: 3), P00188_D12 (SEQ ID NO: 5), P00188_E01 (SEQ ID NO: 7), P00194_G01 (SEQ ID NO: 9), P00194_G05 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00223_F07 (SEQ ID NO: 31), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_B04 (SEQ ID NO: 44), P00240_E05 (SEQ ID NO: 45), P00241_E12 (SEQ ID NO: 47), P00245_D06 (SEQ ID NO: 48), P00246_D12 (SEQ ID NO: 49), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00263_G06 (SEQ ID NO: 60), P00267_F08 (SEQ ID NO: 61), P00269_H08 (SEQ ID NO: 62), P00312_C04 (SEQ ID NO: 64), P00324_H02 (SEQ ID NO: 65), P00628_H02 (SEQ ID NO: 66), P00629_C08 (SEQ ID NO: 68), P00634_G11 (SEQ ID NO: 70), P00641_G11 (SEQ ID NO: 71), P00648_E12 (SEQ ID NO: 73), and P00697_C03 (SEQ ID NO: 75), were identified by analysis of left ventricular heart tissue obtained from an in vivo model of left ventricle myocardial infarction (MI) (Pfeffer, et al., *Circ. Res.* (1985) 57:84–95). Specifically, male Sprague-Dawley rats at age 7–10 weeks were anesthetized with ketamine (80 mg/kg IP) and xylazine (10 mg/kg IP). The thorax and abdomen was shaved, after which the areas were scrubbed with povidone-iodine and 70% isopropyl alcohol a minimum of three times, beginning at the incision line and continuing in a circular motion proceeding toward the periphery. The rats were intubated and placed on a respirator with room air at a rate of 55 breaths/min. A left thoracotomy was performed between the fourth and fifth ribs, after which the heart was exteriorized and the left anterior descending coronary artery (LAD) ligated with silk suture. The same surgical procedure was employed for sham-operated rats, however, the suture was passed through the left ventricular wall and the LAD was not occluded.

Following the surgical procedure, negative pressure in the thoracic was quickly reestablished and the wound closed with a purse-string suture using 3-0 non-absorbable suture material. Butorphanol (0.1 mg/kg. SQ) was provided post surgery as a prophylactic analgesic. The rats were extubated when they recovered their gag reflex and allowed recovering in a warming chamber. Seventy-five percent of the rats had large infarcts on their left ventricle free walls and perioperative mortality rate is about 50%, which is comparable to the published data.

Tissue was collected 2 week, 4 week, 8 week, 12 week and 16 week post-surgery. Blood was collected the day before surgery and the day before sacrifice for measurement of plasma atrial natriuretic peptide (ANP) level. On the day of necropsy, each heart was divided transversely into two halves so that the infarcted area is bisected. One half of the heart was used for histological evaluation, and the other for mRNA microarray analysis.

2. In Vivo Model of Septum Myocardial Infarction

Septum tissue was obtained from diseased rat hearts obtained through the left ventricle rat MI model of Pfeffer, et al., as described above. Poly A+mRNA was prepared from each of these septums for assessment of differentially expressed genes in the disease state, using microarray analysis in a preferred embodiment.

3. Preparation of Normalized cDNA Libraries

Poly A+mRNA was prepared from each of the animals, for assessment of differentially expressed genes in the disease state, using microarray analysis. Total RNA was isolated from homogenized tissue by acid phenol extraction (Chomczynski and Sacchi, *Anal. Biochem.* (1987) 162(1): 156–159). Poly A+mRNA was selected from total RNA by oligo dT hybridization utilizing a polyA Spin mRNA Isolation Kit (New England BioLabs, Beverly, Mass.) according to manufacturers' protocols. A directionally cloned cDNA library was first generated by conventional methods. Briefly, double stranded cDNA was generated by priming first strand synthesis for reverse transcription using oligo dT primers which contain a Not I restriction site. After second strand synthesis, Xba I adapters were added to the 5' end of the cDNA, and the cDNA size was selected for >500 bp and ligated into the corresponding restriction sites of phagemid vector pCR2.1 (Invitrogen, San Diego Calif.).

From the total cDNA library, a normalized library was generated as detailed elsewhere (see, e.g., Bonaldo, et al., *Genome Res.* (1996) 6(9):791–806) and described here briefly. Phagemid vector pCR2.1 contains an F1 origin of replication. Thus, the cDNA library can be propagated as single stranded phage with an appropriate helper virus. Single stranded, circular DNA was extracted from the phage library and served as "tester" DNA in the hybridization step of normalization. The other component of the hybridization, "driver" DNA, was generated from the library by PCR amplification using a set of the following primers specific for the region of the vector, which flanks the cloned inserts:

```
5' CGTATGTTGTGTGGAATTGTGAGCG    (SEQ ID NO: 77)
5' GATGTGCTGCAAGGCGATTAAGTTG    (SEQ ID NO: 78)
```

Purified tester DNA (50 ng) and driver DNA (0.5 µg) were combined in 120 mM NaCl, 50% formamide, 10 mM Tris (pH 8.0), 5 mM EDTA, and 1% SDS. A set of oligonucleotides (10 µg each), corresponding to polylinker sequence (same strand as tester DNA) which is present in the PCR product, was included in the hybridization reaction to block annealing of vector-specific sequences which are in common between tester and driver DNA. The oligonucleotide sequences were as follows:

```
5' GCCGCCAGTGTGCTGGAATTCGGCTAGC    (SEQ ID NO: 79)
5' CGAATTCTGCAGATATCCATCACACTGG    (SEQ ID NO: 80)
5' CTAGAGGGCCCAATTCGCCCTATAG       (SEQ ID NO: 81)
5' TGAGTCGTATTACAATTCACTGGCC       (SEQ ID NO: 82)
5' GCTCGGATCCACTAGTAACG            (SEQ ID NO: 83)
5' TTTTTTTTTTTTTTTTTT              (SEQ ID NO: 84)
```

The reaction mixture, under oil, was heated 3 min. at 80° C., and hybridization performed at 30° C. for 24 hr (calculated $C_o t\sim 5$). Single stranded circles were purified from the reaction mixture by hydroxylapatite (HAP) chromatography, converted to double strand DNA, and electroporated into bacteria to yield a normalized cDNA library representative of genes expressed in the left ventricle of rat. To evaluate the effectiveness of the normalization protocol, the frequency of a few clones (ANP, BNP, actin, and myosin) was assessed in both in the starting library and the normalized library. The frequency of abundant cDNA's (actin and myosin) was reduced and roughly equivalent to rarer cDNA clones (ANP and BNP). Clone frequency in the two libraries was determined with standard screening techniques by immobilizing colonies onto nylon membranes and hybridizing with radiolabeled DNA probes.

Certain genes, unexpressed in a normal tissue and turned on in diseased tissue, may be absent from the normalized cDNA library generated from normal tissue. To obtain disease-specific clones to include on the microarray, one can repeat the normalization strategy using diseased tissue obtained from the appropriate disease model. However, since most genes are expressed commonly between normal and diseased tissue, microarraying normalized libraries from diseased and normal tissue may introduce significant redundancy. a subtracted library can be made using protocols similar to those used to generate normalized libraries. Again, the method of Bonaldo, et al., supra, as described here briefly, is used.

To make a subtracted library, a total cDNA library is generated from the tissue obtained from the disease model (e.g., left ventricle taken from the MI Model). The cDNA library is directionally cloned in pCR2.1 vector and single stranded tester DNA derived as described above for library normalization. The driver DNA is generated by PCR amplification of cloned inserts from the total cDNA library prepared from the left ventricle of normal rat. Hybridization occurs between sequences, which are in common to normal and diseased hearts. For this subtracted library, the reaction is driven more thoroughly (calculated $C_o t\sim 27$) than normalization by using more driver (1.5 µg vs. 0.5 µg) and longer hybridization time (48 hr vs. 24 hr). Purification of non-hybridized, single stranded circles by HAP chromatography, conversion to double strand DNA, and electroporation into bacteria yields a subtracted cDNA library enriched for genes which are expressed in diseased rat hearts. To test that the library is truly subtracted, colony hybridization is performed with probes for ANP, BNP, actin, and myosin. The subtracted library has a high frequency of ANP and BNP clones since they are elevated significantly in the hypertrophic rat heart. Actin and myosin clones are absent since they are expressed equally in normal and diseased left ventricle.

4. Microarray Analysis

High quality DNA is important for the microarray printing process. A microtitre plate protocol for PCR amplification of DNA and its subsequent purification was established that provides acceptable quality and quantity of DNA for printing on microarrays. Specifically, the following PCR probes were synthesized that amplify insert DNA from the vector pCR2.1 that was used for library construction:

```
5' CGTATGTTGTGTGGAATTGTGAGCG    (SEQ ID NO: 85)
5' GATGTGCTGCAAGGCGATTAAGTTG    (SEQ ID NO: 86)
```

After 30 cycles of amplification each PCR product was passed over a gel filtration column to remove unincorporated primers and salts. To maintain robustness, the columns were packed in 96-well filter plates and liquid handling was performed using a robotic liquid handler (Biomek 2000, Beckman).

To test the quality of DNA prepared by this PCR method, 96 purified samples from a single microtitre plate were produced as a microarray. Using the robotic liquid handler, 85 µl of PCR reaction mixture was aliquotted into each well of a thin walled, 0.2 ml 96-well plate. The reaction mixture contained 0.2 mM each dNTP, 1.25 units of Taq polymerase, and 1×Taq buffer (Boehringer Mannheim). Primers, 1 µm each, are from vector regions, which flank the cloning site of pCR2.1 and include a 5' primary amine with a 6-carbon linker to facilitate attachment of DNA product to the glass surface of the microarray chip. 1.0 µl of bacterial culture of individual cDNA clones was added to each well. PCR conditions were: 2 min., 95° C. to denature, then 30 cycles of 95° C., 30 sec./65° C., 40 sec./72° C., 1 min. 30 sec., and a final extension of 72° C., 5 min. using a MJResearch PTC 100 thermocycler.

PCR products were purified by gel filtration over Sephacryl 400 (Sigma). Briefly, 400 µl of pre-swollen Sephacryl 400 was loaded into each well of a 96-well filter plate (PallBiosupport) and spun into a collection plate at 800 g for 1 min. Wells were washed 5 times with 0.2×SSC. PCR reaction mixtures were loaded onto the column and purified DNA (flow-through) was collected at 800 g for 1 min. Samples were dried down at 50° C. overnight and arrayed.

Fluorescent probe pairs were synthesized by reverse transcription of poly A+RNA using, separately, Cy3 dCTP and CyS dCTP (Amersham). In 16.5 µl, 1 µg poly A+RNA and 2 µg of oligo dT 21 mer, were denatured at 65° C., 5 min. and annealed at 25° C., 10 min. Reverse transcription was performed for 2 hours at 37° C. with Superscript RT (Life Technologies, Gaithersburg, Md.) in 1× buffer, 10 units RNase block, 500 µM each dATP/dGTP/dTTP, 280 q µM dCTP, 40 µM CyS or Cy3 dCTP, and 200 units RT. RNA is degraded in 0.1 M NaOH, 65° C. for 10 min. Labeled cDNA was purified by successive filtration with Chroma Spin 30 spin columns (Clontech) following manufacturer's instructions. Samples were dried at room temperature in the dark using a covered Speed-Vac. Probes were applied to the test chip for hybridization and the data collected essentially as described in Schena, et al., cited above The intensity of hybridization signal at each element reflected the level of expression of the mRNA for each gene in the rat ventricle. Digitized signal data was stored and prepared for analysis.

A series of control DNA elements were included on each chip to ensure consistency in labeling and hybridization between experiments and to aid in balancing the signal when two fluorescence channels are used. For each element hybridized with dual labeled probes, absolute and relative intensity of signal was determined. The results from these and other experiments indicate that these methods for production of template DNA and labeled cDNA probes are suitable for generating high quality microarrays within a preferred embodiment of the methods of the present invention. The evaluation of tens of thousands of genes for expression generates a large amount of data that can be manipulated by commercially available software packages that facilitate handling this type and quantity of data. The expression data can be stored, analyzed, and sorted from each experiment using this software. In addition, expression of each clone can be tracked from experiment to experiment using known methodologies.

The novel secreted factor of the present invention was identified from expression data from the following experiments: A 10,000 clone microarray (10K) from a normalized normal rat left ventricle (LV) cDNA library was probed in duplicate. A 3,000 clone array, which included differentially expressed clones from the 10K library, was also probed in duplicate. Included on the microarray with the unidentified genes were a set of known clones. These known clones were included because they represent genes of particular interest and help evaluate the sensitivity of the microarray methodology. Indeed, any genes of particular interest may be included on such microarrays. By way of example, ANP, BNP, endothelin, β-myosin heavy chain, and α-actin are genes that change expression levels in the LVH model, and thus they serve as useful positive controls in the in vivo model exemplified herein.

The intensity of hybridization signal at each element of the microarray reflected the level of expression of the mRNA for each gene. For each element hybridized with dual labeled probes, absolute and relative intensity of signal was determined, which translates into the relative expression levels of the subject genes. The numeric data obtained reflect the relative expression level of the gene in the disease state as compared to the expression level of the gene in the normal, or non-disease state. Positive numbers are indicative of genes expressed at higher levels in the diseased tissue relative to normal tissue, and negative values are indicative of lower expression in disease. Data are the average values from multiple experiments performed with separate DNA arrays (n=4 for MI left ventricle and septum). Array probes were generated from RNA pooled from multiple animals (n=4 for MI).

The data also reflect expression levels of genes in certain disease models over various time points. For example, gene expression in the myocardial infarction model was compared at 2, 4, 8, 12, and 16 weeks for the representative genes in the disease state versus the normal state. Indeed, such experimentation provides valuable data regarding the temporal relationship of gene expression levels in disease states and provides important insights regarding the treatment, diagnosis, and modulation of differentially expressed disease state genes, as discussed in detail infra.

One to two percent of the clones assayed on microarrays were found to be differentially expressed. Secondary chips may be used for more extensive hybridizations, including examination of individual animals, and more thorough evaluation of time points. In a preferred embodiment, clones that reproducibly scored in microarray analysis to be at least about 1.8-fold elevated or decreased were microarrayed on separate secondary chips and their expression levels determined. It is understood, however, that differentially expressed genes exhibiting less than about a two-fold change in expression, e.g., less than one, one-half, or one-quarter, or greater than about a two-fold change in expression, e.g., greater than three, five, ten, twenty, one hundred-fold, or one thousand-fold, are within the scope of the present invention.

5. Microarray Results

Using the foregoing protocols, it was found that in the MI model, the expression level of the gene corresponding to the clones were differentially expressed in heart and kidney. This differential expression suggests the possible involvement of these genes in the development and/or progress of MI. The results are summarized in FIG. 44.

6. Sequence Analysis

The differentially expressed partial and full-length clones P00184_D11 (SEQ ID NO: 1), P00185_D11 (SEQ ID NO: 3), P00188_D12 (SEQ ID NO: 5), P00188_E01 (SEQ ID NO: 7), P00194_G01 (SEQ ID NO: 9), P00194_G05 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00223_F07 (SEQ ID NO: 31), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_B04 (SEQ ID NO: 44), P00240_E05 (SEQ ID NO: 45), P00241_E12 (SEQ ID NO: 47), P00245_D06 (SEQ ID NO: 48), P00246_D12 (SEQ ID NO: 49), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00263_G06 (SEQ ID NO: 60), P00267_F08 (SEQ ID NO: 61), P00269_H08 (SEQ ID NO: 62), P00312_C04 (SEQ ID NO: 64), P00324_H02 (SEQ ID NO: 65), P00628_H02 (SEQ ID NO: 66), P00629_C08 (SEQ ID NO: 68), P00634_G11 (SEQ ID NO: 70), P00641_G11 (SEQ ID NO: 71), P00648_E12 (SEQ ID NO: 73), and P00697_C03 (SEQ ID NO: 75) were sequenced (SEQ ID NOs: 1, 3, 5, 7, 9, 11, 13, 15, 17, 19, 21, 23, 25, 27, 29, 31, 32, 34, 36, 38, 40, 42, 44, 45, 47, 48, 49, 50, 52, 54, 56, 58, 59, 60, 61, 62, 64, 65, 66, 68, 70, 71, 73 and 75), and the deduced amino acid sequence was determined (SEQ ID NOs: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74 and 76). FIGS. 1–43 show the deduced amino acid sequence of the polypeptide encoded by the clones as well as the nucleotide sequences.

The nucleotide sequences of the clones were compared with sequences in the public GenBank, EMBL, DDBJ, PDB and GENSEQ databases. The search was performed using the BLASTN 2.0.8 program with default parameters. Gap penalties: existence: 5; extension: 2. The search revealed no significant homology with sequences present in the searched databases.

7. Northern Blot Analysis

Northern blot analysis suggested that the clones are differentially expressed (see FIG. 44).

Example 2

Identification of the Human Homologue of Rat Clone

The isolated differentially expressed rat gene sequence can be labeled and used to screen a cDNA library constructed from mRNA obtained from an organism of interest. Hybridization conditions will be of a lower stringency when the cDNA library was derived from an organism different from the type of organism from which the labeled sequence was derived. Alternatively, the labeled fragment can be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, Sambrook, et al., supra, and Ausubel, et al., supra.

PCR technology can also be utilized to isolate full-length human cDNA sequences. For example, RNA can be isolated, following standard procedures, from an appropriate human cellular or tissue source. A reverse transcription reaction can be performed on the RNA using an oligonucleotide primer specific for the most 5' end of the amplified fragment for the priming of first strand synthesis. The resulting RNA/DNA hybrid can then be "tailed" with guanines using a standard terminal transferase reaction, the hybrid can be digested with RNase H, and second strand synthesis can then be primed with a poly-C primer. Thus, cDNA sequences upstream of the amplified fragment can easily be isolated. For a review of cloning strategies that can be used, see, e.g., Sambrook, et al., supra, and Ausubel, et al., supra.

Alternatively, the human homologue can be isolated using the CloneCapture cDNA selection Kit (Clontech, Palo Alto, Calif.): a RecA-based system for the rapid enrichment and isolation of cDNA clones of interest without library screening.

Example 3

Expression of the Clones in *E. Coli*

The P00184_D11 (SEQ ID NO: 1), P00185_D11 (SEQ ID NO: 3), P00188_D12 (SEQ ID NO: 5), P00188_E01 (SEQ ID NO: 7), P00194_G01 (SEQ ID NO: 9), P00194_G05 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_E05 (SEQ ID NO: 45), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00269_H08 (SEQ ID NO: 62), P00628_H02 (SEQ ID NO: 66), P00629_C08 (SEQ ID NO: 68), P00641_G11 (SEQ ID NO: 71), P00648_E12 (SEQ ID NO: 73), and P00697_C03 (SEQ ID NO: 75) DNA is initially amplified using selected PCR primers. The primers should contain restriction enzyme sites that correspond to the restriction enzyme sites on the selected expression vector. A variety of expression vectors may be employed. An example of a suitable vector is pBR322 (derived from *E. coli;* see Bolivar, et al., *Gene* (1977) 2:95) which contains genes for ampicillin and tetracycline resistance, or a pBR322-based vector. Other, commercially available vectors include various pUC vectors and Bluescript M13. The vector is digested with restriction enzyme and dephosphorylated. The PCR amplified sequences are then ligated into the vector. The vector will preferably include sequences that encode an antibiotic resistance gene, a promoter, such as a T7 or tryptophan (trp) promoter, a poly-His leader (including the first six STII codons, poly-His sequence, and enterokinase cleavage site), the P00184_D 11 (SEQ ID NO: 1), P00185_D11 (SEQ ID NO: 3), P00188_D12 (SEQ ID NO: 5), P00188_E01 (SEQ ID NO: 7), P00194_G01 (SEQ ID NO: 9), P00194_G05 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_E05 (SEQ ID NO: 45), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00269_H08 (SEQ ID NO: 62), P00628_H02 (SEQ ID NO: 66), P00629_C08 (SEQ ID NO: 68), P00641_G11 (SEQ ID NO: 71), P00648_E12 (SEQ ID NO: 73), and P00697_C03 (SEQ ID NO: 75) coding region, lambda transcriptional terminator, and an argU gene.

The ligation mixture is then used to transform a selected *E. coli* strain using the methods described in Sambrook, et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized protein can then be purified using a metal chelating column under conditions that allow tight binding of the poly-his tagged protein.

Example 4

Expression of the Clones in Yeast

A yeast expression vector is constructed either for intracellular production or secretion of the protein encoded by P00184_D11 (SEQ ID NO: 1), P00185_D11 (SEQ ID NO: 3), P00188_D12 (SEQ ID NO: 5), P00188_E01 (SEQ ID NO: 7), P00194_G01 (SEQ ID NO: 9), P00094_G05 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_E05 (SEQ ID NO: 45), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00269_H08 (SEQ ID NO: 62), P00628_H02 (SEQ ID NO: 66), P00629_C08 (SEQ ID NO: 68), P00641_G11 (SEQ ID NO: 71), P00648_E12 (SEQ ID NO: 73), and P00697_C03 (SEQ ID NO: 75), using an appropriate yeast promoter, such the promoter of 3-phosphoglycerate kinase, or the promoter regions for alcohol oxidase 1 (AOX1, particularly preferred for expression in *Pichia*), alcohol dehydrogenase 2, or isocytochrome C. For secretion, the P00184_D11 (SEQ ID NO: 1), P00185_D11 (SEQ ID NO: 3), P00188_D12 (SEQ ID NO: 5), P00188_E01 (SEQ ID NO: 7), P00194_G01 (SEQ ID NO: 9), P00194_G05 (SEQ ID NO: 1), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_E05 (SEQ ID NO: 45), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00269_H08 (SEQ ID NO: 62), P00628_H02 (SEQ ID NO: 66), P00629_C08 (SEQ ID NO: 68), P00641_G11 (SEQ ID NO: 71), P00648_E12 (SEQ ID NO: 73), and P00697_C03 (SEQ ID NO: 75) coding sequence is linked, at its 5'-end, to a mammalian or yeast signal (secretory leader) sequence, such as a yeast alpha-factor or invertase secretory signal. Alternatively, a commercially available yeast expression system is used that can be purchased, for example, from Clontech Laboratories, Inc. (Palo Alto, Calif., e.g., pYEX 4T family of vectors for Saccharomyces cerevisiae), Invitrogen (Carlsbad, Calif., e.g., pPICZ series Easy Select Pichia Expression Kit) or Stratagene (La Jolla, Calif., e.g., ESP™ Yeast Protein Expression and Purification System for *S. pombe* and pESC vectors for *S. cerevisiae*).

Yeast cells, such as *S. cerevisiae* AB110 strain, or *P. pastoris* GS115 (NRRL Y-15851); GS090 (NRRLY-18014) or PPFI (NRRLY-18017) are then transformed by known techniques, e.g., by the polyethylene glycol method (Hinnen, *Proc. Natl. Acad, Sci. USA* (1978) 75:1929).

The recombinant protein is subsequently isolated and purified by removing the yeast cells from the fermentation medium by centrifugation and then concentrating the medium using selected cartridge filters. The concentrate containing the expressed protein may be further purified using selected column chromatography resins.

Example 5

Expression of the Clones in Mammalian Host Cells

The P00184_D11 (SEQ ID NO:1), P00185_D11 (SEQ ID NO: 3), P00188_D12 (SEQ ID NO: 5), P00188_E01 (SEQ ID NO: 7), P00194_G01 (SEQ ID NO: 9), P00194_G05 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_E05 (SEQ ID NO: 45), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00269_H08 (SEQ ID NO: 62), P00628_H02 (SEQ ID NO: 66), P00629_C08 (SEQ ID NO: 68), P00641_G11 (SEQ ID NO: 71), P00648_E12 (SEQ ID NO: 73), and P00697_C03 (SEQ ID NO: 75) genes are subjected to PCR using primers containing suitable restriction enzyme cleavage sites to allow ligation into a mammalian expression vector such as pCEP4 (Invitrogen). To facilitate the eventual recovery of the expressed protein, it is advisable to use the 3' PCR primer to extend the open reading frame of the cloned gene to include an affinity purification tag such as poly-His (E. Hochuli, et al., *J. Chrom.* (1987) 411:177–184) or calmodulin binding peptide (Hathaway, et al., *J. Biol. Chem.* (1981) 256(15):8183–8189). Recovery of the PCR fragment may be followed by its cleavage at the new flanking restriction sites and ligation into a similarly cleaved pCEP4 preparation. Transformation of bacteria and preparation of plasmids from transformants is followed by verification of the plasmid structure by restriction analysis.

Expression of the P00184_D11 (SEQ ID NO: 1), P00185_D11 (SEQ ID NO: 3), P00188_D12 (SEQ ID NO: 5), P00188_E01 (SEQ ID NO: 7), P00194_G01 (SEQ ID NO: 9), P00194_005 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_E05 (SEQ ID NO: 45), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00269_H08 (SEQ ID NO: 62), P00628_H02 (SEQ ID NO: 66), P00629_C08 (SEQ ID NO: 68), P00641_G11 (SEQ ID NO: 71), P00648_E12 (SEQ ID NO: 73), and P00697_C03 (SEQ ID NO: 75) genes can be accomplished by transient expression in 293 human embryonic kidney cells. For use of vectors such as pCEP4 having the EBV viral origin of replication, 293EBNA cells that are permissive for replication can be used. Transfection is accomplished using a lipid transfection reagent such as Lipofectamine Plus (Life Technologies, Rockville, Md.). Endotoxin-free plasmid DNA (100 µg) is added to 200 µl PLUS reagent and 10 ml DMEM-21 serun free media to give Mix A. This is incubated at room temperature for 15 minutes. Mix B is prepared from 400 µl lipofectamine and 10 ml serum-free DMEM-21. The two mixes are then combined and incubated at room temperature for another 15 minutes. An 850 cm² roller bottle containing the cells to be transfected at 70% confluence is rinsed with serum-free media and 100 ml of serum-free DMEM-2 with 15 mM HEPES pH 7.3 and the DNA-lipid transfection mixture is then added. The cells are then placed in a roller unit at 37° C. for 4 hours after which the volume of media is doubled by addition of DMEM-2 with 15 mM HEPES pH 7.3, 5% FBS and the bottle returned to roller unit overnight. Collect conditioned media every 2–3 days for 2–3 collections.

Example 6

Expression of the Clones in Baculovirus-Infected Insect Cells

Baculovirus-based expression is performed using one of the commercially available baculovirus expression systems such as, for example, from Bac-N-Blue™ (Invitrogen), BacPAK™ Baculovirus Expression System (Clontech), BAC-TO-BAC™ (Life Technologies), or Bac Vector System™ (Novagen). Viral infection of insect cells (e.g., *Spodoptera frugiperda* (Sf9) cells (ATCC CRL 1711)) and protein expression and purification are performed following manufacturers' instructions, or as described by O'Reilley, et al., *Baculovirus Expression Vectors: A Laboratory Manual*, Oxford: Oxford University Press (1994). Optionally, the coding region of the P00184_D11 (SEQ ID NO: 1), P00185_D11 (SEQ ID NO: 3), P00188_D12 (SEQ ID NO: 5), P00188_E01 (SEQ ID NO: 7), P00194_G01 (SEQ ID NO: 9), P00194_G05 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_E05 (SEQ ID NO: 45), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00269_H08 (SEQ ID NO: 62), P00628_H02 (SEQ ID NO: 66), P00629_C08 (SEQ ID NO: 68), P00641_G11 (SEQ ID NO: 71), P00648_E12 (SEQ ID NO: 73), and P00697_C03 (SEQ ID NO: 75) sequence is fused upstream of an epitope tag contained within a baculovirus expression vector, such as a poly-His tag or an immunoglobulin (Ig) tag (like Fc regions of an IgG). The poly-His or Ig tag aids protein purification.

Example 7

Preparation of antibodies that bind the polypeptide encoded by P00184_D11 (SEQ ID NO: 1), P00185_D11 (SEQ ID NO: 3), P00188_D12 (SEQ ID NO: 5), P00188_E01 (SEQ ID NO: 7), P00194_G01 (SEQ ID NO: 9), P00194_G05 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_E05 (SEQ ID NO: 45), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00269_H08 (SEQ ID NO: 62), P00628_H02 (SEQ ID NO: 66), P00629_C08 (SEQ ID NO: 68), P00641_G11 (SEQ ID NO: 71), P00648_E12 (SEQ ID NO: 73), and P00697_C03 (SEQ ID NO: 75)

This example illustrates preparation of monoclonal antibodies that specifically bind the polypeptide encoded by P00184_D11 (SEQ ID NO: 1), P00185_D11 (SEQ ID NO: 3), P00188_D12 (SEQ ID NO: 5), P00188_E01 (SEQ ID NO: 7), P00194_G01 (SEQ ID NO: 9), P00194_G05 (SEQ ID NO: 1), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_E05 (SEQ ID NO: 45), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00269_H08 (SEQ ID NO: 62), P00628_H02 (SEQ ID NO: 66), P00629_C08 (SEQ ID NO: 68), P00641_G11 (SEQ ID NO: 71), P00648_E12 (SEQ ID NO: 73), and P00697_C03 (SEQ ID NO: 75).

Techniques for producing the monoclonal antibodies are known in the art and are described, for instance, in Goding, supra. The immunogen may, for example, be purified protein encoded by the clone or recombinant host cells expressing P00184_D11 (SEQ ID NO: 1), P00185_D11 (SEQ ID NO: 3), P00188_D12 (SEQ ID NO: 5), P00188_E01 (SEQ ID NO: 7), P00094_G01 (SEQ ID NO: 9), P00194_G05 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_E05 (SEQ ID NO: 45), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00269_H08 (SEQ ID NO: 62), P00628_H02 (SEQ ID NO: 66), P00629_C08 (SEQ ID NO: 68), P00641_G11 (SEQ ID NO: 71), P00648_E12 (SEQ ID NO: 73), and P00697_C03 (SEQ ID NO: 75). Mice, such as BALB/c, are immunized with the immunogen emulsified in a selected adjuvant, for example Freund's adjuvant, and injected subcutaneously or intraperitoneally in an amount from 1–100 µg. Approximately 10 to 12 days later, the immunized mice are boosted with additional immunogen emulsified in the selected adjuvant. Thereafter, for several weeks, the mice may get additional boosts. Serum samples may be periodically obtained from the mice by retro-orbital bleeding for testing in ELISA assays to detect antibodies to the polypeptide encoded by P00184_D11 (SEQ ID NO: 1), P00185_D11 (SEQ ID NO: 3), P00188_D 12 (SEQ ID NO: 5), P00188_E01 (SEQ ID NO: 7), P00194_G01 (SEQ ID NO: 9), P00194_G05 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_E05 (SEQ ID NO: 45), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00269_H08 (SEQ ID NO: 62), P00628_H02 (SEQ ID NO: 66), P00629_C08 (SEQ ID NO: 68), P00641_G11 (SEQ ID NO: 71), P00648_E12 (SEQ ID NO: 73), and P00697_C03 (SEQ ID NO: 75).

After a suitable antibody titer has been detected, the animals "positive" for antibodies can be injected with a final intravenous injection of the immunogen. Three to four days later, the mice are sacrificed and the spleen cells are harvested. The spleen cells are then fused to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against the protein encoded by P00184_D11 (SEQ ID NO: 1), P00185_D11 (SEQ ID NO: 3), P00188_D12 (SEQ ID NO: 5), P00188_E01 (SEQ ID NO: 7), P00194_G01 (SEQ ID NO: 9), P00194_G05 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_E05 (SEQ ID NO: 45), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00269_H08 (SEQ ID NO: 62), P00628_H02 (SEQ ID NO: 66), P00629_C08 (SEQ ID NO: 68), P00641_G11 (SEQ ID NO: 71), P00648_E12 (SEQ ID NO: 73), and P00697_C03 (SEQ ID NO: 75).

The positive hybridoma cells can be injected intraperitoneally into syngeneic BALB/c mice to produce ascites containing the antibodies. Antibodies are purified by ammonium sulfate precipitation, protein A or protein G chromatography or other techniques well known in the art.

Example 8

Further Animal Models

The biological function of the P00184_D11 (SEQ ID NO:1), P00185_D11 (SEQ ID NO: 3), P00188_D12 (SEQ ID NO: 5), P00188_E01 (SEQ ID NO: 7), P00194_G01 (SEQ ID NO: 9), P00194_G05 (SEQ ID NO: 11), P00194_H10 (SEQ ID NO: 13), P00199_D08 (SEQ ID NO: 15), P00203_D04 (SEQ ID NO: 17), P00203_E06 (SEQ ID NO: 19), P00209_F06 (SEQ ID NO: 21), P00219_D02 (SEQ ID NO: 23), P00219_F06 (SEQ ID NO: 25), P00220_H05 (SEQ ID NO: 27), P00222_G03 (SEQ ID NO: 29), P00223_F07 (SEQ ID NO: 31), P00225_C01 (SEQ ID NO: 32), P00227_D11 (SEQ ID NO: 34), P00228_F03 (SEQ ID NO: 36), P00233_H08 (SEQ ID NO: 38), P00235_G08 (SEQ ID NO: 40), P00239_C11 (SEQ ID NO: 42), P00240_B04 (SEQ ID NO: 44), P00240_E05 (SEQ ID NO: 45), P00241_E12 (SEQ ID NO: 47), P00245_D06 (SEQ ID NO: 48), P00246_D12 (SEQ ID NO: 49), P00247_A04 (SEQ ID NO: 50), P00248_B04 (SEQ ID NO: 52), P00249_F09 (SEQ ID NO: 54), P00258_A10 (SEQ ID NO: 56), P00262_C10 (SEQ ID NO: 58), P00263_G06 (SEQ ID NO: 60), P00267_F08 (SEQ ID NO: 61), P00269_H08 (SEQ ID NO: 62), P00312_C04 (SEQ ID NO: 64), P00324_H02 (SEQ ID NO: 65), P00628_H02 (SEQ ID NO: 66), P00629_C08 (SEQ ID NO: 68), P00634_G11 (SEQ ID NO: 70), P00641_G11 (SEQ ID NO: 71), P00648_E12 (SEQ ID NO: 73), and P00697_C03 (SEQ ID NO: 75) genes and the encoded protein are further characterized in various animal models of heart, kidney and inflammatory disorders.

1. In Vivo Model of Cardiac Hypertrophy

Rats with left ventricular hypertrophy (LVH) are produced essentially as described in Schunkert, et al., *J. Clin. Invest.* (1990) 86(6):1913–1920. LVH is induced by pressure overload as a result of constriction of the ascending aorta. A stainless steel clip of 0.6-mm internal diameter is placed on the aorta of anesthetized weanling rats. Control animals undergo thoracotomy as a sham operation. Animals usually recover from surgery and appear healthy until about 20 weeks when a few animals may be in demise likely due to heart failure, which typically occurs at this point (Schunkert, et al., 1990, supra). The animals are sacrificed and hearts examined 10 weeks and 20 weeks post-operation. Hypertrophy is evident at both time points as determined by changes in left ventricle weight and thickness. Aortic banded rats and sham operated control animals are sacrificed and measured for heart weight, left ventricle (LV) weight, left ventricle thickness, and LV weight/body weight. Usually there are 6 animals per group. Data are expressed as average with standard deviation.

LVH rats are also examined for expression of ANP, BNP, cardiac α-actin, and/or β-myosin heavy chain mRNA, using Northern blot. Levels of these messages are expected to be elevated in the diseased animals, confirming that the banded rats were pressure overloaded and responded with cardiac hypertrophy. Poly A+mRNA is prepared from each of the animals for assessment of differentially expressed genes in the disease state, using microarray analysis in a preferred embodiment.

2. In Vivo Model of Viral Myocarditis

CVB3 infection in mice results in myocardial disease progression, which can be used as a model for examination of the pathogenesis of virus-induced human myocarditis. The virus is directly injurious to myocardial cells early following infection during the preinflammatory period as determined by light and electron microscopic cytological assessment (Arola, et al., *J. Med. Virol.* (1995) 47:251–259; Chow, et al., *Lab. Invest.* (1991) 64:55–64; McManus, et al., *Clin. Immunol. Immunopathol.* (1993) 68:159–169; Melnick, et al., *J. Expert. Med.* (1951) 93:247–266). Beginning by day two post-infection cytopathic lesions are evident in ventricular myocytes, characterized by cell vacuolar changes, contraction bands and coagulation necrosis (McManus, et al., supra). By day 5 post-infection this myocardial injury becomes obscured by inflammatory infiltrates, cellular calcification, and tissue edema.

In a typical protocol, A/J (H-$2^a$) mice (Jackson Laboratories, Bar Harbor, Me., 4 weeks of age) are acclimatised for one week prior to the onset of the experiment. Any mice that dies naturally during the course of the disease are not included in groups of mice to be used for RNA extraction. Mice are euthanized by $CO_2$ narcosis.

Myocarditic CVB3 (Dr. Charles J. Gauntt; University of Texas, San Antonio, Tex.) is stored at −80° C. Virus is propagated in HeLa cells (American Type Tissue Culture Collection, Rockville, Md.) and is routinely titred before the onset of all experiments using the plaque assay method, with modifications as previously described (Anderson, et al., *J. Virol.* (1996) 70:4632–4645).

Adolescent A/J mice are infected with 1×$10^5$ pfu of myocarditic CVB3 or PBS sham and euthanized on days 3, 9, and 30 post-infection. Ten to fifteen mice per group (CVB3 infected or sham injected) per time-point (days 3, 9, and 30) are euthanized and heart muscle is removed. Following a wash in sterile phosphate buffered saline, a small portion of the apex of the heart is removed and fixed in 4% paraformaldehyde. The remainder of the heart is flash frozen in liquid nitrogen and stored at −80° C. for future RNA isolation.

Sections from the heart are fixed in fresh DPBS-buffered 4% paraformaldehyde overnight at 4° C. Fixed tissue is dehydrated in graded alcohols, cleared in xylene, embedded in paraffin, and sectioned for hematoxylin and eosin, and Masson's trichrome stains. Serial sections are also prepared for in situ hybridization and nick-end labelling stained. The extent and severity of virus-induced injury (including coagulation necrosis, contraction band necrosis, and cytopathic effects), inflammation, and tissue fibrosis and calcification are evaluated and scored as previously described (Chow, et al., supra).

In situ hybridization for CVB3 viral RNA localization is carried out as previously described (Anderson, et al., supra; Hohenadl, et al., *Mol. Cell. Probes* (1991) 5:11–20). Briefly, tissue sections are incubated overnight in hybridization mixture containing digoxigenin-labelled, CVB3 strand-specific riboprobes. Post-hybridization washing is followed by blocking with 2% normal lamb serum. A sheep anti-digoxigenin polyclonal antibody conjugated to alkaline phosphatase (Boehringer Mannheim PQ, Laval, Canada) is developed in Sigma-Fast nitroblue tetrazolium-BCIP [5-bromo-4-chloro-3-indolylphosphate tuluidinium] (Sigma Chemical Co.). The slides are counterstained in fresh carmalum and examined for reaction product by light microscopy. Poly A+mRNA is prepared from each of the animals, as described herein, for assessment of differentially expressed genes in the disease states, using microarray.

3. In Vivo Model of Kidney Disease

In yet another representative example, an in vivo model of kidney disease is used to further characterize the differentially expressed genes of the present invention. For example, a rat model of an inherited form of autosomal dominant polycystic kidney disease (ADPKD) can be used, which develops in Han: SPRD rats (Kaspareit-Rittinghaus, et al., *Transplant Proc.* (1990) 6:2582–2583; Cowley, et al., *Kidney Int.* (1993) 43:522–534). Renal cysts and renal failure is evident in six months old male heterozygous rats (Cy/+), whereas control rats (+/+) show no sign of cysts or renal failure. Diseased (Cy/+) and normal (+/+) animals are sacrificed and the kidneys removed. For cDNA microarray analysis, poly A+mRNA is prepared, as described previously, for assessment of differentially expressed genes in the disease state, using microarray analysis in a preferred embodiment.

All references cited throughout the specification, including the examples, are hereby expressly incorporated by reference.

The invention claimed is:

1. An antibody or fragment thereof that specifically binds to an antigen selected from the group consisting of:
   (a) an antigen encoded by a polynucleotide encoding at least 50 contiguous amino acids from amino acids 1 to 148 of SEQ ID NO: 2;
   (b) an antigen encoded by a polynucleotide encoding a polypeptide having at least 75% sequence identity with amino acids 1 to 203 of SEQ ID NO: 2; and
   (c) an antigen encoded by a polynucleotide of SEQ ID NO: 1.

2. The antibody or fragment thereof of claim 1, wherein the antibody is a monoclonal antibody.

3. The antibody or fragment thereof of claim 2, wherein the monoclonal antibody is recombinantly produced.

4. The antibody or fragment thereof of claim 1, wherein the antibody or fragment thereof is labeled with a detectable marker.

5. The antibody or fragment thereof of claim 4, wherein the detectable marker is alkaline phosphatase.

6. The antibody or fragment thereof of claim 1, wherein the fragment thereof is selected from the group consisting of Fab, F(ab')2, Fv and sFv.

7. The antibody or fragment thereof of claim 1, wherein the antibody is a human antibody, a humanized antibody or a chimeric antibody.

8. A composition comprising an antibody or fragment thereof that specifically binds to an antigen selected from the group consisting of:
   (a) an antigen encoded by a polynucleotide encoding at least 50 contiguous amino acids from amino acids 1 to 148 of SEQ ID NO: 2;
   (b) an antigen encoded by a polynucleotide encoding a polypeptide having at least 75% sequence identity with amino acids 1 to 203 of SEQ ID NO: 2 and
   (c) an antigen encoded by a polynucleotide of SEQ ID NO: 1.

9. The composition of claim 8, further comprising a pharmaceutically acceptable carrier.

10. The composition of claim 8, wherein the antibody or fragment thereof is a monoclonal antibody.

11. The composition of claim 8, wherein the antibody or fragment thereof is labeled with a detectable marker.

12. The composition of claim 11, wherein the detectable marker is alkaline phosphatase.

13. The composition of claim 8, wherein the fragment thereof is selected from the group consisting of Fab, F(ab')2, Fv and sFv.

14. The composition of claim 8, wherein the antibody is a human antibody, a humanized antibody or a chimeric antibody.

15. A kit comprising:
   an antibody or fragment thereof that specifically binds to an antigen selected from the group consisting of an antigen encoded by a polynucleotide encoding at least 50 contiguous amino acids from amino acids 1 to 148 of SEQ ID NO: 2, an antigen encoded by a polynucleotide encoding a polypeptide having at least 75% sequence identity with amino acids 1 to 203 of SEQ ID NO: 2 and an antigen encoded by a polynucleotide of SEQ ID NO: 1.

16. The kit of claim 15, wherein the antibody is a monoclonal antibody.

17. The kit of claim 15, wherein the antibody or fragment thereof is labeled with a detectable marker.

18. The kit of claim 17, wherein the detectable marker is alkaline phosphatase.

19. The kit of claim 15, wherein the fragment thereof is selected from the group consisting of Fab, F(ab')2, Fv and sFv.

20. The kit of claim 15, wherein the antibody is a human antibody, a humanized antibody or a chimeric antibody.

* * * * *